(12) United States Patent
Barbion et al.

(10) Patent No.: US 10,183,943 B2
(45) Date of Patent: Jan. 22, 2019

(54) HETEROCYCLIC COMPOUNDS AND THEIR USE IN PREVENTING OR TREATING BACTERIAL INFECTIONS

(71) Applicant: MUTABILIS, Paris (FR)

(72) Inventors: Julien Barbion, Sannois (FR); Audrey Caravano, Enghien les Bains (FR); Sophie Chasset, Nandy (FR); Francis Chevreuil, Chantilly (FR); Nicolas Lecointe, Paris (FR); Benoît Ledoussal, Pommerit Jaudy (FR); Frédéric Le Strat, Combs la Ville (FR); Sébastien Richard, Paris (FR); Christophe Simon, Chevilly Larue (FR); Sophie Vomscheid, Paris (FR); Julie Brias, Paris (FR); Sophie Briet, Saint Leu la Foret (FR); Fabien Faivre, Drancy (FR); Géraldine Le Fralliec, Bondy (FR); Chrystelle Oliveira, Ermont (FR)

(73) Assignee: MUTABILIS, Paris (FR)

( * ) Notice: Subject to any disclaimer, the term of this patent is extended or adjusted under 35 U.S.C. 154(b) by 0 days.

(21) Appl. No.: 15/571,964

(22) PCT Filed: May 6, 2016

(86) PCT No.: PCT/EP2016/060142
§ 371 (c)(1),
(2) Date: Nov. 6, 2017

(87) PCT Pub. No.: WO2016/177862
PCT Pub. Date: Nov. 10, 2016

(65) Prior Publication Data
US 2018/0093985 A1     Apr. 5, 2018

(30) Foreign Application Priority Data

May 7, 2015 (EP) ..................................... 15305701
Feb. 8, 2016 (EP) ..................................... 16305144

(51) Int. Cl.
| | | |
|---|---|---|
| C07D 471/08 | (2006.01) | |
| A61P 31/04 | (2006.01) | |
| A61K 31/439 | (2006.01) | |
| A61K 31/444 | (2006.01) | |
| A61K 31/497 | (2006.01) | |
| A61K 31/501 | (2006.01) | |
| A61K 31/506 | (2006.01) | |
| A61K 31/546 | (2006.01) | |
| C07D 519/00 | (2006.01) | |

(52) U.S. Cl.
CPC .......... *C07D 471/08* (2013.01); *A61K 31/439* (2013.01); *A61K 31/444* (2013.01); *A61K 31/497* (2013.01); *A61K 31/501* (2013.01); *A61K 31/506* (2013.01); *A61K 31/546* (2013.01); *A61P 31/04* (2018.01); *C07D 519/00* (2013.01)

(58) Field of Classification Search
CPC ..................................................... C07D 471/08
See application file for complete search history.

(56) References Cited

U.S. PATENT DOCUMENTS

2014/0315876 A1   10/2014   Gu et al.

FOREIGN PATENT DOCUMENTS

| WO | 02/010172 A1 | 2/2002 |
| WO | 2013/150296 A1 | 10/2013 |

OTHER PUBLICATIONS

International Search Report and Written Opinion for PCT/EP2016/060142 dated Jul. 27, 2016.
European Seach Report for EP Application 15305701.3 dated Sep. 11, 2015.

*Primary Examiner* — Bruck Kifle
(74) *Attorney, Agent, or Firm* — Thompson Coburn LLP; Steven M. Ritchey

(57) ABSTRACT

The present invention relates to heterocyclic compounds, their process of preparation, pharmaceutical compositions comprising these compounds and use thereof, optionally in combination with other antibacterial agents and/or beta-lactam compounds, for the prevention or treatment of bacterial infections. The present invention also relates to the use of these compounds as β-lactamase inhibitors and/or as antibacterial agents.

24 Claims, No Drawings

HETEROCYCLIC COMPOUNDS AND THEIR USE IN PREVENTING OR TREATING BACTERIAL INFECTIONS

CROSS-REFERENCE TO RELATED APPLICATIONS

This application is a U.S. National Phase application of PCT/EP2016/060142, filed on May 6, 2016, claiming the benefit of European Application No. 15305701.3, filed on May 7, 2015 and European Application No. 16305144.4, filed on Feb. 8, 2016, each of which is incorporated herein by reference in its entirety.

The present invention relates to heterocyclic compounds, their process of preparation, pharmaceutical compositions comprising these compounds and use thereof, optionally in combination with other antibacterial agents and/or beta-lactam compounds, for the prevention or treatment of bacterial infections. The present invention also relates to the use of these compounds as β-lactamase inhibitors and/or as antibacterial agents.

It has been described that there is a continuous evolution of antibacterial resistance which could lead to bacterial strains against which known antibacterial compounds are inefficient.

There is thus a need to provide effective compounds and composition that can overcome bacterial antibiotic resistance.

The objective of the present invention is to provide heterocyclic compounds that can be used as antibacterial agents and/or beta-lactamase inhibitors.

An objective of the present invention is also to provide heterocyclic compounds that can be used for the prevention or for the treatment of bacterial infections.

Another objective of the present invention is to provide heterocyclic compounds that can overcome bacterial antibiotic resistance.

An objective of the invention is also to provide pharmaceutical compositions comprising such heterocyclic compounds, optionally in combination with one or more other antibacterial agent, for the prevention or for the treatment of bacterial infections and which can overcome bacterial antibiotic resistance.

Other objectives will appear throughout the description of the invention.

The present invention thus provides a compound selected from the group consisting of a compound of formula (I) wherein $R^1$ represents A and $R^2$ represents B and a compound of formula (I) wherein $R^1$ represents B and $R^2$ represents A

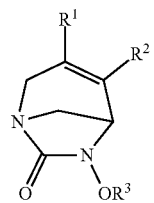

(I)

wherein

A, unsubstituted or substituted by one or more $T^1$, represents a saturated, partially or totally unsaturated or aromatic 4- to 10-membered heterocycle;

B, represents a hydrogen atom; a fluorine atom; $—(CH_2)_m OQ^1$; $—(CH_2)_m—CN$; $—(CH_2)_m—OC(O)Q^1$; $—(CH_2)_m—C(O)OQ^1$; $—(CH_2)_m—OC(O)OQ^1$; $—(CH_2)_m—OC(O)NQ^1Q^2$; $—(CH_2)_m—C(O)NQ^1Q^2$; $—(CH_2)_m—C(O)ONQ^1Q^2$; $—(CH_2)_m—C(O)NQ^1OQ^2$; $—(CH_2)_m—C(O)NQ^1—NQ^1Q^2$; $—(CH_2)_m—NQ^1C(O)Q^2$; $—(CH_2)_m—NQ^1S(O)_2NQ^1Q^2$; $—(CH_2)_m—NQ^1S(O)_2Q^2$; $—(CH_2)_m—NQ^1C(O)OQ^2$; $—(CH_2)_m—NQ^1C(O)NQ^1Q^2$; $—(CH_2)_n—NQ^1Q^2$; $—(CH_2)_n—NH—C(NHQ^3)=NQ^4$; $—(CH_2)_n—NH—CH=NQ^3$; $—(CH_2)_m—C(NHQ^3)=NQ^4$; or an unsubstituted or substituted by one or more $T^2$, $(C_1-C_3)$-alkyl; $(C_1-C_3)$-fluoroalkyl; $O—(C_1-C_3)$-fluoroalkyl; $—(CH_2)_m—(C_3-C_6)$-cycloalkyl; $—(CH_2)_m—(C_3-C_6)$-cyclofluoroalkyl;

$R^3$ represents $SO_3H$, $—CFHCOOH$ or $—CF_2COOH$;

$Q^1$ and $Q^2$, identical or different, independently represent a hydrogen atom; $—(CH_2)_r—NHQ^3$; $—(CH_2)_r—NH—C(NHQ^3)=NQ^4$; $—(CH_2)_r—NH—CH=NQ^3$; $(CH_2)_n—C(NHQ^3)=NQ^4$; $—(CH_2)_r—OQ^3$; $—(CH_2)_n—CONHQ^3$; or an unsubstituted or substituted by one or more $T^2$, $(C_1-C_3)$-alkyl; $(C_1-C_3)$-fluoroalkyl; saturated, partially or totally unsaturated or aromatic-$(CH_2)_m$-(4-, 5- or 6-membered heterocycle comprising at least one nitrogen atom); or $Q^1$, $Q^2$ and the nitrogen atom to which they are bonded, form together an unsubstituted or substituted by one or more $T^2$, saturated or partially unsaturated 4-, 5- or 6-membered heterocycle comprising 1, 2 or 3 heteroatoms;

$Q^3$ and $Q^4$, identical or different, independently represent a hydrogen atom or $(C_1-C_3)$-alkyl;

$T^1$, identical or different, independently represents a fluorine atom; $—(CH_2)_m OQ^1$; $—(CH_2)_m—CN$; $—(CH_2)_m—OC(O)Q^1$; $—(CH_2)_m—C(O)OQ^1$; $—(CH_2)_m—OC(O)OQ^1$; $—(CH_2)_m—OC(O)NQ^1Q^2$; $—(CH_2)_m—C(O)NQ^1Q^2$; $—(CH_2)_m—C(O)ONQ^1Q^2$; $—(CH_2)_m—C(O)NQ^1OQ^2$; $—(CH_2)_m—C(O)NQ^1—NQ^1Q^2$; $—(CH_2)_m—NQ^1C(O)Q^2$; $—(CH_2)_m—NQ^1S(O)_2NQ^1Q^2$; $—(CH_2)_m—NQ^1S(O)_2Q^2$; $—(CH_2)_m—NQ^1C(O)OQ^2$; $—(CH_2)_m—NQ^1C(O)NQ^1Q^2$; $—(CH_2)_m—NQ^1Q^2$; $—(CH_2)_m—NH—C(NHQ^3)=NQ^4$; $—(CH_2)_m—NH—CH=NQ^3$; $—(CH_2)_m—C(NHQ^3)=NQ^4$; $—(X)—(CH_2)_pOQ^1$; $—(X)—(CH_2)_n—CN$; $—(X)—(CH_2)_p—OC(O)Q^1$; $—(X)—(CH_2)_n—C(O)OQ^1$; $—(X)—(CH_2)_p—OC(O)OQ^1$; $—(X)—(CH_2)_p—OC(O)NQ^1Q^2$; $—(X)—(CH_2)_n—C(O)NQ^1Q^2$; $—(X)—(CH_2)_n—C(O)ONQ^1Q^2$; $—(X)—(CH_2)_n—C(O)NQ^1OQ^2$; $—(X)—(CH_2)_n—C(O)NQ^1—NQ^1Q^2$; $—(X)—(CH_2)_p—NQ^1C(O)Q^2$; $—(X)—(CH_2)_p—NQ^1S(O)_2NQ^1Q^2$; $—(X)—(CH_2)_p—NQ^1S(O)_2Q^2$; $—(X)—(CH_2)_p—NQ^1C(O)OQ^2$; $—(X)—(CH_2)_p—NQ^1C(O)NQ^1Q^2$; $—(X)—(CH_2)_p—NQ^1Q^2$; $—(X)—(CH_2)_p—NH—C(NHQ^3)=NQ^4$; $—(X)—(CH_2)_p—NH—CH=NQ^3$; $—(X)—(CH_2)_n—C(NHQ^3)=NQ^4$; $—C(O)—(CH_2)_nOQ^1$; $—C(O)—(CH_2)_n—CN$; $—C(O)—(CH_2)_n—OC(O)Q^1$; $—C(O)—(CH_2)_n—C(O)OQ^1$; $—C(O)—(CH_2)_n—OC(O)OQ^1$; $—C(O)—(CH_2)_n—OC(O)NQ^1Q^2$; $—C(O)—(CH_2)_n—C(O)NQ^1Q^2$; $—C(O)—(CH_2)_n—C(O)ONQ^1Q^2$; $—C(O)—(CH_2)_n—C(O)NQ^1OQ^2$; $—C(O)—(CH_2)_n—C(O)NQ^1—NQ^1Q^2$; $—C(O)—(CH_2)_n—NQ^1C(O)Q^2$; $—C(O)—(CH_2)_n—NQ^1S(O)_2NQ^1Q^2$; $—C(O)—(CH_2)_n—NQ^1S(O)_2Q^2$; $—C(O)—(CH_2)_n—NQ^1C(O)OQ^2$; $—C(O)—(CH_2)_n—NQ^1C(O)NQ^1Q^2$; $—C(O)—(CH_2)_n—NQ^1Q^2$; $—C(O)—(CH_2)_n—NH—C(NHQ^3)$ =NQ$^4$; —C(O)—(CH$_2$)$_n$—NH—CH=NQ$^3$; —C(O)—(CH$_2$)$_n$—C(NHQ$^3$)=NQ$^4$ or T$^1$, identical or different, independently represents an unsubstituted or substituted by one or more T$^2$, —(CH$_2$)$_m$-(4-, 5- or 6-membered saturated, partially or totally unsaturated or aromatic heterocycle); —(X)—(CH$_2$)$_m$-(4-, 5- or 6-membered saturated, partially or totally unsaturated or aromatic heterocycle); (C$_1$-C$_3$)-alkyl; (C$_1$-C$_3$)-fluoroalkyl; —(X)—(C$_1$-C$_3$)-alkyl; —(X)—(C$_1$-C$_3$)-fluoroalkyl; —(CH$_2$)$_m$—(C$_3$-C$_6$)-cycloalkyl; —(X)—(CH$_2$)$_m$—(C$_3$-C$_6$)-cycloalkyl; —(CH$_2$)$_m$—(C$_3$-C$_6$)-cyclofluoroalkyl; —(X)—(CH$_2$)$_m$—(C$_3$-C$_6$)-cyclofluoroalkyl; —C(O)—(CH$_2$)$_m$-(4-, 5- or 6-membered saturated, partially or totally unsaturated or aromatic heterocycle); —C(O)—(C$_1$-C$_3$)-alkyl; —C(O)—(C$_1$-C$_3$)-fluoroalkyl; —C(O)O—(C$_1$-C$_3$)-fluoroalkyl; —C(O)—(CH$_2$)$_m$—(C$_3$-C$_6$)-cycloalkyl; —C(O)—(CH$_2$)$_m$—(C$_3$-C$_6$)-cycloalkyl; —C(O)—(CH$_2$)$_m$—(C$_3$-C$_6$)-cyclofluoroalkyl; —C(O)—(CH$_2$)$_m$—(C$_3$-C$_6$)-cyclofluoroalkyl;

T$^2$, identical or different, independently represents —OH; —NH$_2$; —CONH$_2$;

m, identical or different, independently represents 0, 1, 2 or 3;

n, identical or different, independently represents 1, 2 or 3;

p, identical or different, independently represents 2 or 3;

r is 1, 2 or 3 when the (CH$_2$)$_r$ is directly linked to a carbon atom or 2 or 3 otherwise, preferably r is 2 or 3;

X, identical or different, independently represents O; S; S(O); S(O)$_2$ or N(Q$^3$);

wherein any carbon atom present within a group selected from alkyl, cycloalkyl, fluoroalkyl, cyclofluoroalkyl and heterocycle can be oxidized to form a C=O group;

any sulphur atom present within a heterocycle can be oxidized to form a S=O group or a S(O)$_2$ group;

any nitrogen atom present within a heterocycle or present within group wherein it is trisubstituted thus forming a tertiary amino group, can be further quaternized by a methyl group;

and a racemate, an enantiomer, a diastereoisomer, a geometric isomer or a pharmaceutically acceptable salt thereof.

Preferably, in the compound according to the invention:

A, unsubstituted or substituted by one or more T$^1$, represents a saturated, partially or totally unsaturated or aromatic 4- to 10-membered heterocycle;

B, represents a hydrogen atom; a fluorine atom; —(CH$_2$)$_m$OQ$^1$; —(CH$_2$)$_m$—CN; —(CH$_2$)$_m$—OC(O)Q$^1$; —(CH$_2$)$_m$—C(O)OQ$^1$; —(CH$_2$)$_m$—OC(O)OQ$^1$; —(CH$_2$)$_m$—OC(O)NQ$^1$Q$^2$; —(CH$_2$)$_m$—C(O)NQ$^1$Q$^2$; —(CH$_2$)$_m$—C(O)ONQ$^1$Q$^2$; —(CH$_2$)$_m$—C(O)NQ$^1$OQ$^2$; —(CH$_2$)$_m$—C(O)NQ$^1$—NQ$^1$Q$^2$; —(CH$_2$)$_n$—NQ$^1$C(O)Q$^2$; —(CH$_2$)$_n$—NQ$^1$S(O)$_2$NQ$^1$Q$^2$; —(CH$_2$)$_n$—NQ$^1$S(O)$_2$ Q$^2$; —(CH$_2$)$_n$—NQ$^1$C(O)OQ$^2$; —(CH$_2$)$_n$—NQ$^1$C(O)NQ$^1$Q$^2$; —(CH$_2$)$_n$—NQ$^1$Q$^2$; —(CH$_2$)$_n$—NH—C(NHQ$^3$)=NQ$^4$; —(CH$_2$)$_n$—NH—CH=NQ$^3$; —(CH$_2$)$_m$—C(NHQ$^3$)=NQ$^4$; or an unsubstituted or substituted by one or more T$^2$, (C$_1$-C$_3$)-alkyl; (C$_1$-C$_3$)-fluoroalkyl; O—(C$_1$-C$_3$)-fluoroalkyl; —(CH$_2$)$_m$—(C$_3$-C$_6$)-cycloalkyl; —(CH$_2$)$_m$—(C$_3$-C$_6$)-cyclofluoroalkyl;

R$^3$ represents —SO$_3$H, —CFHCOOH or —CF$_2$COOH;

Q$^1$ and Q$^2$, identical or different, independently represent a hydrogen atom; —(CH$_2$)$_p$—NHQ$^3$; —(CH$_2$)$_p$—NH—C(NHQ$^3$)=NQ$^4$; —(CH$_2$)$_p$—NH—CH=NQ$^3$; (CH$_2$)$_n$—C(NHQ$^3$)=NQ$^4$; —(CH$_2$)$_p$—OQ$^3$; —(CH$_2$)$_n$—CONHQ$^3$; or an unsubstituted or substituted by one or more T$^2$, (C$_1$-C$_3$)-alkyl; (C$_1$-C$_3$)-fluoroalkyl; saturated, partially or totally unsaturated or aromatic-(CH$_2$)$_m$-(4-, 5- or 6-membered heterocycle comprising at least one nitrogen atom); or Q$^1$, Q$^2$ and the nitrogen atom to which they are bonded, form together an unsubstituted or substituted by one or more T$^2$, saturated or partially unsaturated 4-, 5- or 6-membered heterocycle comprising 1, 2 or 3 heteroatoms;

Q$^3$ and Q$^4$, identical or different, independently represent a hydrogen atom or (C$_1$-C$_3$)-alkyl;

T$^1$, identical or different, independently represents a fluorine atom; —(CH$_2$)$_m$OQ$^1$; —(CH$_2$)$_m$—CN; —(CH$_2$)$_m$—OC(O)Q$^1$; —(CH$_2$)$_m$—C(O)OQ$^1$; —(CH$_2$)$_m$—OC(O)OQ$^1$; —(CH$_2$)$_m$—OC(O)NQ$^1$Q$^2$; —(CH$_2$)$_m$—C(O)NQ$^1$Q$^2$; —(CH$_2$)$_m$—C(O)ONQ$^1$Q$^2$; —(CH$_2$)$_m$—C(O)NQ$^1$Q$^2$; —(CH$_2$)$_m$—C(O)NQ$^1$—NQ$^1$Q$^2$; —(CH$_2$)$_m$—NQ$^1$C(O)Q$^2$; —(CH$_2$)$_m$—NQ$^1$S(O)$_2$NQ$^1$Q$^2$; —(CH$_2$)$_m$—NQ$^1$S(O)$_2$Q$^2$; —(CH$_2$)$_m$—NQ$^1$C(O)OQ$^2$; —(CH$_2$)$_m$—NQ$^1$C(O)NQ$^1$Q$^2$; —(CH$_2$)$_m$—NQ$^1$Q$^2$; —(CH$_2$)$_m$—NH—C(NHQ$^3$)=NQ$^4$; —(CH$_2$)$_m$—NH—CH=NQ$^3$; —(CH$_2$)$_m$—C(NHQ$^3$)=NQ$^4$; —(X)—(CH$_2$)$_p$OQ$^1$; —(X)—(CH$_2$)$_n$—CN; —(X)—(CH$_2$)$_p$—OC(O)Q$^1$; —(X)—(CH$_2$)$_n$—C(O)OQ$^1$; —(X)—(CH$_2$)$_p$—OC(O)OQ$^1$; —(X)—(CH$_2$)$_p$—OC(O)NQ$^1$Q$^2$; —(X)—(CH$_2$)$_n$—C(O)NQ$^1$Q$^2$; —(X)—(CH$_2$)$_n$—C(O)ONQ$^1$Q$^2$; —(X)—(CH$_2$)$_n$—C(O)NQ$^1$OQ$^2$; —(X)—(CH$_2$)$_n$—C(O)NQ$^1$-Q$^1$Q$^2$; —(X)—(CH$_2$)$_p$—NQ$^1$C(O)Q$^2$; —(X)—(CH$_2$)$_p$—NQ$^1$S(O)$_2$NQ$^1$Q$^2$; —(X)—(CH$_2$)$_p$—NQ$^1$S(O)$_2$Q$^2$; —(X)—(CH$_2$)$_p$—NQ$^1$C(O)OQ$^2$; —(X)—(CH$_2$)$_p$—NQ$^1$C(O)NQ$^1$Q$^2$; —(X)—(CH$_2$)$_p$—NQ$^1$Q$^2$; —(X)—(CH$_2$)$_p$—NH—C(NHQ$^3$)=NQ$^4$; (X)—(CH$_2$)$_p$—NH—CH=NQ$^3$; —(X)—(CH$_2$)$_n$—C(NHQ$^3$)=NQ$^4$; or T$^1$, identical or different, independently represents an unsubstituted or substituted by one or more T$^2$, —(CH$_2$)$_m$-(4-, 5- or 6-membered saturated, partially or totally unsaturated or aromatic heterocycle); —(X)—(CH$_2$)$_m$-(4-, 5- or 6-membered saturated, partially or totally unsaturated or aromatic heterocycle); (C$_1$-C$_3$)-alkyl; (C$_1$-C$_3$)-fluoroalkyl; O—(C$_1$-C$_3$)-fluoroalkyl; —(CH$_2$)$_m$—(C$_3$-C$_6$)-cycloalkyl; —(X)—(CH$_2$)$_m$—(C$_3$-C$_6$)-cycloalkyl; —(CH$_2$)$_m$—(C$_3$-C$_6$)-cyclofluoroalkyl; —(X)—(CH$_2$)$_m$—(C$_3$-C$_6$)-cyclofluoroalkyl;

T$^2$, identical or different, independently represents —OH; —NH$_2$; —CONH$_2$;

m, identical or different, independently represents 0, 1, 2 or 3;

n, identical or different, independently represents 1, 2 or 3;

p, identical or different, independently represents 2 or 3;

X, identical or different, independently represents O; S; S(O); S(O)$_2$ or N(Q$^3$);

wherein any carbon atom present within a group selected from alkyl, cycloalkyl, fluoroalkyl, cyclofluoroalkyl and heterocycle can be oxidized to form a C=O group;

any sulphur atom present within a heterocycle can be oxidized to form a S=O group or a S(O)$_2$ group;

any nitrogen atom present within a heterocycle or present within group wherein it is trisubstituted thus forming a tertiary amino group, can be further quaternized by a methyl group.

Preferably, the compound according to the invention is selected from the compounds of formulae (D) and (B)

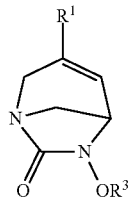
(D)

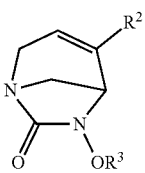
(B)

wherein $R^1$, $R^2$ and $R^3$ are defined according to formula (I).

Also preferably, the compound according to the invention is selected from a compound of formula (C)

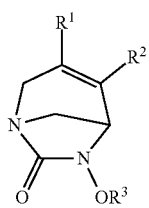
(C)

wherein $R^1$, $R^2$ and $R^3$ are defined according to formula (I) provided that B does not represent a hydrogen atom.

More preferably, the compound according to the invention is selected from compounds of formulae (I*), (D*), (B*), (C*)

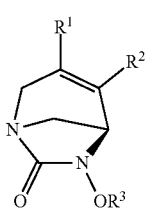
(I*)

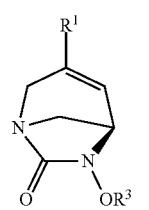
(D*)

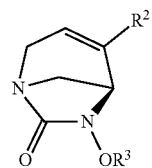
(B*)

(C*)

wherein $R^1$, $R^2$ and $R^3$ are respectively defined according to formulae (I), (D), (B) and (C).

For the compound according to the invention, A, unsubstituted or substituted by one or more $T^1$, represents a saturated, partially or totally unsaturated or aromatic 4- to 10-membered heterocycle. In a preferred manner, A, unsubstituted or substituted by one or more $T^1$, represents a carbon-linked saturated, partially or totally unsaturated or aromatic 4- to 10-membered heterocycle.

Preferably, A, unsubstituted or substituted by one or more $T^1$, represents a 4-, 5- or 6-membered monocyclic heterocycle or an 8- to 10-membered bicyclic heterocycle. More preferably, A, unsubstituted or substituted by one or more $T^1$, represents a 4-, 5- or 6-membered monocyclic heterocycle comprising at least one nitrogen atom or an 8- to 10-membered bicyclic heterocycle comprising at least one nitrogen atom.

Equally preferably, A, unsubstituted or substituted by one or more $T^1$, represents a 5- or 6-membered monocyclic heterocycle comprising at least one nitrogen atom and further comprising at least one further heteroatom or heteroatomic group selected from O, S, S(O), S(O)$_2$ and N or an 8- to 10-membered bicyclic heterocycle comprising at least one nitrogen atom and at least one further heteroatom or heteroatomic group selected from O, S, S(O), S(O)$_2$ and N. Such heterocycles can advantageously comprise 1, 2 or 3 further heteroatom or heteroatomic group selected from O, S, S(O), S(O)$_2$ and N.

More preferably, A, unsubstituted or substituted by one or more $T^1$, represents a 4-, 5- or 6-membered monocyclic heterocycle and even more preferably a 4-, 5- or 6-membered monocyclic heterocycle comprising at least one nitrogen atom and possibly comprising at least one further heteroatom or heteroatomic group, for example 1, 2 or 3 further heteroatom or heteroatomic group selected from O, S, S(O), S(O)$_2$ and N.

The invention notably provides a compound wherein A represents
  an unsubstituted or substituted by one or more $T^1$, saturated, partially or totally unsaturated or aromatic 4-, 5- or 6-membered heterocycle comprising at least one nitrogen atom; or
  an unsubstituted or substituted by one or more $T^1$, saturated, partially or totally unsaturated or aromatic 4-, 5- or 6-membered heterocycle comprising at least one nitrogen atom and at least one further heteroatom or heteroatomic group selected from O, S, S(O), S(O)$_2$ and N.

Preferred compounds according to the invention are compounds of formulae (D) and (B) wherein A, unsubstituted or substituted by one or more $T^1$, represents a group selected from azetidinyl, oxetanyl, oxazolyl, oxazolidinyl, oxadiazolyl, pyrrolyl, pyrrolidinyl, pyridyl, tetrahydropyridinyl, piperidinyl, morpholinyl, pyrazolyl, pyrimidinyl, pyrazinyl, tetrazolyl, imidazolyl, thienyl, furanyl, thiadiazolyl, isothiazolyl, triazolyl, tetrazolyl, pyrazolyl, isoxazolyl, 2-pyrrolidinonyl, imidazol-2,4-dione, 1,2,4-oxadiazol-5-one, 1,5-dihydropyrrolyl-2-one, pyrazinone, pyridazinone, pyridone, pyrimidone, dioxanyl, pyrrolidinyl, imidazolidinyl, pyranyl, tetrahydrofuranyl, dioxolanyl, tetrahydropyranyl. Corresponding compounds of formulae (D*) and (B*) according to the invention are equally preferred.

Equally preferred compounds according to the invention are compounds of formula (C) wherein A, unsubstituted or substituted by one or more $T^1$, represents a group selected from azetidinyl, oxetanyl, oxazolyl, oxazolidinyl, oxadiazolyl, pyrrolyl, pyrrolidinyl, pyridyl, tetrahydropyridinyl, piperidinyl, morpholinyl, pyrazolyl, pyrimidinyl, pyrazinyl, tetrazolyl, imidazolyl, thienyl, thiazolyl, furanyl, thiadiazolyl, isothiazolyl, triazolyl, tetrazolyl, pyrazolyl, isoxazolyl, 2-pyrrolidinonyl, imidazol-2,4-dione, 1,2,4-oxadiazol-5-one, 1,5-dihydropyrrolyl-2-one, pyrazinone, pyridazinone, pyridone, pyrimidone, dioxanyl, pyrrolidinyl, imidazolidinyl, pyranyl, tetrahydrofuranyl, dioxolanyl, tetrahydropyranyl. Corresponding compounds of formula (C*) according to the invention are equally preferred.

Preferably, in the compounds of the invention, B represents H or an unsubstituted or substituted by one or more $T^2$, $(C_1-C_3)$-alkyl, $-(CH_2)_m-C(O)NQ^1Q^2$, $-(CH_2)_m-NQ^1C(O)Q^2$ wherein $T^2$, m, $Q^1$ and $Q^2$ are as defined above, preferably $Q^1$ and $Q^2$ are H or $(C_1-C_3)$-alkyl. Preferably, in the compounds of the invention B represents H or $(C_1-C_3)$-alkyl. Preferably, in the compounds of the invention, B represents H or an unsubstituted or substituted by one or more $T^2$, $(C_1-C_3)$-alkyl, $-(CH_2)_m-C(O)NQ^1Q^2$, wherein $T^2$, m, $Q^1$ and $Q^2$ are as defined above, preferably $Q^1$ and $Q^2$ are H or $(C_1-C_3)$-alkyl. Preferably, in the compounds of the invention B represents H or $(C_1-C_3)$-alkyl.

Preferably, in the compounds of the invention, $T^1$ represents an unsubstituted or substituted by one or more $T^2$, $(C_1-C_3)$-alkyl; $-(CH_2)_mOQ^1$; $-(CH_2)_mC(O)OQ^1$; $(CH_2)_mNQ^1Q^2$, $-(CH_2)_m-C(O)NQ^1OQ^2$; $-(CH_2)_m-C(O)NQ^1-NQ^1Q^2$; $-(CH_2)_m-NQ^1C(O)Q^2$; $-(CH_2)_m-NQ^1S(O)_2NQ^1Q^2$; $-(CH_2)_m-C(O)NQ^1Q^2$; $-(CH_2)_m-NQ^1C(O)NQ^1Q^2$; $-(CH_2)_m-NQ^1Q^2$; $-(CH_2)_m-NH-C(NHQ^3)=NQ^4$; an unsubstituted or substituted by one or more $T^2$, $-C(O)(C_1-C_3)$-alkyl; $-C(O)(CH_2)_nOQ^1$, $-C(O)(CH_2)_nC(O)OQ^1$, $-C(O)(CH_2)_n-NQ^1Q^2$, $-C(O)(CH_2)_n-C(O)NQ^1OQ^2$; $-C(O)(CH_2)_n-C(O)NQ^1-NQ^1Q^2$; $-C(O)(CH_2)_n-NQ^1C(O)Q^2$; $-C(O)(CH_2)_n-NQ^1S(O)_2 NQ^1Q^2$; $-C(O)(CH_2)_n-NQ^1C(O)NQ^1Q^2$; $-C(O)(CH_2)_n-NQ^1Q^2$; $-C(O)(CH_2)_n-NH-C(NHQ^3)=NQ^4$; $-(X)-(C_1-C_3)$-alkyl; $-(X)-(CH_2)_pOQ^1$, $-(X)-(CH_2)_nC(O)OQ^1$, $-(X)-(CH_2)_pNQ^1Q^2$, $-(X)-(CH_2)_n-C(O)NQ^1OQ^2$; $-(X)-(CH_2)_n-C(O)NQ^1-NQ^1Q^2$; $-(X)-(CH_2)_p-NQ^1C(O)Q^2$; $-(X)-(CH_2)_p-NQ^1S(O)_2NQ^1Q^2$; $-(X)-(CH_2)_p-NQ^1C(O)NQ^1Q^2$; $-(X)-(CH_2)_p-NQ^1Q^2$; $-(X)-(CH_2)_p-NH-C(NHQ^3)=NQ^4$; wherein $T^2$, m, n, p, $Q^1$, $Q^2$, $Q^3$ and $Q^4$ are as defined above, preferably $Q^1$, $Q^2$, $Q^3$ and $Q^4$ each identical or different represent H or $-(C_1-C_3)$-alkyl. Preferably, in the compounds of the invention, $T^1$ represents a $-(C_1-C_3)$-alkyl, $-(CH_2)_mOQ^1$; $-(CH_2)_m-C(O)OQ^1$; $-(CH_2)_m-C(O)NQ^1Q^2$; $-(CH_2)_m-NQ^1C(O)Q^2$; $-(CH_2)_m-NQ^1C(O)NQ^1Q^2$; $-(CH_2)_m-NQ^1Q^2$; $-C(O)-(C_1-C_3)$-alkyl, $-C(O)-(CH_2)_nOQ^1$; $-C(O)-(CH_2)_n-C(O)OQ^1$; $-C(O)-(CH_2)_n-C(O)NQ^1Q^2$; $-C(O)-(CH_2)_n-NQ^1C(O)Q^2$; $-C(O)-(CH_2)_n-NQ^1C(O)NQ^1Q^2$; $-C(O)-(CH_2)_n-NQ^1Q^2$; $-(X)-(C_1-C_3)$-alkyl; $-(X)-(CH_2)_pOQ^1$; $-(X)-(CH_2)_n-C(O)OQ^1$; $-(X)-(CH_2)_n-C(O)NQ^1Q^2$; $-(X)-(CH_2)_p-NQ^1C(O)Q^2$; $-(X)-(CH_2)_p-NQ^1C(O)NQ^1Q^2$; $-(X)-(CH_2)_p-NQ^1Q^2$; wherein $T^2$, m, n, p, $Q^1$, $Q^2$, $Q^3$ and $Q^4$ are as defined above, preferably $Q^1$, $Q^2$, $Q^3$ and $Q^4$ each identical or different represent H or $-(C_1-C_3)$-alkyl. Preferably, in the compounds of the invention, $T^1$ represents an unsubstituted or substituted by one or more $T^2$, $(C_1-C_3)$-alkyl; $(CH_2)_mOQ^1$, $(CH_2)_mC(O)OQ^1$, $(CH_2)_mNQ^1Q^2$, wherein $T^2$, m $Q^1$ and $Q^2$ are as defined above. Preferably, in the compounds of the invention, $T^1$ represents a $(C_1-C_3)$-alkyl; $(CH_2)_mOQ^1$, $(CH_2)_mNQ^1Q^2$, wherein m $Q^1$ and $Q^2$ are as defined above, preferably $Q^1$ and $Q^2$ represents H or $(C_1-C_3)$-alkyl.

Preferably, in the compounds of the invention, $T^1$ represents an unsubstituted or substituted by one or more $T^2$, $(C_1-C_3)$-alkyl; $(CH_2)_mOQ^1$, $-(CH_2)_m-C(O)NQ^1Q^2$; $(CH_2)_mC(O)OQ^1$, $(CH_2)_mNQ^1Q^2$, wherein $T^2$, m $Q^1$ and $Q^2$ are as defined above. Preferably, in the compounds of the invention, $T^1$ represents a $(C_1-C_3)$-alkyl; $OQ^1$, $C(O)OQ^1$, $(CH_2)_mNQ^1Q^2$, $C(O)NQ^1Q^2$; wherein m $Q^1$ and $Q^2$ are as defined above, preferably $Q^1$ and $Q^2$ represents H or $(C_1-C_3)$-alkyl.

The present invention also relates to the combination of each of the preferred features for the substituent.

Preferably in the compounds of the invention:

A represents an unsubstituted or substituted by one or more $T^1$, represents a saturated, partially or totally unsaturated or aromatic 4- to 10-membered heterocycle. In a preferred manner, A, unsubstituted or substituted by one or more $T^1$, represents a carbon-linked saturated, partially or totally unsaturated or aromatic 4- to 10-membered heterocycle; or A represents, unsubstituted or substituted by one or more $T^1$, represents a 5- or 6-membered monocyclic heterocycle comprising at least one nitrogen atom and further comprising at least one further heteroatom or heteroatomic group selected from O, S, S(O), S(O)$_2$ and N or an 8- to 10-membered bicyclic heterocycle comprising at least one nitrogen atom and at least one further heteroatom or heteroatomic group selected from O, S, S(O), S(O)$_2$ and N. Such heterocycles can advantageously comprise 1, 2 or 3 further heteroatom or heteroatomic group selected from O, S, S(O), S(O)$_2$ and N; and B represents H or an unsubstituted or substituted by one or more $T^2$, $(C_1-C_3)$-alkyl, $-(CH_2)_m-C(O)NQ^1Q^2$, $-(CH_2)_m-NQ^1C(O)Q^2$ wherein $T^2$, m, $Q^1$ and $Q^2$ are as defined above, preferably $Q^1$ and $Q^2$ are H or $(C_1-C_3)$-alkyl. Preferably, in the compounds of the invention B represents H or $(C_1-C_3)$-alkyl; and $T^1$ represents an unsubstituted or substituted by one or more $T^2$, $(C_1-C_3)$-alkyl; $(CH_2)_mOQ^1$, $(CH_2)_mC(O)OQ^1$, $(CH_2)_mNQ^1Q^2$, $-(CH_2)_m-C(O)NQ^1Q^2$; $-(CH_2)_m-C(O)NQ^1-NQ^1Q^2$; $-(CH_2)_m-NQ^1C(O)Q^2$; $-(CH_2)_m-C(O)NQ^1Q^2$; $-(CH_2)_m-NQ^1S(O)_2NQ^1Q^2$; $-(CH_2)_m-NQ^1C(O)NQ^1Q^2$; $-(CH_2)_m-NQ^1Q^2$; $-(CH_2)_m-NH-C(NHQ^3)=NQ^4$; an unsubstituted or substituted by one or more $T^2$, $-C(O)(C_1-C_3)$-alkyl; $-C(O)(CH_2)_nOQ^1$, $-C(O)(CH_2)_n-C(O)OQ^1$, $-C(O)(CH_2)_n-NQ^1Q^2$, $-C(O)-(CH_2)_n-C(O)NQ^1OQ^2$; $-C(O)(CH_2)_n-C(O)NQ^1-NQ^1Q^2$; $-C(O)(CH_2)_n-NQ^1C(O)Q^2$; $-C(O)(CH_2)_n-NQ^1S(O)_2NQ^1Q^2$; $-C(O)(CH_2)_n-NQ^1C(O)NQ^1Q^2$; $-C(O)(CH_2)_n-NQ^1Q^2$; $-C(O)(CH_2)_n-NH-C(NHQ^3)=NQ^4$; $-(X)-(C_1-C_3)$-alkyl; $-(X)-(CH_2)_pOQ^1$, —(X)—$(CH_2)_n$C(O)OQ$^1$, —(X)—$(CH_2)_p$NQ$^1$Q$^2$, —(X)—$(CH_2)_n$—C(O)NQ$^1$Q$^2$; —(X)—$(CH_2)_n$—C(O)NQ$^1$-NQ$^1$Q$^2$; —(X)—$(CH_2)_p$—NQ$^1$C(O)Q$^2$; —(X)—$(CH_2)_p$—NQ$^1$S(O)$_2$ NQ$^1$Q$^2$; —(X)—$(CH_2)_p$—NQ$^1$C(O)NQ$^1$Q$^2$; —(X)—$(CH_2)_p$—NQ$^1$Q$^2$; —(X)—$(CH_2)_p$—NH—C(NHQ$^3$)=NQ$^4$; wherein T$^2$, m, n, p, Q$^1$, Q$^2$, Q$^3$ and Q$^4$ are as defined above, preferably Q$^1$, Q$^2$, Q$^3$ and Q$^4$ each identical or different represent H or —(C$_1$-C$_3$)-alkyl. Preferably, in the compounds of the invention, T$^1$ represents a —(C$_1$-C$_3$)-alkyl, —$(CH_2)_m$OQ$^1$; —$(CH_2)_m$—C(O)OQ$^1$; —$(CH_2)_m$—C(O)NQ$^1$Q$^2$; —$(CH_2)_m$—NQ$^1$C(O)Q$^2$; —$(CH_2)_m$—NQ$^1$C(O)NQ$^1$Q$^2$; —$(CH_2)_m$—NQ$^1$Q$^2$; —C(O)—(C$_1$-C$_3$)-alkyl, —C(O)—$(CH_2)_n$OQ$^1$; —C(O)—$(CH_2)_n$—C(O)OQ$^1$; —C(O)—$(CH_2)_n$—C(O)NQ$^1$Q$^2$; —C(O)—$(CH_2)_n$—NQ$^1$C(O)Q$^2$; —C(O)—$(CH_2)_n$—NQ$^1$C(O)NQ$^1$Q$^2$; —C(O)—$(CH_2)_n$—NQ$^1$Q$^2$; —(X)—(C$_1$-C$_3$)-alkyl; —(X)—$(CH_2)_p$OQ$^1$—(X)—$(CH_2)_n$—C(O)OQ$^1$; —(X)—$(CH_2)_n$—C(O)NQ$^1$Q$^2$; —(X)—$(CH_2)_p$—NQ$^1$C(O)Q$^2$; —(X)—$(CH_2)_p$—NQ$^1$C(O)NQ$^1$Q$^2$; —(X)—$(CH_2)_p$—NQ$^1$Q$^2$; wherein T$^2$, m, n, p, Q$^1$, Q$^2$, Q$^3$ and Q$^4$ are as defined above, preferably Q$^1$, Q$^2$, Q$^3$ and Q$^4$ each identical or different represent H or —(C$_1$-C$_3$)-alkyl. Preferably, in the compounds of the invention, T$^1$ represents an unsubstituted or substituted by one or more T$^2$, (C$_1$-C$_3$)-alkyl; $(CH_2)_m$OQ$^1$, $(CH_2)_m$C(O)OQ$^1$, $(CH_2)_m$NQ$^1$Q$^2$, wherein T$^2$, m Q$^1$ and Q$^2$ are as defined above. Preferably, in the compounds of the invention, T$^1$ represents a (C$_1$-C$_3$)-alkyl; OQ$^1$, C(O)OQ$^1$, $(CH_2)_m$NQ$^1$Q$^2$, wherein m Q$^1$ and Q$^2$ are as defined above, preferably Q$^1$ and Q$^2$ represents H or (C$_1$-C$_3$)-alkyl.

Preferably, in the compounds of the invention, T$^1$ represents an unsubstituted or substituted by one or more T$^2$, (C$_1$-C$_3$)-alkyl; $(CH_2)_m$OQ$^1$, —$(CH_2)_m$—C(O)NQ$^1$Q$^2$; $(CH_2)_m$C(O)OQ$^1$, $(CH_2)_m$NQ$^1$Q$^2$, wherein T$^2$, m Q$^1$ and Q$^2$ are as defined above. Preferably, in the compounds of the invention, T$^1$ represents a (C$_1$-C$_3$)-alkyl; OQ$^1$, C(O)OQ$^1$, —C(O)NQ$^1$Q$^2$; $(CH_2)_m$NQ$^1$Q$^2$, wherein m Q$^1$ and Q$^2$ are as defined above, preferably Q$^1$ and Q$^2$ represents H or (C$_1$-C$_3$)-alkyl.

Preferably in the compounds of the invention:

A represents, unsubstituted or substituted by one or more T$^1$, represents a 5- or 6-membered monocyclic heterocycle comprising at least one nitrogen atom and further comprising at least one further heteroatom or heteroatomic group selected from O, S, S(O), S(O)$_2$ and N or an 8- to 10-membered bicyclic heterocycle comprising at least one nitrogen atom and at least one further heteroatom or heteroatomic group selected from O, S, S(O), S(O)$_2$ and N. Such heterocycles can advantageously comprise 1, 2 or 3 further heteroatom or heteroatomic group selected from O, S, S(O), S(O)$_2$ and N; and B represents H or an unsubstituted or substituted by one or more T$^2$, (C$_1$-C$_3$)-alkyl, —$(CH_2)_m$—C(O)NQ$^1$Q$^2$, —$(CH_2)_m$—NQ$^1$C(O)Q$^2$ wherein T$^2$, m, Q$^1$ and Q$^2$ are as defined above, preferably Q$^1$ and Q$^2$ are H or (C$_1$-C$_3$)-alkyl. Preferably, B represents H or (C$_1$-C$_3$)-alkyl; and T$^1$ represents a —(C$_1$-C$_3$)-alkyl, —$(CH_2)_m$OQ$^1$; —$(CH_2)_m$—C(O)OQ$^1$; —$(CH_2)_m$—C(O)NQ$^1$Q$^2$; —$(CH_2)_m$—NQ$^1$C(O)Q$^2$; —$(CH_2)_m$—NQ$^1$C(O)NQ$^1$Q$^2$; —$(CH_2)_m$—NQ$^1$Q$^2$; —C(O)—(C$_1$-C$_3$)-alkyl, —C(O)—$(CH_2)_n$OQ$^1$; —C(O)—$(CH_2)_n$—C(O)OQ$^1$; —C(O)—$(CH_2)_n$—C(O)NQ$^1$Q$^2$; —C(O)—$(CH_2)_n$—NQ$^1$C(O)Q$^2$; —C(O)—$(CH_2)_n$—NQ$^1$C(O)NQ$^1$Q$^2$; —C(O)—$(CH_2)_n$—NQ$^1$Q$^2$; —(X)—(C$_1$-C$_3$)-alkyl; —(X)—$(CH_2)_p$OQ$^1$; —(X)—$(CH_2)_n$—C(O)OQ$^1$; —(X)—$(CH_2)_n$—C(O)NQ$^1$Q$^2$; —(X)—$(CH_2)_p$—NQ$^1$C(O)Q$^2$; —(X)—$(CH_2)_p$—NQ$^1$C(O)NQ$^1$Q$^2$; —(X)—$(CH_2)_p$—NQ$^1$Q$^2$; wherein T$^2$, m, n, p, Q$^1$, Q$^2$, Q$^3$ and Q$^4$ are as defined above, preferably Q$^1$, Q$^2$, Q$^3$ and Q$^4$ each identical or different represent H or —(C$_1$-C$_3$)-alkyl. Preferably, T$^1$ represents an unsubstituted or substituted by one or more T$^2$, (C$_1$-C$_3$)-alkyl; $(CH_2)_m$OQ$^1$, $(CH_2)_m$C(O)OQ$^1$, $(CH_2)_m$NQ$^1$Q$^2$, wherein T$^2$, m Q$^1$ and Q$^2$ are as defined above. Preferably, in the compounds of the invention, T$^1$ represents a (C$_1$-C$_3$)-alkyl; OQ$^1$, C(O)OQ$^1$, $(CH_2)_m$NQ$^1$Q$^2$, wherein m Q$^1$ and Q$^2$ are as defined above, preferably Q$^1$ and Q$^2$ represents H or (C$_1$-C$_3$)-alkyl. Preferably, T$^1$ represents an unsubstituted or substituted by one or more T$^2$, (C$_1$-C$_3$)-alkyl; $(CH_2)_m$OQ$^1$, —$(CH_2)_m$—C(O)NQ$^1$Q$^2$; $(CH_2)_m$C(O)OQ$^1$, $(CH_2)_m$NQ$^1$Q$^2$, wherein T$^2$, m Q$^1$ and Q$^2$ are as defined above. Preferably, in the compounds of the invention, T$^1$ represents a (C$_1$-C$_3$)-alkyl; OQ$^1$, C(O)OQ$^1$, $(CH_2)_m$NQ$^1$Q$^2$, —C(O)NQ$^1$Q$^2$; wherein m Q$^1$ and Q$^2$ are as defined above, preferably Q$^1$ and Q$^2$ represents H or (C$_1$-C$_3$)-alkyl.

Preferably in the compounds of the invention:

A represents an unsubstituted or substituted by one or more T$^1$, represents a saturated, partially or totally unsaturated or aromatic 4- to 10-membered heterocycle. In a preferred manner, A, unsubstituted or substituted by one or more T$^1$, represents a carbon-linked saturated, partially or totally unsaturated or aromatic 4- to 10-membered heterocycle; or A represents, unsubstituted or substituted by one or more T$^1$, represents a 5- or 6-membered monocyclic heterocycle comprising at least one nitrogen atom and further comprising at least one further heteroatom or heteroatomic group selected from O, S, S(O), S(O)$_2$ and N or an 8- to 10-membered bicyclic heterocycle comprising at least one nitrogen atom and at least one further heteroatom or heteroatomic group selected from O, S, S(O), S(O)$_2$ and N. Such heterocycles can advantageously comprise 1, 2 or 3 further heteroatom or heteroatomic group selected from O, S, S(O), S(O)$_2$ and N; and B represents H or an unsubstituted or substituted by one or more T$^2$, (C$_1$-C$_3$)-alkyl, —$(CH_2)_m$—C(O)NQ$^1$Q$^2$, wherein T$^2$, m, Q$^1$ and Q$^2$ are as defined above, preferably Q$^1$ and Q$^2$ are H or (C$_1$-C$_3$)-alkyl. Preferably, in the compounds of the invention B represents H or (C$_1$-C$_3$)-alkyl; and T$^1$ represents an unsubstituted or substituted by one or more T$^2$, (C$_1$-C$_3$)-alkyl; $(CH_2)_m$OQ$^1$, $(CH_2)_m$C(O)OQ$^1$, $(CH_2)_m$NQ$^1$Q$^2$, —$(CH_2)_m$—C(O)NQ$^1$OQ$^2$; —$(CH_2)_m$—C(O)NQ$^1$-NQ$^1$Q$^2$; —$(CH_2)_m$—NQ$^1$C(O)Q$^2$; —$(CH_2)_m$—C(O)NQ$^1$Q$^2$; —$(CH_2)_m$—NQ$^1$S(O)$_2$NQ$^1$Q$^2$; —$(CH_2)_m$—NQ$^1$C(O)NQ$^1$Q$^2$; —$(CH_2)_m$—NQ$^1$Q$^2$; —$(CH_2)_m$—NH—C(NHQ$^3$)=NQ$^4$; an unsubstituted or substituted by one or more T$^2$, —C(O)(C$_1$-C$_3$)-alkyl; —C(O)$(CH_2)_n$OQ$^1$, —C(O)$(CH_2)_n$—C(O)OQ$^1$, —C(O)$(CH_2)_n$—NQ$^1$Q$^2$, —C(O)—$(CH_2)_n$—C(O)NQ$^1$OQ$^2$; —C(O)$(CH_2)_n$—C(O)NQ$^1$—NQ$^1$Q$^2$; —C(O)$(CH_2)_n$—NQ$^1$C(O)Q$^2$; —C(O)$(CH_2)_n$—NQ$^1$S(O)$_2$NQ$^1$Q$^2$; —C(O)$(CH_2)_n$—NQ$^1$C(O)NQ$^1$Q$^2$; —C(O)$(CH_2)_n$—NQ$^1$Q$^2$; —C(O)$(CH_2)_n$—NH—C(NHQ$^3$)=NQ$^4$; —(X)—(C$_1$-C$_3$)-alkyl; —(X)—$(CH_2)_p$OQ$^1$, —(X)—$(CH_2)_n$—C(O)OQ$^1$, —(X)—$(CH_2)_p$NQ$^1$Q$^2$, —(X)—$(CH_2)_n$—C(O)NQ$^1$OQ$^2$; —(X)—$(CH_2)_n$—C(O)NQ$^1$—NQ$^1$Q$^2$; —(X)—$(CH_2)_p$—NQ$^1$C(O)Q$^2$; —(X)—$(CH_2)_p$—NQ$^1$S(O)$_2$NQ$^1$Q$^2$; —(X)—$(CH_2)_p$—NQ$^1$C(O)NQ$^1$Q$^2$; —(X)—$(CH_2)_p$—NQ$^1$Q$^2$; —(X)—$(CH_2)_p$—NH—C(NHQ$^3$)=NQ$^4$; wherein T$^2$, m, n, p, Q$^1$, Q$^2$, Q$^3$ and Q$^4$ are as defined above, preferably Q$^1$, Q$^2$, Q$^3$ and Q$^4$ each identical or different represent H or —(C$_1$-C$_3$)-alkyl. Preferably, in the compounds of the invention, T$^1$ represents a —(C$_1$-C$_3$)-alkyl, —$(CH_2)_m$OQ$^1$; —$(CH_2)_m$—C(O)OQ$^1$; —$(CH_2)_m$—C(O)NQ$^1$Q$^2$; —$(CH_2)_m$—NQ$^1$C(O)Q$^2$; —$(CH_2)_m$—NQ$^1$C(O)NQ$^1$Q$^2$; —$(CH_2)_m$—NQ$^1$Q$^2$; —C(O)—(C$_1$-C$_3$)-alkyl, —C(O)—$(CH_2)_n$—OQ$^1$; —C(O)—$(CH_2)_n$—C(O)

$OQ^1$; —C(O)—$(CH_2)_n$—C(O)$NQ^1Q^2$; —C(O)—$(CH_2)_n$—$NQ^1C(O)Q^2$; —C(O)—$(CH_2)_n$—$NQ^1C(O)NQ^1Q^2$; —C(O)—$(CH_2)_n$—$NQ^1Q^2$; —(X)—$(C_1-C_3)$-alkyl; —(X)—$(CH_2)_p OQ^1$-(X)—$(CH_2)_n$—$C(O)OQ^1$; —(X)—$(CH_2)_n$—$C(O)NQ^1Q^2$; —(X)—$(CH_2)_p$—$NQ^1C(O)Q^2$; —(X)—$(CH_2)_p$—$NQ^1C(O)NQ^1Q^2$; —(X)—$(CH_2)_p$—$NQ^1Q^2$; wherein $T^2$, m, n, p, $Q^1$, $Q^2$, $Q^3$ and $Q^4$ are as defined above, preferably $Q^1$, $Q^2$, $Q^3$ and $Q^4$ each identical or different represent H or —$(C_1-C_3)$-alkyl. Preferably, in the compounds of the invention, $T^1$ represents an unsubstituted or substituted by one or more $T^2$, $(C_1-C_3)$-alkyl; $(CH_2)_m OQ^1$, $(CH_2)_m C(O)OQ^1$, $(CH_2)_m NQ^1Q^2$, wherein $T^2$, m $Q^1$ and $Q^2$ are as defined above. Preferably, in the compounds of the invention, $T^1$ represents a $(C_1-C_3)$-alkyl; $OQ^1$, $C(O)OQ^1$, $(CH_2)_m NQ^1Q^2$, wherein m $Q^1$ and $Q^2$ are as defined above, preferably $Q^1$ and $Q^2$ represents H or $(C_1-C_3)$-alkyl.

Preferably, in the compounds of the invention, $T^1$ represents an unsubstituted or substituted by one or more $T^2$, $(C_1-C_3)$-alkyl; $(CH_2)_m OQ^1$, —$(CH_2)_m$—$C(O)NQ^1Q^2$; $(CH_2)_m C(O)OQ^1$, $(CH_2)_m NQ^1Q^2$, wherein $T^2$, m $Q^1$ and $Q^2$ are as defined above.

Preferably, in the compounds of the invention, $T^1$ represents a $(C_1-C_3)$-alkyl; $OQ^1$, $C(O)OQ^1$, —$C(O)NQ^1Q^2$; $(CH_2)_m NQ^1Q^2$, wherein m $Q^1$ and $Q^2$ are as defined above, preferably $Q^1$ and $Q^2$ represents H or $(C_1-C_3)$-alkyl.

Preferably in the compounds of the invention:

A represents, unsubstituted or substituted by one or more $T^1$, represents a 5- or 6-membered monocyclic heterocycle comprising at least one nitrogen atom and further comprising at least one further heteroatom or heteroatomic group selected from O, S, S(O), $S(O)_2$ and N or an 8- to 10-membered bicyclic heterocycle comprising at least one nitrogen atom and at least one further heteroatom or heteroatomic group selected from O, S, S(O), $S(O)_2$ and N. Such heterocycles can advantageously comprise 1, 2 or 3 further heteroatom or heteroatomic group selected from O, S, S(O), $S(O)_2$ and N; and B represents H or an unsubstituted or substituted by one or more $T^2$, $(C_1-C_3)$-alkyl, —$(CH_2)_m$—$C(O)NQ^1Q^2$, wherein $T^2$, m, $Q^1$ and $Q^2$ are as defined above, preferably $Q^1$ and $Q^2$ are H or $(C_1-C_3)$-alkyl. Preferably, B represents H or $(C_1-C_3)$-alkyl; and $T^1$ represents a —$(C_1-C_3)$-alkyl, —$(CH_2)_m OQ^1$; —$(CH_2)_m$—$C(O)OQ^1$; —$(CH_2)_m$—$C(O)NQ^1Q^2$; —$(CH_2)_m$—$NQ^1C(O)Q^2$; —$(CH_2)_m$—$NQ^1C(O)NQ^1Q^2$; —$(CH_2)_m$—$NQ^1Q^2$; —C(O)—$(C_1-C_3)$-alkyl, —C(O)—$(CH_2)_n OQ^1$; —C(O)—$(CH_2)_n$—$C(O)OQ^1$; —C(O)—$(CH_2)_n$—$C(O)NQ^1Q^2$; —C(O)—$(CH_2)_n$—$NQ^1C(O)Q^2$; —C(O)—$(CH_2)_n$—$NQ^1C(O)NQ^1Q^2$; —C(O)—$(CH_2)_n$—$NQ^1Q^2$; —(X)—$(C_1-C_3)$-alkyl; —(X)—$(CH_2)_p OQ^1$; —(X)—$(CH_2)_n$—$C(O)OQ^1$; —(X)—$(CH_2)_n$—$C(O)NQ^1Q^2$; —(X)—$(CH_2)_p$—$NQ^1C(O)Q^2$; —(X)—$(CH_2)_p$—$NQ^1C(O)NQ^1Q^2$;—(X)—$(CH_2)_p$—$NQ^1Q^2$; wherein $T^2$, m, n, p, $Q^1$, $Q^2$, $Q^3$ and $Q^4$ are as defined above, preferably $Q^1$, $Q^2$, $Q^3$ and $Q^4$ each identical or different represent H or —$(C_1-C_3)$-alkyl. Preferably, $T^1$ represents an unsubstituted or substituted by one or more $T^2$, $(C_1-C_3)$-alkyl; $(CH_2)_m OQ^1$, $(CH_2)_m C(O)OQ^1$, $(CH_2)_m NQ^1Q^2$, wherein $T^2$, m $Q^1$ and $Q^2$ are as defined above. Preferably, in the compounds of the invention, $T^1$ represents a $(C_1-C_3)$-alkyl; $OQ^1$, $C(O)OQ^1$, $(CH_2)_m NQ^1Q^2$, wherein m $Q^1$ and $Q^2$ are as defined above, preferably $Q^1$ and $Q^2$ represents H or $(C_1-C_3)$-alkyl.

Preferably, $T^1$ represents an unsubstituted or substituted by one or more $T^2$, $(C_1-C_3)$-alkyl; $(CH_2)_m OQ^1$, —$(CH_2)_m$—$C(O)NQ^1Q^2$; $(CH_2)_m C(O)OQ^1$, $(CH_2)_m NQ^1Q^2$, wherein $T^2$, m $Q^1$ and $Q^2$ are as defined above. Preferably, in the compounds of the invention, $T^1$ represents a $(C_1-C_3)$-alkyl; $OQ^1$, $C(O)OQ^1$, $(CH_2)_m NQ^1Q^2$, —$C(O)NQ^1Q^2$; wherein m $Q^1$ and $Q^2$ are as defined above, preferably $Q^1$ and $Q^2$ represents H or $(C_1-C_3)$-alkyl.

Preferably in the compounds of the invention:

A represents, unsubstituted or substituted by one or more $T^1$, represents a 5- or 6-membered monocyclic heterocycle comprising at least one nitrogen atom and further comprising at least one further heteroatom or heteroatomic group selected from O, S, S(O), $S(O)_2$ and N or an 8- to 10-membered bicyclic heterocycle comprising at least one nitrogen atom and at least one further heteroatom or heteroatomic group selected from O, S, S(O), $S(O)_2$ and N. Such heterocycles can advantageously comprise 1, 2 or 3 further heteroatom or heteroatomic group selected from O, S, S(O), $S(O)_2$ and N; and B represents H or $(C_1-C_3)$-alkyl; and $T^1$ represents an unsubstituted or substituted by one or more $T^2$, $(C_1-C_3)$-alkyl; $(CH_2)_m OQ^1$, $(CH_2)_m C(O)OQ^1$, $(CH_2)_m NQ^1Q^2$, —$(CH_2)_m$—$C(O)NQ^1Q^2$; —$(CH_2)_m$—$C(O)NQ^1$-$NQ^1Q^2$; —$(CH_2)_m$—$NQ^1C(O)Q^2$; —$(CH_2)_m$—$NQ^1S(O)_2 NQ^1Q^2$; —$(CH_2)_m$—$NQ^1C(O)NQ^1Q^2$; —$(CH_2)_m$—

Preferably in the compounds of the invention:

A represents, unsubstituted or substituted by one or more $T^1$, represents a 5- or 6-membered monocyclic heterocycle comprising at least one nitrogen atom and further comprising at least one further heteroatom or heteroatomic group selected from O, S, S(O), $S(O)_2$ and N or an 8- to 10-membered bicyclic heterocycle comprising at least one nitrogen atom and at least one further heteroatom or heteroatomic group selected from O, S, S(O), $S(O)_2$ and N. Such heterocycles can advantageously comprise 1, 2 or 3 further heteroatom or heteroatomic group selected from O, S, S(O), $S(O)_2$ and N; and B represents H or $(C_1-C_3)$-alkyl; and $T^1$ represents an unsubstituted or substituted by one or more $T^2$, $(C_1-C_3)$-alkyl; $(CH_2)_m OQ^1$, $(CH_2)_m C(O)OQ^1$, $(CH_2)_m NQ^1Q^2$, —$(CH_2)_m$—$C(O)NQ^1Q^2$; wherein $T^2$, m $Q^1$ and $Q^2$ are as defined above. Preferably, in the compounds of the invention, $T^1$ represents a $(C_1-C_3)$-alkyl; $OQ^1$, $C(O)OQ^1$, $(CH_2)_m NQ^1Q^2$, —$C(O)NQ^1Q^2$; wherein m $Q^1$ and $Q^2$ are as defined above, preferably $Q^1$ and $Q^2$ represents H or $(C_1-C_3)$-alkyl.

Preferably in the compounds of the invention:

A represents an unsubstituted or substituted by one or more $T^1$, represents a saturated, partially or totally unsaturated or aromatic 4- to 10-membered heterocycle. In a preferred manner, A, unsubstituted or substituted by one or more $T^1$, represents a carbon-linked saturated, partially or totally unsaturated or aromatic 4- to 10-membered heterocycle; or A represents, unsubstituted or substituted by one or more $T^1$, represents a 5- or 6-membered monocyclic heterocycle comprising at least one nitrogen atom and further comprising at least one further heteroatom or heteroatomic group selected from O, S, S(O), $S(O)_2$ and N or an 8- to 10-membered bicyclic heterocycle comprising at least one nitrogen atom and at least one further heteroatom or heteroatomic group selected from O, S, S(O), $S(O)_2$ and N. Such heterocycles can advantageously comprise 1, 2 or 3 further heteroatom or heteroatomic group selected from O, S, S(O), $S(O)_2$ and N; and B represents H; and $T^1$ represents an unsubstituted or substituted by one or more $T^2$, $(C_1-C_3)$-alkyl; $(CH_2)_m OQ^1$, $(CH_2)_m C(O)OQ^1$, $(CH_2)_m NQ^1Q^2$, —$(CH_2)_m$—$C(O)NQ^1Q^2$; —$(CH_2)_m$—$C(O)NQ^1$-$NQ^1Q^2$; —$(CH_2)_m$—$NQ^1C(O)Q^2$; —$(CH_2)_m$—$NQ^1S(O)_2NQ^1Q^2$; —$(CH_2)_m$—$NQ^1C(O)NQ^1Q^2$; —$(CH_2)_m$—

NQ$^1$Q$^2$; —(CH$_2$)$_m$—NH—C(NHQ$^3$)=NQ$^4$; an unsubstituted or substituted by one or more T$^2$, —C(O)(C$_1$-C$_3$)-alkyl; —C(O)(CH$_2$)$_n$OQ$^1$, —C(O)(CH$_2$)$_n$—C(O)OQ$^1$, —C(O)(CH$_2$)$_n$—NQ$^1$Q$^2$; —C(O)—(CH$_2$)$_n$—C(O)NQ$^1$Q$^2$; —C(O)(CH$_2$)$_n$—C(O)NQ$^1$-NQ$^1$Q$^2$; —C(O)(CH$_2$)$_n$—NQ$^1$C(O)Q$^2$; —C(O)(CH$_2$)$_n$—NQ$^1$S(O)$_2$NQ$^1$Q$^2$; —C(O)(CH$_2$)$_n$—NQ$^1$C(O)NQ$^1$Q$^2$; —C(O)(CH$_2$)$_n$—NQ$^1$Q$^2$; —C(O)(CH$_2$)$_n$—NH—C(NHQ$^3$)=NQ$^4$; —(X)—(C$_1$-C$_3$)-alkyl; —(X)—(CH$_2$)$_p$OQ$^1$, —(X)—(CH$_2$)$_n$C(O)OQ$^1$, —(X)—(CH$_2$)$_p$NQ$^1$Q$^2$, —(X)—(CH$_2$)$_n$—C(O)NQ$^1$Q$^2$; —(X)—(CH$_2$)$_n$—C(O)NQ$^1$-NQ$^1$Q$^2$; —(X)—(CH$_2$)$_p$—NQ$^1$C(O)Q$^2$; —(X)—(CH$_2$)$_p$—NQ$^1$S(O)$_2$NQ$^1$Q$^2$; —(X)—(CH$_2$)$_p$—NQ$^1$C(O)NQ$^1$Q$^2$; —(X)—(CH$_2$)$_p$—NQ$^1$Q$^2$; —(X)—(CH$_2$)$_p$—NH—C(NHQ$^3$)=NQ$^4$; wherein T$^2$, m, n, p, Q$^1$, Q$^2$, Q$^3$ and Q$^4$ are as defined above, preferably Q$^1$, Q$^2$, Q$^3$ and Q$^4$ each identical or different represent H or —(C$_1$-C$_3$)-alkyl. Preferably, in the compounds of the invention, T$^1$ represents a —(C$_1$-C$_3$)-alkyl, —(CH$_2$)$_m$OQ$^1$; —(CH$_2$)$_m$—C(O)OQ$^1$; —(CH$_2$)$_m$—C(O)NQ$^1$Q$^2$; —(CH$_2$)$_m$—NQ$^1$C(O)Q$^2$; —(CH$_2$)$_m$—NQ$^1$C(O)NQ$^1$Q$^2$; —(CH$_2$)$_m$—NQ$^1$Q$^2$; —C(O)—(C$_1$-C$_3$)-alkyl, —C(O)—(CH$_2$)$_n$OQ$^1$; —C(O)—(CH$_2$)$_n$—C(O)OQ$^1$; —C(O)—(CH$_2$)$_n$—C(O)NQ$^1$Q$^2$; —C(O)—(CH$_2$)$_n$—NQ$^1$C(O)Q$^2$; —C(O)—(CH$_2$)$_n$—NQ$^1$C(O)NQ$^1$Q$^2$; C(O)—(CH$_2$)$_n$—NQ$^1$Q$^2$; —(X)—(C$_1$-C$_3$)-alkyl; —(X)—(CH$_2$)$_p$OQ$^1$; —(X)—(CH$_2$)$_n$—C(O)OQ$^1$; —(X)—(CH$_2$)$_n$—C(O)NQ$^1$Q$^2$; —(X)—(CH$_2$)$_p$—NQ$^1$C(O)Q$^2$; —(X)—(CH$_2$)$_p$—NQ$^1$C(O)NQ$^1$Q$^2$; —(X)—(CH$_2$)$_p$—NQ$^1$Q$^2$; wherein T$^2$, m, n, p, Q$^1$, Q$^2$, Q$^3$ and Q$^4$ are as defined above, preferably Q$^1$, Q$^2$, Q$^3$ and Q$^4$ each identical or different represent H or —(C$_1$-C$_3$)-alkyl. Preferably, in the compounds of the invention, T$^1$ represents an unsubstituted or substituted by one or more T$^2$, (C$_1$-C$_3$)-alkyl; (CH$_2$)$_m$OQ$^1$, —(CH$_2$)$_m$—C(O)NQ$^1$Q$^2$; (CH$_2$)$_m$C(O)OQ$^1$, (CH$_2$)$_m$NQ$^1$Q$^2$, wherein T$^2$, m Q$^1$ and Q$^2$ are as defined above. Preferably, in the compounds of the invention, T$^1$ represents a (C$_1$-C$_3$)-alkyl; OQ$^1$, C(O)OQ$^1$, (CH$_2$)$_m$NQ$^1$Q$^2$, —C(O)NQ$^1$Q$^2$; wherein m Q$^1$ and Q$^2$ are as defined above, preferably Q$^1$ and Q$^2$ represents H or (C$_1$-C$_3$)-alkyl.

Preferably in the compounds of the invention:

A represents, unsubstituted or substituted by one or more T$^1$, represents a 5- or 6-membered monocyclic heterocycle comprising at least one nitrogen atom and further comprising at least one further heteroatom or heteroatomic group selected from O, S, S(O), S(O)$_2$ and N or an 8- to 10-membered bicyclic heterocycle comprising at least one nitrogen atom and at least one further heteroatom or heteroatomic group selected from O, S, S(O), S(O)$_2$ and N. Such heterocycles can advantageously comprise 1, 2 or 3 further heteroatom or heteroatomic group selected from O, S, S(O), S(O)$_2$ and N; and B represents H; and T$^1$ represents a —(C$_1$-C$_3$)-alkyl, —(CH$_2$)$_m$OQ$^1$; —(CH$_2$)$_m$—C(O)OQ$^1$; —(CH$_2$)$_m$—C(O)NQ$^1$Q$^2$; —(CH$_2$)$_m$—NQ$^1$C(O)Q$^2$; —(CH$_2$)$_m$—NQ$^1$C(O)NQ$^1$Q$^2$; —(CH$_2$)$_m$—NQ$^1$Q$^2$; —C(O)—(C$_1$-C$_3$)-alkyl, —C(O)—(CH$_2$)$_n$OQ$^1$; —C(O)—(CH$_2$)$_n$—C(O)OQ$^1$; —C(O)—(CH$_2$)$_n$—C(O)NQ$^1$Q$^2$; —C(O)—(CH$_2$)$_n$—NQ$^1$C(O)Q$^2$; —C(O)—(CH$_2$)$_n$—NQ$^1$C(O)NQ$^1$Q$^2$; —C(O)—(CH$_2$)$_n$—NQ$^1$Q$^2$; —(X)—(C$_1$-C$_3$)-alkyl; —(X)—(CH$_2$)$_p$OQ$^1$; —(X)—(CH$_2$)$_n$—C(O)OQ$^1$; —(X)—(CH$_2$)$_n$—C(O)NQ$^1$Q$^2$; —(X)—(CH$_2$)$_p$—NQ$^1$C(O)Q$^2$; —(X)—(CH$_2$)$_p$—NQ$^1$C(O)NQ$^1$Q$^2$; —(X)—(CH$_2$)$_p$—NQ$^1$Q$^2$; wherein T$^2$, m, n, p, Q$^1$, Q$^2$, Q$^3$ and Q$^4$ are as defined above, preferably Q$^1$, Q$^2$, Q$^3$ and Q$^4$ each identical or different represent H or —(C$_1$-C$_3$)-alkyl. Preferably, T$^1$ represents an unsubstituted or substituted by one or more T$^2$, (C$_1$-C$_3$)-alkyl; (CH$_2$)$_m$OQ$^1$, (CH$_2$)$_m$C(O)OQ$^1$, —(CH$_2$)$_m$—C(O)NQ$^1$Q$^2$; (CH$_2$)$_m$NQ$^1$Q$^2$, wherein T$^2$, m Q$^1$ and Q$^2$ are as defined above. Preferably, in the compounds of the invention, T$^1$ represents a (C$_1$-C$_3$)-alkyl; OQ$^1$, C(O)OQ$^1$, (CH$_2$)$_m$NQ$^1$Q$^2$, —C(O)NQ$^1$Q$^2$; wherein m Q$^1$ and Q$^2$ are as defined above, preferably Q$^1$ and Q$^2$ represents H or (C$_1$-C$_3$)-alkyl.

Preferably in the compounds of the invention:

A represents, unsubstituted or substituted by one or more T$^1$, represents a 5- or 6-membered monocyclic heterocycle comprising at least one nitrogen atom and further comprising at least one further heteroatom or heteroatomic group selected from O, S, S(O), S(O)$_2$ and N or an 8- to 10-membered bicyclic heterocycle comprising at least one nitrogen atom and at least one further heteroatom or heteroatomic group selected from 0, S, S(O), S(O)$_2$ and N. Such heterocycles can advantageously comprise 1, 2 or 3 further heteroatom or heteroatomic group selected from O, S, S(O), S(O)$_2$ and N; and B represents H; and T$^1$ represents an unsubstituted or substituted by one or more T$^2$, (C$_1$-C$_3$)-alkyl; —(CH$_2$)$_m$—C(O)NQ$^1$Q$^2$; (CH$_2$)$_m$OQ$^1$, (CH$_2$)$_m$C(O)OQ$^1$, (CH$_2$)$_m$NQ$^1$Q$^2$, wherein T$^2$, m Q$^1$ and Q$^2$ are as defined above. Preferably, in the compounds of the invention, T$^1$ represents a (C$_1$-C$_3$)-alkyl; OQ$^1$, C(O)OQ$^1$, (CH$_2$)$_m$NQ$^1$Q$^2$, —C(O)NQ$^1$Q$^2$; wherein m Q$^1$ and Q$^2$ are as defined above, preferably Q$^1$ and Q$^2$ represents H or (C$_1$-C$_3$)-alkyl.

The term "alkyl", as used herein, refers to an aliphatic-hydrocarbon group which may be straight or branched, having 1 to 3 carbon atoms in the chain unless specified otherwise. Preferred alkyl groups have 1 or 2 carbon atoms in the chain. Specific examples of alkyl groups include, but are not limited to, methyl, ethyl, n-propyl, isopropyl. Preferably, the alkyl group is methyl or ethyl.

The term "fluoroalkyl", as used herein, refers to an alkyl group substituted with at least one fluorine atom. The term "alkyl" is as defined above. Specific examples of fluoroalkyl groups include but are not limited to trifluoromethyl, difluoromethyl, fluoromethyl.

The term "cycloalkyl" refers to a saturated monocyclic or bicyclic non-aromatic hydrocarbon ring of 3 to 6 carbon atoms, preferably 3 to 4 carbon atoms, which can comprise one or more unsaturation. Specific examples of monocyclic cycloalkyl groups include cyclopropyl, cyclobutyl, cyclopentyl, cyclohexyl. Preferably, the cycloalkyl group is cyclopropyl or cyclobutyl.

The term "fluorocycloalkyl" refers to a cycloalkyl group substituted with at least one fluorine atom. The term "cycloalkyl" is as defined above. Specific examples of fluorocycloalkyl groups include fluorocyclopropyl, difluorocyclopropyl, fluorocyclobutyl, difluorocyclobutyl.

The term "heterocycle", as used herein and without contrary definition specifically mentioned, either alone or in combination with another radical, refers to a monocyclic saturated, partially or totally unsaturated or aromatic hydrocarbon radical, preferably to a 4- to 10-membered hydrocarbon radical, comprising at least one heteroatom, such as N, O, S, S(O) or S(O)$_2$. Preferably, the heterocycle is a monocyclic saturated, partially or totally unsaturated or aromatic hydrocarbon radical, preferably a 4- to 6-membered hydrocarbon radical, comprising at least one nitrogen atom and at least one further heteroatom, such as N, O, S, S(O) or S(O)$_2$. The carbon atoms of the heterocycle can also be oxidized to form a C(O) group. Suitable heterocycles are also disclosed in the Handbook of Chemistry and Physics, 76th Edition, CRC Press, Inc., 1995-1996, pages 2-25 to 2-26. Exemplary heterocycle groups include but are not limited to azetidinyl, oxetanyl, oxazolyl, oxazolidinyl, oxadiazolyl, pyrrolyl, pyrrolidinyl, pyridyl, tetrahydropyridinyl, piperidinyl, morpholinyl, pyrazolyl, pyrimidinyl, pyrazinyl, tetrazolyl, imidazolyl, thienyl, thiazolyl, furanyl, thiadiazolyl, isothiazolyl, triazolyl, tetrazolyl, pyrazolyl, isoxazolyl, 2-pyrrolidinonyl, imidazol-2,4-dione, 1,2,4-oxadiazol-5-one, 1,5-dihydropyrrolyl-2-one, pyrazinone, pyridazinone, pyridone, pyrimidone, dioxanyl, pyrrolidinyl, imidazolidinyl, pyranyl, tetrahydrofuranyl, dioxolanyl, tetrahydropyranyl. Preferably, in the compounds according to the invention, the heterocycle is linked to the structure of the compounds by a carbon atom of the heterocycle (also said carbon-linked heterocycle).

Moreover some compounds according to this invention may contain a basic amino group and thus may form an inner zwitterionic salt (or zwitterion) with the acidic group (R$^3$)—OSO$_3$H, —OCFHCO$_2$H or —OCF$_2$CO$_2$H and such inner zwitterionic salts are also included in this invention.

The expression "optionally substituted" means "non-substituted or substituted by chemical groups that are further defined" or "unsubstituted or substituted chemical groups that are further defined".

The term "racemate" is employed herein to refer to an equal amount of two specific enantiomers.

The term "enantiomer" is employed herein to refer to one of the two specific stereoisomers which is a non-superimposable mirror image with one other but is related to one other by reflection.

The compounds according to the invention may include one or more asymmetric carbon atoms and may thus exist in the form of optical isomers as well as in the form of racemic or non-racemic mixtures thereof. The compounds according to the invention can be utilized as a single isomer or as a mixture of stereochemical isomeric forms.

Diastereoisomers, i.e., non-superimposable stereochemical isomers can be separated by conventional means such as chromatography, distillation, crystallization or sublimation. The optical isomers (enantiomers) can be obtained by using optically active starting materials, by resolution of the racemic mixtures according to conventional processes, for example by formation of diastereoisomeric salts by treatment with an optically active acid or base or by using chiral chromatography column.

As used herein, the expression "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention can be synthesized from the parent compound which comprises a basic or an acidic moiety, by conventional chemical methods. Furthermore, the expression "pharmaceutically acceptable salt" refers to relatively non-toxic, inorganic and organic acid or base addition salts of the compounds of the present invention. These salts can be prepared in situ during the final isolation and purification of the compounds. In particular, the acid addition salts can be prepared by separately reacting the purified compound in its purified form with an organic or inorganic acid and by isolating the salt thus formed. Among the examples of acid addition salts are the hydrobromide, hydrochloride, hydroiodide, sulfamate, sulfate, bisulfate, phosphate, nitrate, acetate, propionate, succinate, oxalate, valerate, oleate, palmitate, stearate, laurate, borate, benzoate, lactate, tosylate, citrate, maleate, fumarate, tartrate, naphthylate, mesylate, glucoheptanate, glucoronate, glutamate, lactobionate, malonate, salicylate, methylenebis-b-hydroxynaphthoate, gentisic acid, isethionate, di-p-toluoyltartrate, ethanesulfonate, benzenesulfonate, cyclohexyl sulfamate, quinateslaurylsulfonate salts, and the like. Examples of base addition salts include ammonium salts such as tromethamine, meglumine, epolamine, etc, metal salts such as sodium, lithium, potassium, calcium, zinc or magnesium salts with organic bases such as dicyclohexylamine salts, N-methyl-D-glucamine. Lists of suitable salts may be found in Remington's Pharmaceutical Sciences, 17th ed., Mack Publishing Company, Easton, Pa., 1985, p. 1418, P. H. Stahl, C. G. Wermuth, Handbook of Pharmaceutical salts—Properties, Selection and Use, Wiley-VCH, 2002 and S. M. Berge et al. "Pharmaceutical Salts" J. Pharm. Sci, 66: p. 1-19 (1977).

Compounds according to the invention also include isotopically-labelled compounds wherein one or more atoms is replaced by an atom having the same atomic number, but an atomic mass or mass number different from the atomic mass or mass number usually found in nature. Examples of isotopes suitable for inclusion in the compounds described above and are not limited to $^2$H, $^3$H, $^{11}$C, $^{13}$C, $^{14}$C, $^{18}$F, $^{19}$F, $^{13}$N, $^{15}$N, $^{33}$S, $^{34}$S, $^{35}$S, $^{36}$S, $^{17}$O or $^{18}$O. Isotopically-labelled compounds are useful in drug and/or substrate tissue distribution studies. Substitution with heavier isotopes such as deuterium ($^2$H) affords greater metabolic stability (for example increased in vivo half-life or reduced dosage requirements). Isotopically-labelled compounds are prepared by any suitable method or by processes using an appropriate isotopically-labelled reagent in replacement of the non-labelled reagent otherwise employed.

The invention provides compounds having antibacterial properties and/or compounds acting as β-lactamase inhibitors.

The invention also provides a process for the preparation of a compound according to the invention. In particular the invention provides a process for the preparation of compound selected within the compounds of formulae (I), (D), (B), (C), (I*), (D*), (B*), (C*) according to the invention.

General processes according to the invention is represented in schemes 1, 2, 3 and 4 wherein R$^2$ represents various substituents.

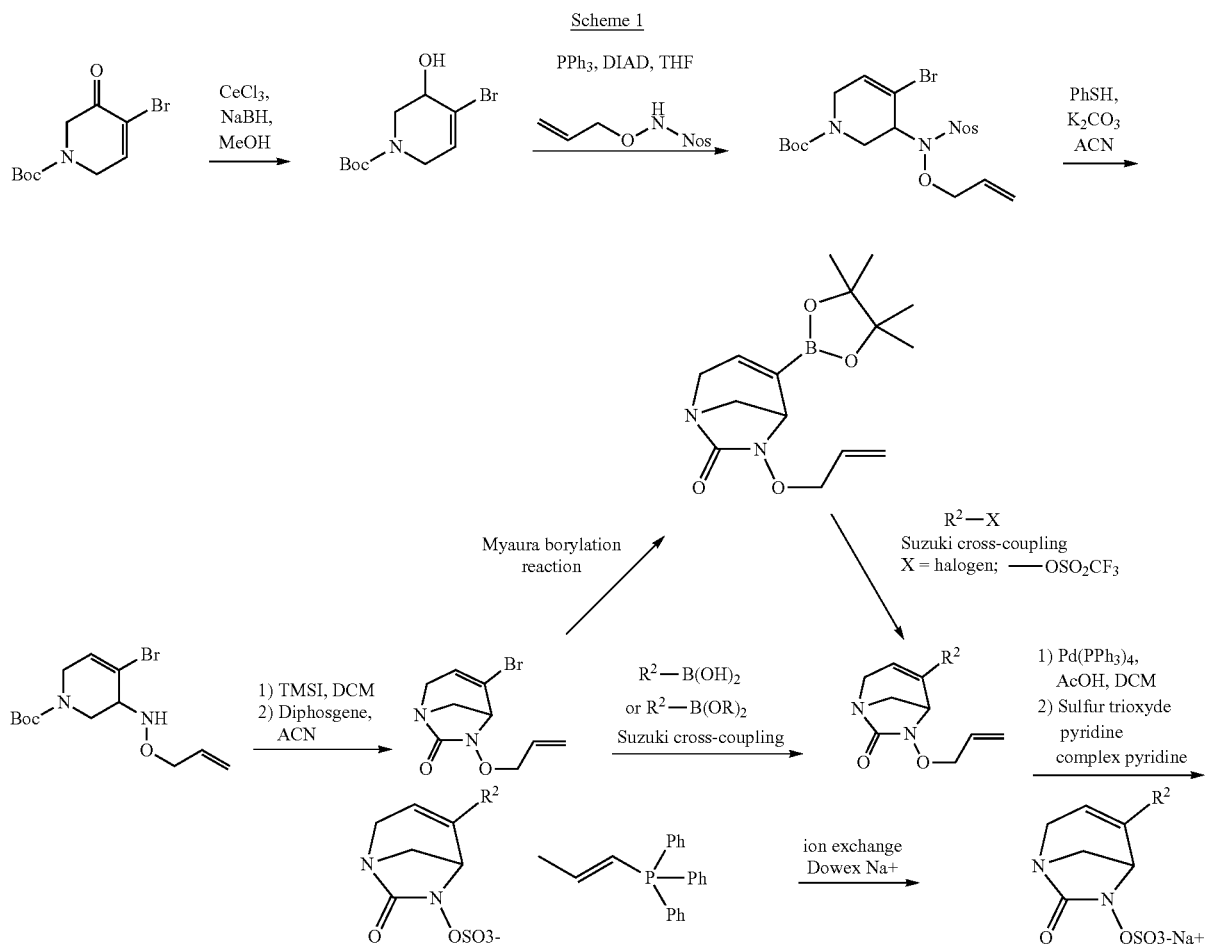
Scheme 1
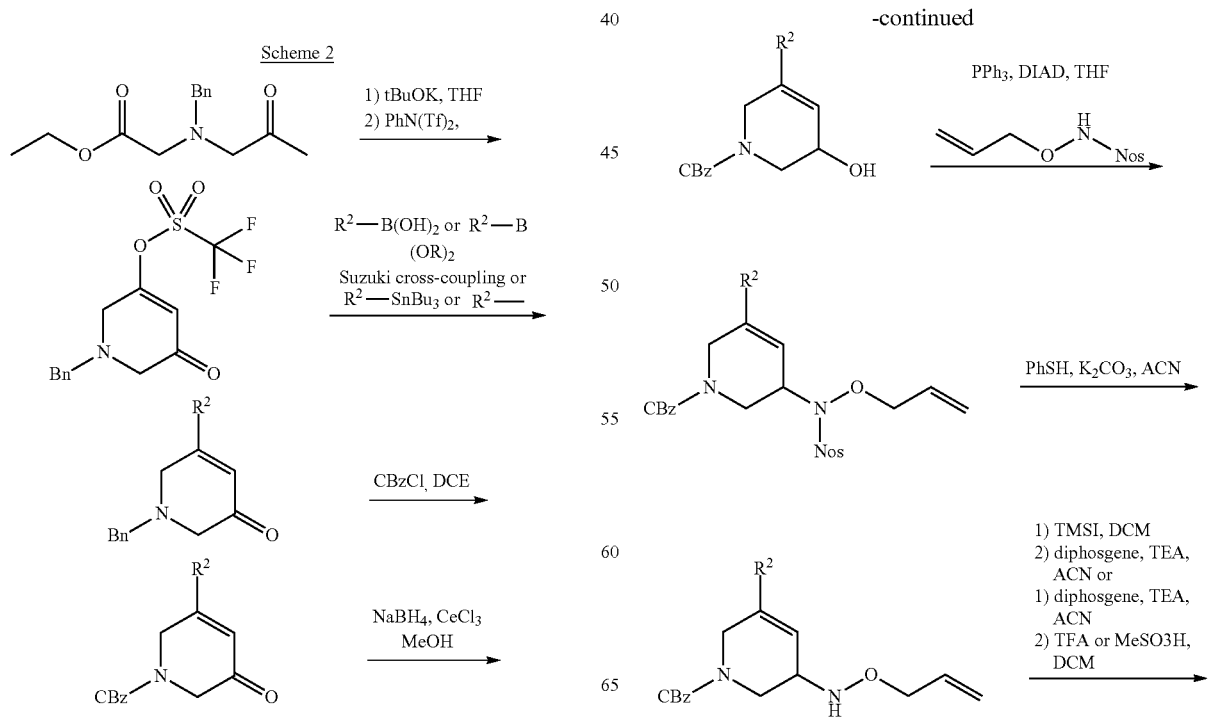
Scheme 2

19
-continued
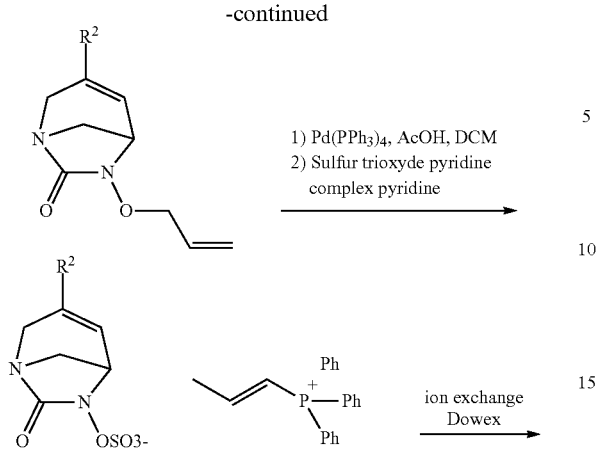
20
-continued
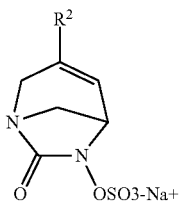
Scheme 3
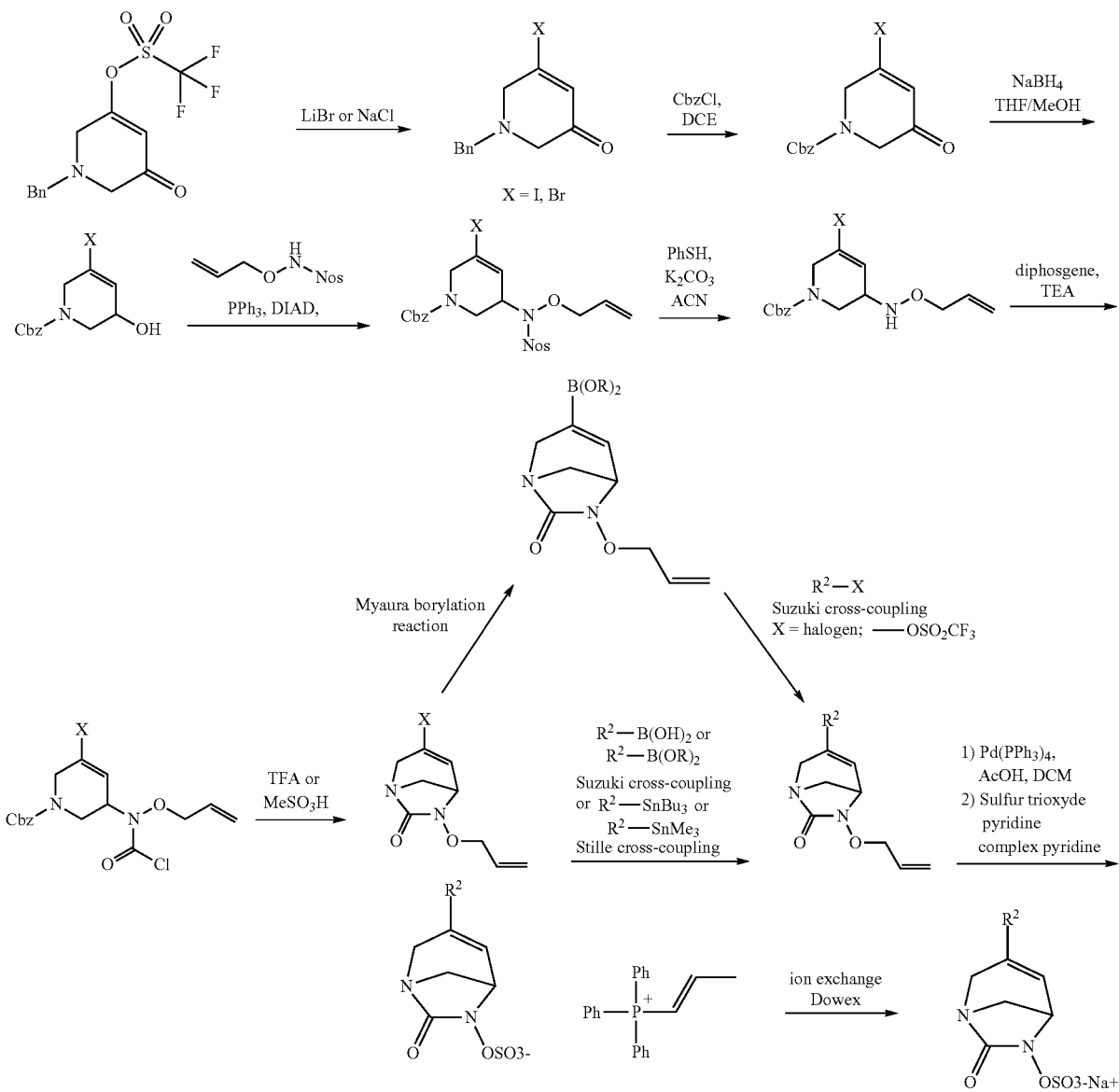

Scheme 4
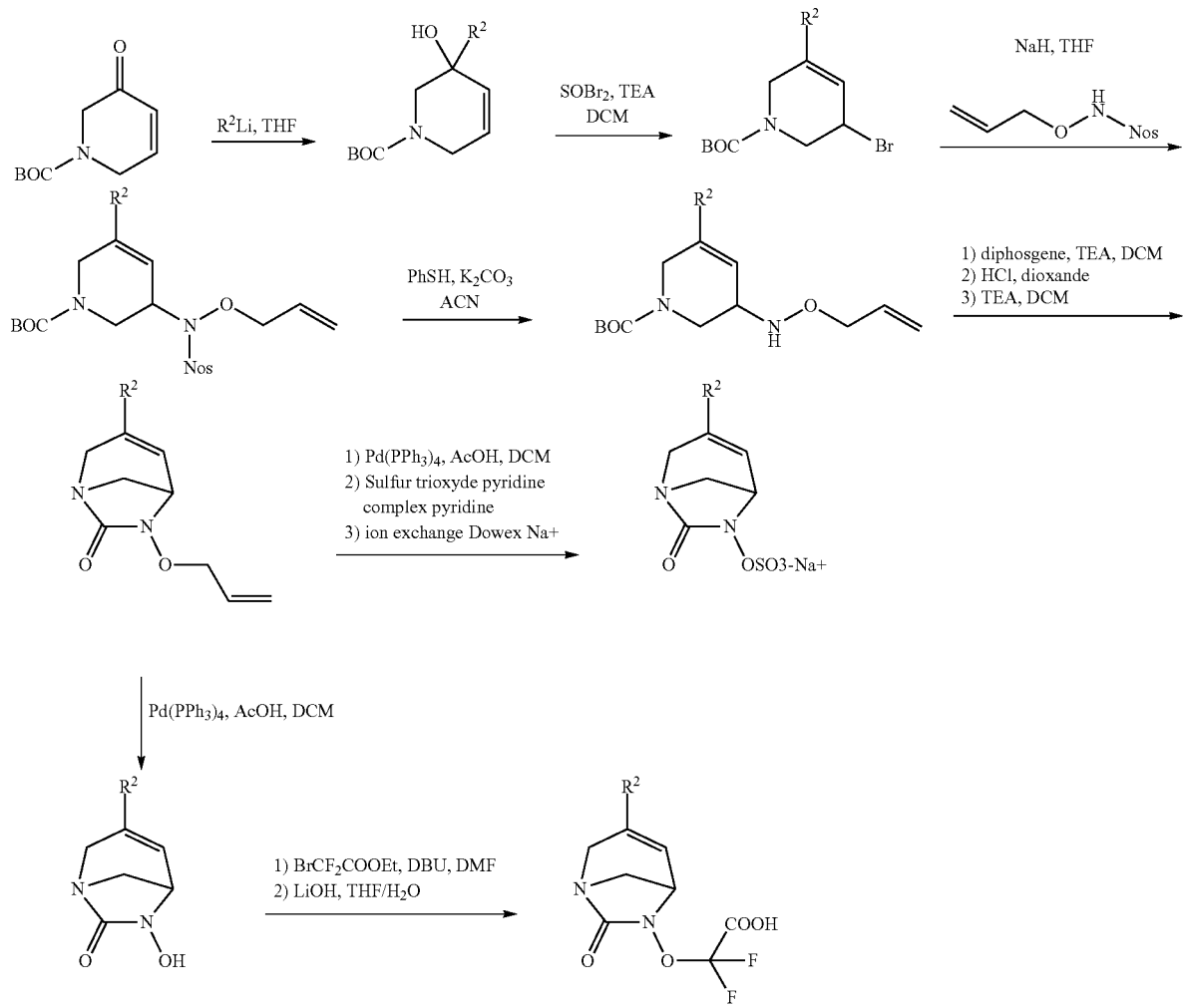
The processes of schemes 1, 2, 3 and 4 can be adapted for preparing further compounds according to the invention. Further processes for the preparation of compounds according to the invention can be derived from the processes of schemes 1, 2, 3 and 4.
The invention relates also to compounds of formula
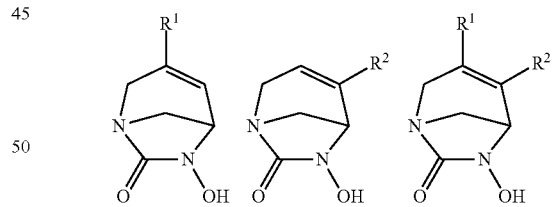
preferably of formula
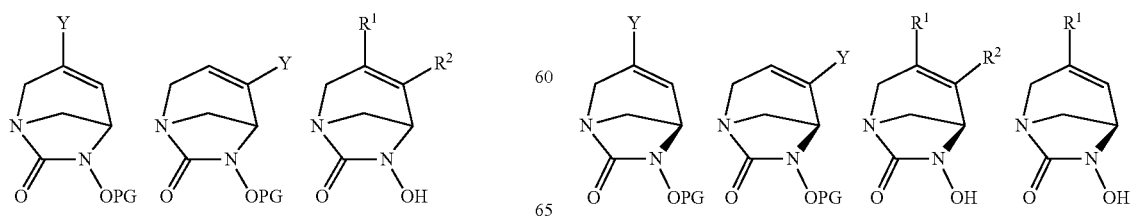

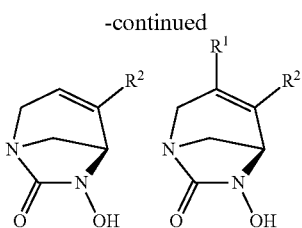

wherein R¹, R² are as defined above, Y is halogen, —B(OR)₂ or SnR₃ wherein R is alkyl or the OR are linked together with the B to form a cycle comprising for example 5 members; and PG, is a protective group, for example chosen among allyl, benzyl, tertbutyldimethylsilyl (TBDMS), tert-butoxycarbonyl (Boc), etc. The compounds are especially intermediates compounds for the preparation of compounds of formula (I), (D), (B), (C), (B1), (I*), (D*), (B*), (C*) according to the invention.

The invention also provides particular processes represented in the schemes of the experimental part that is provided herein for the preparation of compounds according to the invention wherein R¹, R² and R³ represent various substituents. These processes can also be adapted for preparing further compounds according to the invention. Further processes for the preparation of compounds according to the invention can be derived from these processes.

The invention also provides the use of the compounds according to the invention in the control of bacteria. The compound according to the invention is then usually used in combination with at least one pharmaceutically acceptable excipient.

The expression "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also provides a composition, preferably a pharmaceutical composition, comprising at least one compound according to the invention in mixture with a pharmaceutically acceptable excipient. The composition according to the invention may thus comprise at least one compound selected from compounds of formulae (I), (D), (B), (C), (I*), (D*), (B*) and (C*) in mixture with a pharmaceutically acceptable excipient.

The composition according to the invention can further comprise at least one or more antibacterial agent(s), preferably at least one of these antibacterial agents is a beta-lactam.

The term "beta-lactam" or "β-lactam" refers to antibacterial compounds comprising a β-lactam unit, i.e. a β-lactam chemical group or moiety.

The term "pharmaceutically acceptable carrier" or "pharmaceutically acceptable excipient" is employed for any excipient, solvent, dispersion medium, absorption retardant, diluent or adjuvant etc., such as preserving or antioxidant agents, fillers, binders, disintegrating agents, wetting agents, emulsifying agents, suspending agents, solvents, dispersion media, coatings, antibacterial agents, isotonic and absorption delaying agents and the like, that does not produce a secondary reaction, for example an allergic reaction, in humans or animals. Typical, non-limiting examples of excipients include mannitol, lactose, magnesium stearate, sodium saccharide, talcum, cellulose, sodium crosscarmellose, glucose, gelatine, starch, lactose, dicalcium phosphate, sucrose, kaolin, magnesium carbonate, wetting agents, emulsifying agents, solubilizing agents, sterile water, saline, pH buffers, non-ionic surfactants, lubricants, stabilizing agents, binding agents and edible oils such as peanut oil, sesame oils and the like. In addition, various excipients commonly used in the art may be included. Pharmaceutically acceptable carriers or excipients are well known to a person skilled in the art, and include those described in Remington's Pharmaceutical Sciences (Mack Publishing Company, Easton, USA, 1985), Merck Index (Merck & Company, Rahway, N.J.), Gilman et al (Eds. The pharmacological basis of therapeutics, 8th Ed., Pergamon press., 1990). Except insofar as any conventional media or adjuvant is incompatible with the active ingredient according to the invention, its use in the therapeutic compositions is contemplated.

The expression "antibacterial agent" as used herein, refers to any substance, compound or their combination capable of inhibiting, reducing or preventing growth of bacteria, inhibiting or reducing ability of bacteria to produce infection in a subject, or inhibiting or reducing ability of bacteria to multiply or remain infective in the environment, or decreasing infectivity or virulence of bacteria.

The antibacterial agent can be selected among the following families: aminoglycosides, beta-lactams, glycylcyclines, tetracyclines, quinolones, fluoroquinolones, glycopeptides, lipopeptides, macrolides, ketolides, lincosamides, streptogramins, oxazolidinones and polymyxins alone or in mixture. Preferably, the further antibacterial agent is selected among the beta-lactam families, and more preferably among penicillin, cephalosporins, penems, carbapenems and monobactam, alone or in mixture.

Among the penicillin the antibacterial agent is preferably selected in the group consisting of amoxicillin, ampicillin, azlocillin, mezocillin, apalcillin, hetacillin, bacampicillin, carbenicillin, sulbenicillin, temocillin, ticarcillin, piperacillin, mecillinam, pivmecillinam, methicillin, ciclacillin, talampacillin, aspoxicillin, oxacillin, cloxacillin, dicloxacillin, flucloxacillin, nafcillin, and pivampicillin, alone or in mixture.

Among the cephalosporin, the antibacterial agent is preferably selected in the group consisting of cefatriazine, cefazolin, cefoxitin, cephalexin, cephradine, ceftizoxime, cephacetrile, cefbuperazone, cefprozil, ceftobiprole, ceftobiprole medocaril, ceftaroline, ceftaroline fosaminyl, cefalonium, cefminox, ceforanide, cefotetan, ceftibuten, cefcapene pivoxil, cefditoren pivoxil, cefdaloxime cefroxadine, ceftolozane and S-649266, cephalothin, cephaloridine, cefaclor, cefadroxil, cefamandole, cefazolin, cephalexin, cephradine, ceftizoxime, cephacetrile, cefotiam, cefotaxime, cefsulodin, cefoperazone, cefmenoxime, cefmetazole, cephaloglycin, cefonicid, cefodizime, cefpirome, ceftazidime, ceftriaxone, cefpiramide, cefbuperazone, cefozopran, cefepime, cefoselis, cefluprenam, cefuzonam, cefpimizole, cefclidine, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbef, and latamoxef, alone or in mixture.

Among the carbapenem, the antibacterial agent is preferably selected in the group consisting of imipenem, doripenem, meropenem, biapenem, ertapenem and panipenem, alone or in mixture.

Among the monobactam, the antibacterial agent is preferably selected in the group consisting of aztreonam, tigemonam, carumonam, BAL30072 and nocardicin A, alone or in mixture.

The present invention also relates to a composition comprising at least a compound of formulae (I), (D), (B), (C) (I*), (D*), (B*), (C*) according to the invention and ceftazidime.

The present invention also provides a kit comprising:
a pharmaceutical composition according to the invention, and
at least one other composition comprising one or more antibacterial agents, preferably at least one of these antibacterial agents is a beta-lactam.

The two compositions can each be prepared separately with one specific pharmaceutically acceptable carrier, and can then be mixed, especially extemporaneously.

The present invention also relates to a kit comprising:
a pharmaceutical composition comprising at least a compound of formulae (I), (D), (B), (C), (I*), (D*), (B*), (C*) according to the invention; and
a pharmaceutical composition comprising ceftazidime.

The present invention also refers to a compound selected within the compounds of formulae (I), (D), (B), (C), (I*), (D*), (B*) and (C*) according to the invention for its use as a medicine.

The present invention also refers to a compound selected within the compounds of formulae (I), (D), (B), (C), (I*), (D*), (B*) and (C*) according to the invention for its use for the preparation of a medicine.

The present invention also refers to a compound selected within the compounds of formulae (I), (D), (B), (C), (I*), (D*), (B*) and (C*) according to the invention for its use as an antibacterial agent.

The present invention also refers to the use of a compound selected within the compounds of formulae (I), (D), (B), (C), (I*), (D*), (B*) and (C*) according to the invention or to the use of a pharmaceutical composition according to the invention for the preparation of an antibacterial agent comprising medicine.

The present invention also refers to the use of a compound selected within the compounds of formulae (I), (D), (B), (C), (I*), (D*), (B*) and (C*) according to the invention or to the use of a pharmaceutical composition according to the invention for the preparation of a beta-lactamase inhibitor comprising medicine.

The present invention also refers to the use of a compound selected within the compounds of formulae (I), (D), (B), (C), (I*), (D*), (B*) and (C*) according to the invention or to the use of a pharmaceutical composition according to the invention for the preparation of a medicine comprising an antibacterial agent and a beta-lactamase inhibitor.

The present invention also refers to the use of a compound selected within the compounds of formulae (I), (D), (B), (C), (I*), (D*), (B*) and (C*) according to the invention or to the use of a pharmaceutical composition according to the invention or to the use of a kit according to the invention for the treatment or for the prevention of at least one bacterial infection.

The present invention also refers to the use of a compound selected within the compounds of formulae (I), (D), (B), (C), (I*), (D*), (B*) and (C*) according to the invention or to the use of a pharmaceutical composition according to the invention or to the use of a kit according to the invention for the preparation of a medicine useful in the treatment or in the prevention of at least one bacterial infection.

The terms "prevention", "prevent" and "preventing" as used herein are intended to mean the administration of a compound or composition according to the invention in order to prevent infection by bacteria or to prevent occurrence of related infection and/or diseases.

The terms "prevention", "prevent" and "preventing" also encompass the administration of a compound or composition according to the present invention in order preventing at least one bacterial infection, by administration to a patient susceptible to be infected, or otherwise at a risk of being infected by this bacteria.

The terms "treatment", "treat" and "treating" as used herein are intended to mean in particular the administration of a treatment comprising a compound or composition according to the invention to a patient suffering from an infection. The terms "treatment", "treat" and "treating" as used herein, also refer to administering a compound or composition according to the invention, optionally in combination with one or more further antibacterial agent, in order:
to reduce or to eliminate either bacterial infection or one or more symptoms associated with a bacterial infection, or
to retard the progression of a bacterial infection or of one or more symptoms associated with a bacterial infection, or
to reduce the severity of a bacterial infection or of one or more symptoms associated with a bacterial infection, or
to suppress the clinical manifestation of a bacterial infection, or
to suppress the manifestation of adverse symptoms caused by a bacterial infection.

The expression "infection" or "bacterial infection" as used herein, include the presence of bacteria, in or on a subject, which, if its growth were inhibited, would result in a benefit to the subject. As such, the term "infection" or "bacterial infection" in addition to referring to the presence of bacteria also refer to normal flora, which is not desirable. The term "infection" includes infection caused by bacteria. Examples of such bacterial infections are urinary tract infection (UTI), kidney infections (pyelonephritis), gynecological and obstetrical infections, respiratory tract infection (RTI), acute exacerbation of chronic bronchitis (AECB), Community-acquired pneumonia (CAP), hospital-acquired pneumonia (HAP), ventilator associated pneumonia (VAP), intra-abdominal pneumonia (IAI), acute otitis media, acute sinusitis, sepsis, catheter-related sepsis, chancroid, *chlamydia*, skin infections, bacteremia.

The term "growth" as used herein, refers to the growth of one or more microorganisms and includes reproduction or population expansion of a microorganism, such as bacteria. The term also includes maintenance of on-going metabolic processes of a microorganism, including processes that keep the microorganism alive.

According to the invention, bacteria are chosen amongst gram-positive bacteria or gram-negative bacteria, preferably gram-negative bacteria. According to the invention, bacteria can be also chosen among bacteria producing "beta-lactamase" or "β-lactamase". These bacteria are well known by the person skilled in the art. The term "beta-lactamase" or "β-lactamase" as used herein, refers to any enzyme or protein or any other substance that is able to break down a beta-lactam ring. The term "beta-lactamase" or "β-lactamase" includes enzymes that are produced by bacteria and that have the ability to hydrolyze, either partially or completely, the beta-lactam ring present in a compound such as an antibacterial agent.

Among the gram-positive bacteria, the bacteria according to the invention is preferably chosen among *Staphylococcus, Streptococcus, Staphylococcus* species (including *Staphylococcus aureus, Staphylococcus epidermidis*), *Streptococcus* species (including *Streptococcus pneumonia, Streptococcus agalactiae*), *Enterococcus* species (including *Enterococcus faecalis* and *Enterococcus faecium*).

Among the gram-negative bacteria, the bacteria according to the invention is preferably chosen among *Acinetobacter* species (including *Acinetobacter baumannii*), *Citrobacter* species, *Escherichia* species (including *Escherichia coli*), *Haemophilus* influenza, *Morganella morganii, Klebsiella* species (including *Klebsiella pneumonia*), *Enterobacter* species (including *Enterobacter cloacae*), *Neisseria gonorrhoeae, Burkholderia* species (including *Burkholderia cepacia*), (*Proteus* species (including *Proteus mirabilis*), *Serratia* species (including *Serratia marcescens*), *Pseudomonas aeruginosa*.

The invention thus preferably refers to a compound selected within the compounds of formulae (I), (D), (B), (C), (I*), (D*), (B*) and (C*) according to the invention or to a pharmaceutical composition according to the invention or to a kit according to the invention for its use for the treatment or for the prevention of a bacterial infection, preferably caused by bacteria producing one or more beta-lactamases. Preferably, the bacteria are chosen amongst gram-positive bacteria or gram-negative bacteria, more preferably gram-negative bacteria.

The present invention also refers to the use of a compound selected within the compounds of formulae (I), (D), (B), (C), (I*), (D*), (B*) and (C*) according to the invention or to a pharmaceutical composition according to the invention for the preparation of a medicine for the treatment or for the prevention of a bacterial infection, preferably caused by bacteria producing one or more beta-lactamases. Preferably, the bacteria are chosen amongst gram-positive bacteria or gram-negative bacteria, more preferably gram-negative bacteria.

The present invention also refers to a kit according to the invention, for its simultaneous, separated or sequential administration to a patient in need thereof in the treatment or in the prevention of bacterial infections, preferably caused by bacteria producing one or more beta-lactamases. Preferably, the bacteria are chosen amongst gram-positive bacteria or gram-negative bacteria, more preferably gram-negative bacteria.

The present invention also refers to a compound selected within the compounds of formulae (I), (D), (B), (C), (I*), (D*), (B*) and (C*) according to the invention for its use in combination with one or more further antibacterial agents, preferably at least one of the further antibacterial agents being a beta lactam compound, for the treatment or for the prevention of bacterial infections, preferably caused by bacteria producing one or more beta-lactamases. Preferably, the bacteria are chosen amongst gram-positive bacteria or gram-negative bacteria, more preferably gram-negative bacteria, and wherein a compound selected within the compounds of formulae (I), (D), (B), (C), (I*), (D*), (B*) and (C*) according to the invention and the further antibacterial agent are administered simultaneously, separately or sequentially.

The present invention also refers to the use of a compound selected within the compounds of formulae (I), (D), (B), (C), (I*), (D*), (B*) and (C*) according to the invention or of a pharmaceutical composition according to the invention or of a kit according to the invention for the prevention or for the treatment of bacterial infections, preferably of a bacterial infection, preferably caused by bacteria producing one or more beta-lactamases. Preferably, the bacteria are chosen amongst gram-positive bacteria or gram-negative bacteria, more preferably gram-negative bacteria.

The present invention also relates to a method for the treatment or prevention of bacterial infections, preferably caused by bacteria producing one or more beta-lactamases comprising the administration of a therapeutically effective amount of a compound selected within the compounds of formulae (I), (D), (B), (C), (I*), (D*), (B*) and (C*) according to the invention, or of a pharmaceutical composition according to the invention or of a kit according to the invention to a patient in need thereof. Preferably, the bacteria are chosen amongst gram-positive bacteria or gram-negative bacteria, more preferably gram-negative bacteria.

The term "patient" means a person or an animal at risk of being infected by bacteria or, a person or an animal being infected by bacteria, preferably by gram-positive and by gram-negative bacteria, more preferably by gram-negative bacteria. As used herein, the term "patient" refers to a warm-blooded person or animal such as a mammal, preferably a human or a human child, who is afflicted with, or has the potential to be afflicted with one or more infections and conditions described herein. The identification of those subjects who are in need of treatment of herein-described diseases and conditions is well within the ability and knowledge of one skilled in the art. A veterinarian or a physician skilled in the art can readily identify, by the use of clinical tests, physical examination, medical or family history or biological and diagnostic tests, those subjects who are in need of such a treatment.

The expression "therapeutically effective amount" or "pharmaceutically effective amount" as used herein, refer to an amount of a compound according to the invention, which when administered to a patient in need thereof, is sufficient to effect treatment for disease-states, conditions, or disorders for which the compound has utility. Such an amount would be sufficient to elicit the biological or medical response of a tissue system, or patient that is sought by a researcher or a clinician. The amount of a compound according to the invention which constitutes a "therapeutically effective amount" will vary, notably depending on the compound itself and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a "therapeutically effective amount" can be determined by one of ordinary skilled in the art having regard to its own knowledge, and this disclosure. Preferably, the compound according to the invention is administered in an amount comprised between 0.1 to 30 g per day.

The compound according to the invention may be provided in an aqueous physiological buffer solution for parenteral administration. The compound of the present invention is also capable of being administered in unit dose forms, wherein the expression "unit dose" means a single dose which is capable of being administered to a patient, and which can be readily handled and packaged, remaining as a physically and chemically stable unit dose comprising either the active compound itself, or as a pharmaceutically acceptable composition, as described herein. The compound provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches.

The pharmaceutical composition may be conveniently administered in unit dosage form and may be prepared by any method well-known in the pharmaceutical art, for example, as described in Remington: The Science and Practice of Pharmacy, 20$^{th}$ ed.; Gennaro, A. R., Ed.; Lippincott Williams & Wilkins: Philadelphia, Pa., 2000.

Preferred formulations include pharmaceutical compositions wherein a compound according to the present invention is formulated for oral or parenteral administration. For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings and flavorings. In addition, the active compounds may be incorporated into fast dissolved, modified-release or sustained-release preparations and formulations, and wherein such sustained-release formulations are preferably bi-modal. Preferred tablets contain lactose, cornstarch, magnesium silicate, crosscarmellose sodium, povidone, magnesium stearate or talc in any combination.

Liquid preparations for parenteral administration include sterile aqueous or non-aqueous solutions, suspensions and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compound. Intravenous vehicles can include fluid and nutrient replenishers, electrolyte replenishers, such as those based on Ringer's dextrose, and the like. Other potentially useful parenteral delivery systems for the active compound include ethylene-vinyl acetate copolymer particles, osmotic pumps, implantable infusion systems and liposomes.

Alternative modes of administration include formulations for inhalation, which include such means as dry powder, aerosol, or drops. They may be aqueous solutions comprising, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations.

Formulations suitable for transdermal administration can be presented as discrete patches and can be lipophilic emulsions or buffered, aqueous solutions, dissolved and/or dispersed in a polymer or an adhesive.

EXAMPLES

The following examples are provided for the purpose of illustrating the present invention and by no means should be interpreted to limit the scope of the present invention.

The first part represents the preparation of the compounds (intermediates and final compounds) whereas the second part describes the evaluation of antibacterial activity of compounds according to the invention.

Preparation of the Compounds and Biological Activity:
  Abbreviations or symbols used herein include:
ACHN: 1,1'-azobis(cyclohexanecarbonitrile)
ACN: acetonitrile
AcOH: acetic acid
Bn: benzyl
Boc: tert-butoxycarbonyl
Boc$_2$O: tert-butoxycarbonyl anhydride
BocON: [2-(tert-butoxycarbonyloxyimino)-2-phenylacetonitrile]
bs: broad singlet
Burgess reagent: methyl N-(triethylammoniosulfonyl)carbamate
Cbz: carboxybenzyl
CbzCl: benzyl chloroformate
CFU: colony-forming units
CLSI: clinical laboratory standards institute
d: doublet
DBU: 1,8-diazabicyclo[5.4.0]undec-7-ene
DCM: dichloromethane
DCE: 1,2-dichloroethane
dd: doublet of doublet
ddd: doublet of doublet of doublet
ddt: doublet of doublet of triplet
dq: doublet of quartet
dt: doublet of triplet
DTA: di-tert-butylazodicarboxylate
DEAD: diethyl azodicarboxylate
Dess-Martin periodinane: 1,1,1-tris(acetyloxy)-1,1-dihydro-1,2-benziodoxol-3-(1H)-one
DIAD: diisopropyl azodicarboxylate
DIPEA: N,N-diisopropylethylamine
DMAP: 4-dimethylaminopyridine
DMF: N,N-dimethylformamide
DMSO: dimethylsulfoxide
EtOAc: ethyl acetate
Et$_2$O: diethyl ether
h: hours
HATU: 1-[Bis(dimethylamino)methylene]-1H-1,2,3-triazolo[4,5-b]pyridinium-3-oxid hexafluorophosphate
iPrOH: isopropanol
m: multiplet
min: minutes
MeOH: methanol
MeONa: sodium methoxide
MIC: minimum inhibitory concentration
MS: mass spectrometry MsCl: methanesulfonyl chloride
NBS: N-bromosuccinimide
NMR: nuclear magnetic resonance spectroscopy
Ns: nosyl, nitrobenzenesulfonyl
Pd(Ph₃)₄: tetrakis(triphenylphosphine)palladium(0)
PG: protective group
PhSH: thiophenol
PMe₃: trimethylphosphine
PPh₃: triphenylphosphine
Ppm: parts per million
q: quartet
rt: room temperature
s: singlet
SEM: [2-(trimethylsilyl)ethoxy]methyl
t: triplet
td: triplet of doublet
TBAF: tetra-n-butylammonium fluoride
TBDMSOTf: trifluoromethanesulfonic acid tert-butyldimethylsilyl ester
TBSOTf: trimethylsilyl trifluoromethanesulfonate
tBuOK: potassium tert-butoxide
TEA: triethylamine
Tf: trifluoromethanesulfonate
TFA: trifluoroacetic acid
THF: tetrahydrofuran
THP: tetrahydropyranyl
TLC: thin layer chromatography
TMSI: Iodotrimethylsilane
Tr: trityl (triphenylmethyl)

Example 1

Synthesis of Sodium (7-oxo-4-pyrazol-4-yl-1,6-diaza-bicyclo[3.2.1]oct-3-en-6-yl) sulfate

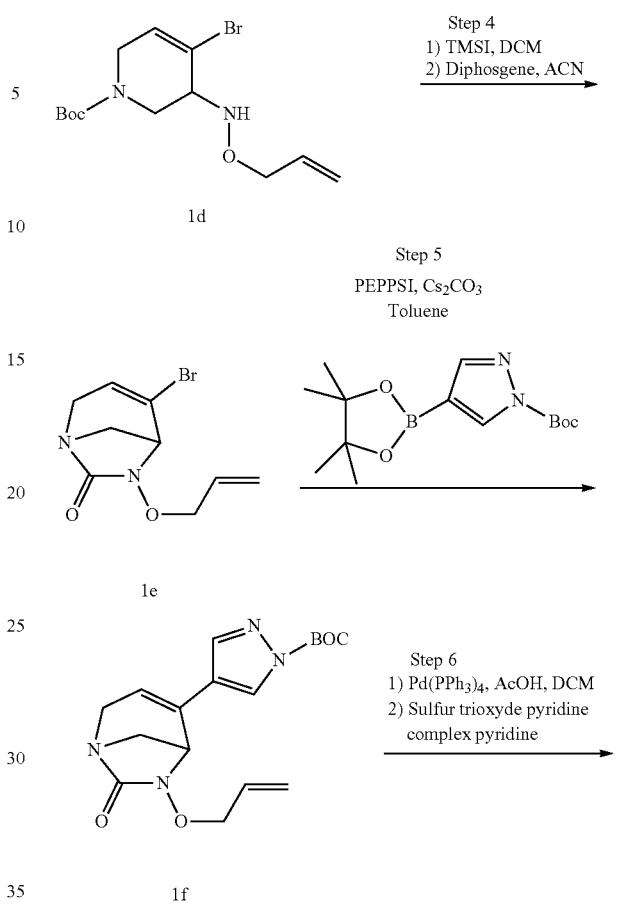

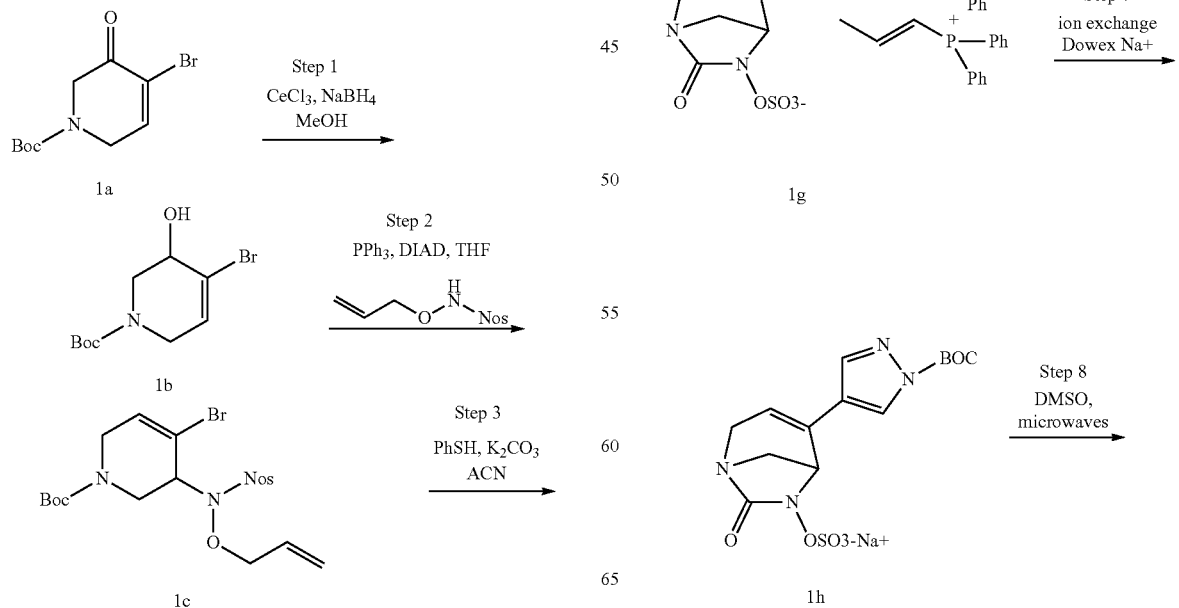

-continued

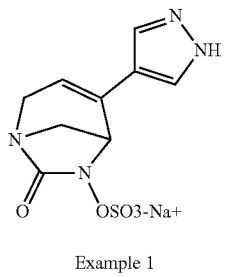

Example 1

Step 1: Preparation of Intermediate tert-butyl 4-bromo-3-hydroxy-3,6-dihydro-2H-pyridine-1-carboxylate (1b)

In a 250 mL round bottom flask under inert atmosphere, tert-butyl 4-bromo-3-oxo-3,6-dihydro-2H-pyridine-1-carboxylate (1a, prepared according to *Tetrahedron Lett.*, 1994, 35, 3589-3592) (2.875 g, 10.41 mmol) was diluted with anhydrous MeOH (50 mL). The clear solution was cooled down to 0° C. with an ice bath and heptahydrate cerium chloride (111) was then added (4.46 g, 11.97 mmol). NaBH$_4$ (0.492 g, 13.01 mmol) was added by portion over 20 min. The resulting suspension was stirred until complete conversion of the starting material. Reaction mixture was filtered on Celite®, washed with MeOH (50 mL). The filtrate was diluted with EtOAc (250 mL) and cooled down to 0° C. 0.1 M aqueous hydrochloric acid was added to reach pH 5-6. Aqueous layer was extracted with EtOAc (3×75 mL). Combined organic layers were dried over Na$_2$SO$_4$, filtered and concentrated under reduced pressure. Crude residue was purified by flash chromatography on silica gel (heptane/EtOAc 60/40) to give desired tert-butyl 4-bromo-3-hydroxy-3,6-dihydro-2H-pyridine-1-carboxylate (1b) (2.85 g, 10.24 mmol, 98%).

MS m/z ([M-(tert-butyl)+H]$^+$) 222-224.

$^1$H NMR (400 MHz, CDCl$_3$): δ (ppm) 1.49 (s, 9H), 2.50 (bs, 1H), 3.66 (dd, J=13.7/4.0 Hz, 1H), 3.73-3.90 (m, 2H), 4.08 (d, J=18.3 Hz, 1H), 4.24 (bs, 1H), 6.20 (bs, 1H).

Step 2: Preparation of Intermediate tert-butyl 3-[allyloxy-(4-nitrophenyl)sulfonyl-amino]-4-bromo-3,6-dihydro-2H-pyridine-1-carboxylate (1c)

Under inert atmosphere, to a solution of tert-butyl 4-bromo-3-hydroxy-3,6-dihydro-2H-pyridine-1-carboxylate (1b) (2.85 g, 10.25 mmol) in THF (100 mL) was added N-(allyloxy)-2-nitrobenzenesulfonamide (3.97 g, 15.37 mmol), PPh$_3$ (8.06 g, 30.74 mmol) and DIAD (6.05 mL, 30.74 mmol). The pale yellow solution turned to an orange suspension. The reaction was stirred for 12 h at rt and was then concentrated under reduced pressure. The pale orange residue was taken up in DCM (50 mL) and concentrated under reduced pressure to give an orange oil. Purification by flash chromatography on silica gel (toluene/Et$_2$O 85/15) gave pure tert-butyl 3-[allyloxy-(4-nitrophenyl)sulfonyl-amino]-4-bromo-3,6-dihydro-2H-pyridine-1-carboxylate (1c) (3.73 g, 7.20 mmol, 71%) as a pale yellow oil.

MS m/z ([M-(tert-Butyl)+H]$^+$) 462-464.

$^1$H NMR (300 MHz, CDCl$_3$): δ (ppm) 1.39 (bs, 9H), 3.11-3.42 (m, 1H), 3.64 (d, J=18.8 Hz, 1H), 3.93-4.56 (m, 4H), 4.64 (bs, 1H), 5.17-5.33 (m, 2H), 5.75-5.92 (m, 1H), 6.43 (bs, 1H), 7.64 (d, J=7.1 Hz, 1H), 7.72-7.87 (m, 2H), 8.18 (d, J=7.1 Hz, 1H).

Step 3: Preparation of Intermediate tert-butyl 3-allyloxyamino-4-bromo-5,6-dihydropyridine-1(2H)-carboxylate (1d)

In a 100 mL round bottom flask under inert atmosphere, tert-butyl 3-[allyloxy-(4-nitrophenyl)sulfonyl-amino]-4-bromo-3,6-dihydro-2H-pyridine-1-carboxylate (1c) (3.72 g, 7.18 mmol) was diluted at rt with ACN (70 mL). To the clear yellow solution were added thiophenol (3.68 mL, 35.88 mmol) and K$_2$CO$_3$ (7.44 g, 53.82 mmol). The resulting yellow suspension turned to orange and was stirred for 12 h. The mixture was filtered on 0.45 μm PTFE membrane and the filtrate was concentrated under reduced pressure. The crude compound was purified by flash chromatography on silica gel (toluene/acetone 98/2) to give desired tert-butyl 3-allyloxyamino-4-bromo-5,6-dihydropyridine-1(2H)-carboxylate (1d) (1.84 g, 5.51 mmol, 77%).

MS m/z ([M+H]$^+$) 331-333.

$^1$H NMR (300 MHz, CDCl$_3$): δ (ppm) 1.52 (bs, 9H), 3.32 (dd, J=13.6/3.7 Hz, 1H), 3.57-3.83 (m, 2H), 4.05-4.40 (m, 4H), 5.17-5.39 (m, 2H), 5.82 (bs, 1H), 5.90-6.08 (m, 1H), 6.26 (bs, 1H).

Step 4: Preparation of Intermediate 6-allyloxy-4-bromo-1,6-diaza-bicyclo[3.2.1]oct-3-en-7-one (1e)

In a 250 mL round bottom flask under inert atmosphere, tert-butyl 3-allyloxyamino-4-bromo-5,6-dihydropyridine-1(2H)-carboxylate (1d) (1.84 g, 5.51 mmol) was diluted in anhydrous DCM (150 mL). TMSI (1.23 mL, 8.26 mmol) was then slowly added over 10 min. The resulting yellow suspension was stirred at rt for 10 min until complete conversion of the starting material. The reaction mixture was cooled down to 0° C. with an ice bath and quenched with MeOH (10 mL). The resulting pale yellow solution was concentrated to dryness under reduced pressure to give a brown gum (2.09 g) containing crude 3-allyloxyamino-4-bromo-5,6-dihydropyridine which was engaged without further purification in the next step.

In a 500 mL round bottom flask under inert atmosphere, crude 3-allyloxyamino-4-bromo-5,6-dihydropyridine was diluted with anhydrous ACN (150 mL). The yellow solution was cooled down to 0° C. and TEA (3.07 mL, 22.03 mmol) was added. Diphosgene (366 μL, 3.03 mmol) diluted in ACN (60 mL) was slowly added over 1 h. The reaction mixture was stirred at 0° C. for 1 hour until complete conversion of the starting material. The pale brown solution was concentrated under reduced pressure and the brown residue was taken up in EtOAc (200 mL), then washed with saturated aqueous sodium hydrogenocarbonate solution (50 mL) and brine (50 mL). The organic layer was dried over Na$_2$SO$_4$, filtered and concentrated under reduced pressure. The crude material was purified by flash chromatography on silica gel (toluene/EtOAc 85/15) and gave pure 6-allyloxy-4-bromo-1,6-diaza-bicyclo[3.2.1]oct-3-en-7-one (1e) as a pale yellow solid (638 mg, 2.46 mmol, 45% over 2 steps).

MS m/z ([M+H]$^+$) 259-261.

$^1$H NMR (400 MHz, CDCl$_3$): δ (ppm) 3.20 (d, J=10.9 Hz, 1H), 3.53 (dd, J=10.9/3.1 Hz, 1H), 3.72 (dd, J=18.0/2.1 Hz, 1H), 3.85 (dd, J=18.0/3.4 Hz, 1H), 4.05-4.09 (m, 1H), 4.39-4.56 (m, 2H), 5.31-5.46 (m, 2H), 6.00-6.13 (m, 2H).

Step 5: Preparation of Intermediate tert-butyl 4-(6-allyloxy-7-oxo-1,6-diazabicyclo[3.2.1]oct-3-en-4-yl)pyrazole-1-carboxylate (1f)

In a 5 mL sealed tube under inert atmosphere, 6-allyloxy-4-bromo-1,6-diaza-bicyclo[3.2.1]oct-3-en-7-one (1e) (79.3 mg, 0.306 mmol) was diluted at rt with anhydrous toluene (3.1 mL). Anhydrous Cs$_2$CO$_3$ (133 mg, 0.408 mmol) and tert-butyl 4-(4,4,5,5-tetramethyl-1,3,2-dioxaborolan-2-yl)pyrazole-1-carboxylate (60 mg, 0.204 mmol) were added. Argon was bubbled through the resulting white suspension for 10 min and PEPPSI catalyst was then added (10.4 mg, 0.015 mmol). The mixture was heated under microwaves at 100° C. for 50 min to reach maximal conversion of the starting material. The mixture was filtered through 0.45 μm membrane, the brown filtrate was diluted with EtOAc (10 mL) and washed with brine (2×2 mL). Aqueous layers were extracted with EtOAc (2×2 mL). Organic layers were dried over Na$_2$SO$_4$, filtered and concentrated under reduced pressure to give crude material (148 mg). Further purification by flash chromatography on silica gel (DCM/EtOAc 100/0 to 70/30) gave pure tert-butyl 4-(6-allyloxy-7-oxo-1,6-diazabicyclo [3.2.1]oct-3-en-4-yl)pyrazole-1-carboxylate (10 as a yellowish oil (34 mg, 0.098 mmol, 32%).

MS m/z ([M+H]$^+$) 347.

$^1$H NMR (300 MHz, CDCl$_3$): δ (ppm) 1.51 (s, 9H), 3.04 (d, J=10.8 Hz, 1H), 3.45 (dd, J=10.9/2.8 Hz, 1H), 3.68 (dd, J=18.8/2.0 Hz, 1H), 3.80 (dd, J=18.8/2.8 Hz, 1H), 3.93 (bd, J=2.7 Hz, 1H), 4.21-4.38 (m, 2H), 5.13-5.28 (m, 2H), 5.68-5.72 (m, 1H), 5.80-5.95 (m, 1H), 7.58 (d, J=0.9 Hz, 1H), 7.87 (bs, 1H).

Step 6: Preparation of Intermediate triphenyl-(propenyl)-phosphonium tert-butyl 4-(7-oxo-1,6-diazabicyclo[3.2.1]oct-3-en-4-yl)pyrazole-1-carboxylate sulfate (1g)

To a solution of tert-butyl 4-(6-allyloxy-7-oxo-1,6-diazabicyclo [3.2.1]oct-3-en-4-yl)pyrazole-1-carboxylate (10 (27 mg, 0.078 mmol) in anhydrous DCM (1 mL) were added glacial AcOH (9 μL, 0.156 mmol) and Pd(PPh$_3$)$_4$ (45 mg, 0.039 mmol). After 45 min of stirring at rt, pyridine (1 mL) and sulfur trioxide pyridine complex (62 mg, 0.390 mmol) were added to the reaction mixture. The resulting white suspension was protected from light and stirred overnight until the reaction was completed. The suspension was filtered, the solids were washed with DCM (3×5 mL), the filtrate was concentrated under vacuum and then purified by flash chromatography on silica gel (DCM/acetone: 100/0 to 25/75) to afford triphenyl-(propenyl)-phosphonium tert-butyl 4-(7-oxo-1,6-diazabicyclo[3.2.1]oct-3-en-4-yl)pyrazole-1-carboxylate sulfate (1g) (35 mg).

MS m/z ([M−H]$^−$) 385.

MS m/z ([M+H]$^+$) 303 (triphenyl-propenyl-phosphonium).

Step 7: Preparation of Intermediate Sodium tert-butyl 4-(7-oxo-1,6-diaza-bicyclo[3.2.1]oct-3-en-4-yl)pyrazole-1-carboxylate sulfate (1 h)

Triphenyl-(propenyl)-phosphonium tert-butyl 4-(7-oxo-1,6-diaza-bicyclo[3.2.1]oct-3-en-4-yl)pyrazole-1-carboxylate sulfate (1g) (35 mg) dissolved in H$_2$O (200 μL) was applied on a Dowex sodium form column (Dowex® 50WX8 hydrogen form stored with an aqueous solution of 2N NaOH and washed until neutral pH with H$_2$O). The fractions containing the desired compound were combined, frozen and lyophilized to afford sodium tert-butyl 4-(7-oxo-1,6-diazabicyclo[3.2.1]oct-3-en-4-yl)pyrazole-1-carboxylate sulfate (1h) (17.5 mg, 0.265 mmol, 55% over 2 steps) as a white amorphous solid.

MS m/z ([M−H]$^−$) 385.

Step 8: Preparation of Sodium (7-oxo-4-pyrazol-4-yl-1,6-diaza-bicyclo[3.2.1]oct-3-en-6-yl) sulfate (Example 1)

In a 2 mL sealed tube, sodium tert-butyl 4-(7-oxo-1,6-diaza-bicyclo[3.2.1]oct-3-en-4-yl)pyrazole-1-carboxylate sulfate (1h) (14.4 mg, 0.035 mmol) was diluted with DMSO (600 μL). The resulting solution was saturated with argon and heated under microwaves at 140° C. for 5 min. The solution turned yellow and was directly frozen and lyophilized. The residue was taken up with H$_2$O (2 mL), filtered over 0.20 μm membrane and lyophilized once more. The pale yellow solid was dissolved in H$_2$O (200 μL) and was applied on a Dowex sodium form column (Dowex® 50WX8 hydrogen form stored with an aqueous solution of 2N NaOH and washed until neutral pH with H$_2$O). The fractions containing the desired compound were combined, frozen and lyophilized to afford sodium (7-oxo-4-pyrazol-4-yl-1,6-diaza-bicyclo[3.2.1]oct-3-en-6-yl) sulfate (Example 1) (5.4 mg, 0.018 mmol, 49%) as a pale yellow solid.

MS m/z ([M−H]$^−$) 285.

$^1$H NMR (400 MHz, D$_2$O): δ (ppm) 3.46 (d, J=11.2 Hz, 1H), 3.71 (dd, J=11.2/3.6 Hz, 1H), 3.82 (dd, J=18.6/3.6 Hz, 1H), 3.99 (dd, J=18.6/1.7 Hz, 1H), 4.65-4.67 (m, 1H), 5.91-5.94 (m, 1H), 7.78-7.83 (bs, 2H).

Example 2

Synthesis of Sodium [4-(2-methylpyrazol-3-yl)-7-oxo-1,6-diazabicyclo[3.2.1]oct-3-en-6-yl] sulfate

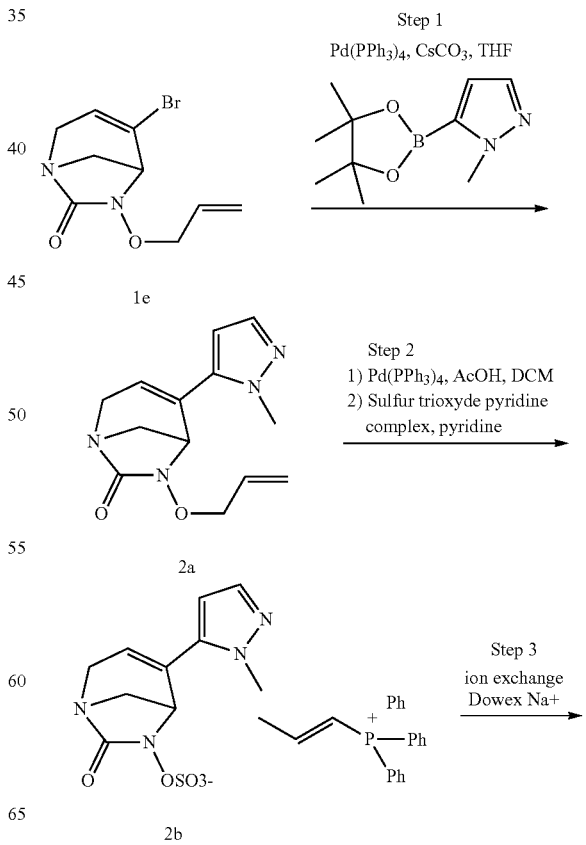

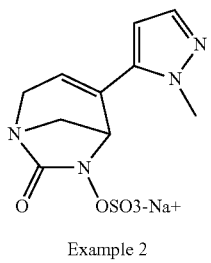

Example 2

Step 1: Preparation of Intermediate 6-allyloxy-4-(2-methylpyrazol-3-yl)-1,6-diazabicyclo[3.2.1]oct-3-en-7-one (2a)

In a Wheaton vial, 6-allyloxy-4-bromo-1,6-diazabicyclo[3.2.1]oct-3-en-7-one (1e) (30 mg, 0.116 mmol), 1-methyl-1H-pyrazole-5-boronic acid pinacol ester (28.9 mg, 0.139 mmol) and anhydrous CsCO$_3$ (75.4 mg, 0.232 mmol) were dissolved in anhydrous THF (1.3 mL). The solution was degassed by bubbling argon for 10 min and Pd(PPh$_3$)$_4$ (4.0 mg, 0.003 mmol) was added. The reaction mixture was heated at 60° C. for 90 min. H$_2$O (1 mL) was added and the mixture was extracted with EtOAc (2×1 mL). The organic layer was dried over Na$_2$SO$_4$, filtered and concentrated under vacuum to afford a crude material which was purified by preparative TLC (toluene/acetone: 8/2) to give the desired product 6-allyloxy-4-(2-methylpyrazol-3-yl)-1,6-diazabicyclo[3.2.1]oct-3-en-7-one (2a) (8.8 mg, 0.034 mmol, 29%).

MS m/z ([M+H]$^+$) 261.

$^1$H NMR (300 MHz, CDCl$_3$): δ (ppm) 3.23 (m, 1H), 3.58-3.63 (m, 1H), 3.83-4.05 (m, 3H), 3.86 (s, 3H), 4.28-4.44 (m, 2H), 5.23-5.31 (m, 2H), 5.74-5.77 (m, 1H), 5.82-5.96 (m, 1H), 6.17 (d, J=2.0 Hz, 1H), 7.43 (d, J=2.0 Hz, 1H).

Step 2: Preparation of Intermediate triphenyl-(propenyl)-phosphonium [4-(2-methylpyrazol-3-yl)-7-oxo-1,6-diazabicyclo[3.2.1]oct-3-en-6-yl] sulfate (2b)

Using the procedure described in example 1 (step 6), the intermediate 6-allyloxy-4-(2-methylpyrazol-3-yl)-1,6-diazabicyclo[3.2.1]oct-3-en-7-one (2a) (52 mg, 0.198 mmol) is converted into triphenyl-(propenyl)-phosphonium [4-(2-methylpyrazol-3-yl)-7-oxo-1,6-diazabicyclo[3.2.1]oct-3-en-6-yl] sulfate (2b) (56.7 mg) as an amorphous solid after purification by flash chromatography on silica gel (DCM/acetone 80/20 to 0/100).

MS m/z ([M+H]$^+$) 301.
MS m/z ([M−H]$^-$) 299.
MS m/z ([M+H]$^+$) 303 (triphenyl-propenyl-phosphonium).

Step 3: Preparation of Sodium [4-(2-methylpyrazol-3-yl)-7-oxo-1,6-diazabicyclo[3.2.1]oct-3-en-6-yl] sulfate (Example 2)

Using the procedure described in example 1 (step 7), triphenyl-(propenyl)-phosphonium [4-(2-methylpyrazol-3-yl)-7-oxo-1,6-diazabicyclo[3.2.1]oct-3-en-6-yl] sulfate (2b) (56.7 mg) is converted after ion exchange (Dowex sodium form column) into sodium [4-(2-methylpyrazol-3-yl)-7-oxo-1,6-diazabicyclo[3.2.1]oct-3-en-6-yl] sulfate (Example 2) (34.6 mg, 0.107 mmol, 54% over 2 steps) as a white amorphous solid after lyophilization.

MS m/z ([M+H]$^+$) 301.
MS m/z ([M−H]$^-$) 299.
$^1$H NMR (300 MHz, D$_2$O): δ (ppm) 3.53-357 (m, 1H), 3.73-3.95 (m, 5H), 4.07-4.14 (m, 1H), 4.53-4.54 (m, 1H), 6.00 (bs, 1H), 6.41 (d, J=2.2 Hz, 1H), 7.52 (d, J=2.2 Hz, 1H).

Example 3

Synthesis of Sodium [4-(oxazol-5-yl)-7-oxo-1,6-diazabicyclo[3.2.1]oct-3-en-6-yl] sulfate

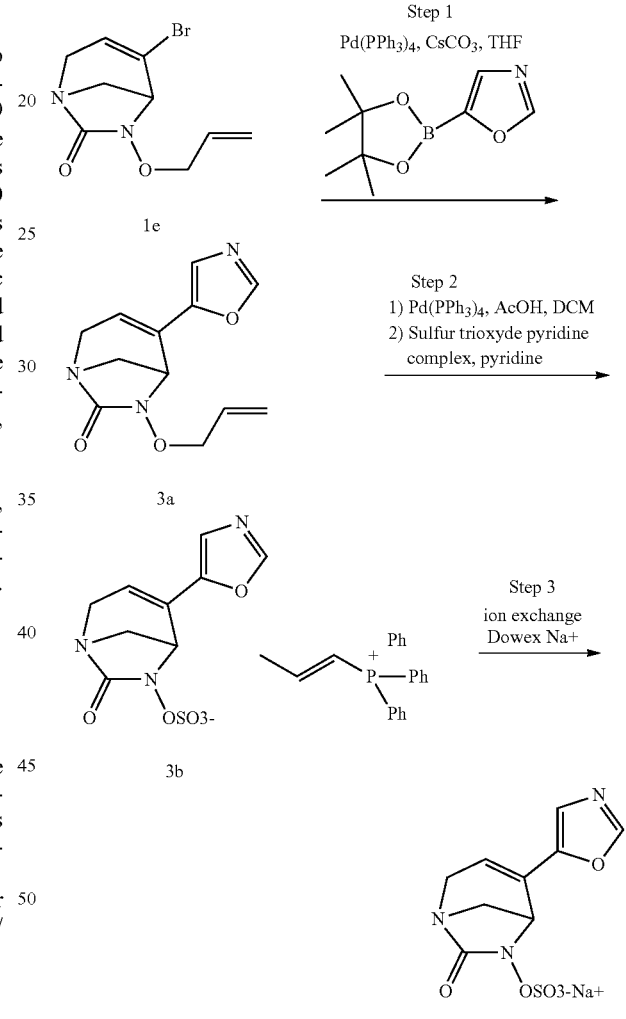

Example 3

Step 1: Preparation of Intermediate 6-allyloxy-4-(oxazol-5-yl)-1,6-diazabicyclo[3.2.1]oct-3-en-7-one (3a)

Using the procedure described in example 2 (step 1), the intermediate 6-allyloxy-4-bromo-1,6-diazabicyclo[3.2.1]oct-3-en-7-one (1e) (30 mg, 0.116 mmol) is converted into 6-allyloxy-4-(oxazol-5-yl)-1,6-diazabicyclo[3.2.1]oct-3-en-7-one (3a) (2.4 mg, 0.010 mmol, 8.4%) using 5-(4,4,5,5- tetramethyl-1,3,2-dioxaborolan-2-yl)oxazole (27.1 mg, 0.139 mmol) and after purification by preparative TLC (toluene/acetone: 8/2).

MS m/z ([M+H]$^+$) 248, ([M+Na]$^+$) 270.

$^1$H NMR (300 MHz, CDCl$_3$): δ (ppm) 3.17 (d, J=10.9 Hz, 1H), 3.60 (dd, J=10.9/3.0 Hz, 1H), 3.84-4.00 (m, 2H), 4.17-4.18 (m, 1H), 4.35-4.46 (m, 2H), 5.29-5.36 (m, 2H), 5.94-6.07 (m, 2H), 7.01 (s, 1H), 7.81 (s, 1H).

Step 2: Preparation of Intermediate triphenyl-(propenyl)-phosphonium [4-(oxazol-5-yl)-7-oxo-1,6-diazabicyclo[3.2.1]oct-3-en-6-yl] sulfate (3b)

Using the procedure described in example 1 (step 6), the intermediate 6-allyloxy-4-(oxazol-5-yl)-1,6-diazabicyclo[3.2.1]oct-3-en-7-one (3a) (47 mg, 0.190 mmol) is converted into triphenyl-(propenyl)-phosphonium [4-(oxazol-5-yl)-7-oxo-1,6-diazabicyclo[3.2.1]oct-3-en-6-yl] sulfate (3b) (60.6 mg) as an amorphous solid after purification by flash chromatography on silica gel (DCM/acetone 80/20 to 10/90).

MS m/z ([M+H]$^+$) 288.

MS m/z ([M−H]$^-$) 286.

MS m/z ([M+H]$^+$) 303 (triphenyl-propenyl-phosphonium).

Step 3: Preparation of Sodium [4-(oxazol-5-yl)-7-oxo-1,6-diazabicyclo[3.2.1]oct-3-en-6-yl]sulfate (Example 3)

Using the procedure described in example 1 (step 7), triphenyl-(propenyl)-phosphonium [4-(oxazol-5-yl)-7-oxo-1,6-diazabicyclo[3.2.1]oct-3-en-6-yl] sulfate (3b) (60.6 mg) is converted after ion exchange (Dowex sodium form column) into sodium [4-(oxazol-5-yl)-7-oxo-1,6-diazabicyclo[3.2.1]oct-3-en-6-yl] sulfate (Example 3) (25.2 mg, 0.081 mmol, 43% over 2 steps) as a white amorphous solid after lyophilization.

MS m/z ([M+H]$^+$) 288

MS m/z ([M−H]$^-$) 286.

$^1$H NMR (300 MHz, D$_2$O): δ (ppm) 3.49 (dd, J=11.4/0.7 Hz, 1H), 3.75 (ddd, J=11.4/3.1/0.7 Hz, 1H), 3.87-4.12 (m, 2H), 4.73-4.74 (m, 1H), 6.22-6.24 (m, 1H), 7.22 (s, 1H), 8.12 (s, 1H).

Example 4

Synthesis of Sodium [4-(oxazol-2-yl)-7-oxo-1,6-diazabicyclo[3.2.1]oct-3-en-6-yl] sulfate

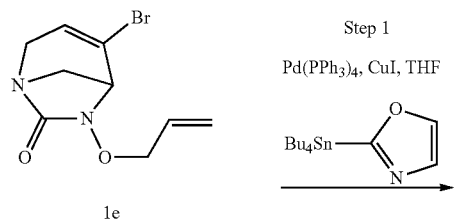

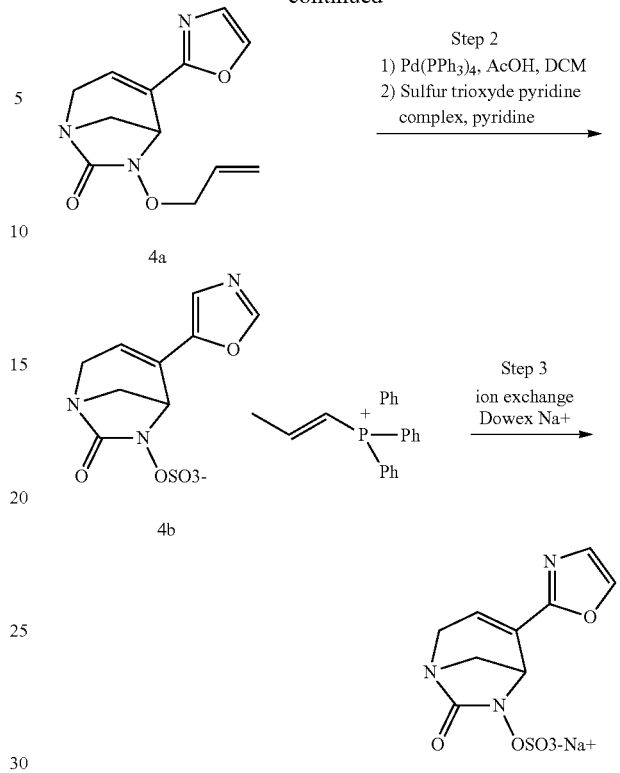

Example 4

Step 1: Preparation of Intermediate 6-allyloxy-4-(oxazol-2-yl)-1,6-diazabicyclo[3.2.1]oct-3-en-7-one (4a)

In a Wheaton vial, 6-allyloxy-4-bromo-1,6-diazabicyclo[3.2.1]oct-3-en-7-one (1e) (30 mg, 0.116 mmol), 2-(tri-n-butylstannyl)oxazole (53.9 mg, 0.0.151 mmol) and anhydrous CuI (22.0 mg, 0.116 mmol) were dissolved in anhydrous DMF (1.2 mL). The solution was degassed by bubbling argon for 5 min and Pd(PPh$_3$)$_4$ (13.4 mg, 0.012 mmol) was added. The reaction was stirred for 2 h at 80° C. EtOAc (1 mL) was added, followed by a saturated solution of potassium fluoride (1 mL). The mixture was stirred at rt for 1 h. The organic layer was separated, washed with brine (2 mL), dried over Na$_2$SO$_4$, filtered, and concentrated under vacuum to afford a crude material which was purified by preparative TLC (toluene/acetone: 7/3) to give the desired 6-allyloxy-4-(oxazol-2-yl)-1,6-diazabicyclo[3.2.1]oct-3-en-7-one (4a) (8.4 mg, 0.034 mmol, 29%).

MS m/z ([M+H]$^+$) 248, ([M+Na]$^+$) 270.

$^1$H NMR (300 MHz, CDCl$_3$): δ (ppm) 3.14 (d, J=11.0 Hz, 1H), 3.60 (dd, J=11.0/3.0 Hz, 1H), 3.83-4.03 (m, 2H), 4.36-4.46 (m, 2H), 4.75-4.76 (m, 1H), 5.24-5.35 (m, 2H), 5.95-6.05 (m, 1H), 6.50-6.51 (m, 1H), 7.14 (d, J=0.8 Hz, 1H), 7.60 (bs, 1H).

Step 2: Preparation of Intermediate triphenyl-(propenyl)-phosphonium [4-(oxazol-2-yl)-7-oxo-1,6-diazabicyclo[3.2.1]oct-3-en-6-yl] sulfate (4b)

Using the procedure described in example 1 (step 6), the intermediate 6-allyloxy-4-(oxazol-2-yl)-1,6-diazabicyclo[3.2.1]oct-3-en-7-one (4a) (71 mg, 0.287 mmol) is converted into triphenyl-(propenyl)-phosphonium [4-(oxazol-2-yl)-7-oxo-1,6-diazabicyclo[3.2.1]oct-3-en-6-yl] sulfate (4b) as an amorphous solid after purification by flash chromatography on silica gel (DCM/acetone from 80/20 to 10/90).

MS m/z ([M+H]$^+$) 288.
MS m/z ([M−H]$^−$) 286.
MS m/z ([M+H]$^+$) 303 (triphenyl-propenyl-phosphonium).

Step 3: Preparation of Sodium [4-(oxazol-2-yl)-7-oxo-1,6-diazabicyclo[3.2.1]oct-3-en-6-yl]sulfate (Example 4)

Using the procedure described in example 1 (step 7), triphenyl-(propenyl)-phosphonium [4-(oxazol-2-yl)-7-oxo-1,6-diazabicyclo[3.2.1]oct-3-en-6-yl] sulfate (4b) is converted after ion exchange (Dowex sodium form column) into sodium [4-(oxazol-2-yl)-7-oxo-1,6-diazabicyclo[3.2.1]oct-3-en-6-yl] sulfate (Example 4) (24.4 mg, 0.079 mmol, 27% over 2 steps) as a white amorphous solid after lyophilization.

MS m/z ([M+H]$^+$) 288.
MS m/z ([M−H]$^−$) 286.
$^1$H NMR (300 MHz, D$_2$O): δ (ppm) 3.47 (dd, J=11.4/0.7 Hz 1H), 3.79 (ddd, J=11.4/3.7/0.7 Hz 1H), 3.92-4.16 (m, 2H), 5.01-5.02 (m, 1H), 6.69-6.71 (m, 1H), 7.23 (d, J=0.9 Hz, 1H), 7.86 (d, J=0.9 Hz, 1H).

Example 5

Synthesis of Sodium (7-oxo-4-isoxazol-4-yl-1,6-diaza-bicyclo[3.2.1]oct-3-en-6-yl) sulfate

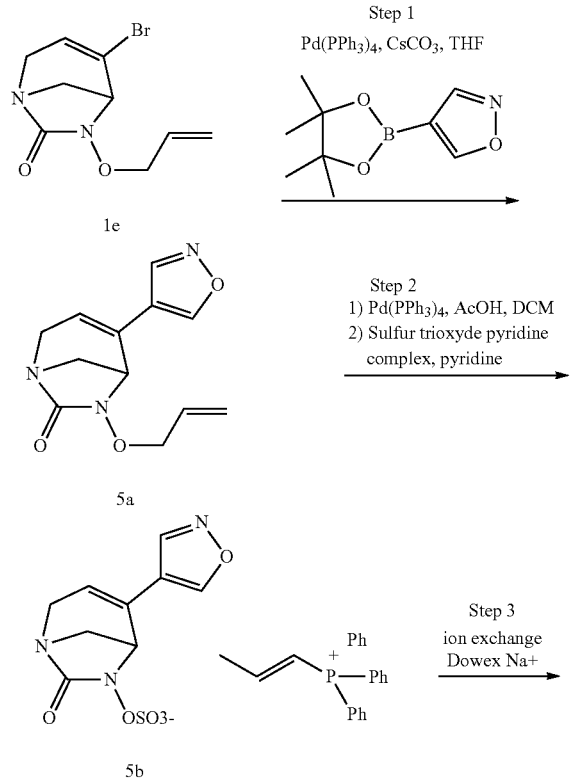

Example 5

Step 1: Preparation of Intermediate 6-allyloxy-4-isoxazol-4-yl-1,6-diazabicyclo[3.2.1]oct-3-en-7-one (5a)

In a Wheaton vial, 6-allyloxy-4-bromo-1,6-diazabicyclo[3.2.1]oct-3-en-7-one (1e) (30 mg, 0.116 mmol), 4-(4,4,5,5-tetramethyl-1,3,2-dioxaborolan-2-yl)isoxazole (27.1 mg, 0.139 mmol) and anhydrous Cs$_2$CO$_3$ (75.4 mg, 0.232 mmol) were dissolved in anhydrous THF (1.3 mL). The solution was degassed by bubbling argon for 10 min and Pd(PPh$_3$)$_4$ (4.0 mg, 0.003 mmol) was added. The reaction was stirred for 45 min at rt. H$_2$O (1 mL) was added and the mixture was extracted with EtOAc (2×1 mL). The organic layer was dried over Na$_2$SO$_4$, filtered, and concentrated under vacuum to afford a crude material which was purified by preparative TLC (toluene/acetone: 8/2) to give the desired product 6-allyloxy-4-isoxazol-4-yl-1,6-diazabicyclo[3.2.1]oct-3-en-7-one (5a) (3.0 mg, 0.012 mmol, 10%).

MS m/z ([M+H]$^+$) 248.
$^1$H NMR (400 MHz, CDCl$_3$): δ (ppm) 3.23 (dd, J=10.9/0.4 Hz, 1H), 3.64 (ddd, J=10.9/3.4/0.4 Hz, 1H), 3.87 (dd, J=18.8/2.1 Hz, 1H), 3.99 (dd, J=18.8/3.4 Hz, 1H), 4.04-4.08 (m, 1H), 4.39-4.57 (m, 2H), 5.34-5.48 (m, 2H), 5.85-5.90 (m, 1H), 5.96-6.13 (m, 1H), 8.36 (s, 1H), 8.42 (s, 1H).

Step 2: Preparation of Intermediate triphenyl-(propenyl)-phosphonium (7-oxo-4-isoxazol-4-yl-1,6-diaza-bicyclo[3.2.1]oct-3-en-6-yl) sulfate (5b)

Using the procedure described in example 1 (step 6), the intermediate 6-allyloxy-4-isoxazol-4-yl-1,6-diazabicyclo[3.2.1]oct-3-en-7-one (5a) (35 mg, 0.142 mmol) was converted into triphenyl-(propenyl)-phosphonium (7-oxo-4-isoxazol-4-yl-1,6-diaza-bicyclo[3.2.1]oct-3-en-6-yl) sulfate (5b) (57 mg) as an amorphous solid after purification by flash chromatography on silica gel (DCM/acetone 100/0 to 0/100).

MS m/z ([M+H]$^+$) 288.
MS m/z ([M−H]$^−$) 286.
MS m/z ([M+H]$^+$) 303 (triphenyl-propenyl-phosphonium).

Step 3: Preparation of Sodium (7-oxo-4-isoxazol-4-yl-1,6-diaza-bicyclo[3.2.1]oct-3-en-6-yl) sulfate (Example 5)

Using the procedure described in example 1 (step 7), triphenyl-(propenyl)-phosphonium (7-oxo-4-isoxazol-4-yl-1,6-diaza-bicyclo[3.2.1]oct-3-en-6-yl) sulfate (5b) (57 mg) was converted after ion exchange (Dowex sodium form column) into sodium (7-oxo-4-isoxazol-4-yl-1,6-diaza-bicyclo[3.2.1]oct-3-en-6-yl) sulfate (Example 5) (19.4 mg, 0.062 mmol, 44% over 2 steps) as a white amorphous solid after lyophilization.

MS m/z ([M+H]$^+$) 288.

MS m/z ([M−H]$^−$) 286.

$^1$H NMR (400 MHz, D$_2$O): δ (ppm) 3.50 (d, J=11.4 Hz, 1H), 3.74 (dd, J=11.4/3.0 Hz, 1H), 3.87 (dd, J=18.8/3.5 Hz, 1H), 4.04 (dd, J=18.8/2.0 Hz, 1H), 4.65-4.69 (m, 1H), 6.06-6.11 (m, 1H), 8.65 (s, 1H), 8.75 (s, 1H).

Example 6

Synthesis of Lithium difluoro-(4-isoxazol-4-yl-7-oxo-1,6-diaza-bicyclo[3.2.1]oct-3-en-6-yloxy)-acetate

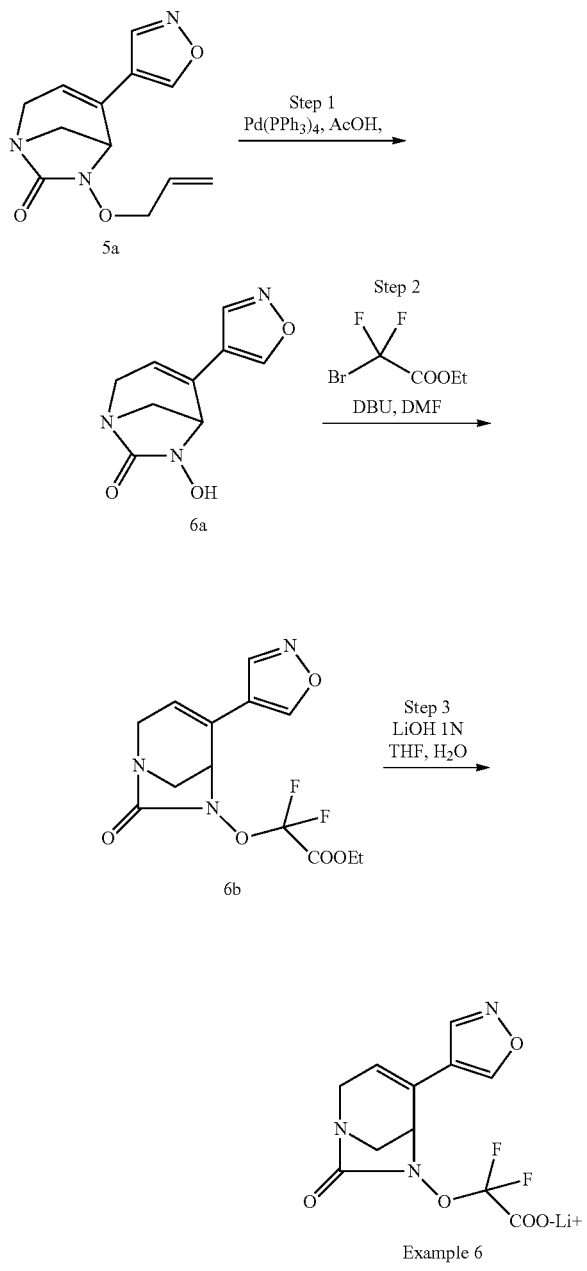

Example 6

Step 1: Preparation of Intermediate 6-hydroxy-4-isoxazol-4-yl-1,6-diazabicyclo[3.2.1]oct-3-en-7-one (6a)

To a solution of 6-allyloxy-4-isoxazol-4-yl-1,6-diazabicyclo[3.2.1]oct-3-en-7-one (5a) (400 mg, 1.62 mmol) and glacial AcOH (185 µL, 3.24 mmol) in anhydrous DCM (16 mL) was added in one portion Pd(PPh$_3$)$_4$ (935 mg, 0.81 mmol) at rt. After stirring 20 min, the mixture was evaporated under nitrogen flux. The oily residue was purified by chromatography on silica gel (DCM/Acetone 7/3) to afford 6-hydroxy-4-isoxazol-4-yl-1,6-diazabicyclo[3.2.1]oct-3-en-7-one (6a) (275 mg, 1.33 mmol, 82%).

MS m/z ([M+H]$^+$) 208.

$^1$H NMR (300 MHz, CDCl$_3$): δ (ppm) 3.22 (d, J=11.3 Hz, 1H), 3.63 (dd, J=3.2/11.3 Hz, 1H), 3.84 (dd, J=2.2/18.8 Hz, 1H), 3.93 (dd, J=3.2/18.8 Hz, 1H), 4.07 (dd, J=1.1/2.5 Hz, 1H), 5.84-5.86 (m, 1H), 8.35 (s, 1H), 8.47 (s, 1H).

Step 2: Preparation of Intermediate ethyl 2,2-difluoro-2-[(4-isoxazol-4-yl-7-oxo-1,6-diazabicyclo[3.2.1]oct-3-en-6-yl)oxy]acetate (6b)

6-hydroxy-4-isoxazol-4-yl-1,6-diazabicyclo[3.2.1]oct-3-en-7-one (6a) (227 mg, 1.09 mmol) was solubilized in DMF (12 mL) at −20° C. with DBU (179 µL, 1.20 mmol) and ethyl 2-bromo-2,2-difluoro-acetate (702 µL, 5.48 mmol). After stirring 1 h, the reaction mixture was evaporated under nitrogen flux. The residue was purified by chromatography on silica gel (DCM/Et$_2$O 9/1) to provide ethyl 2,2-difluoro-2-[(4-isoxazol-4-yl-7-oxo-1,6-diazabicyclo[3.2.1]oct-3-en-6-yl)oxy]acetate (6b) which was triturated with MTBE (214 mg, 0.65 mmol, 59%).

MS m/z ([M+H]$^+$) 330.

$^1$H NMR (300 MHz, CDCl$_3$): δ (ppm) 1.34 (t, J=7.2 Hz, 3H), 3.29 (d, J=11.4 Hz, 1H), 3.70 (dd, J=2.7/11.4 Hz, 1H), 3.93 (dd, J=2.1/18.8 Hz, 1H), 4.05 (dd, J=3.4/18.8 Hz, 1H), 4.28 (d, J=2.7 Hz, 1H), 4.36 (q, J=7.2 Hz, 2H), 5.91-5.95 (m, 1H), 8.37 (s, 1H), 8.52 (s, 1H).

Step 3: Preparation of Lithium difluoro-(4-isoxazol-4-yl-7-oxo-1,6-diaza-bicyclo[3.2.1]oct-3-en-6-yloxy)-acetate (Example 6)

Ethyl 2,2-difluoro-2-[(4-isoxazol-4-yl-7-oxo-1,6-diazabicyclo[3.2.1]oct-3-en-6-yl)oxy]acetate (6b) (188 mg, 0.57 mmol) was solubilized in THF (3.3 mL) and H$_2$O (2.1 mL) at 0° C. A solution of LiOH 1N (730 µL, 0.73 mmol) was then dropped. The mixture was stirred for 1 h at 0° C. The reaction mixture was acidified with HCl 0.5N (330 µL, 0.16 mmol) and concentrated to remove THF. The resulting aqueous layer was frozen and lyophilized. The resulting salt was solubilized with iPrOH and filtrated on a silica gel cake. The filtrate was concentrated and the residue was triturated with MTBE to provide lithium difluoro-(4-isoxazol-4-yl-7-oxo-1,6-diaza-bicyclo[3.2.1]oct-3-en-6-yloxy)-acetate (Example 6) (131 mg, 0.43 mmol, 76%) as a white solid.

MS m/z ([M+H]$^+$) 208.

$^1$H NMR (400 MHz, DMSO-d$_6$): δ (ppm) 3.29 (d, J=11.2 Hz, 1H), 3.42 (dd, J=2.8/11.3 Hz, 1H), 3.73-3.81 (m, 1H), 3.92 (dd, J=1.7/18.6 Hz, 1H), 4.44 (d, J=2.3 Hz, 1H), 6.03-6.07 (m, 1H), 8.96 (s, 1H), 9.28 (s, 1H).

Example 7

Synthesis of Sodium [4-(4-pyridyl)-7-oxo-1,6-diazabicyclo[3.2.1]oct-3-en-6-yl] sulfate

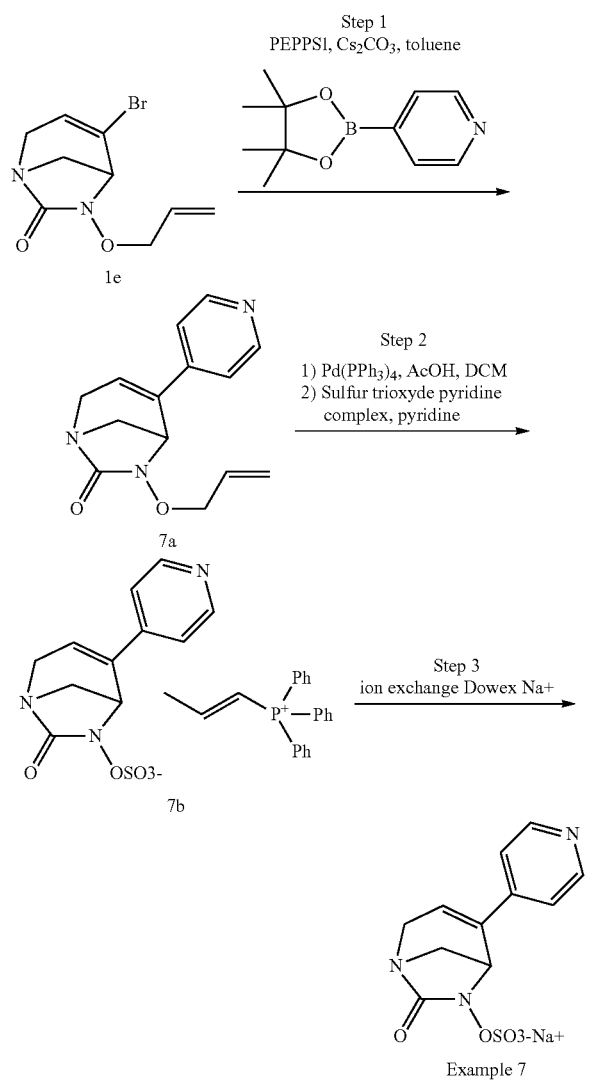

Example 7

Step 1: Preparation of Intermediate 6-allyloxy-4-(4-pyridyl)-1,6-diazabicyclo[3.2.1]oct-3-en-7-one (7a)

In a Wheaton vial, 6-allyloxy-4-bromo-1,6-diazabicyclo[3.2.1]oct-3-en-7-one (1e) (30 mg, 0.116 mmol), 4-pyridine-boronic acid pinacol ester (28.5 mg, 0.139 mmol) and $Cs_2CO_3$ (75.4 mg, 0.232 mmol) were dissolved in anhydrous toluene (1.2 mL). The solution was degassed by bubbling argon for 10 min and PEPPSI catalyst (3.9 mg, 0.004 mmol) was added. The reaction was stirred for 2 h at 100° C. under microwave. $H_2O$ (1 mL) was added and the mixture was extracted with EtOAc (2×1 mL). The organic layer was dried over $Na_2SO_4$, filtered and concentrated under reduced pressure to afford a crude material which was purified by preparative TLC (toluene/acetone 55/45) to give the desired 6-allyloxy-4-(4-pyridyl)-1,6-diazabicyclo[3.2.1]oct-3-en-7-one (7a) (6.0 mg, 0.023 mmol, 20%).

MS m/z ([M+H]$^+$) 258.

$^1$H NMR (300 MHz, CDCl$_3$): δ (ppm) 3.21 (d, J=10.9 Hz, 1H), 3.69 (dd, J=10.9/3.0 Hz, 1H), 3.90 (dd, J=19.0/2.0 Hz, 1H), 4.03 (dd, J=19.0/2.0 Hz, 1H), 4.29 (d, J=2.3 Hz, 1H), 4.43-4.58 (m, 2H), 5.34-5.36 (m, 1H), 5.37-5.42 (m, 1H), 6.00-6.10 (m, 1H), 6.13-6.17 (m, 1H), 7.26-7.30 (m, 2H), 8.59-8.63 (m, 2H).

Step 2: Preparation of Intermediate triphenyl-(propenyl)-phosphonium [4-(4-pyridyl)-7-oxo-1,6-diazabicyclo[3.2.1]oct-3-en-6-yl] sulfate (7b)

Using the procedure described in example 1 (step 6), the intermediate 6-allyloxy-4-(4-pyridyl)-1,6-diazabicyclo[3.2.1]oct-3-en-7-one (7a) (50 mg, 0.194 mmol) was converted into triphenyl-(propenyl)-phosphonium [4-(4-pyridyl)-7-oxo-1,6-diazabicyclo[3.2.1]oct-3-en-6-yl] sulfate (7b) as an amorphous solid after purification by flash chromatography on silica gel (DCM/acetone 50/50 to acetone/pyridine 96/4).

MS m/z ([M+H]$^+$) 298.

MS m/z ([M−H]$^-$) 296.

MS m/z ([M+H]$^+$) 303 (triphenyl-propenyl-phosphonium).

Step 3: Preparation of Sodium [4-(4-pyridyl)-7-oxo-1,6-diazabicyclo[3.2.1]oct-3-en-6-yl]sulfate (Example 7)

Using the procedure described in example 1 (step 7), triphenyl-(propenyl)-phosphonium [4-(4-pyridyl)-7-oxo-1,6-diazabicyclo[3.2.1]oct-3-en-6-yl] sulfate (7b) was converted after ion exchange (Dowex sodium form column) into sodium [4-(4-pyridyl)-7-oxo-1,6-diazabicyclo[3.2.1]oct-3-en-6-yl] sulfate (Example 7) (3.9 mg, 0.013 mmol, 7% over 2 steps) as a white amorphous solid after lyophilization.

MS m/z ([M+H]$^+$) 298.

MS m/z ([M−H]$^-$) 296.

$^1$H NMR (400 MHz, D$_2$O): δ (ppm) 3.47 (d, J=11.3 Hz, 1H), 3.78 (dd, J=11.3/3.2 Hz, 1H), 3.92 (dd, J=19.2/3.5 Hz, 1H), 4.07 (dd, J=19.2/2.2 Hz, 1H), 4.82-4.85 (m, 1H), 6.39-6.42 (m, 1H), 7.47-7.50 (m, 2H), 8.47-8.51 (m, 2H).

Example 8

Synthesis of Sodium [4-(N-methyl-6-oxo-3-pyridyl)-7-oxo-1,6-diazabicyclo[3.2.1]oct-3-en-6-yl] sulfate

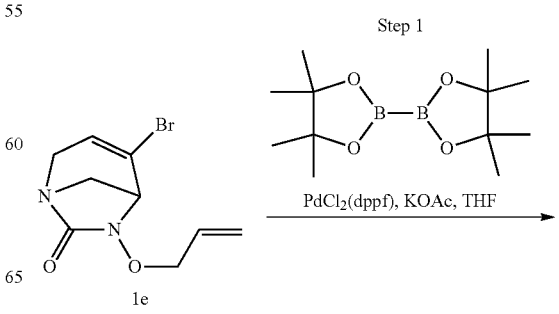

Step 1

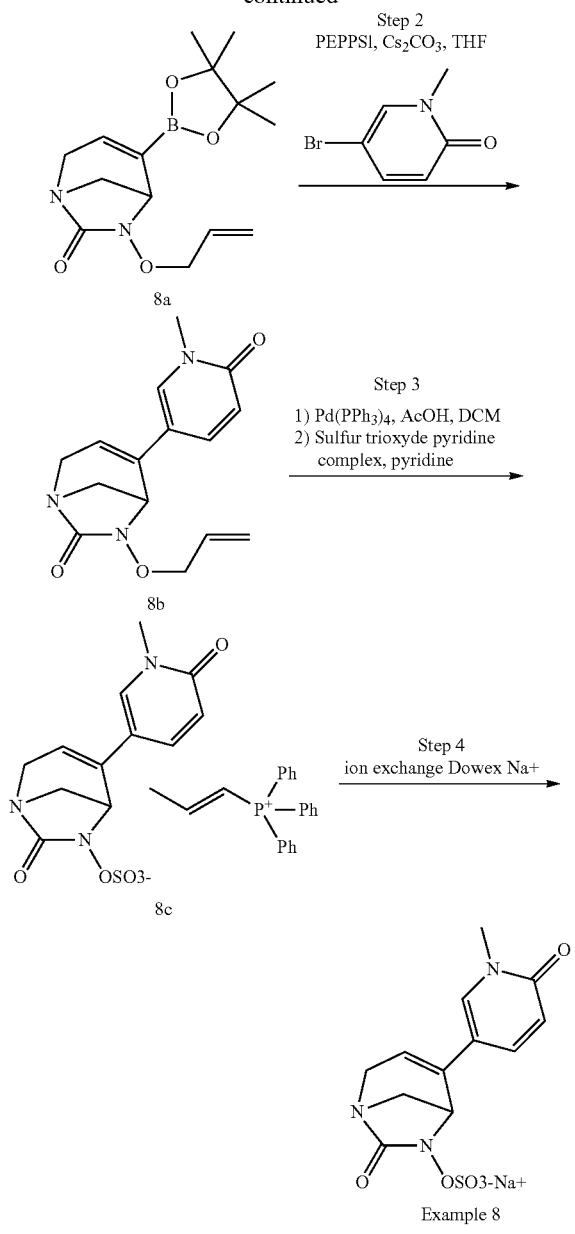

Step 1: Preparation of Intermediate (6-allyloxy-4-(4,4,5,5-tetramethyl-1,3,2-dioxaborolan-2-yl)-1,6-diazabicyclo[3.2.1]oct-3-en-7-one (8a)

In a Wheaton vial, 6-allyloxy-4-bromo-1,6-diazabicyclo[3.2.1]oct-3-en-7-one (1e) (10.0 mg, 0.039 mmol), KOAc (11.4 mg, 0.116 mmol) and bis(pinacolato)diboron (11.8 mg, 0.046 mmol) were dissolved in anhydrous THF (0.5 mL). The solution was degassed by bubbling argon for 10 min and Pd(dppf)Cl$_2$ (1.6 mg, 0.002 mmol) was added. The reaction was stirred for 60 min at 80° C. under microwaves. H2O (1 mL) was added and the mixture was extracted with EtOAc (2×1 mL). The organic layer was dried over Na$_2$SO$_4$, filtered, and concentrated under vacuum to afford a crude material which was purified by chromatography on silica gel (cyclohexane/EtOAc 8/2) to give the desired product (6-allyloxy-4-(4,4,5,5-tetramethyl-1,3,2-dioxaborolan-2-yl)-1,6-diazabicyclo[3.2.1] oct-3-en-7-one (8a) (2.2 mg, 0.007 mmol, 19%).

MS m/z ([M+H]$^+$) 307.

$^1$H NMR (300 MHz, CDCl$_3$): δ (ppm) 1.24 (s, 6H), 1.25 (s, 6H), 3.04 (d, J=10.7 Hz, 1H), 3.45 (dd, J=10.7/2.9 Hz, 1H), 3.74 (dd, J=19.2/1.9 Hz, 1H), 3.86 (dd, J=19.2/3.1 Hz, 1H), 4.10 (d, J=2.9 Hz, 1H), 4.34-4.48 (m, 2H), 5.25 (dq, J=10.4/1.2 Hz, 1H), 5.35 (dq, J=17.2/1.5 Hz, 1H), 5.96-6.08 (m, 1H), 6.41-6.45 (m, 1H).

Step 2: Preparation of Intermediate 6-allyloxy-4-(N-methyl-6-oxo-3-pyridyl)-1,6-diazabicyclo[3.2.1] oct-3-en-7-one (8b)

In a Wheaton vial, (6-allyloxy-4-(4,4,5,5-tetramethyl-1,3,2-dioxaborolan-2-yl)-1,6-diazabicyclo[3.2.1]oct-3-en-7-one (8a) (30 mg, 0.098 mmol), 5-bromo-N-methylpyridin-2 (1H)-one (22.1 mg, 0.118 mmol) and Cs$_2$CO$_3$ (63.8 mg, 0.196 mmol) were dissolved in anhydrous THF (0.7 mL). The solution was degassed by bubbling argon for 10 min and PEPPSI catalyst (3.3 mg, 0.005 mmol) was added. The reaction was stirred for 2h at 80° C. under microwaves. The mixture was filtered and concentrated under reduced pressure to afford a crude material which was purified by preparative TLC (DCM/EtOAc 60/40) to give the 6-allyloxy-4-(N-methyl-6-oxo-3-pyridyl)-1,6-diazabicyclo[3.2.1] oct-3-en-7-one (8b) (4.0 mg, 0.014 mmol, 14%).

MS m/z ([M+H]$^+$) 288.

$^1$H NMR (300 MHz, CDCl$_3$): δ (ppm) 3.09 (d, J=10.8 Hz, 1H), 3.47 (s, 3H), 3.55 (dd, J=10.8/3.0 Hz, 1H), 3.74 (dd, J=18.7/2.1 Hz, 1H), 3.87 (dd, J=18.7/3.4 Hz, 1H), 3.98-4.01 (m, 1H), 4.33-4.51 (m, 2H), 5.25-5.36 (m, 2H), 5.60-5.64 (m, 1H), 5.89-6.05 (m, 1H), 6.47-6.52 (m, 1H), 7.20-7.35 (m, 2H).

Step 3: Preparation of Intermediate triphenyl-(propenyl)-phosphonium [4-(N-methyl-6-oxo-3-pyridyl)-7-oxo-1,6-diazabicyclo[3.2.1]oct-3-en-6-yl] sulfate (8c)

Using the procedure described in example 1 (step 6), the intermediate 6-allyloxy-4-(N-methyl-6-oxo-3-pyridyl)-1,6-diazabicyclo[3.2.1]oct-3-en-7-one (8b) (33 mg, 0.115 mmol) was converted into triphenyl-(propenyl)-phosphonium [4-(N-methyl-6-oxo-3-pyridyl)-7-oxo-1,6-diazabicyclo[3.2.1]oct-3-en-6-yl] sulfate (8c) as an amorphous solid after purification by flash chromatography on silica gel (DCM/acetone 50/50 to 0/100).

MS m/z ([M+H]$^+$) 328.
MS m/z ([M−H]$^−$) 326.
MS m/z ([M+H]$^+$) 303 (triphenyl-propenyl-phosphonium).

Step 4: Preparation of Sodium [4-(N-methyl-6-oxo-3-pyridyl)-7-oxo-1,6-diazabicyclo[3.2.1]oct-3-en-6-yl] sulfate (Example 8)

Using the procedure described in example 1 (step 7), triphenyl-(propenyl)-phosphonium [4-(N-methyl-6-oxo-3-pyridyl)-7-oxo-1,6-diazabicyclo[3.2.1]oct-3-en-6-yl] sulfate (8c) was converted after ion exchange (Dowex sodium form column) into sodium [4-(N-methyl-6-oxo-3-pyridyl)-7-oxo-1,6-diazabicyclo[3.2.1]oct-3-en-6-yl] sulfate (Example 8) (10.8 mg, 0.031 mmol, 27% over 2 steps) as a white amorphous solid after lyophilization.

MS m/z ([M+H]$^+$) 328.
MS m/z ([M−H]$^−$) 326.

¹H NMR (400 MHz, D₂O): δ (ppm) 3.46 (d, J=11.3 Hz, 1H), 3.58 (s, 3H), 3.71-3.76 (m, 1H), 3.85 (dd, J=18.9/3.6 Hz, 1H), 4.02 (dd, J=18.8/2.1 Hz, 1H), 4.68-4.71 (m, 1H), 5.96-6.00 (m, 1H), 6.61-6.65 (m, 1H), 7.74-7.78 (m, 2H).

Example 9

Synthesis of Sodium [4-(3-pyridyl)-7-oxo-1,6-diazabicyclo[3.2.1]oct-3-en-6-yl]sulfate

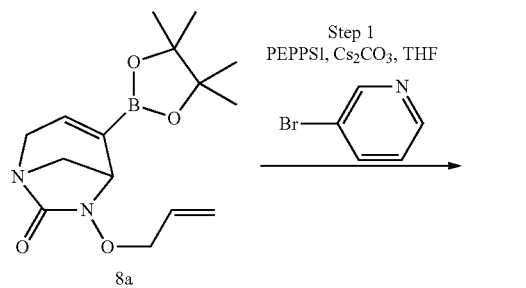

8a

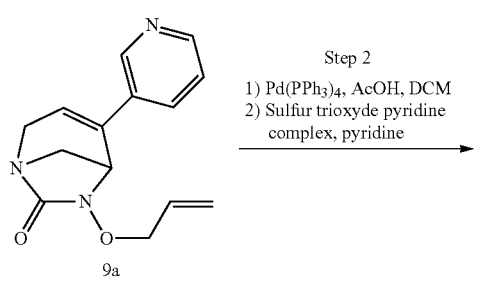

9a

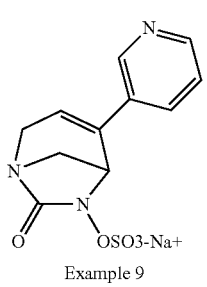

Example 9

Step 1: Preparation of Intermediate 6-allyloxy-4-(3-pyridyl)-1,6-diazabicyclo[3.2.1]oct-3-en-7-one (9a)

In a vial, (6-allyloxy-4-(4,4,5,5-tetramethyl-1,3,2-dioxaborolan-2-yl)-1,6-diazabicyclo[3.2.1]oct-3-en-7-one (8a) (200 mg, 0.653 mmol), 3-bromopyridine (155 mg, 0.980 mmol), dry Cs₂CO₃ (424 mg, 1.306 mmol) were dissolved in anhydrous THF (4 mL). The solution was degassed under argon for 5 min and PEPPSI catalyst (89 mg, 0.130 mmol) was added. The reaction was stirred at 80° C. for 1 h under microwaves. The mixture was filtered and concentrated under reduced pressure to afford a crude material which was purified by chromatography on silica gel (DCM/acetone 100/0 to 50/50) to give the desired product 6-allyloxy-4-(3-pyridyl)-1,6-diazabicyclo[3.2.1]oct-3-en-7-one (9a) (68 mg, 0.264 mmol, 27%) as a gum.

MS m/z ([M+H]⁺) 258.

¹H NMR (300 MHz, CDCl₃): δ (ppm) 3.21 (d, J=10.8 Hz, 1H), 3.65 (dd, J=10.8/3.0 Hz, 1H), 3.86 (dd, J=18.8/2.1 Hz, 1H), 3.99 (dd, J=18.8/3.4 Hz, 1H), 4.22-4.24 (m, 1H), 4.41-4.54 (m, 2H), 5.29-5.33 (m, 1H), 5.33-5.40 (m, 1H), 5.94-5.97 (m, 1H), 5.98-6.07 (m, 1H), 7.26-7.30 (m, 1H), 7.66-7.70 (m, 1H), 8.52 (dd, J=4.8/1.6 Hz, 1H), 8.61-8.64 (m, 1H)

Step 2: Preparation of Intermediate triphenyl-(propenyl)-phosphonium [4-(3-pyridyl)-7-oxo-1,6-diazabicyclo[3.2.1]oct-3-en-6-yl] sulfate (9b)

Using the procedure described in example 1 (step 6), the intermediate 6-allyloxy-4-(3-pyridyl)-1,6-diazabicyclo[3.2.1]oct-3-en-7-one (9a) (102 mg, 0.397 mmol) was converted into triphenyl-(propenyl)-phosphonium [4-(3-pyridyl)-7-oxo-1,6-diazabicyclo[3.2.1]oct-3-en-6-yl] sulfate (9b) as an amorphous solid. Crude product was used in the next step without purification.

MS m/z ([M+H]⁺) 298.

MS m/z ([M-H]⁻) 296.

MS m/z ([M+H]⁺) 303 (triphenyl-propenyl-phosphonium).

Step 3: Preparation of Sodium [4-(3-pyridyl)-7-oxo-1,6-diazabicyclo[3.2.1]oct-3-en-6-yl]sulfate (Example 9)

Using the procedure described in example 1 (step 7), triphenyl-(propenyl)-phosphonium [4-(3-pyridyl)-7-oxo-1,6-diazabicyclo[3.2.1]oct-3-en-6-yl] sulfate (9b) was converted after ion exchange (Dowex sodium form column) into sodium [4-(3-pyridyl)-7-oxo-1,6-diazabicyclo[3.2.1]oct-3-en-6-yl] sulfate. After lyophilization, the residue was purified by chromatography on C18 (H₂O/ACN 99/1). After a passage on G10 column (H₂O elution), sodium [4-(3-pyridyl)-7-oxo-1,6-diazabicyclo[3.2.1]oct-3-en-6-yl] sulfate (Example 9) (5.3 mg, 0.017 mmol, 5% over 2 steps) was recovered as a white amorphous solid after lyophilization.

MS m/z ([M+H]⁺) 298.

MS m/z ([M-H]⁻) 296.

¹H NMR (400 MHz, D₂O): δ (ppm) 3.49 (d, J=11.3 Hz, 1H), 3.76 (dd, J=11.3/3.1 Hz, 1H), 3.90 (dd, J=18.9/3.4 Hz, 1H), 4.05 (dd, J=18.9/1.9 Hz, 1H), 4.76-4.78 (m, 1H), 6.16-6.19 (m, 1H), 7.44 (dd, J=8.0/4.9 Hz, 1H), 7.86-7.91 (m, 1H), 8.40-8.44 (m, 1H), 8.56-8.59 (m, 1H).

Example 10

Synthesis of Sodium [4-(pyrimidin-5-yl)-7-oxo-1,6-diazabicyclo[3.2.1]oct-3-en-6-yl] sulfate

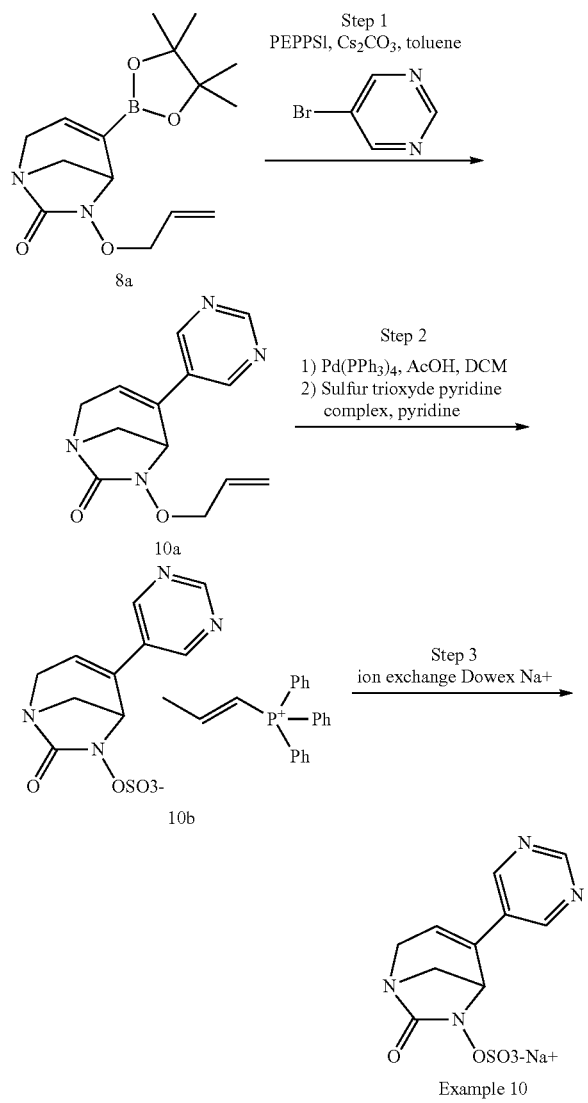

Step 1: Preparation of Intermediate 6-allyloxy-4-(pyrimidin-5-yl)-1,6-diazabicyclo[3.2.1]oct-3-en-7-one (10a)

In a Wheaton vial, (6-allyloxy-4-(4,4,5,5-tetramethyl-1,3,2-dioxaborolan-2-yl)-1,6-diazabicyclo[3.2.1]oct-3-en-7-one (8a) (250 mg, 0.816 mmol), 5-bromopyrimidine (156 mg, 0.980 mmol), dry $Cs_2CO_3$ (530 mg, 1.630 mmol) were dissolved in anhydrous toluene (5 mL). The solution was degassed under argon for 5 min and PEPPSI catalyst (28 mg, 0.041 mmol) was added. The reaction was stirred at 100° C. for 1.5 h under microwaves. The mixture was filtered and concentrated under reduced pressure to afford a crude material which was purified by chromatography on silica gel (DCM/acetone 100/0 to 50/50) to give the desired product 6-allyloxy-4-(pyrimidin-5-yl)-1,6-diazabicyclo[3.2.1]oct-3-en-7-one (10a) (55 mg, 0.213 mmol, 26%) as a gum.

MS m/z ([M+H]$^+$) 259.

$^1$H NMR (300 MHz, CDCl$_3$): δ (ppm) 3.21 (d, J=10.9 Hz, 1H), 3.66 (dd, J=10.9/3.0 Hz, 1H), 3.86 (dd, J=19.0/2.1 Hz, 1H), 4.00 (dd, J=19.0/3.4 Hz, 1H), 4.18-4.21 (m, 1H), 4.39-4.54 (m, 2H), 5.29-5.40 (m, 2H), 5.94-6.06 (m, 2H), 8.73 (s, 2H), 9.11 (s, 1H).

Step 2: Preparation of Intermediate triphenyl-(propenyl)-phosphonium [4-(pyrimidin-5-yl)-7-oxo-1,6-diazabicyclo[3.2.1]oct-3-en-6-yl] sulfate (10b)

Using the procedure described in example 1 (step 6), the intermediate 6-allyloxy-4-(pyrimidin-5-yl)-1,6-diazabicyclo[3.2.1]oct-3-en-7-one (10a) (102 mg, 0.397 mmol) was converted into triphenyl-(propenyl)-phosphonium [4-(pyrimidin-5-yl)-7-oxo-1,6-diazabicyclo[3.2.1]oct-3-en-6-yl] sulfate (10b) as an amorphous solid. Crude product was used in the next step without purification.

MS m/z ([M+H]$^+$) 299.

MS m/z ([M−H]$^-$) 297.

MS m/z ([M+H]$^+$) 303 (triphenyl-propenyl-phosphonium).

Step 3: Preparation of Sodium [4-(pyrimidin-5-yl)-7-oxo-1,6-diazabicyclo[3.2.1]oct-3-en-6-yl] sulfate (Example 10)

Using the procedure described in example 1 (step 7), triphenyl-(propenyl)-phosphonium [4-(pyrimidin-5-yl)-7-oxo-1,6-diazabicyclo[3.2.1]oct-3-en-6-yl] sulfate (10b) was converted after ion exchange (Dowex sodium form column) into sodium [4-(pyrimidin-5-yl)-7-oxo-1,6-diazabicyclo[3.2.1]oct-3-en-6-yl] sulfate. After lyophilization, the residue was purified by chromatography on C18 (H$_2$O/ACN 99/1) to give sodium [4-(pyrimidin-5-yl)-7-oxo-1,6-diazabicyclo[3.2.1]oct-3-en-6-yl] sulfate (Example 10) (2.4 mg, 0.007 mmol, 4% over 2 steps) as a white amorphous solid after lyophilization.

MS m/z ([M+H]$^+$) 299.

MS m/z ([M−H]$^-$) 297.

$^1$H NMR (400 MHz, D$_2$O): δ (ppm) 3.53 (d, J=11.4 Hz, 1H), 3.81 (dd, J=11.4/3.2 Hz, 1H), 3.96 (dd, J=19.2/3.5 Hz, 1H), 4.10 (dd, J=19.2/2.1 Hz, 1H), 4.82-4.85 (m, 1H), 6.34-6.37 (m, 1H), 8.87 (s, 2H), 9.04 (s, 1H).

Example 11

Synthesis of Sodium [4-(2-pyridyl)-7-oxo-1,6-diazabicyclo[3.2.1]oct-3-en-6-yl]sulfate

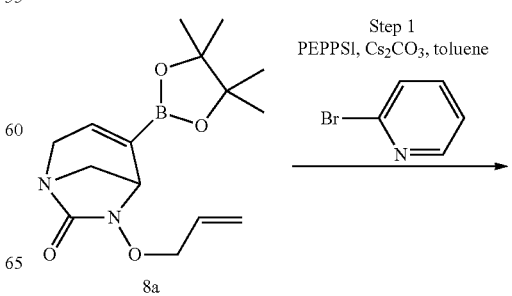

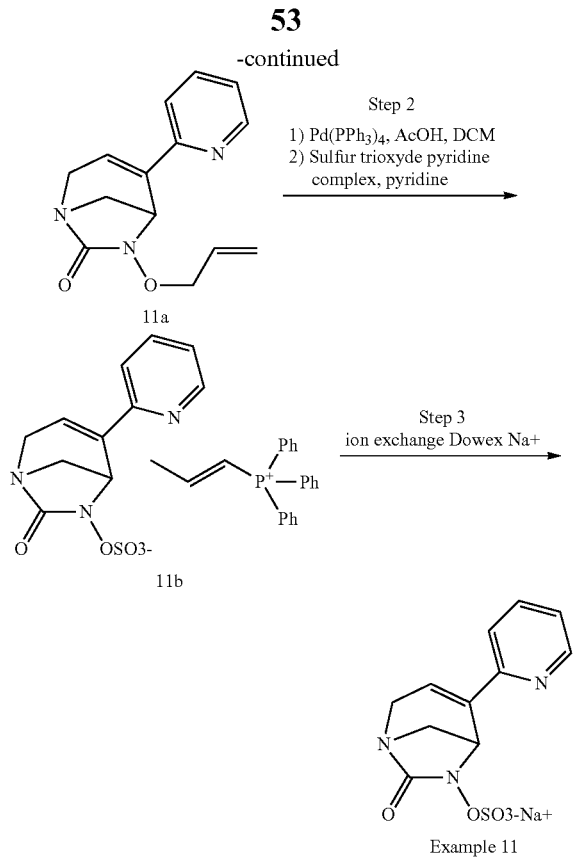

MS m/z ([M+H]⁺) 298.
MS m/z ([M−H]⁻) 296.
MS m/z ([M+H]⁺) 303 (triphenyl-propenyl-phosphonium).

Step 3: Preparation of Sodium [4-(2-pyridyl)-7-oxo-1,6-diazabicyclo[3.2.1]oct-3-en-6-yl]sulfate (Example 11)

Using the procedure described in example 1 (step 7), triphenyl-(propenyl)-phosphonium [4-(2-pyridyl)-7-oxo-1,6-diazabicyclo[3.2.1]oct-3-en-6-yl] sulfate (11 b) was converted after ion exchange (Dowex sodium form column) into sodium [4-(2-pyridyl)-7-oxo-1,6-diazabicyclo[3.2.1]oct-3-en-6-yl] sulfate. After lyophilization, the residue was purified by chromatography on C18 (H₂O/ACN 99/1) to give sodium [4-(2-pyridyl)-7-oxo-1,6-diazabicyclo[3.2.1]oct-3-en-6-yl] sulfate (Example 11) (1.2 mg, 0.004 mmol, 1% over 2 steps) as a white amorphous solid after lyophilization.

MS m/z ([M+H]⁺) 298.
MS m/z ([M−H]⁻) 296.
$^1$H NMR (400 MHz, D₂O): δ (ppm) 3.49 (d, J=11.3 Hz, 1H), 3.80 (dd, J=11.3/3.2 Hz, 1H), 3.94 (dd, J=19.1/3.5 Hz, 1H), 4.10 (dd, J=19.1/2.1 Hz, 1H), 5.02-5.04 (m, 1H), 6.48-6.51 (m, 1H), 7.35-7.40 (m, 1H), 7.58-7.63 (m, 1H), 7.87-7.92 (m, 1H), 8.48-8.51 (m, 1H).

Example 12

Synthesis of Sodium [4-(pyrazin-2-yl)-7-oxo-1,6-diazabicyclo[3.2.1]oct-3-en-6-yl] sulfate Step 1: Preparation of Intermediate 6-allyloxy-4-(2-pyridyl)-1,6-diazabicyclo[3.2.1]oct-3-en-7-one (11a)

Using the procedure described in example 10 (step 1), the intermediate (6-allyloxy-4-(4,4,5,5-tetramethyl-1,3,2-dioxaborolan-2-yl)-1,6-diazabicyclo[3.2.1]oct-3-en-7-one (8a) (50 mg, 0.163 mmol) is converted into 6-allyloxy-4-(2-pyridyl)-1,6-diazabicyclo[3.2.1]oct-3-en-7-one (11a) (19 mg, 0.074 mmol, 45%) using 2-bromopyridine (31 mg, 0.196 mmol), PEPPSI catalyst (22 mg, 0.032 mmol) and after purification by chromatography on silica gel (DCM/acetone 100/0 to 80/20).

MS m/z ([M+H]⁺) 258.
$^1$H NMR (300 MHz, CDCl₃): δ (ppm) 3.17 (d, J=10.9 Hz, 1H), 3.63 (dd, J=10.9/3.1 Hz, 1H), 3.87 (dd, J=19.0/2.2 Hz, 1H), 4.00 (dd, J=19.0/3.4 Hz, 1H), 4.31-4.45 (m, 2H), 4.98-5.02 (m, 1H), 5.19-5.25 (m, 1H), 5.28-5.30 (m, 1H), 5.84-5.99 (m, 1H), 6.30-6.34 (m, 1H), 7.16 (ddd, J=7.5/4.9 Hz, J=1.0 Hz, 1H), 7.43-7.48 (m, 1H), 7.65 (dd, J=7.7/1.8 Hz, 1H), 8.54 (ddd, J=4.9/1.8/1.0 Hz, 1H).

Step 2: Preparation of Intermediate triphenyl-(propenyl)-phosphonium [4-(2-pyridyl)-7-oxo-1,6-diazabicyclo[3.2.1]oct-3-en-6-yl] sulfate (11b)

Using the procedure described in example 1 (step 6), the intermediate 6-allyloxy-4-(2-pyridyl)-1,6-diazabicyclo[3.2.1]oct-3-en-7-one (11a) (100 mg, 0.389 mmol) was converted into triphenyl-(propenyl)-phosphonium [4-(2-pyridyl)-7-oxo-1,6-diazabicyclo[3.2.1]oct-3-en-6-yl] sulfate (11b) as an amorphous solid which was used in the next step without purification.

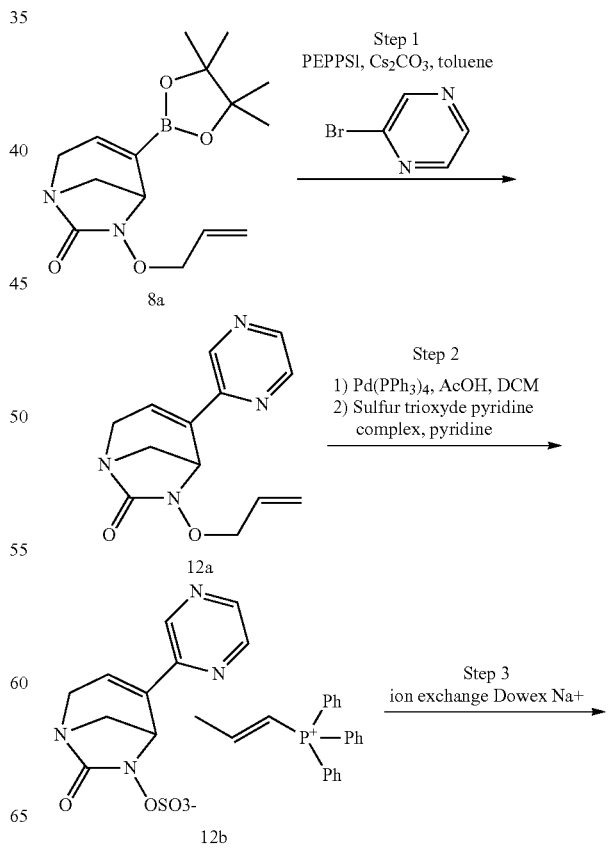

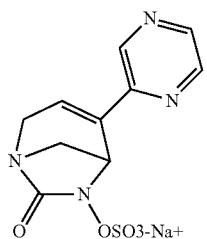

Example 12

Step 1: Preparation of Intermediate 6-allyloxy-4-(pyrazin-2-yl)-1,6-diazabicyclo[3.2.1]oct-3-en-7-one (12a)

Using the procedure described in example 10 (step 1), the intermediate (6-allyloxy-4-(4,4,5,5-tetramethyl-1,3,2-dioxaborolan-2-yl)-1,6-diazabicyclo[3.2.1]oct-3-en-7-one (8a) (250 mg, 0.817 mmol) is converted into 6-allyloxy-4-(pyrazin-2-yl)-1,6-diazabicyclo[3.2.1]oct-3-en-7-one (12a) (57 mg, 0.221 mmol, 27%) using 2-bromopyrazine (195 mg, 1.220 mmol), PEPPSI catalyst (111 mg, 0.163 mmol) and after purification by chromatography on silica gel (DCM/acetone 100/0 to 80/20).

MS m/z ([M+H]$^+$) 259.

$^1$H NMR (300 MHz, CDCl$_3$): δ (ppm) 3.18 (d, J=10.9 Hz, 1H), 3.67 (dd, J=10.9/2.9 Hz, 1H), 3.91 (dd, J=19.2/2.2 Hz, 1H), 4.04 (dd, J=19.2/3.4 Hz, 1H), 4.32-4.45 (m, 2H), 4.91-4.94 (m, 1H), 5.21-5.32 (m, 2H), 5.86-6.00 (m, 1H), 6.48-6.52 (m, 1H), 8.44 (d, J=2.5 Hz, 1H), 8.50 (dd, J=2.5/1.5 Hz, 1H), 8.77 (d, J=1.5 Hz, 1H).

Step 2: Preparation of Intermediate triphenyl-(propenyl)-phosphonium [4-(pyrazin-2-yl)-7-oxo-1,6-diazabicyclo[3.2.1]oct-3-en-6-yl] sulfate (12b)

Using the procedure described in example 1 (step 6), the intermediate 6-allyloxy-4-(pyrazin-2-yl)-1,6-diazabicyclo[3.2.1]oct-3-en-7-one (12a) (57 mg, 0.220 mmol) was converted into triphenyl-(propenyl)-phosphonium [4-(pyrazin-2-yl)-7-oxo-1,6-diazabicyclo[3.2.1]oct-3-en-6-yl] sulfate (12b) as an amorphous solid which was used in the next step without purification.

MS m/z ([M+H]$^+$) 298.
MS m/z ([M–H]$^−$) 296.
MS m/z ([M+H]$^+$) 303 (triphenyl-propenyl-phosphonium).

Step 3: Preparation of Sodium [4-(pyrazin-2-yl)-7-oxo-1,6-diazabicyclo[3.2.1]oct-3-en-6-yl]sulfate (Example 12)

Using the procedure described in example 1 (step 7), triphenyl-(propenyl)-phosphonium [4-(pyrazin-2-yl)-7-oxo-1,6-diazabicyclo[3.2.1]oct-3-en-6-yl] sulfate (12b) was converted after ion exchange (Dowex sodium form column) into sodium [4-(pyrazin-2-yl)-7-oxo-1,6-diazabicyclo[3.2.1]oct-3-en-6-yl] sulfate. After lyophilization, the residue was purified by chromatography on C18 (H$_2$O/ACN 99/1) to give sodium [4-(pyrazin-2-yl)-7-oxo-1,6-diazabicyclo[3.2.1]oct-3-en-6-yl] sulfate (Example 12) (1.2 mg, 0.004 mmol, 2% over 2 steps) as a white amorphous solid after lyophilization.

MS m/z ([M+H]$^+$) 298.
MS m/z ([M–H]$^−$) 296.

$^1$H NMR (400 MHz, D$_2$O): δ (ppm) 3.50 (d, J=11.4 Hz, 1H), 3.82 (dd, J=11.4/3.1 Hz, 1H), 3.98 (dd, J=19.4/3.5 Hz, 1H), 4.13 (dd, J=19.4/2.0 Hz, 1H), 5.12-5.15 (m, 1H), 6.65-6.68 (m, 1H), 8.49-8.52 (m, 1H), 8.58-8.61 (m, 1H), 8.79-8.81 (m, 1H).

Example 13

Synthesis of Sodium [4-(N-methyl-2-oxo-4-pyridyl)-7-oxo-1,6-diazabicyclo[3.2.1]oct-3-en-6-yl] sulfate

Step 1: Preparation of Intermediate 6-allyloxy-4-(N-methyl-2-oxo-4-pyridyl)-1,6-diazabicyclo[3.2.1]oct-3-en-7-one (13a)

Using the procedure described in example 10 (step 1), the intermediate (6-allyloxy-4-(4,4,5,5-tetramethyl-1,3,2-dioxaborolan-2-yl)-1,6-diazabicyclo[3.2.1]oct-3-en-7-one (8a) (250 mg, 0.817 mmol) is converted into 6-allyloxy-4-(N-methyl-2-oxo-4-pyridyl)-1,6-diazabicyclo[3.2.1]oct-3-en-7-one (13a) (100 mg, 0.348 mmol, 43%) using 4-bromo-N-methyl-pyridin-2-one (230 mg, 1.220 mmol), PEPPSI catalyst (111 mg, 0.163 mmol) and after purification by chromatography on silica gel (DCM/acetone 100/0 to 50/50).

MS m/z ([M+H]$^+$) 288.

$^1$H NMR (300 MHz, CDCl$_3$): δ (ppm) 3.12 (d, J=10.9 Hz, 1H), 3.50 (s, 3H), 3.61 (dd, J=10.9/3.0 Hz, 1H), 3.83 (dd, J=19.1/2.0 Hz, 1H), 3.95 (dd, J=19.1/3.4 Hz, 1H), 4.19-4.22 (m, 1H), 4.37-4.48 (m, 2H), 5.28-5.39 (m, 2H), 5.96-6.05 (m, 1H), 6.05-6.08 (m, 1H), 6.19 (dd, J=7.1/2.0 Hz, 1H), 6.49 (d, J=1.9 Hz, 1H), 7.22 (d, J=7.1 Hz, 1H).

Step 2: Preparation of Intermediate triphenyl-(propenyl)-phosphonium [4-(N-methyl-2-oxo-4-pyridyl)-7-oxo-1,6-diazabicyclo[3.2.1]oct-3-en-6-yl] sulfate (13b)

Using the procedure described in example 1 (step 6), the intermediate 6-allyloxy-4-(N-methyl-2-oxo-4-pyridyl)-1,6-diazabicyclo[3.2.1]oct-3-en-7-one (13a) (57 mg, 0.220 mmol) was converted into triphenyl-(propenyl)-phosphonium [4-(N-methyl-2-oxo-4-pyridyl)-7-oxo-1,6-diazabicyclo[3.2.1]oct-3-en-6-yl] sulfate (13b) as an amorphous solid after purification by flash chromatography on silica gel (DCM/acetone 50/50 to 0/100).

MS m/z ([M+H]$^+$) 328.

MS m/z ([M−H]$^-$) 326.

MS m/z ([M+H]$^+$) 303 (triphenyl-propenyl-phosphonium).

Step 3: Preparation of Sodium [4-(1-methyl-2-oxo-4-pyridyl)-7-oxo-1,6-diazabicyclo[3.2.1]oct-3-en-6-yl] sulfate (Example 13)

Using the procedure described in example 1 (step 7), triphenyl-(propenyl)-phosphonium [4-(N-methyl-2-oxo-4-pyridyl)-7-oxo-1,6-diazabicyclo[3.2.1]oct-3-en-6-yl] sulfate (13b) was converted after ion exchange (Dowex sodium form column) into sodium [4-(N-methyl-2-oxo-4-pyridyl)-7-oxo-1,6-diazabicyclo[3.2.1]oct-3-en-6-yl] sulfate (Example 13) (18.2 mg, 0.052 mmol, 15% over 2 steps) as a white amorphous solid after lyophilization.

MS m/z ([M+H]$^+$) 328.

MS m/z ([M−H]$^-$) 326.

$^1$H NMR (400 MHz, D$_2$O): δ (ppm) 3.40 (d, J=11.3 Hz, 1H), 3.49 (s, 3H), 3.75 (dd, J=10.8/3.1 Hz, 1H), 3.87 (dd, J=19.4/3.4 Hz, 1H), 4.05 (dd, J=19.4/2.0 Hz, 1H), 4.69-4.72 (m, 1H), 6.30-6.33 (m, 1H), 6.51-6.55 (m, 1H), 6.55-6.58 (m, 1H), 7.52 (d, J=7.1 Hz, 1H).

Example 14

Synthesis of Sodium [4-(4-methyl-5-oxo-pyrazin-2-yl)-7-oxo-1,6-diazabicyclo [3.2.1]oct-3-en-6-yl] sulfate

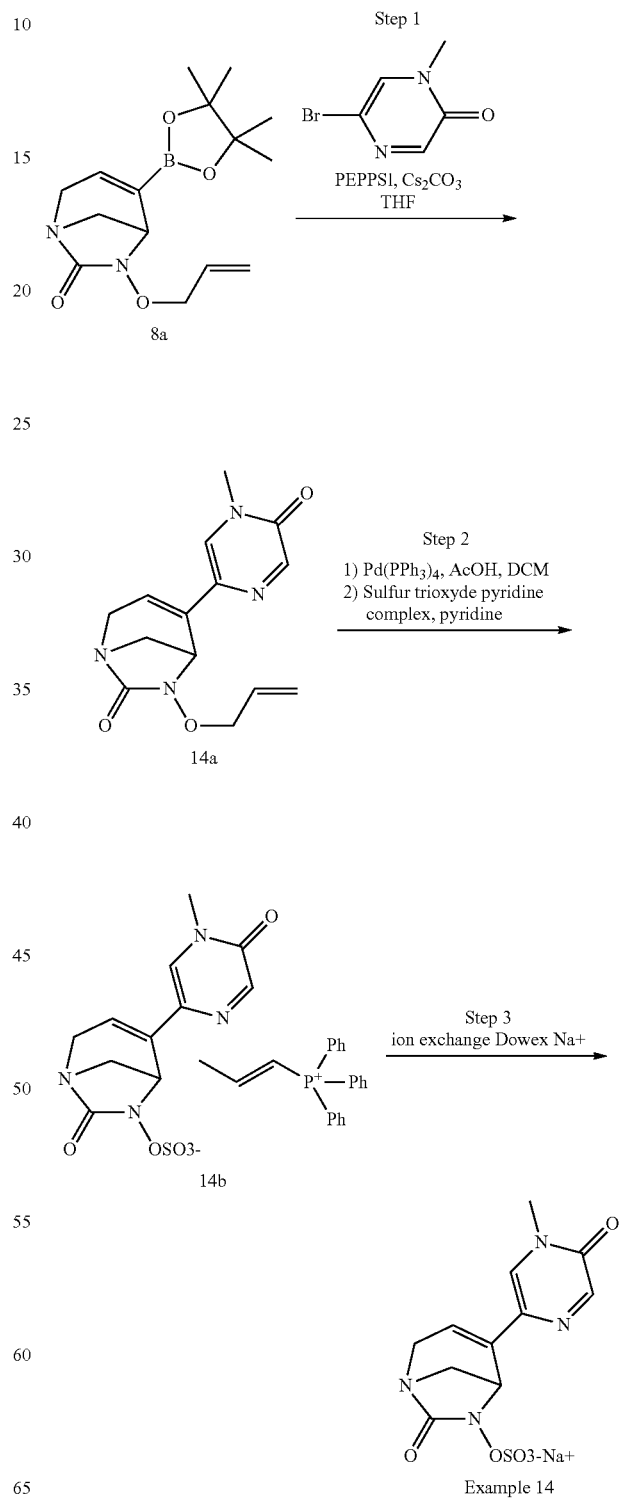

Example 14

Step 1: Preparation of Intermediate 6-allyloxy-4-(4-methyl-5-oxo-pyrazin-2-yl)-1,6-diazabicyclo[3.2.1]oct-3-en-7-one (14a)

Using the procedure described in example 9 (step 1), the intermediate (6-allyloxy-4-(4,4,5,5-tetramethyl-1,3,2-dioxaborolan-2-yl)-1,6-diazabicyclo[3.2.1]oct-3-en-7-one (8a) (200 mg, 0.653 mmol) is converted into 6-allyloxy-4-(4-methyl-5-oxo-pyrazin-2-yl)-1,6-diazabicyclo[3.2.1]oct-3-en-7-one (14a) (65 mg, 0.225 mmol, 35%) using 5-bromo-1-methyl-pyrazin-2-one (150 mg, 0.790 mmol), PEPPSI catalyst (89 mg, 0.130 mmol) and after purification by chromatography on silica gel (DCM/acetone 100/0 to 50/50).

MS m/z ([M+H]$^+$) 289.

$^1$H NMR (300 MHz, CDCl$_3$): δ (ppm) 3.15 (d, J=10.9 Hz, 1H), 3.52 (s, 3H), 3.58-3.64 (m, 1H), 3.82-3.97 (m, 2H), 4.32-4.47 (m, 2H), 4.51 (d, J=2.7 Hz, 1H), 5.26-5.36 (m, 2H), 5.90-6.01 (m, 1H), 6.04-6.08 (m, 1H), 7.24 (bs, 1H), 8.10 (bs, 1H).

Step 2: Preparation of Intermediate triphenyl-(propenyl)-phosphonium [4-(4-methyl-5-oxo-pyrazin-2-yl)-7-oxo-1,6-diazabicyclo[3.2.1]oct-3-en-6-yl] sulfate (14b)

Using the procedure described in example 1 (step 6), the intermediate 6-allyloxy-4-(4-methyl-5-oxo-pyrazin-2-yl)-1,6-diazabicyclo[3.2.1]oct-3-en-7-one (14a) (65 mg, 0.225 mmol) was converted into triphenyl-(propenyl)-phosphonium [4-(4-methyl-5-oxo-pyrazin-2-yl)-7-oxo-1,6-diazabicyclo[3.2.1]oct-3-en-6-yl] sulfate (14b) as an amorphous solid after purification by flash chromatography on silica gel (DCM/acetone 50/50 to 0/100).

MS m/z ([M+H]$^+$) 329.

MS m/z ([M−H]$^-$) 327.

MS m/z ([M+H]$^+$) 303 (triphenyl-propenyl-phosphonium).

Step 3: Preparation of Sodium [4-(4-methyl-5-oxo-pyrazin-2-yl)-7-oxo-1,6-diazabicyclo[3.2.1]oct-3-en-6-yl] sulfate (Example 14)

Using the procedure described in example 1 (step 7), triphenyl-(propenyl)-phosphonium [4-(4-methyl-5-oxo-pyrazin-2-yl)-7-oxo-1,6-diazabicyclo[3.2.1]oct-3-en-6-yl] sulfate (14b) was converted after ion exchange (Dowex sodium form column) into sodium [4-(4-methyl-5-oxo-pyrazin-2-yl)-7-oxo-1,6-diazabicyclo[3.2.1]oct-3-en-6-yl] sulfate (Example 14) (20 mg, 0.057 mmol, 26% over 2 steps) as a white amorphous solid after lyophilization.

MS m/z ([M+H]$^+$) 329.

MS m/z ([M−H]$^-$) 327.

$^1$H NMR (400 MHz, DMSO): δ (ppm) 3.21 (d, J=11.0 Hz, 1H), 3.39 (s, 3H), 3.45 (dd, J=11.0/3.0 Hz, 1H), 3.68 (dd, J=18.7/3.6 Hz, 1H), 3.80 (dd, J=18.7/1.9 Hz, 1H), 4.62 (d, J=1.9 Hz, 1H), 6.18-6.22 (m, 1H), 7.94 (bs, 1H), 8.01 (d, J=0.9 Hz, 1H).

Example 15

Synthesis of Sodium [4-(N-methyl-2-oxo-pyrimidin-5-yl)-7-oxo-1,6-diazabicyclo[3.2.1]oct-3-en-6-yl] sulfate

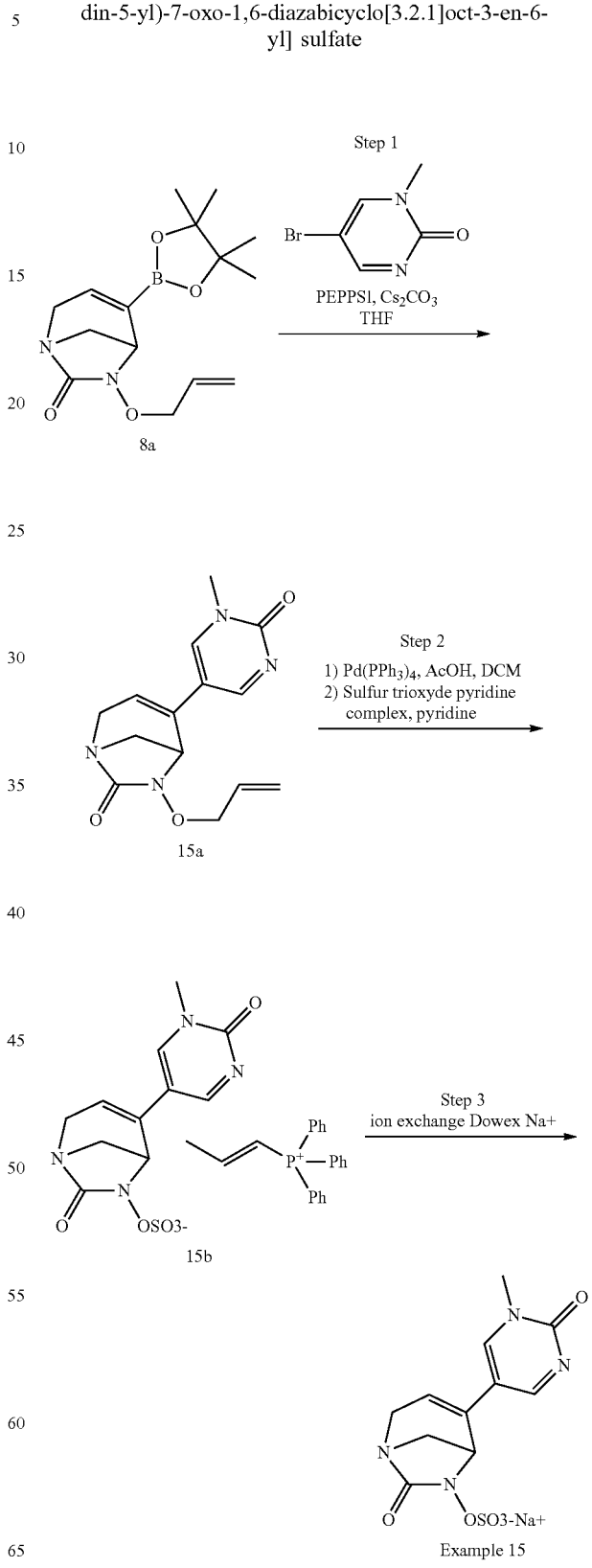

Example 15

Step 1: Preparation of Intermediate 6-allyloxy-4-(N-methyl-2-oxo-pyrimidin-5-yl)-1,6-diazabicyclo[3.2.1]oct-3-en-7-one (15a)

Using the procedure described in example 9 (step 1), the intermediate (6-allyloxy-4-(4,4,5,5-tetramethyl-1,3,2-dioxaborolan-2-yl)-1,6-diazabicyclo[3.2.1]oct-3-en-7-one (8a) (200 mg, 0.653 mmol) is converted into 6-allyloxy-4-(N-methyl-2-oxo-pyrimidin-5-yl)-1,6-diazabicyclo[3.2.1]oct-3-en-7-one (15a) (55 mg, 0.190 mmol, 30%) using 5-bromo-N-methyl-pyrimidin-2-one (150 mg, 0.790 mmol), PEPPSI catalyst (89 mg, 0.130 mmol) and after purification by chromatography on silica gel (DCM/acetone 100/0 to 50/50).

MS m/z ([M+H]$^+$) 289.

$^1$H NMR (300 MHz, CDCl$_3$): δ (ppm) 3.18 (d, J=10.6 Hz, 1H), 3.56 (s, 3H), 3.62 (dd, J=10.9/2.9 Hz, 1H), 3.83 (dd, J=18.8/2.0 Hz, 1H), 3.95 (dd, J=18.8/3.3 Hz, 1H), 4.00-4.04 (m, 1H), 4.39-4.57 (m, 2H), 5.33-5.43 (m, 2H), 5.77-5.81 (m, 1H), 5.95-6.10 (m, 1H), 7.68 (d, J=3.3 Hz, 1H), 8.63 (d, J=3.3 Hz, 1H).

Step 2: Preparation of Intermediate triphenyl-(propenyl)-phosphonium [4-(N-methyl-2-oxo-pyrimidin-5-yl)-7-oxo-1,6-diazabicyclo[3.2.1]oct-3-en-6-yl] sulfate (15b)

Using the procedure described in example 1 (step 6), the intermediate 6-allyloxy-4-(N-methyl-2-oxo-pyrimidin-5-yl)-1,6-diazabicyclo[3.2.1]oct-3-en-7-one (15a) (55 mg, 0.190 mmol) was converted into triphenyl-(propenyl)-phosphonium [4-(N-methyl-2-oxo-pyrimidin-5-yl)-7-oxo-1,6-diazabicyclo[3.2.1]oct-3-en-6-yl] sulfate (15b) as an amorphous solid after purification by flash chromatography on silica gel (DCM/acetone 50/50 to 0/100).

MS m/z ([M+H]$^+$) 329.

MS m/z ([M−H]$^-$) 327.

MS m/z ([M+H]$^+$) 303 (triphenyl-propenyl-phosphonium).

Step 3: Preparation of Sodium [4-(N-methyl-2-oxo-pyrimidin-5-yl)-7-oxo-1,6-diazabicyclo[3.2.1]oct-3-en-6-yl] sulfate (Example 15)

Using the procedure described in example 1 (step 7), triphenyl-(propenyl)-phosphonium [4-(N-methyl-2-oxo-pyrimidin-5-yl)-7-oxo-1,6-diazabicyclo[3.2.1]oct-3-en-6-yl] sulfate (15b) was converted after ion exchange (Dowex sodium form column) into sodium [4-(N-methyl-2-oxo-pyrimidin-5-yl)-7-oxo-1,6-diazabicyclo[3.2.1]oct-3-en-6-yl] sulfate (Example 15) (5.9 mg, 0.017 mmol, 9% over 2 steps) as a white amorphous solid after lyophilization.

MS m/z ([M+H]$^+$) 329.

MS m/z ([M−H]$^-$) 327.

$^1$H NMR (400 MHz, D$_2$O): δ (ppm) 3.49 (d, J=11.3 Hz, 1H), 3.61 (s, 3H), 3.75 (dd, J=11.4/3.1 Hz, 1H), 3.89 (dd, J=18.9/3.5 Hz, 1H), 4.04 (dd, J=18.9/2.0 Hz, 1H), 4.66-4.69 (m, 1H), 6.07-6.11 (m, 1H), 8.22 (d, J=3.2 Hz, 1H), 8.74 (d, J=3.2 Hz, 1H).

Example 16

Synthesis of Sodium [4-(N-methyl-2-oxo-3-pyridyl)-7-oxo-1,6-diazabicyclo[3.2.1]oct-3-en-6-yl] sulfate

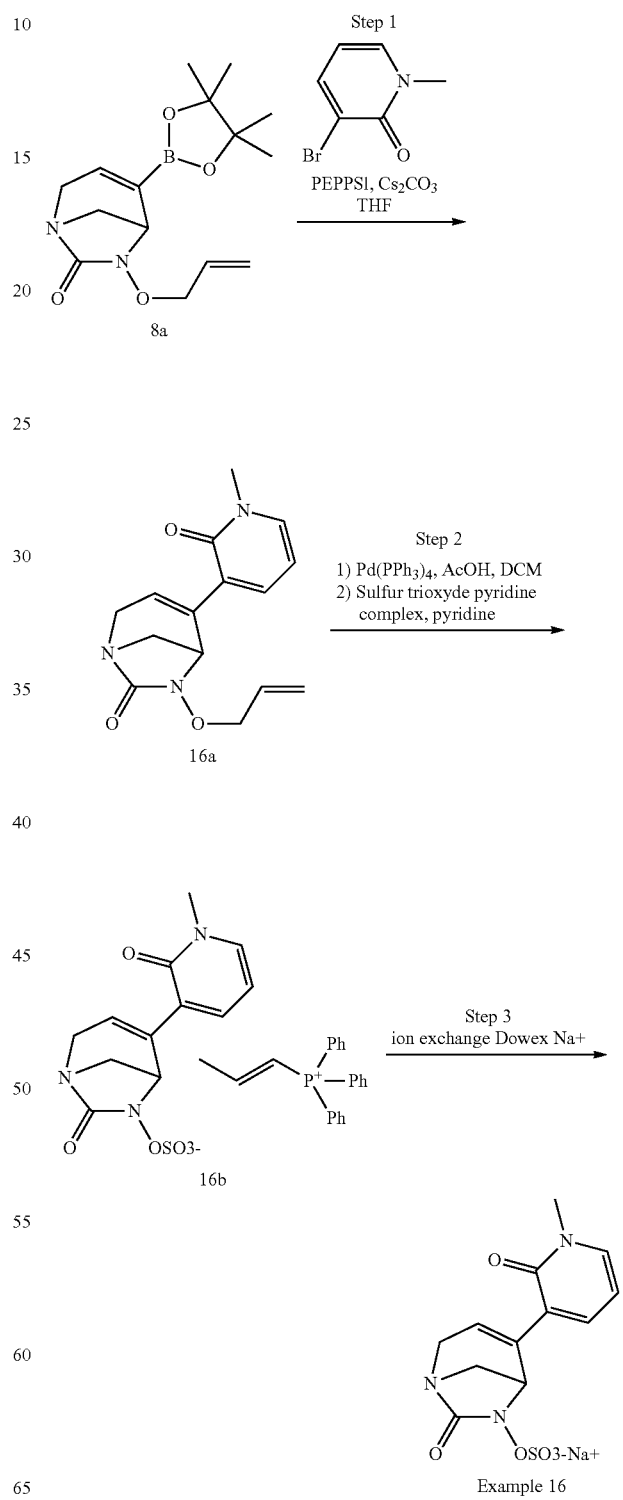

Example 16

Step 1: Preparation of Intermediate 6-allyloxy-4-(N-methyl-2-oxo-3-pyridyl)-1,6-diazabicyclo[3.2.1]oct-3-en-7-one (16a)

Using the procedure described in example 9 (step 1), the intermediate (6-allyloxy-4-(4,4,5,5-tetramethyl-1,3,2-dioxaborolan-2-yl)-1,6-diazabicyclo[3.2.1]oct-3-en-7-one (8a) (200 mg, 0.653 mmol) is converted into 6-allyloxy-4-(N-methyl-2-oxo-3-pyridyl)-1,6-diazabicyclo[3.2.1]oct-3-en-7-one (16a) (117 mg, 0.407 mmol, 63%) using 3-bromo-N-methyl-pyridin-2-one (149 mg, 0.790 mmol), PEPPSI catalyst (89 mg, 0.130 mmol) and after purification by chromatography on silica gel (DCM/acetone 100/0 to 50/50).

MS m/z ([M+H]$^+$) 288.

$^1$H NMR (300 MHz, CDCl$_3$): δ (ppm) 3.32 (d, J=10.8 Hz, 1H), 3.55 (s, 3H), 3.55-3.59 (m, 1H), 3.87 (d, J=2.6 Hz, 2H), 4.25-4.40 (m, 2H), 4.51 (d, J=2.6 Hz, 1H), 5.18-5.28 (m, 2H), 5.82-5.95 (m, 2H), 6.18 (t, J=6.8 Hz, 1H), 7.27 (dd, J=6.8/2.0 Hz, 1H), 7.37 (dd, J=6.9/2.0 Hz, 1H).

Step 2: Preparation of Intermediate triphenyl-(propenyl)-phosphonium [4-(N-methyl-2-oxo-3-pyridyl)-7-oxo-1,6-diazabicyclo[3.2.1]oct-3-en-6-yl] sulfate (16b)

Using the procedure described in example 1 (step 6), the intermediate 6-allyloxy-4-(N-methyl-2-oxo-3-pyridyl)-1,6-diazabicyclo[3.2.1]oct-3-en-7-one (16a) (117 mg, 0.407 mmol) was converted into triphenyl-(propenyl)-phosphonium [4-(N-methyl-2-oxo-3-pyridyl)-7-oxo-1,6-diazabicyclo[3.2.1]oct-3-en-6-yl] sulfate (16b) as an amorphous solid after purification by flash chromatography on silica gel (DCM/acetone 50/50 to 0/100).

MS m/z ([M+H]$^+$) 328.

MS m/z ([M−H]$^−$) 326.

MS m/z ([M+H]$^+$) 303 (triphenyl-propenyl-phosphonium).

Step 3: Preparation of Sodium [4-(N-methyl-2-oxo-3-pyridyl)-7-oxo-1,6-diazabicyclo[3.2.1]oct-3-en-6-yl] sulfate (Example 16)

Using the procedure described in example 1 (step 7), triphenyl-(propenyl)-phosphonium [4-(N-methyl-2-oxo-3-pyridyl)-7-oxo-1,6-diazabicyclo[3.2.1]oct-3-en-6-yl] sulfate (16b) was converted after ion exchange (Dowex sodium form column) into sodium [4-(N-methyl-2-oxo-3-pyridyl)-7-oxo-1,6-diazabicyclo[3.2.1]oct-3-en-6-yl] sulfate (Example 16) (24 mg, 0.068 mmol, 17% over 2 steps) as a white amorphous solid after lyophilization.

MS m/z ([M+H]$^+$) 328.

MS m/z ([M−H]$^−$) 326.

$^1$H NMR (400 MHz, D$_2$O): δ (ppm) 3.54 (d, J=11.2 Hz, 1H), 3.56 (s, 3H), 3.74 (dd, J=11.2/3.2 Hz, 1H), 3.84 (dd, J=18.8/3.4 Hz, 1H), 4.07 (dd, J=18.8/2.0 Hz, 1H), 4.74-4.76 (m, 1H), 6.15-6.18 (m, 1H), 6.50 (t, J=6.9 Hz, 1H), 7.58-7.63 (m, 2H).

Example 17

Synthesis of Sodium [4-(1-methyl-6-oxo-pyridazin-3-yl)-7-oxo-1,6-diazabicyclo[3.2.1]oct-3-en-6-yl] sulfate

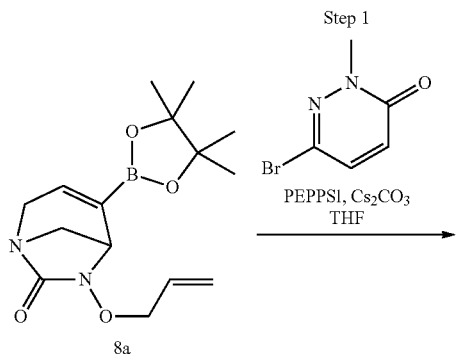

Step 1

PEPPSI, Cs$_2$CO$_3$
THF

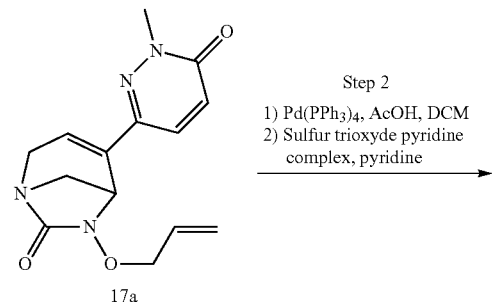

17a

Step 2
1) Pd(PPh$_3$)$_4$, AcOH, DCM
2) Sulfur trioxyde pyridine complex, pyridine

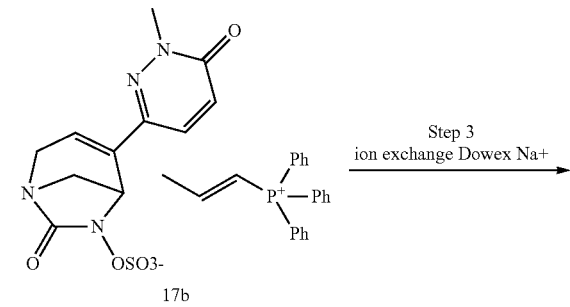

17b

Step 3
ion exchange Dowex Na+

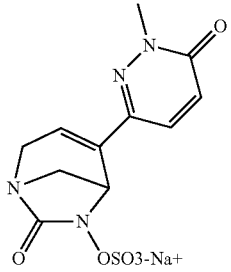

Example 17

Step 1: Preparation of Intermediate 6-allyloxy-4-(1-methyl-6-oxo-pyridazin-3-yl)-1,6-diazabicyclo[3.2.1]oct-3-en-7-one (17a)

Using the procedure described in example 9 (step 1), the intermediate (6-allyloxy-4-(4,4,5,5-tetramethyl-1,3,2-dioxaborolan-2-yl)-1,6-diazabicyclo[3.2.1]oct-3-en-7-one (8a) (200 mg, 0.653 mmol) is converted into 6-allyloxy-4-(1-methyl-6-oxo-pyridazin-3-yl)-1,6-diazabicyclo[3.2.1]oct-3-en-7-one (17a) (140 mg, 0.486 mmol, 75%) using 6-bromo-2-methyl-pyridazin-3-one (150 mg, 0.790 mmol), PEPPSI catalyst (89 mg, 0.130 mmol) and after purification by chromatography on silica gel (DCM/acetone 100/0 to 50/50).

MS m/z ([M+H]$^+$) 289.

$^1$H NMR (400 MHz, CDCl$_3$): δ (ppm) 3.10 (d, J=11.0 Hz, 1H), 3.61 (dd, J=11.0/3.0 Hz, 1H), 3.78 (s, 3H), 3.85 (dd, J=19.1/2.1 Hz, 1H), 3.98 (dd, J=19.1/3.4 Hz, 1H), 4.33-4.45 (m, 2H), 4.90 (d, J=2.4 Hz, 1H), 5.24-5.34 (m, 2H), 5.89-6.00 (m, 1H), 6.09-6.12 (m, 1H), 6.91 (d, J=9.7 Hz, 1H), 7.43 (d, J=9.7 Hz, 1H).

Step 2: Preparation of Intermediate triphenyl-(propenyl)-phosphonium [4-(1-methyl-6-oxo-pyridazin-3-yl)-7-oxo-1,6-diazabicyclo[3.2.1]oct-3-en-6-yl] sulfate (17b)

Using the procedure described in example 1 (step 6), the intermediate 6-allyloxy-4-(1-methyl-6-oxo-pyridazin-3-yl)-1,6-diazabicyclo[3.2.1]oct-3-en-7-one (17a) (140 mg, 0.486 mmol) was converted into triphenyl-(propenyl)-phosphonium [4-(1-methyl-6-oxo-pyridazin-3-yl)-7-oxo-1,6-diazabicyclo[3.2.1]oct-3-en-6-yl] sulfate (17b) as an amorphous solid after purification by flash chromatography on silica gel (DCM/acetone 50/50 to 0/100).

MS m/z ([M+H]$^+$) 329.

MS m/z ([M−H]$^-$) 327.

MS m/z ([M+H]$^+$) 303 (triphenyl-propenyl-phosphonium).

Step 3: Preparation of Sodium [4-(1-methyl-6-oxo-pyridazin-3-yl)-7-oxo-1,6-diazabicyclo[3.2.1]oct-3-en-6-yl] sulfate (Example 17)

Using the procedure described in example 1 (step 7), triphenyl-(propenyl)-phosphonium [4-(1-methyl-6-oxo-pyridazin-3-yl)-7-oxo-1,6-diazabicyclo[3.2.1]oct-3-en-6-yl] sulfate (17b) was converted after ion exchange (Dowex sodium form column) into sodium [4-(1-methyl-6-oxo-pyridazin-3-yl)-7-oxo-1,6-diazabicyclo[3.2.1]oct-3-en-6-yl] sulfate (Example 17) (36 mg, 0.103 mmol, 22% over 2 steps) as a white amorphous solid after lyophilization.

MS m/z ([M+H]$^+$) 329.

MS m/z ([M−H]$^-$) 327.

$^1$H NMR (400 MHz, D$_2$O): δ (ppm) 3.44 (d, J=11.3 Hz, 1H), 3.78 (dd, J=11.4/3.1 Hz, 1H), 3.81 (s, 3H), 3.93 (dd, J=19.2/3.5 Hz, 1H), 4.09 (dd, J=19.2/2.1 Hz, 1H), 5.20 (d, J=2.2 Hz, 1H), 6.41-6.44 (m, 1H), 7.05 (d, J=9.6 Hz, 1H), 7.79 (d, J=9.6 Hz, 1H).

Example 18

Synthesis of Sodium [4-(N-methyl-6-oxo-2-pyridyl)-7-oxo-1,6-diazabicyclo[3.2.1]oct-3-en-6-yl] sulfate

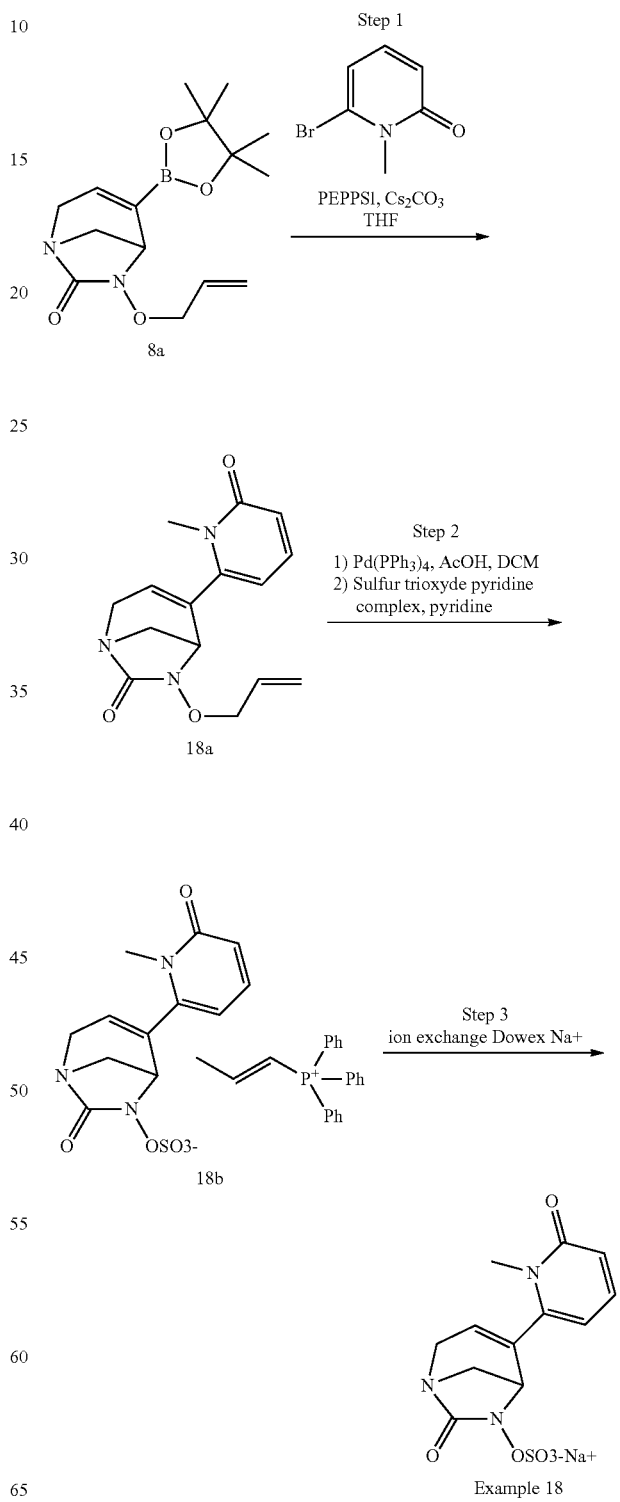

Example 18

Step 1: Preparation of Intermediate 6-allyloxy-4-(N-methyl-6-oxo-2-pyridyl)-1,6-diazabicyclo[3.2.1]oct-3-en-7-one (18a)

Using the procedure described in example 9 (step 1), the intermediate (6-allyloxy-4-(4,4,5,5-tetramethyl-1,3,2-dioxaborolan-2-yl)-1,6-diazabicyclo[3.2.1]oct-3-en-7-one (8a) (200 mg, 0.653 mmol) is converted into 6-allyloxy-4-(N-methyl-6-oxo-2-pyridyl)-1,6-diazabicyclo[3.2.1]oct-3-en-7-one (18a) (51 mg, 0.177 mmol, 28%) using 6-bromo-N-methyl-pyridin-2-one (150 mg, 0.790 mmol), PEPPSI catalyst (89 mg, 0.130 mmol) and after purification by chromatography on silica gel (DCM/acetone 100/0 to 50/50).

MS m/z ([M+H]$^+$) 288.

$^1$H NMR (400 MHz, CDCl$_3$): δ (ppm) 3.23 (d, J=10.9 Hz, 1H), 3.41 (s, 3H), 3.65 (dd, J=10.9/2.9 Hz, 1H), 3.86 (dd, J=18.9/1.9 Hz, 1H), 3.94-4.01 (m, 2H), 4.23-4.40 (m, 2H), 5.20-5.28 (m, 2H), 5.76-5.87 (m, 2H), 6.15 (dd, J=6.8/1.3 Hz, 1H), 6.54 (dd, J=9.1/1.3 Hz, 1H), 7.28 (dd, J=9.1/6.8 Hz, 1H).

Step 2: Preparation of Intermediate triphenyl-(propenyl)-phosphonium [4-(N-methyl-6-oxo-2-pyridyl)-7-oxo-1,6-diazabicyclo[3.2.1]oct-3-en-6-yl] sulfate (18b)

Using the procedure described in example 1 (step 6), the intermediate 6-allyloxy-4-(N-methyl-6-oxo-2-pyridyl)-1,6-diazabicyclo[3.2.1]oct-3-en-7-one (18a) (51 mg, 0.177 mmol) was converted into triphenyl-(propenyl)-phosphonium [4-(N-methyl-6-oxo-2-pyridyl)-7-oxo-1,6-diazabicyclo[3.2.1]oct-3-en-6-yl] sulfate (18b) as an amorphous solid after purification by flash chromatography on silica gel (DCM/acetone 50/50 to 0/100).

MS m/z ([M+H]$^+$) 328.

MS m/z ([M–H]$^-$) 326.

MS m/z ([M+H]$^+$) 303 (triphenyl-propenyl-phosphonium).

Step 3: Preparation of Sodium [4-(N-methyl-6-oxo-2-pyridyl)-7-oxo-1,6-diazabicyclo[3.2.1]oct-3-en-6-yl] sulfate (Example 18)

Using the procedure described in example 1 (step 7), triphenyl-(propenyl)-phosphonium [4-(N-methyl-6-oxo-2-pyridyl)-7-oxo-1,6-diazabicyclo[3.2.1]oct-3-en-6-yl] sulfate (18b) was converted after ion exchange (Dowex sodium form column) into sodium [4-(N-methyl-6-oxo-2-pyridyl)-7-oxo-1,6-diazabicyclo[3.2.1]oct-3-en-6-yl] sulfate (Example 18) (7.5 mg, 0.021 mmol, 12% over 2 steps) as a white amorphous solid after lyophilization.

MS m/z ([M+H]$^+$) 328.

MS m/z ([M–H]$^-$) 326.

$^1$H NMR (400 MHz, D$_2$O): δ (ppm) 3.49 (s, 3H), 3.68 (d, J=11.4 Hz, 1H), 3.80 (dd, J=11.4/2.9 Hz, 1H), 3.94 (dd, J=19.0/3.3 Hz, 1H), 4.11 (dd, J=19.0/1.8 Hz, 1H), 4.54 (d, J=2.2 Hz, 1H), 6.08-6.11 (m, 1H), 6.56 (dd, J=7.0/0.8 Hz, 1H), 6.63 (dd, J=9.0/0.8 Hz, 1H), 7.63 (dd, J=9.0/7.0 Hz, 1H).

Example 19

Synthesis of Sodium [4-(1-methyl-6-oxo-pyridazin-4-yl)-7-oxo-1,6-diazabicyclo[3.2.1]oct-3-en-6-yl] sulfate

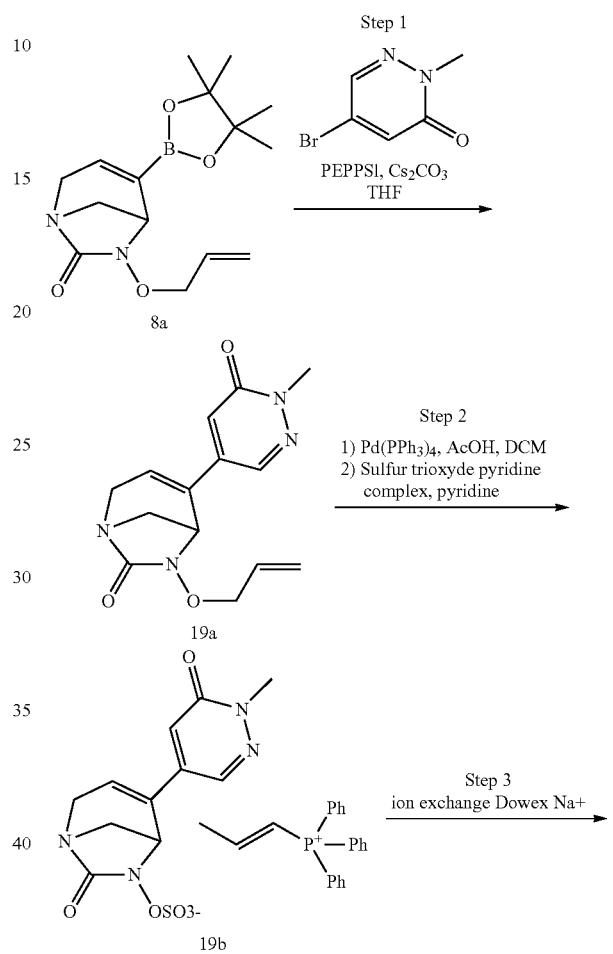

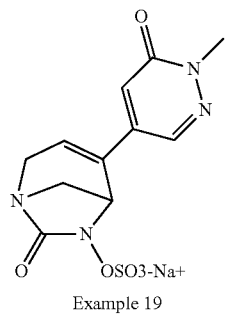

Example 19

Step 1: Preparation of Intermediate 6-allyloxy-4-(1-methyl-6-oxo-pyridazin-4-yl)-1,6-diazabicyclo[3.2.1]oct-3-en-7-one (19a)

Using the procedure described in example 9 (step 1), the intermediate (6-allyloxy-4-(4,4,5,5-tetramethyl-1,3,2-dioxaborolan-2-yl)-1,6-diazabicyclo[3.2.1]oct-3-en-7-one (8a) (200 mg, 0.653 mmol) is converted into 6-allyloxy-4-(1-methyl-6-oxo-pyridazin-4-yl)-1,6-diazabicyclo[3.2.1]oct-3- en-7-one (19a) (65 mg, 0.225 mmol, 35%) using 5-bromo-2-methyl-pyridazin-3-one (186 mg, 0.790 mmol), PEPPSI catalyst (89 mg, 0.130 mmol) and after purification by chromatography on silica gel (DCM/acetone 100/0 to 20/80).

MS m/z ([M+H]$^+$) 289.

$^1$H NMR (400 MHz, CDCl$_3$): δ (ppm) 3.10 (d, J=10.8 Hz, 1H), 3.63 (dd, J=10.8/3.2 Hz, 1H), 3.75 (s, 3H), 3.86 (dd, J=19.6/2.0 Hz, 1H), 3.98 (dd, J=19.2/3.2 Hz, 1H), 4.15 (d, J=2.0 Hz, 1H), 4.38-4.48 (m, 2H), 5.30-5.38 (m, 2H), 5.95-6.05 (m, 1H), 6.18 (s, 1H), 6.78 (d, J=2.0 Hz, 1H), 7.80 (d, J=2.0 Hz, 1H).

Step 2: Preparation of Intermediate triphenyl-(propenyl)-phosphonium [4-(1-methyl-6-oxo-pyridazin-4-yl)-7-oxo-1,6-diazabicyclo[3.2.1]oct-3-en-6-yl] sulfate (19b)

Using the procedure described in example 1 (step 6), the intermediate 6-allyloxy-4-(1-methyl-6-oxo-pyridazin-4-yl)-1,6-diazabicyclo[3.2.1]oct-3-en-7-one (19a) (65 mg, 0.225 mmol) was converted into triphenyl-(propenyl)-phosphonium [4-(1-methyl-6-oxo-pyridazin-4-yl)-7-oxo-1,6-diazabicyclo[3.2.1]oct-3-en-6-yl] sulfate (19b) as an amorphous solid after purification by flash chromatography on silica gel (DCM/acetone 50/50 to 0/100).

MS m/z ([M+H]$^+$) 329.
MS m/z ([M−H]$^−$) 327.
MS m/z ([M+H]$^+$) 303 (triphenyl-propenyl-phosphonium).

Step 3: Preparation of Sodium [4-(1-methyl-6-oxo-pyridazin-4-yl)-7-oxo-1,6-diazabicyclo[3.2.1]oct-3-en-6-yl] sulfate (Example 19)

Using the procedure described in example 1 (step 7), triphenyl-(propenyl)-phosphonium [4-(1-methyl-6-oxo-pyridazin-4-yl)-7-oxo-1,6-diazabicyclo[3.2.1]oct-3-en-6-yl] sulfate (19b) was converted after ion exchange (Dowex sodium form column) into sodium [4-(1-methyl-6-oxo-pyridazin-4-yl)-7-oxo-1,6-diazabicyclo[3.2.1]oct-3-en-6-yl] sulfate (Example 19) (7.4 mg, 0.021 mmol, 10% over 2 steps) as a white amorphous solid after lyophilization.

MS m/z ([M+H]$^+$) 329.
MS m/z ([M−H]$^−$) 327.

$^1$H NMR (400 MHz, D$_2$O): δ (ppm) 3.48 (d, J=11.6 Hz, 1H), 3.77 (s, 3H), 3.79 (dd, J=11.6/2.8 Hz, 1H), 3.96 (dd, J=19.2/2.8 Hz, 1H), 4.12 (dd, J=19.2/2.0 Hz, 1H), 4.80 (m, 1H), 6.53-6.58 (m, 1H), 7.04 (d, J=2.0 Hz, 1H), 8.18 (d, J=2.0 Hz, 1H).

Example 20: Synthesis of Sodium [4-(N-methyl-6-oxo-pyrimidin-4-yl)-7-oxo-1,6-diazabicyclo[3.2.1]oct-3-en-6-yl] sulfate Step 1

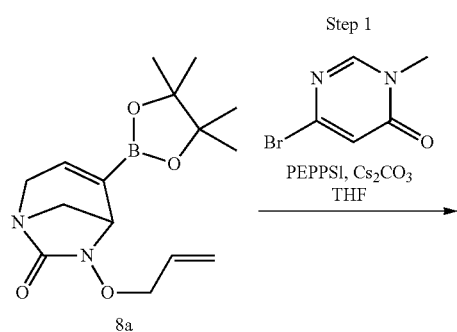

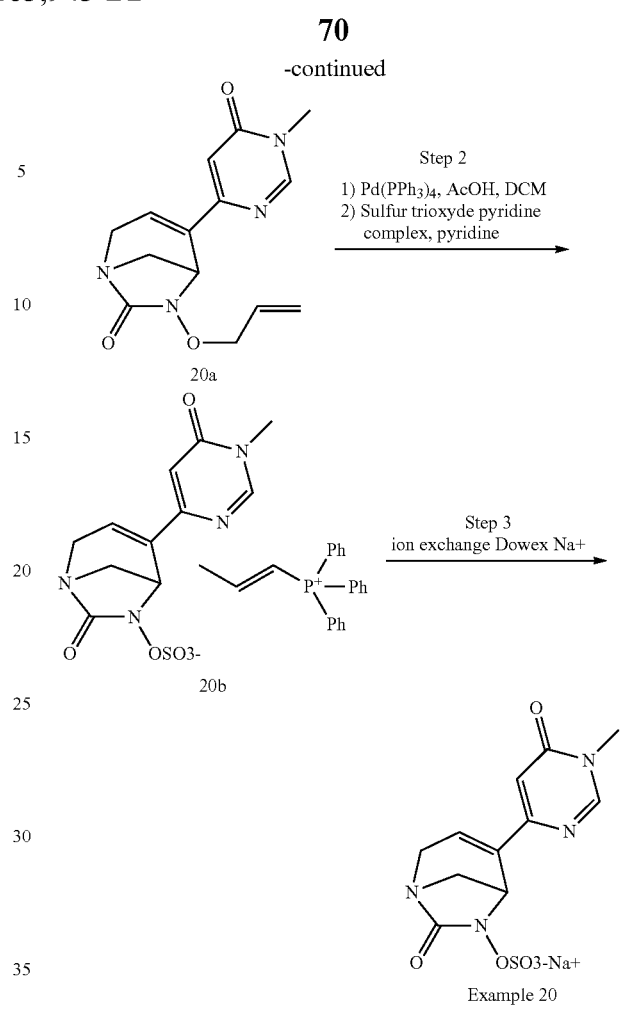

Step 1: Preparation of Intermediate 6-allyloxy-4-(N-methyl-6-oxo-pyrimidin-4-yl)-1,6-diazabicyclo[3.2.1]oct-3-en-7-one (20a)

Using the procedure described in example 9 (step 1), the intermediate (6-allyloxy-4-(4,4,5,5-tetramethyl-1,3,2-dioxaborolan-2-yl)-1,6-diazabicyclo[3.2.1]oct-3-en-7-one (8a) (200 mg, 0.653 mmol) is converted into 6-allyloxy-4-(N-methyl-6-oxo-pyrimidin-4-yl)-1,6-diazabicyclo[3.2.1]oct-3-en-7-one (20a) (10 mg, 0.035 mmol, 6%) using 4-bromo-N-methyl-pyrimidin-6-one (149 mg, 0.790 mmol), PEPPSI catalyst (89 mg, 0.130 mmol) and after purification by chromatography on silica gel (DCM/acetone 100/0 to 40/60).

MS m/z ([M+H]$^+$) 289.

$^1$H NMR (400 MHz, CDCl$_3$): δ (ppm) 3.10 (d, J=11.2 Hz, 1H), 3.49 (s, 3H), 3.50 (d, J=11.2 Hz, 1H), 3.62 (dd, J=11.2/3.2 Hz, 1H), 3.88 (dd, J=19.6/2.0 Hz, 1H), 4.00 (dd, J=19.6/3.2 Hz, 1H), 4.36-4.46 (m, 2H), 5.29-5.37 (m, 2H), 5.95-6.06 (m, 1H), 6.45 (s, 1H), 6.72 (m, 1H), 8.04 (s, 1H).

Step 2: Preparation of Intermediate triphenyl-(propenyl)-phosphonium [4-(N-methyl-6-oxo-pyrimidin-4-yl)-7-oxo-1,6-diazabicyclo[3.2.1]oct-3-en-6-yl] sulfate (20b)

Using the procedure described in example 1 (step 6), the intermediate 6-allyloxy-4-(N-methyl-6-oxo-pyrimidin-4- yl)-1,6-diazabicyclo[3.2.1]oct-3-en-7-one (20a) (49 mg, 0.170 mmol) was converted into triphenyl-(propenyl)-phosphonium [4-(N-methyl-6-oxo-pyrimidin-4-yl)-7-oxo-1,6-diazabicyclo[3.2.1]oct-3-en-6-yl] sulfate (20b) as an amorphous solid after purification by flash chromatography on silica gel (DCM/acetone 50/50 to 0/100).

MS m/z ([M+H]+) 329.

MS m/z ([M−H]−) 327.

MS m/z ([M+H]+) 303 (triphenyl-propenyl-phosphonium).

Step 3: Preparation of Sodium [4-(N-methyl-6-oxo-pyrimidin-4-yl)-7-oxo-1,6-diazabicyclo[3.2.1]oct-3-en-6-yl] sulfate (Example 20)

Using the procedure described in example 1 (step 7), triphenyl-(propenyl)-phosphonium [4-(N-methyl-6-oxo-pyrimidin-4-yl)-7-oxo-1,6-diazabicyclo[3.2.1]oct-3-en-6-yl] sulfate (20b) was converted after ion exchange (Dowex sodium form column) into sodium [4-(N-methyl-6-oxo-pyrimidin-4-yl)-7-oxo-1,6-diazabicyclo[3.2.1]oct-3-en-6-yl] sulfate (Example 20) (2.5 mg, 0.007 mmol, 5% over 2 steps) as a white amorphous solid after lyophilization.

MS m/z ([M+H]+) 329.

MS m/z ([M−H]−) 327.

$^1$H NMR (400 MHz, D$_2$O): δ (ppm) 3.45 (d, J=11.2 Hz, 1H), 3.53 (s, 3H), 3.79 (dd, J=11.2/3.2 Hz, 1H), 3.96 (dd, J=19.6/3.2 Hz, 1H), 4.13 (dd, J=19.6/2.0 Hz, 1H), 4.91 (d, J=2.0 Hz, 1H), 6.68 (s, 1H), 6.76-6.80 (m, 1H), 8.38 (s, 1H).

Example 21: Synthesis of Sodium (7-oxo-3-thiazol-2-yl-4-methyl-1,6-diaza-bicyclo[3.2.1]oct-3-en-6-yl) sulfate

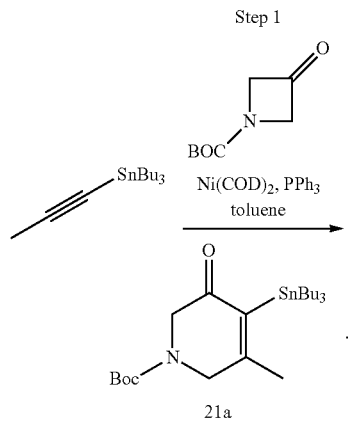

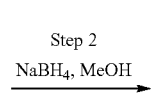

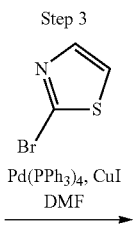

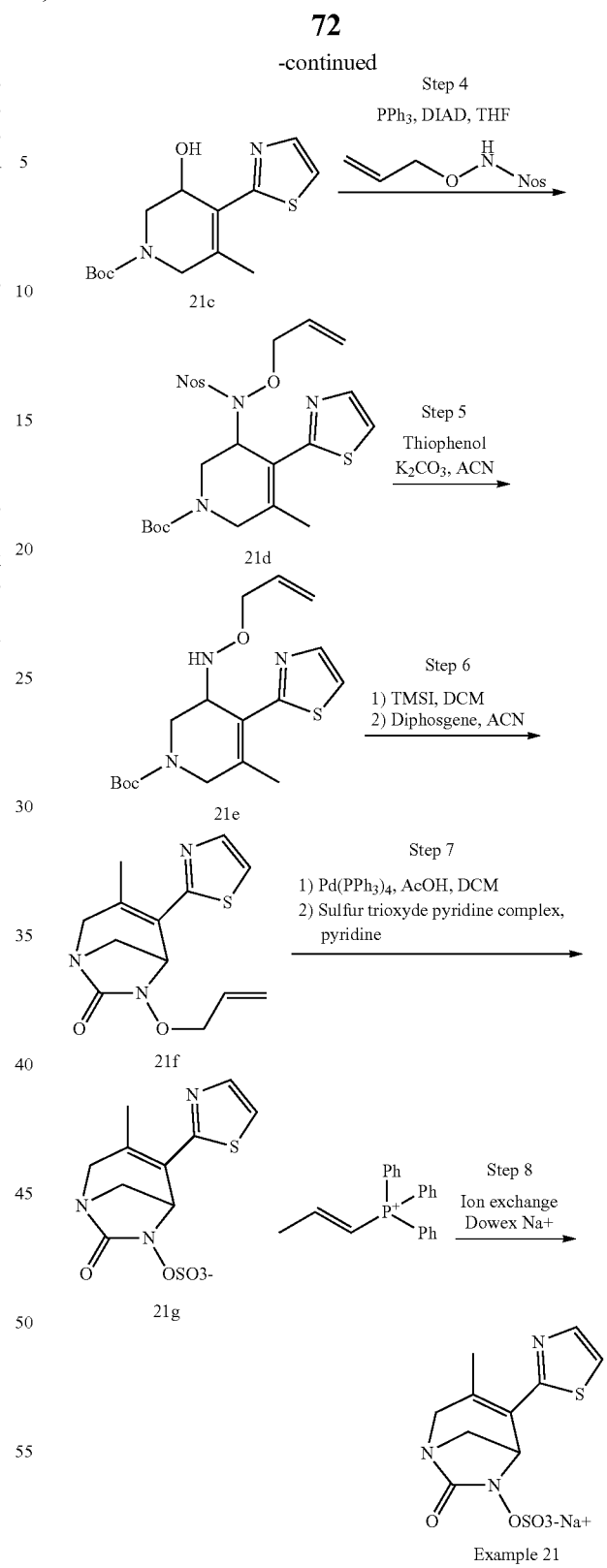

Step 1: Preparation of Intermediate tert-butyl 4-methyl-5-oxo-3-(tributylstannyl)-5,6-dihydropyridine-1(2H)-carboxylate (21a)

Under inert atmosphere, Ni(COD)$_2$ (322 mg, 1.20 mmol) and PPh$_3$ (613 mg, 2.34 mmol) were added to a solution of 3-Boc-azetidinone (4 g, 23.36 mmol) and tributyl(prop-1-ynyl)stannane (8.9 g, 26.87 mmol) in degassed toluene (140 mL). The reaction mixture was stirred at 60° C. for 2 h, concentrated in vacuo, and purified by flash chromatography on silica gel (petroleum ether/Et$_2$O 100/0 to 80/20) to provide tert-butyl 4-methyl-5-oxo-3-(tributylstannyl)-5,6-dihydropyridine-1(2H)-carboxylate (21a) (6.45 g, 12.89 mmol, 55%) as a colorless oil.

MS m/z ([M+Na]$^+$) 524.

$^1$H NMR (400 MHz, CDCl$_3$): δ (ppm) 0.88-1.47 (m, 36H), 2.01 (t, J=2.5 Hz, 3H), 4.00 (bs, 2H), 4.06 (bs, 2H).

Step 2: Preparation of Intermediate tert-butyl 4-methyl-5-hydroxy-3-(tributylstannyl)-5,6-dihydropyridine-1(2H)-carboxylate (21b)

A solution of tert-butyl 4-methyl-5-oxo-3-(tributylstannyl)-5,6-dihydropyridine-1(2H)-carboxylate (21a) (3 g, 6.00 mmol) in dry MeOH (50 mL) under inert atmosphere was cooled down to 0° C. with an ice bath. NaBH$_4$ (295 mg, 7.80 mmol) was added by portions over 15 min. The reaction was stirred at 0° C. for 1 h. Another portion of NaBH$_4$ was added to the clear yellow solution (90 mg, 2.40 mmol). After 3 h, the reaction was stopped, concentrated to approximately 20 mL under reduced pressure. The resulting solution was diluted with EtOAc (100 mL), washed with brine (30 mL). The organic layer was dried over Na$_2$SO$_4$, filtered and concentrated under reduced pressure. The crude residue was purified by flash chromatography on silica gel (heptane/EtOAc 100/0 to 70/30) to give desired tert-butyl 4-methyl-5-hydroxy-3-(tributylstannyl)-5,6-dihydropyridine-1(2H)-carboxylate (21b) (1.62 g, 3.23 mmol, 54%) as a white solid and a clean fraction of recovered starting keto derivative (21a) (703 mg, 1.41 mmol, 23%).

MS m/z ([M+Na]$^+$) 526.

Step 3: Preparation of Intermediate tert-butyl 4-methyl-3-hydroxy-5-(thiazol-2-yl)-5,6-dihydropyridine-1(2H)-carboxylate (21c)

Two 25 mL sealed tube were charged with tert-butyl 4-methyl-5-hydroxy-3-(tributylstannyl)-5,6-dihydropyridine-1(2H)-carboxylate (21b) (810 mg, 1.613 mmol) and diluted with DMF (16 mL). In each tube, 2-bromothiazole (397 mg, 2.42 mmol) was added followed by CuI (I) (307 mg, 1.61 mmol). Both suspensions were degassed with argon and Pd(PPh$_3$)$_4$ (186 mg, 0.161 mmol) was added. The reactions were stirred at 50° C. under argon until complete conversion of starting material. The resulting clear green solutions were combined, concentrated under reduced pressure. The residue was taken up in DCM (20 mL), filtered on PTFE 0.45 μm. The filtrate was concentrated under reduced pressure and purified by flash chromatography on silica gel (heptane/EtOAc 100/0 to 30/70) then on reverse phase (H$_2$O/ACN 98/2 to 40/60) to give desired intermediate tert-butyl 4-methyl-5-hydroxy-3-(thiazol-2-yl)-5,6-dihydropyridine-1(2H)-carboxylate (21c) (348 mg, 1.17 mmol, 36%).

MS m/z ([M+H]$^+$) 297.

Step 4: Preparation of Intermediate tert-butyl 4-methyl-3-[allyloxy-(2-nitro-benzenesulfonyl)-amino]-5-(thiazol-2-yl)-5,6-dihydropyridine-1(2H)-carboxylate (21d)

Using the procedure described in example 1 (step 2), the intermediate tert-butyl 4-methyl-5-hydroxy-3-(thiazol-2-yl)-5,6-dihydropyridine-1(2H)-carboxylate (21c) (348 mg, 1.17 mmol) was converted into tert-butyl 4-methyl-5-[allyloxy-(2-nitro-benzenesulfonyl)-amino]-3-(thiazol-2-yl)-5,6-dihydropyridine-1(2H)-carboxylate (21d) (351 mg, 0.654 mmol, 56%) as a pale yellow oil after purification by flash chromatography on silica gel (heptane/EtOAc 100/0 to 50/50).

MS m/z ([M+H]$^+$) 537.

Step 5: Preparation of Intermediate tert-butyl 4-methyl-3-allyloxyamino-5-(thiazol-2-yl)-5,6-dihydropyridine-1(2H)-carboxylate (21e)

Using the procedure described in example 1 (step 3), the intermediate tert-butyl 4-methyl-5-[allyloxy-(2-nitro-benzenesulfonyl)-amino]-3-(thiazol-2-yl)-5,6-dihydropyridine-1(2H)-carboxylate (21d) (533 mg, 0.933 mmol) was converted into tert-butyl 4-methyl-5-allyloxyamino-3-(thiazol-2-yl)-5,6-dihydropyridine-1(2H)-carboxylate (21e) (280 mg, 0.797 mmol, 80%) after purification by flash chromatography on silica gel (toluene/Et$_2$O 90/10 to 20/80).

MS m/z ([M+H]$^+$) 352.

Step 6: Preparation of Intermediate 3-allyloxyamino-4-methyl-5-thiazol-2-yl-5,6-dihydropyridine (21f)

Using the procedure described in example 1 (step 4), the intermediate tert-butyl 4-methyl-3-allyloxyamino-5-(thiazol-2-yl)-5,6-dihydropyridine-1(2H)-carboxylate (21e) (280 mg, 0.797 mmol) was converted into 6-allyloxy-4-methyl-3-thiazol-2-yl-1,6-diaza-bicyclo[3.2.1]oct-3-en-7-one (21f) as a pale yellow solid (140 mg, 0.505 mmol, 63% over 2 steps) after purification by flash chromatography on silica gel (heptane/EtOAc 100/0 to 0/100).

MS m/z ([M+H]$^+$) 278.

$^1$H NMR (400 MHz, CDCl$_3$): δ (ppm) 2.01 (s, 3H), 3.22 (d, J=10.6 Hz, 1H), 3.62 (dd, J=10.7/2.5 Hz, 1H), 3.81 (dd, J=18.2/1.0 Hz, 1H), 3.91 (d, J=18.2 Hz, 1H), 4.37-4.49 (m, 2H), 4.96 (d, J=3.1 Hz, 1H), 5.25-5.35 (m, 2H), 5.91-6.04 (m, 1H), 7.42 (d, J=3.3 Hz, 1H), 7.87 (d, J=3.3 Hz, 1H).

Step 7: Preparation of Intermediate triphenyl-(propenyl)-phosphonium (7-oxo-4-methyl-3-thiazol-2-yl-1,6-diaza-bicyclo[3.2.1]oct-3-en-6-yl) sulfate (21Q)

Using the procedure described in example 1 (step 6), the intermediate 6-allyloxy-4-methyl-3-thiazol-2-yl-1,6-diaza-bicyclo[3.2.1]oct-3-en-7-one (21f) (140 mg, 0.505 mmol) was converted into triphenyl-(propenyl)-phosphonium (7-oxo-4-methyl-3-thiazol-2-yl-1,6-diaza-bicyclo[3.2.1]oct-3-en-6-yl) sulfate (21g) (245 mg) after purification by flash chromatography on silica gel (DCM/acetone 100/0 to 25/75).

MS m/z ([M+H]$^+$) 317.
MS m/z ([M−H]$^−$) 316.
MS m/z ([M+H]$^+$) 303 (triphenyl-propenyl-phosphonium).

Step 8: Preparation of Sodium (7-oxo-4-methyl-3-thiazol-2-yl-1,6-diaza-bicyclo[3.2.1]oct-3-en-6-yl) sulfate (Example 21)

Using the procedure described in example 1 (step 7), triphenyl-(propenyl)-phosphonium (7-oxo-4-methyl-3-thiazol-2-yl-1,6-diaza-bicyclo[3.2.1]oct-3-en-6-yl) sulfate (21g) (245 mg) was converted after ion exchange (Dowex sodium form column) into sodium (7-oxo-4-methyl-3-thiazol-2-yl-1,6-diaza-bicyclo[3.2.1]oct-3-en-6-yl) sulfate (Example 21) (89.8 mg, 0.265 mmol, 55% over 2 steps) as a white amorphous solid after lyophilization.

MS m/z ([M−H]⁻) 316.

¹H NMR (400 MHz, D₂O): δ (ppm) 1.89 (s, 3H), 3.49 (d, J=11.0 Hz, 1H), 3.75 (dd, J=11.0/3.0 Hz, 1H), 3.83 (d, J=18.6 Hz, 1H), 4.04 (d, J=18.6 Hz, 1H), 4.88 (d, J=3.1 Hz, 1H), 7.64 (d, J=3.3 Hz, 1H), 7.83 (d, J=3.3 Hz, 1H).

Example 22

Synthesis of Sodium [4-(4-(2-methoxy-2-oxo-methyl)-thiazol-5-yl)-7-oxo-1,6-diazabicyclo[3.2.1]oct-3-en-6-yl] sulfate

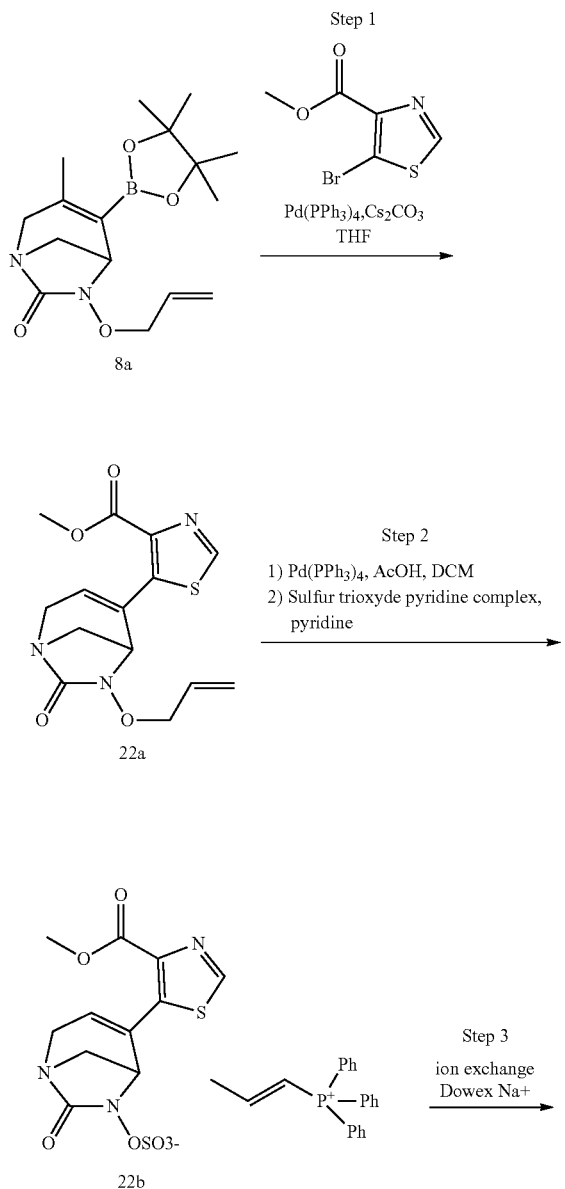

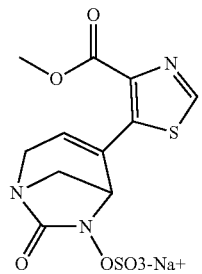

Example 22

Step 1: Preparation of Intermediate 6-allyloxy-4-(4-(2-methoxy-2-oxo-methyl)-thiazol-5-yl)-1,6-diazabicyclo[3.2.1]oct-3-en-7-one (22a)

In a Wheaton vial, (6-allyloxy-4-(4,4,5,5-tetramethyl-1,3,2-dioxaborolan-2-yl)-1,6-diazabicyclo[3.2.1]oct-3-en-7-one (8a) (300 mg, 0.980 mmol), methyl 5-bromothiazole-4-carboxylate (261 mg, 1.176 mmol), dry Cs₂CO₃ (639 mg, 1.96 mmol) were dissolved in anhydrous THF (9.8 mL). The solution was degassed under argon for 5 min and Pd(PPh₃)₄ catalyst (226 mg, 0.196 mmol) was added. The reaction was stirred at 80° C. for 8 h under microwaves. The mixture was filtered and concentrated under reduced pressure to afford a crude material which was purified by chromatography on silica gel (cyclohexane/EtOAc 60/40 to 0/100) to give the desired product 6-allyloxy-4-(4-(2-methoxy-2-oxo-methyl)-thiazol-5-yl)-1,6-diazabicyclo[3.2.1]oct-3-en-7-one (22a) (177 mg, 0.551 mmol, 56%) as a gum.

MS m/z ([M+H]⁺) 322.

¹H NMR (300 MHz, CDCl₃): δ (ppm) 3.48 (d, J=11.0 Hz, 1H), 3.61-3.68 (m, 1H), 3.81-4.01 (m, 5H), 4.16-4.20 (m, 1H), 4.20-4.39 (m, 2H), 5.13-5.28 (m, 2H), 5.71-5.90 (m, 2H), 8.68 (s, 1H).

Step 2: Preparation of Intermediate triphenyl-(propenyl)-phosphonium [4-(4-(2-methoxy-2-oxo-methyl)-thiazol-5-yl)-7-oxo-1,6-diazabicyclo[3.2.1]oct-3-en-6-yl] sulfate (22b)

Using the procedure described in example 1 (step 6), the intermediate 6-allyloxy-4-(4-(2-methoxy-2-oxo-methyl)-thiazol-5-yl)-1,6-diazabicyclo[3.2.1]oct-3-en-7-one (22a) (155 mg, 0.482 mmol) was converted into triphenyl-(propenyl)-phosphonium [4-(4-(2-methoxy-2-oxo-methyl)-thiazol-5-yl)-7-oxo-1,6-diazabicyclo[3.2.1]oct-3-en-6-yl] sulfate (22b) as an amorphous solid after purification by flash chromatography on silica gel (DCM/acetone 50/50 to 0/100).

MS m/z ([M+H]⁺) 362.

MS m/z ([M−H]⁻) 360.

MS m/z ([M+H]⁺) 303 (triphenyl-propenyl-phosphonium).

Step 3: Preparation of Sodium [4-(4-(2-methoxy-2-oxo-methyl)-thiazol-5-yl)-7-oxo-1,6-diazabicyclo[3.2.1]oct-3-en-6-yl] sulfate (Example 22)

Using the procedure described in example 1 (step 7), triphenyl-(propenyl)-phosphonium [4-(4-(2-methoxy-2-oxo-methyl)-thiazol-5-yl)-7-oxo-1,6-diazabicyclo[3.2.1]oct-3-en-6-yl] sulfate (22b) was converted after ion exchange (Dowex sodium form column) into sodium [4-(4-

(2-methoxy-2-oxo-methyl)-thiazol-5-yl)-7-oxo-1,6-diazabicyclo[3.2.1]oct-3-en-6-yl] sulfate (Example 22) (36 mg, 0.094 mmol, 19% over 2 steps) as a white amorphous solid after lyophilization.

MS m/z ([M+H]$^+$) 362.
MS m/z ([M−H]$^-$) 360.
$^1$H NMR (400 MHz, D$_2$O): δ (ppm) 3.63-3.68 (m, 1H), 3.82 (dd, J=11.3/3.1 Hz, 1H), 3.90-3.96 (m, 5H), 4.61 (dd, J=2.8/1.2 Hz, 1H), 5.95-6.09 (m, 1H), 8.94 (s, 1H).

Example 23

Synthesis of Sodium [4-(1,3-dimethyluracil-5-yl)-7-oxo-1,6-diazabicyclo[3.2.1]oct-3-en-6-yl] sulfate

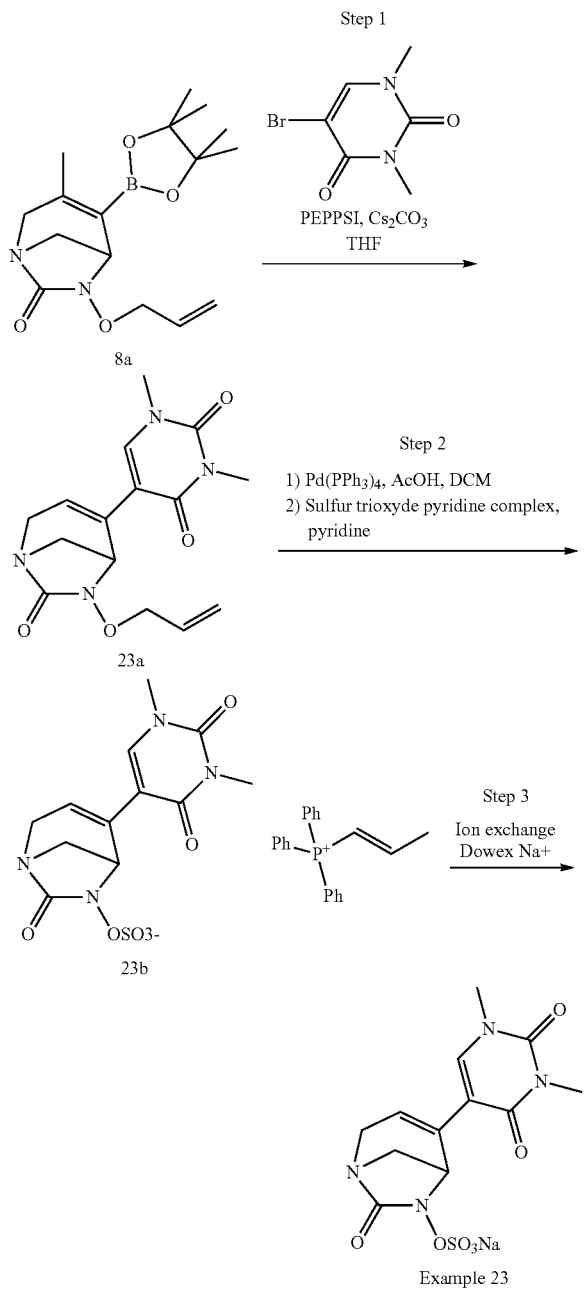

Step 1: Preparation of Intermediate 6-allyloxy-4-(1,3-dimethyluracil-5-yl)-1,6-diazabicyclo[3.2.1]oct-3-en-7-one (23a)

Using the procedure described in example 9 (step 1), the intermediate (6-allyloxy-4-(4,4,5,5-tetramethyl-1,3,2-dioxaborolan-2-yl)-1,6-diazabicyclo[3.2.1]oct-3-en-7-one (8a) (411 mg, 1.342 mmol) is converted into 6-allyloxy-4-(1,3-dimethyluracil-5-yl)-1,6-diazabicyclo[3.2.1]oct-3-en-7-one (23a) (73 mg, 0.229 mmol, 17%) as a yellow oil, using 5-bromo-1,3-dimethyluracil (353 mg, 1.611 mmol), PEPPSI catalyst (182 mg, 0.268 mmol) and after purification by chromatography on silica gel (DCM/acetone 100/0 to 30/70).

MS m/z ([M+H]$^+$) 319.
$^1$H NMR (300 MHz, CDCl$_3$): δ (ppm) 3.35 (s, 3H), 3.36 (s, 3H), 3.85 (d, J=2.7 Hz, 2H), 4.32-4.40 (m, 3H), 5.24-5.33 (m, 2H), 5.72-5.75 (m, 2H), 5.87-6.00 (m, 1H), 7.12 (d, J=7.8 Hz, 1H), 7.25 (d, J=3.9 Hz, 1H).

Step 2: Preparation of Intermediate triphenyl-(propenyl)-phosphonium [4-(1,3-dimethyluracil-5-yl)-7-oxo-1,6-diazabicyclo[3.2.1]oct-3-en-6-yl] sulfate (23b)

Using the procedure described in example 1 (step 6), the intermediate 6-allyloxy-4-(1,3-dimethyluracil-5-yl)-1,6-diazabicyclo[3.2.1]oct-3-en-7-one (23a) (73 mg, 0.229 mmol) was converted into triphenyl-(propenyl)-phosphonium [4-(1,3-dimethyluracil-5-yl)-7-oxo-1,6-diazabicyclo[3.2.1]oct-3-en-6-yl] sulfate (23b) (26 mg) as a yellow amorphous solid after purification by flash chromatography on silica gel (DCM/acetone 90/10 to 50/50).

MS m/z ([M−H]$^-$) 357.
MS m/z ([M+H]$^+$) 303 (triphenyl-propenyl-phosphonium).

Step 3: Preparation of Sodium [4-(1,3-dimethyluracil-5-yl)-7-oxo-1,6-diazabicyclo[3.2.1]oct-3-en-6-yl] sulfate (Example 23)

Using the procedure described in example 1 (step 7), triphenyl-(propenyl)-phosphonium [4-(1,3-dimethyluracil-5-yl)-7-oxo-1,6-diazabicyclo[3.2.1]oct-3-en-6-yl] sulfate (23b) (26 mg) was converted after ion exchange (Dowex sodium form column) into sodium [4-(1,3-dimethyluracil-5-yl)-7-oxo-1,6-diazabicyclo[3.2.1]oct-3-en-6-yl] sulfate (Example 23) (10 mg, 0.027 mmol, 11% over 2 steps) as a white amorphous solid after lyophilization.

MS m/z ([M+H]$^+$) 359.
MS m/z ([M−H]$^-$) 357.
$^1$H NMR (400 MHz, D$_2$O): δ (ppm) 3.30 (s, 3H), 3.42 (s, 3H), 3.51 (d, J=11.2 Hz, 1H), 3.71 (dd, J=11.2/3.2 Hz, 1H), 3.81 (dd, J=18.8/3.2 Hz, 1H), 4.04 (dd, J=18.8/2.0 Hz, 1H), 4.65 (d, J=2.8 Hz, 1H), 6.07 (m, 1H), 7.69 (s, 1H).

Example 24

Synthesis of Sodium [4-(2-methoxypyrimidin-5-yl)-7-oxo-1,6-diazabicyclo[3.2.1]oct-3-en-6-yl] sulfate

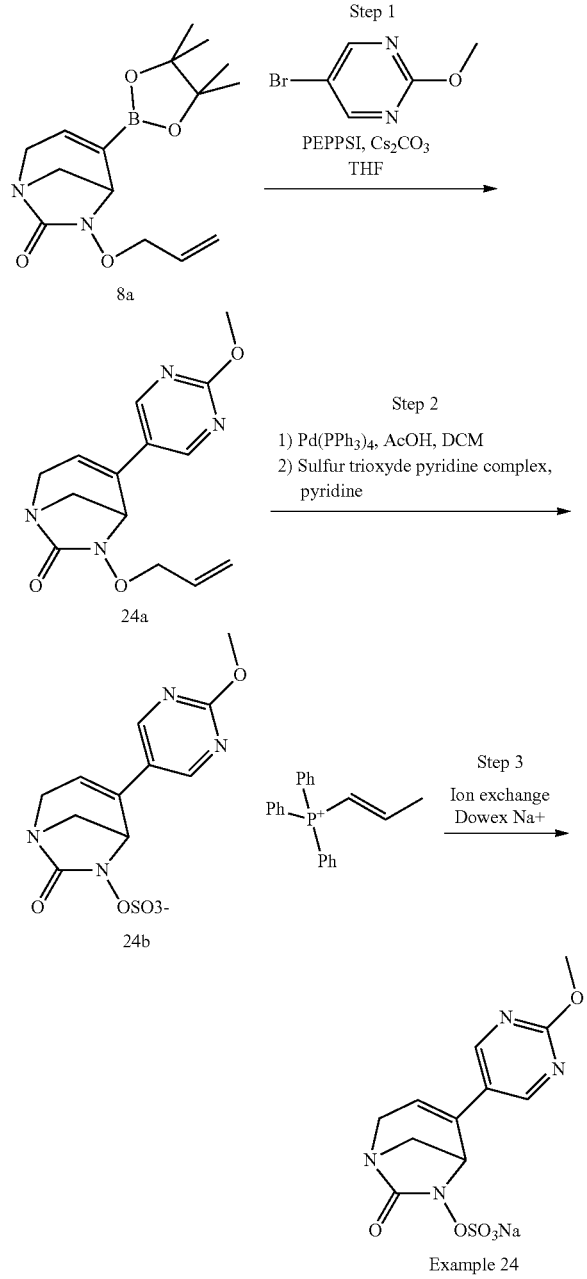

Step 1: Preparation of Intermediate 6-allyloxy-4-(2-methoxypyrimidin-5-yl)-1,6-diazabicyclo[3.2.1]oct-3-en-7-one (24a)

Using the procedure described in example 9 (step 1), the intermediate (6-allyloxy-4-(4,4,5,5-tetramethyl-1,3,2-dioxaborolan-2-yl)-1,6-diazabicyclo[3.2.1]oct-3-en-7-one (8a) (404 mg, 1.324 mmol) is converted into 6-allyloxy-4-(2-methoxypyrimidin-5-yl)-1,6-diazabicyclo[3.2.1]oct-3-en-7-one (24a) (111 mg, 0.385 mmol, 29%) as a yellow oil, using 5-bromo-2-methoxypyrimidine (300 mg, 1.589 mmol), PEPPSI catalyst (180 mg, 0.265 mmol) and after purification by chromatography on silica gel (DCM/acetone 100/0 to 70/30).

MS m/z ([M+H]$^+$) 289.

$^1$H NMR (400 MHz, CDCl$_3$): δ (ppm) 3.20 (d, J=11.2 Hz, 1H), 3.64 (dd, J=10.8/3.0 Hz, 1H), 3.75-3.88 (m, 1H), 3.98 (dd, J=10.8/3.0 Hz, 1H), 4.02 (s, 3H), 4.14 (m, 1H), 4.37-4.53 (m, 2H), 5.22-5.40 (m, 2H), 5.88-5.90 (m, 1H), 5.94-6.09 (m, 1H), 8.51 (s, 2H).

Step 2: Preparation of Intermediate triphenyl-(propenyl)-phosphonium [4-(2-methoxypyrimidin-5-yl)-7-oxo-1,6-diazabicyclo[3.2.1]oct-3-en-6-yl] sulfate (24b)

Using the procedure described in example 1 (step 6), the intermediate 6-allyloxy-4-(2-methoxypyrimidin-5-yl)-1,6-diazabicyclo[3.2.1]oct-3-en-7-one (24a) (111 mg, 0.385 mmol) was converted into triphenyl-(propenyl)-phosphonium [4-(2-methoxypyrimidin-5-yl)-7-oxo-1,6-diazabicyclo[3.2.1]oct-3-en-6-yl] sulfate (24b) (60 mg) as a yellow amorphous solid after purification by flash chromatography on silica gel (DCM/acetone 90/10 to 50/50).

MS m/z ([M−H]$^-$) 327.

MS m/z ([M+H]$^+$) 303 (triphenyl-propenyl-phosphonium).

Step 3: Preparation of Sodium [4-(2-methoxypyrimidin-5-yl)-7-oxo-1,6-diazabicyclo[3.2.1]oct-3-en-6-yl] sulfate (Example 24)

Using the procedure described in example 1 (step 7), triphenyl-(propenyl)-phosphonium [4-(2-methoxypyrimidin-5-yl)-7-oxo-1,6-diazabicyclo[3.2.1]oct-3-en-6-yl] sulfate (24b) (60 mg) was converted after ion exchange (Dowex sodium form column) into sodium [4-(2-methoxypyrimidin-5-yl)-7-oxo-1,6-diazabicyclo[3.2.1]oct-3-en-6-yl] sulfate (Example 24) (31 mg, 0.088 mmol, 25% over 2 steps) as a light-yellow amorphous solid after lyophilization.

MS m/z ([M+H]$^+$) 329.

MS m/z ([M−H]$^-$) 327.

$^1$H NMR (400 MHz, D$_2$O): δ (ppm) 3.52 (d, J=11.2 Hz, 1H), 3.78 (dd, J=11.2/3.2 Hz, 1H), 3.92 (dd, J=18.8/3.2 Hz, 1H), 4.02 (s, 3H), 4.07 (dd, J=18.8/2.0 Hz, 1H), 4.77 (m, 1H), 6.18 (m, 1H), 8.63 (s, 2H).

Example 25

Synthesis of Sodium [3-(oxazol-2-yl)-7-oxo-1,6-diazabicyclo[3.2.1]oct-3-en-6-yl] sulfate

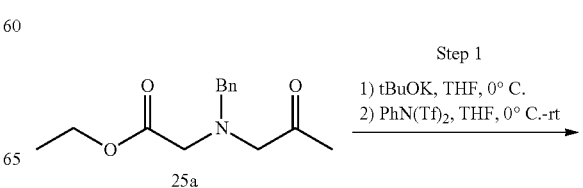

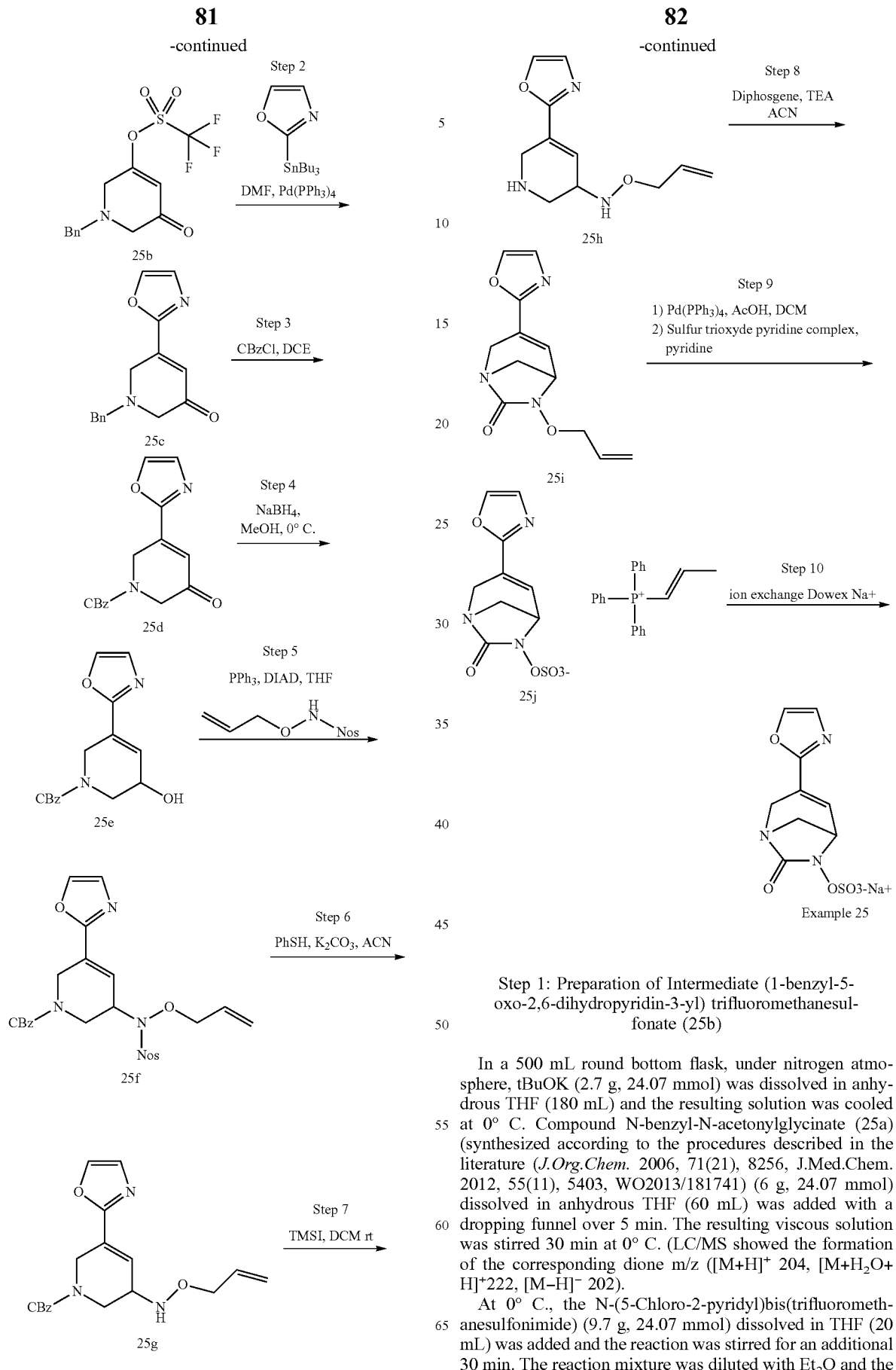

Step 1: Preparation of Intermediate (1-benzyl-5-oxo-2,6-dihydropyridin-3-yl) trifluoromethanesulfonate (25b)

In a 500 mL round bottom flask, under nitrogen atmosphere, tBuOK (2.7 g, 24.07 mmol) was dissolved in anhydrous THF (180 mL) and the resulting solution was cooled at 0° C. Compound N-benzyl-N-acetonylglycinate (25a) (synthesized according to the procedures described in the literature (*J.Org.Chem.* 2006, 71(21), 8256, J.Med.Chem. 2012, 55(11), 5403, WO2013/181741) (6 g, 24.07 mmol) dissolved in anhydrous THF (60 mL) was added with a dropping funnel over 5 min. The resulting viscous solution was stirred 30 min at 0° C. (LC/MS showed the formation of the corresponding dione m/z ([M+H]$^+$ 204, [M+H$_2$O+H]$^+$222, [M−H]$^-$ 202).

At 0° C., the N-(5-Chloro-2-pyridyl)bis(trifluoromethanesulfonimide) (9.7 g, 24.07 mmol) dissolved in THF (20 mL) was added and the reaction was stirred for an additional 30 min. The reaction mixture was diluted with Et$_2$O and the solution was washed with H$_2$O. The organic layer was dried over Na$_2$SO$_4$, filtered and concentrated in vacuo. The residue was purified by chromatography on silica gel (toluene/acetone 100/0 to 95/5 or cyclohexane/ethyl acetate 100/0 to 50/50) to provide (1-benzyl-5-oxo-2,6-dihydropyridin-3-yl) trifluoromethanesulfonate (25b) which was triturated in a mixture of petroleum ether/ether (9/1) at −78° C. After filtration, compound (25b) was obtained as a white crystalline solid (5.80 g, 17.29 mmol, 71%) and stored in the freezer.

MS m/z ([M+H]$^+$) 336.

$^1$H NMR (300 MHz, CDCl$_3$): δ (ppm) 3.27 (s, 2H), 3.49 (s, 2H), 3.73 (s, 2H), 6.17 (t, J=1.3 Hz, 1H).

Step 2: Preparation of Intermediate 1-benzyl-5-oxazol-2-yl-2,6-dihydropyridin-3-one (25c)

In a sealed flask, (1-benzyl-5-oxo-2,6-dihydropyridin-3-yl) trifluoromethanesulfonate (25b) (3.12 g, 9.305 mmol) and 2-(tributylstannanyl)-1,3-oxazole (5 g, 13.96 mmol) were dissolved in anhydrous DMF (93 mL). The solution was degassed under argon for 10 min and Pd(Ph$_3$)$_4$ (1.08 g, 0.931 mmol) was added. The reaction was stirred at 60° C. for 45 min until complete conversion of starting material (25b). The mixture was concentrated under reduced pressure to afford a crude material which was purified by flash chromatography on silica gel (toluene/acetone 100/0 to 70/30) to give the desired coupling compound 1-benzyl-5-oxazol-2-yl-2,6-dihydropyridin-3-one (25c) (1.35 g, 5.31 mmol, 57%) as a yellow oil.

MS m/z ([M+H]$^+$) 255.

$^1$H NMR (400 MHz, CDCl$_3$): δ (ppm) 3.26 (bs, 2H), 3.79 (s, 2H), 3.82 (bs, 2H), 6.83 (t, J=1.7 Hz, 1H), 7.31 (d, J=0.6 Hz, 1H), 7.32-7.38 (m, 5H), 7.77 (d, J=0.6 Hz, 1H).

Step 3: Preparation of Intermediate benzyl 3-oxazol-2-yl-5-oxo-2,6-dihydropyridine-1-carboxylate (25d)

1-benzyl-5-oxazol-2-yl-2,6-dihydropyridin-3-one (25c) (649 mg, 2.55 mmol) was dissolved in DCE (25 mL) and benzyl chloroformate (1.1 mL, 7.66 mmol) was added. The reaction mixture was stirred 4 days at rt. The reaction was concentrated in vacuo and the crude residue was purified by flash chromatography on silica gel (toluene/acetone 100/0 to 70/30) to give benzyl 3-oxazol-2-yl-5-oxo-2,6-dihydropyridine-1-carboxylate (25d) (663 mg, 2.22 mmol, 87%).

MS m/z ([M+H]$^+$) 299.

$^1$H NMR (400 MHz, CDCl$_3$): δ (ppm) 4.28 (s, 2H), 4.81 (bs, 2H), 5.22 (bs, 2H), 6.87 (t, J=1.6 Hz, 1H), 7.32-7.44 (m, 6H), 7.79 (d, J=0.6 Hz, 1H).

Step 4: Preparation of Intermediate benzyl 3-hydroxy-5-oxazol-2-yl-3,6-dihydro-2H-pyridine-1-carboxylate (25e)

Benzyl 3-oxazol-2-yl-5-oxo-2,6-dihydropyridine-1-carboxylate (25d) (680 mg, 2.28 mmol) was dissolved in MeOH (23 mL) at 0° C. NaBH$_4$ (103 mg, 2.74 mmol) was added by small portions and the reaction mixture was stirred at 0° C. for 30 min. The reaction was concentrated in vacuo approximately to 4-5 mL of MeOH then diluted with EtOAc and washed with brine. The organic layer was dried over Na$_2$SO$_4$, filtered and concentrated. The benzyl 3-hydroxy-5-oxazol-2-yl-3,6-dihydro-2H-pyridine-1-carboxylate (25e) was used in the next step without further purification.

MS m/z ([M+H]$^+$) 301.

Step 5: Preparation of Intermediate benzyl-3-[allyloxy-(2-nitrophenyl)sulfonyl-amino]-5-oxazol-2-yl-3,6-dihydro-2H-pyridine-1-carboxylate (25f)

Under inert atmosphere at room temperature, DIAD (539 μL, 2.74 mmol) in anhydrous THF (2 mL) was added drop by drop to a solution of benzyl 3-hydroxy-5-oxazol-2-yl-3,6-dihydro-2H-pyridine-1-carboxylate (25e) (2.28 mmol) dissolved in dry THF (23 mL) in presence of N-allyloxy-2-nitro-benzenesulfonamide (813 mg, 3.15 mmol) and PPh$_3$ (718 mg, 2.74 mmol). After stirring 1 h at rt, the reaction mixture was concentrated under vacuum and purified by flash chromatography on silica gel (toluene/acetone 100/0 to 70/30) then by chromatography on C18 reverse phase (H$_2$O/ACN 80/20 to 0/100) to afford benzyl-3-[allyloxy-(2-nitrophenyl)sulfonyl-amino]-5-oxazol-2-yl-3,6-dihydro-2H-pyridine-1-carboxylate (25f) (1.08 g, 2.00 mmol, 88%) as a white foam.

MS m/z ([M+H]$^+$) 541.

Step 6: Preparation of Intermediate benzyl 3-(allyloxyamino)-5-oxazol-2-yl-3,6-dihydro-2H-pyridine-1-carboxylate (25g)

Under inert atmosphere, K$_2$CO$_3$ (481 mg, 3.48 mmol) was added to a solution of benzyl-3-[allyloxy-(2-nitrophenyl)sulfonyl-amino]-5-oxazol-2-yl-3,6-dihydro-2H-pyridine-1-carboxylate (25f) (251 mg, 0.464 mmol) in anhydrous ACN (8 mL) in presence of PhSH (238 μL, 2.32 mmol). After stirring 12 h at rt, the reaction mixture was filtered on Celite® and the cake was washed with DCM (10 mL). The filtrate was concentrated and the crude residue was purified by flash chromatography on silica gel (toluene/acetone 100/0 to 80/20) to give benzyl 3-(allyloxyamino)-5-oxazol-2-yl-3,6-dihydro-2H-pyridine-1-carboxylate (25g) (138 mg, 0.388 mmol, 84%) as a yellow foam.

MS m/z ([M+H]$^+$) 356.

Step 7: Preparation of Intermediate N-allyloxy-5-oxazol-2-yl-1,2,3,6-tetrahydropyridin-3-amine (25h)

Under inert atmosphere, TMSI (87 μL, 0.582 mmol) was added to a solution of benzyl 3-(allyloxyamino)-5-oxazol-2-yl-3,6-dihydro-2H-pyridine-1-carboxylate (25g) (138 mg, 0.388 mmol) in anhydrous DCM (3.9 mL). After stirring 3 h at rt, the reaction mixture was filtered on Celite® and the cake was washed with DCM (10 mL). The filtrate was concentrated and the crude residue was diluted with EtOAc (50 mL) and washed with a saturated aqueous solution of NaHCO$_3$ (15 mL) and brine (15 mL). The organic layer was dried over Na$_2$SO$_4$, filtered and dried under reduced pressure. The crude residue was purified by flash chromatography on C18 reverse phase (H$_2$O/ACN 98/2 to 30/70) to give N-allyloxy-5-oxazol-2-yl-1,2,3,6-tetrahydropyridin-3-amine (25h) (81 mg, 0.366 mmol, 94%) as a colorless oil.

MS m/z ([M+H]$^+$) 222.

Step 8: Preparation of Intermediate 6-allyloxy-3-oxazol-2-yl-1,6-diazabicyclo[3.2.1]oct-3-en-7-one (25i)

Under inert atmosphere, N-allyloxy-5-oxazol-2-yl-1,2,3,6-tetrahydropyridin-3-amine (25h) (80 mg, 0.362 mmol) was dissolved in anhydrous ACN (30 mL) and cooled down to 0° C. with an ice bath. TEA was added (201 μL, 1.45 mmol) followed by diphosgene (24 μL, 0.199 mmol dissolved in 5 mL of anhydrous ACN). After stirring 1 h at 0° C. and 3 h at rt, the reaction mixture was concentrated under reduced pressure. The residue was diluted in EtOAc (15 mL) washed with a saturated aqueous solution of NaHCO$_3$ (5 mL). The aqueous layer was extracted with EtOAc (5 mL) and the combined organic layers were dried over Na$_2$SO$_4$, filtered and dried under reduced pressure. The crude mixture was purified by flash chromatography on C18 reverse phase (H$_2$O/ACN 80/20 to 0/100) to give 6-allyloxy-3-oxazol-2-yl-1,6-diazabicyclo[3.2.1]oct-3-en-7-one (25i) (19 mg, 0.077 mmol, 21%).

MS m/z ([M+H]$^+$) 248

$^1$H NMR (400 MHz, CDCl$_3$): δ (ppm) 3.17 (d, J=10.9 Hz, 1H), 3.56-3.54 (m, 1H), 4.07-4.17 (m, 2H), 4.34-4.51 (m, 3H), 5.31-5.45 (m, 2H), 5.97-6.14 (m, 1H), 7.16 (d, J=0.7 Hz, 1H), 7.17-7.19 (m, 2H), 7.62 (d, J=0.7 Hz, 1H).

Step 9: Preparation of Intermediate triphenyl-(propenyl)-phosphonium [3-(oxazol-2-yl)-7-oxo-1,6-diazabicyclo[3.2.1]oct-3-en-6-yl] sulfate (25j)

Using the procedure described in example 1 (step 6), the intermediate 6-allyloxy-3-oxazol-2-yl-1,6-diazabicyclo[3.2.1]oct-3-en-7-one (25i) (19 mg, 0.077 mmol) was converted into triphenyl-(propenyl)-phosphonium [3-(oxazol-2-yl)-7-oxo-1,6-diazabicyclo[3.2.1]oct-3-en-6-yl] sulfate (25j) after purification by flash chromatography on silica gel (DCM/acetone 100/0 to 0/100).

MS m/z ([M−H]$^−$) 286

MS m/z ([M+H]$^+$) 303 (triphenyl-propenyl-phosphonium).

Step 10: Preparation of Sodium [3-(oxazol-2-yl)-7-oxo-1,6-diazabicyclo[3.2.1]oct-3-en-6-yl]sulfate (Example 25)

Using the procedure described in example 1 (step 7), triphenyl-(propenyl)-phosphonium [3-(oxazol-2-yl)-7-oxo-1,6-diazabicyclo[3.2.1]oct-3-en-6-yl] sulfate (25j) was converted after ion exchange (Dowex sodium form column) into sodium [3-(oxazol-2-yl)-7-oxo-1,6-diazabicyclo[3.2.1]oct-3-en-6-yl] sulfate (Example 25) (3.9 mg, 0.013 mmol, 17% over 2 steps) as a white solid, after lyophilization.

MS m/z ([M−H]$^−$) 286.

$^1$H NMR (400 MHz, D$_2$O): δ (ppm) 3.23 (d, J=11.3 Hz, 1H), 3.45-3.53 (m, 1H), 3.96 (dd, J=17.8/1.5 Hz, 1H), 4.05 (dd, J=17.8/2.0 Hz, 1H), 4.34 (dd, J=5.2/2.5 Hz, 1H), 6.97 (d, J=0.8 Hz, 1H), 6.99-7.04 (m, 1H), 7.62 (d, J=0.8 Hz, 1H).

Example 26

Synthesis of Sodium [3-(isoxazol-4-yl)-7-oxo-1,6-diazabicyclo[3.2.1]oct-3-en-6-yl] sulfate

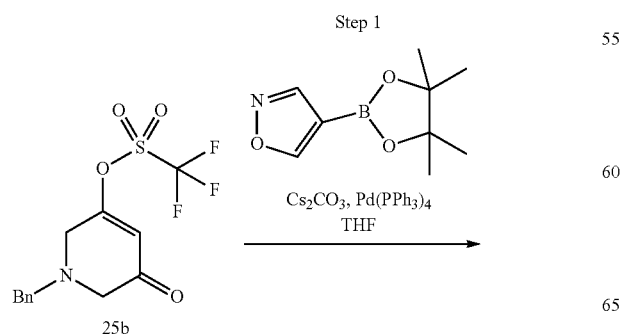

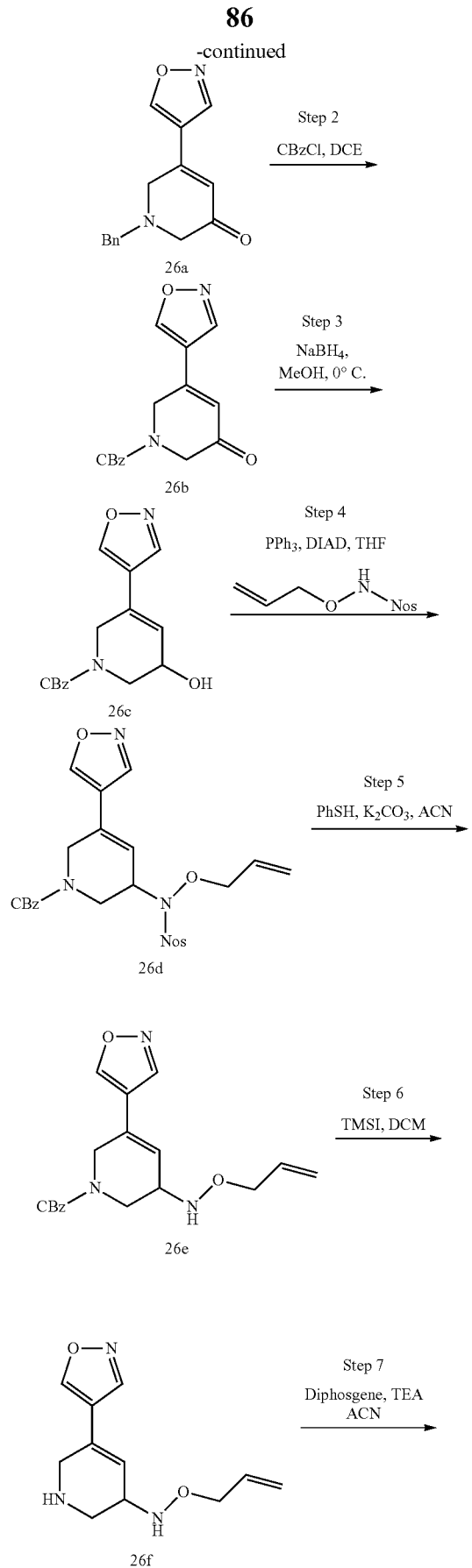

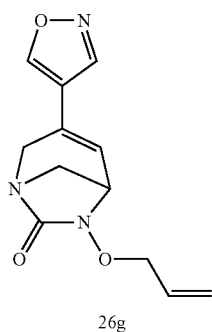

Step 8
1) Pd(PPh₃)₄, AcOH, DCM
2) Sulfur trioxyde pyridine complex, pyridine

26g

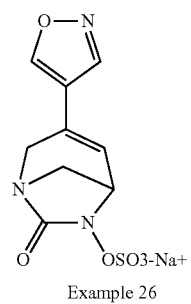

Step 9
ion exchange Dowex Na+

26h

Example 26

Step 1: Preparation of Intermediate 1-benzyl-5-isoxazol-4-yl-2,6-dihydropyridin-3-one (26a)

In a sealed flask, (1-benzyl-5-oxo-2,6-dihydropyridin-3-yl) trifluoromethanesulfonate (25b) (750 mg, 2.24 mmol) and 4-isoxazoleboronic acid pinacol ester (1.62 g, 3.58 mmol.) were dissolved in anhydrous THF (23 mL) in presence of Cs₂CO₃ (1.46 g, 4.47 mmol). The suspension was degassed under argon for 10 min and Pd(PPh₃)₄ (124 mg, 0.108 mmol) was added. The reaction was stirred at 55° C. for 30 min until complete conversion of starting material (25b). The mixture was filtered and concentrated under reduced pressure to afford a crude material which was purified by flash chromatography on silica gel (toluene/acetone 100/0 to 70/30) to give the desired coupling compound 1-benzyl-5-isoxazol-4-yl-2,6-dihydropyridin-3-one (26a) (445 mg, 1.74 mmol, 78%) as a yellow oil.

MS m/z ([M+H]⁺) 255.

$^1$H NMR (400 MHz, CDCl₃): δ (ppm) 3.31 (bs, 2H), 3.56 (s, 2H), 3.80 (s, 2H), 6.40 (t, J=1.4 Hz, 1H), 7.34-7.42 (m, 5H), 8.49 (s, 1H), 8.60 (s, 1H).

Step 2: Preparation of Intermediate benzyl 3-isoxazol-4-yl-5-oxo-2,6-dihydropyridine-1-carboxylate (26b)

1-benzyl-5-isoxazol-4-yl-2,6-dihydropyridin-3-one (26a) (601 mg, 2.36 mmol) was dissolved in DCE (20 mL) and benzyl chloroformate (1.7 mL, 11.82 mmol) was added. The reaction mixture was stirred 16 h at rt. The reaction was concentrated in vacuo and the crude residue was purified by flash chromatography on silica gel (toluene/acetone 100/0 to 70/30) and by chromatography on C18 reverse phase (H₂O/ACN 80/20 to 0/100) to give compound benzyl 3-isoxazol-4-yl-5-oxo-2,6-dihydropyridine-1-carboxylate (26b) (632 mg, 2.12 mmol, 90%).

MS m/z ([M+H]⁺) 299.

$^1$H NMR (400 MHz, CDCl₃): δ (ppm) 4.26 (s, 2H), 4.57 (bs, 2H), 5.21 (s, 2H), 6.43 (t, J=1.7 Hz, 1H), 7.32-7.42 (m, 5H), 8.53 (s, 1H), 8.77 (bs, 1H).

Step 3: Preparation of Intermediate benzyl 3-hydroxy-5-isoxazol-4-yl-3,6-dihydro-2H-pyridine-1-carboxylate (26c)

Benzyl 3-isoxazol-4-yl-5-oxo-2,6-dihydropyridine-1-carboxylate (26b) (632 mg, 2.12 mmol) was dissolved in MeOH (20 mL) at 0° C. NaBH₄ (96 mg, 2.54 mmol) was added by small portions and the reaction mixture was stirred at 0° C. for 5 min. The reaction was concentrated in vacuo approximatively to 4-5 mL of MeOH then diluted with EtOAc and washed with brine. The organic layer was dried over Na₂SO₄, filtered and concentrated. The residue benzyl 3-hydroxy-5-isoxazol-4-yl-3,6-dihydro-2H-pyridine-1-carboxylate (26c) was used in the next step without further purification.

MS m/z ([M+H]⁺) 301.

Step 4: Preparation of Intermediate benzyl-3-[allyloxy-(2-nitrophenyl)sulfonyl-amino]-5-isoxazol-4-yl-3,6-dihydro-2H-pyridine-1-carboxylate (26d)

Using the procedure described in example 25 (step 5), the intermediate benzyl 3-hydroxy-5-isoxazol-4-yl-3,6-dihydro-2H-pyridine-1-carboxylate (26c) (2.10 mmol) was converted into benzyl-3-[allyloxy-(2-nitrophenyl)sulfonyl-amino]-5-isoxazol-4-yl-3,6-dihydro-2H-pyridine-1-carboxylate (26d) as yellow foam (632 mg, 1.17 mmol, 56%), after purification by flash chromatography on silica gel (DCM/acetone 90/10 to 50/50).

MS m/z ([M+H]⁺) 541.

Step 5: Preparation of Intermediate benzyl 3-(allyloxyamino)-5-isoxazol-4-yl-3,6-dihydro-2H-pyridine-1-carboxylate (26e)

Using the procedure described in example 25 (step 6), the intermediate benzyl-3-[allyloxy-(2-nitrophenyl)sulfonyl-amino]-5-isoxazol-4-yl-3,6-dihydro-2H-pyridine-1-carboxylate (26d) (632 mg, 1.17 mmol) was converted into benzyl 3-(allyloxyamino)-5-isoxazol-4-yl-3,6-dihydro-2H-pyridine-1-carboxylate (26e) (92 mg, 0.259 mmol, 22%) as a yellow foam, after purification by flash chromatography on silica gel (toluene/acetone 100/0 to 80/20) and by chromatography on C18 reverse phase (H₂O/ACN 80/20 to 15/85).

MS m/z ([M+H]⁺) 356

Step 6: Preparation of Intermediate N-allyloxy-5-isoxazol-4-yl-1,2,3,6-tetrahydropyridin-3-amine (26f)

Using the procedure described in example 25 (step 7), the intermediate benzyl 3-(allyloxyamino)-5-isoxazol-4-yl-3,6-dihydro-2H-pyridine-1-carboxylate (25e) (92 mg, 0.259 mmol) was converted into N-allyloxy-5-isoxazol-4-yl-1,2,3,6-tetrahydropyridin-3-amine (26f) (45 mg, 0.203 mmol, 79%) as a yellowish oil, after purification by chromatography on Q$^{18}$ reverse phase (H$_2$O/ACN 98/2 to 30/70).

MS m/z ([M+H]$^+$) 222.

Step 7: Preparation of Intermediate 6-allyloxy-3-isoxazol-4-yl-1,6-diazabicyclo[3.2.1]oct-3-en-7-one (26g)

Using the procedure described in example 25 (step 8), the intermediate N-allyloxy-5-isoxazol-4-yl-1,2,3,6-tetrahydropyridin-3-amine (26f) (45 mg, 0.203 mmol) was converted into 6-allyloxy-3-isoxazol-4-yl-1,6-diazabicyclo[3.2.1]oct-3-en-7-one (26g) (9 mg, 0.036 mmol, 18%) after purification by chromatography on C18 reverse phase (H$_2$O/ACN 100/0 to 20/80).

MS m/z ([M+H]$^+$) 248.

$^1$H NMR (400 MHz, CDCl$_3$): δ (ppm) 3.17 (d, J=10.6 Hz, 1H), 3.54-3.60 (m, 1H), 3.94 (dd, J=17.3/2.2 Hz, 1H), 4.02 (dd, J=5.3/2.2 Hz, 1H), 4.08 (dd, J=17.3/0.9 Hz, 1H), 4.36-4.50 (m, 2H), 5.29-5.42 (m, 2H), 5.97-6.08 (m, 1H), 6.54-6.58 (m, 1H), 8.34 (s, 2H).

Step 8: Preparation of Intermediate triphenyl-(propenyl)-phosphonium [3-(isoxazol-4-yl)-7-oxo-1,6-diazabicyclo[3.2.1]oct-3-en-6-yl] sulfate (26h)

Using the procedure described in example 1 (step 6), the intermediate 6-allyloxy-3-isoxazol-4-yl-1,6-diazabicyclo[3.2.1]oct-3-en-7-one (26g) (9 mg, 0.036 mmol) was converted into triphenyl-(propenyl)-phosphonium [3-(isoxazol-4-yl)-7-oxo-1,6-diazabicyclo[3.2.1]oct-3-en-6-yl] sulfate (26h) after purification by flash chromatography on silica gel (DCM/acetone 100/0 to 0/100).

MS m/z ([M−H]$^−$) 286.

Step 9: Preparation of Sodium Salt of [3-(isoxazol-4-yl)-7-oxo-1,6-diazabicyclo[3.2.1]oct-3-en-6-yl] sulfate (Example 26)

Using the procedure described in example 1 (step 7), triphenyl-(propenyl)-phosphonium [3-(isoxazol-4-yl)-7-oxo-1,6-diazabicyclo[3.2.1]oct-3-en-6-yl] sulfate (26h) was converted after ion exchange (Dowex sodium form column) into sodium [3-(isoxazol-4-yl)-7-oxo-1,6-diazabicyclo[3.2.1]oct-3-en-6-yl] sulfate (Example 26) (3.8 mg, 0.012 mmol, 34% over 2 steps) as a white solid, after lyophilization.

MS m/z ([M−H]$^−$) 286.

$^1$H NMR (400 MHz, D$_2$O): δ (ppm) 3.36 (d, J=11.4 Hz, 1H), 3.58 (dd, J=11.4/2.4 Hz, 1H), 3.96 (dd, J=17.7/0.6 Hz, 1H), 4.11 (dd, J=17.7/2.2 Hz, 1H), 4.36 (dd, J=5.3/2.7 Hz, 1H), 6.57-6.64 (m, 1H), 8.56 (s, 1H), 8.59 (s, 1H).

Example 27

Synthesis of the Sodium [3-(1,3-benzothiazol-2-yl)-7-oxo-1,6-diazabicyclo[3.2.1]oct-3-en-6-yl] sulfate

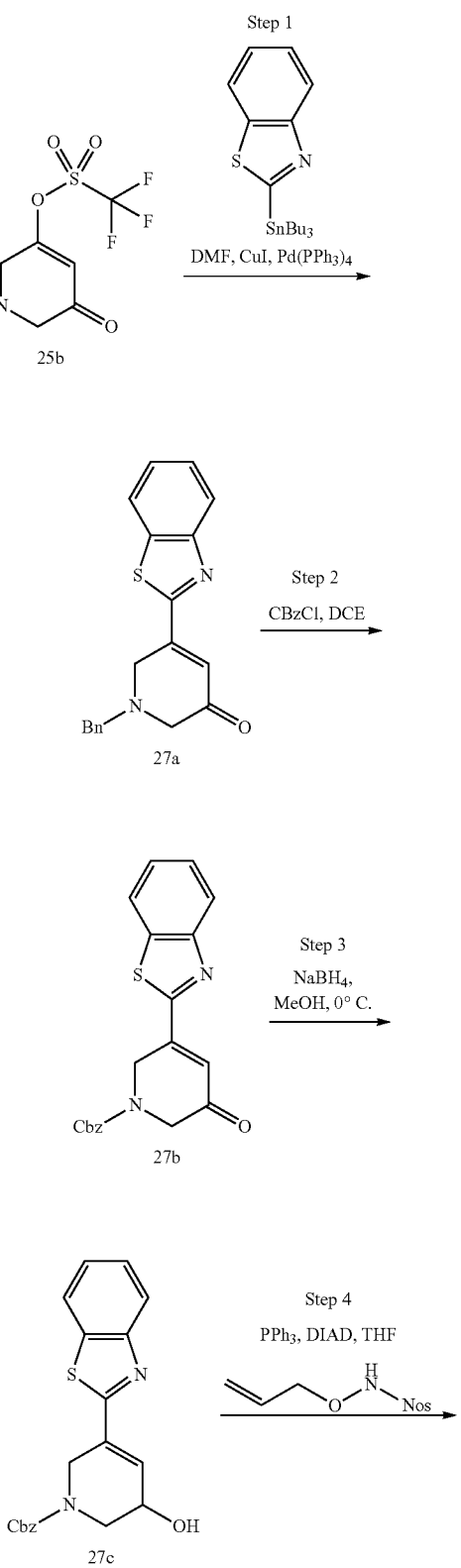

-continued

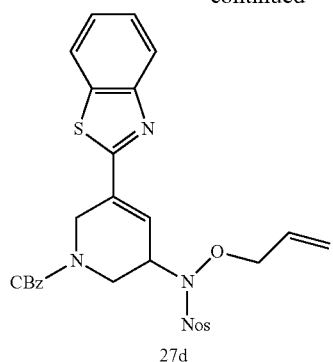

27d

Step 5
PhSH, K₂CO₃,
ACN
→

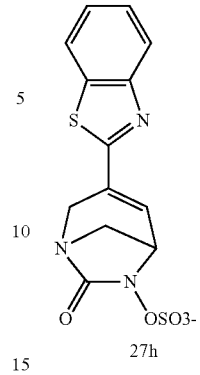

27h

Step 9
ion exchange Dowex Na+
→

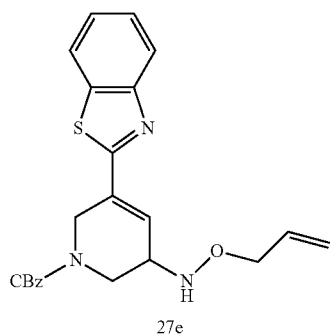

27e

Step 6
Diphosgene, TEA
DCM
→

Example 27

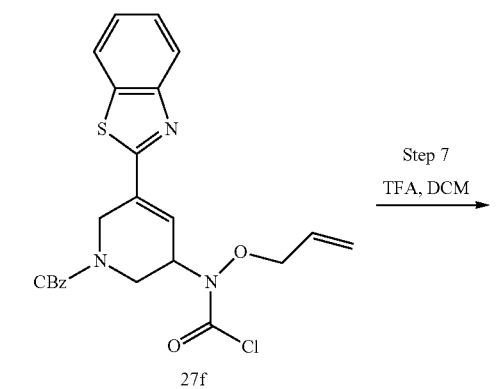

27f

Step 7
TFA, DCM
→

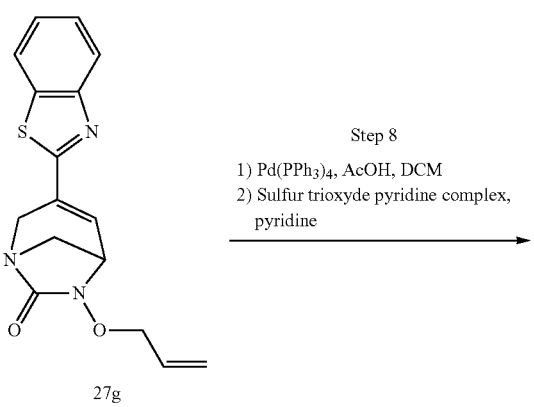

27g

Step 8
1) Pd(PPh₃)₄, AcOH, DCM
2) Sulfur trioxyde pyridine complex, pyridine
→

Step 1: Preparation of Intermediate 5-(1,3-benzothiazol-2-yl)-1-benzyl-2,6-dihydropyridin-3-one (27a)

In a sealed flask, (1-benzyl-5-oxo-2,6-dihydropyridin-3-yl) trifluoromethanesulfonate (25b) (1.51 g, 4.503 mmol) and 2-(tributylstannyl)-1,3-benzothiazole (2.1 g, 4.954 mmol) were dissolved in anhydrous DMF (45 mL). The solution was degassed under argon for 10 min and CuI (I) (0.858 g, 4.503 mmol) and Pd(Ph₃)₄ (0.520 g, 0.45 mmol) were successively added. The reaction was stirred at 60° C. for 45 min until complete conversion of starting material (25b). The reaction mixture was filtered on Isolute Si-TMT, the filtrate was concentrated under reduced pressure to afford a crude material which was purified by flash chromatography on silica gel (toluene/acetone 100/0 to 70/30) to give the desired coupling compound 5-(1,3-benzothiazol-2-yl)-1-benzyl-2,6-dihydropyridin-3-one (27a) (0.761 g, 2.375 mmol, 53%) as a yellow solid.

MS m/z ([M+H]⁺) 321.

¹H NMR (400 MHz, CDCl₃): δ (ppm) 3.28 (bs, 2H), 3.84 (s, 2H), 4.05 (bs, 2H), 6.79 (t, J=1.7 Hz, 1H), 7.28-7.37 (m, 5H), 7.44-7.54 (m, 2H), 7.87-7.94 (m, 1H), 8.03-8.09 (m, 1H).

Step 2: Preparation of Intermediate benzyl 3-(1,3-benzothiazol-2-yl)-5-oxo-2,6-dihydropyridine-1-carboxylate (27b)

Using the procedure described in example 26 (step 2), the intermediate 5-(1,3-benzothiazol-2-yl)-1-benzyl-2,6-dihydropyridin-3-one (27a) (761 mg, 2.375 mmol) was converted into benzyl 3-(1,3-benzothiazol-2-yl)-5-oxo-2,6-dihydropyridine-1-carboxylate (27b) (621 mg, 1.704 mmol, 72%) as a yellow solid, after purification by flash chromatography on silica gel (cyclohexane/ethyl acetate 100/0 to 70/30).

MS m/z ([M+H]⁺) 365.

¹H NMR (300 MHz, CDCl₃): δ (ppm) 4.32 (bs, 2H), 5.02 (bs, 2H), 5.23 (bs, 2H), 6.82 (t, J=1.8 Hz, 1H), 7.32-7.39 (m, 5H), 7.46-7.58 (m, 2H), 7.91-7.94 (m, 1H), 8.10-8.13 (m, 1H).

Step 3: Preparation of Intermediate benzyl 5-(1,3-benzothiazol-2-yl)-3-hydroxy-3,6-dihydro-2H-pyridine-1-carboxylate (27c)

Benzyl 3-(1,3-benzothiazol-2-yl)-5-oxo-2,6-dihydropyridine-1-carboxylate (27b) (0.798 g, 2.19 mmol) was dissolved in a mixture of THF/MeOH 1/5 (26 mL) at 0° C. NaBH₄ (99 mg, 2.628 mmol) was added by small portions and the reaction mixture was stirred at 0° C. for 30 min. The reaction was concentrated in vacuo approximatively to 4-5 mL of MeOH then diluted with EtOAc and washed with brine. The organic layer was dried over Na₂SO₄, filtered and concentrated. The crude residue was purified by flash chromatography on silica gel (cyclohexane/EtOAc 95/5 to 40/60) to give the compound benzyl 5-(1,3-benzothiazol-2-yl)-3-hydroxy-3,6-dihydro-2H-pyridine-1-carboxylate (27c) (434 mg, 1.184 mmol, 54%) as a yellow gum.

MS m/z ([M+H]⁺) 367.

¹H NMR (300 MHz, CDCl₃): δ (ppm) 3.53-3.96 (m, 2H), 4.40-4.78 (m, 3H), 5.20 (s, 2H), 6.74-6.79 (m, 1H), 7.30-7.49 (m, 7H), 7.82-7.85 (m, 1H), 7.98-8.01 (m, 1H).

Step 4: Preparation of Intermediate benzyl-3-[allyloxy-(2-nitrophenyl)sulfonyl-amino]-5-(1,3-benzothiazol-2-yl)-3,6-dihydro-2H-pyridine-1-carboxylate (27d)

Using the procedure described in example 25 (step 5), the intermediate benzyl 5-(1,3-benzothiazol-2-yl)-3-hydroxy-3,6-dihydro-2H-pyridine-1-carboxylate (27c) (434 mg, 1.184 mmol) was converted into benzyl-3-[allyloxy-(2-nitrophenyl)sulfonyl-amino]-5-(1,3-benzothiazol-2-yl)-3,6-dihydro-2H-pyridine-1-carboxylate (27d) (631 mg, 1.040 mmol, 88%) as a white foam, after purification by flash chromatography on silica gel (cyclohexane/EtOAc 100/0 to 50/50) followed by chromatography on C18 reverse phase (H₂O/ACN 70/30 to 0/100).

MS m/z ([M+H]⁺) 607, ([2M+H]⁺) 1213.

Step 5: Preparation of Intermediate benzyl 3-(allyloxyamino)-5-(1,3-benzothiazol-2-yl)-3,6-dihydro-2H-pyridine-1-carboxylate (27e)

Using the procedure described in example 25 (step 6), the intermediate benzyl-3-[allyloxy-(2-nitrophenyl)sulfonyl-amino]-5-(1,3-benzothiazol-2-yl)-3,6-dihydro-2H-pyridine-1-carboxylate (27d) (752 mg, 1.24 mmol) was converted into benzyl 3-(allyloxyamino)-5-(1,3-benzothiazol-2-yl)-3,6-dihydro-2H-pyridine-1-carboxylate (27e) (355 mg, 0.842 mmol, 68%) as a yellow gum, after purification by flash chromatography on silica gel (cyclohexane/EtOAc 100/0 to 0/100).

MS m/z ([M+H]⁺) 422, ([2M+H]⁺) 843.

Step 6: Preparation of benzyl 3-[allyloxy(chlorocarbonyl)amino]-5-(1,3-benzothiazol-2-yl)-3,6-dihydro-2H-pyridine-1-carboxylate (27f)

To a solution of benzyl 3-(allyloxyamino)-5-(1,3-benzothiazol-2-yl)-3,6-dihydro-2H-pyridine-1-carboxylate (27e) (302 mg, 0.716 mmol) in anhydrous DCM (7.2 mL) at 0° C. under nitrogen atmosphere were added TEA (200 μL, 1.433 mmol) followed by diphosgene (112 μL, 0.931 mmol). The mixture was stirred at 0° C. for 5 min, diluted with DCM (10 mL) and washed with brine (5 mL). The organic layer was dried over Na₂SO₄, and concentrated in vacuo to provide compound benzyl 3-[allyloxy(chlorocarbonyl)amino]-5-(1,3-benzothiazol-2-yl)-3,6-dihydro-2H-pyridine-1-carboxylate (27f) which was used in the next step without further purification.

MS m/z ([M+H]⁺) 484/486.

Step 7: Preparation of Intermediate 6-allyloxy-3-(1,3-benzothiazol-2-yl)-1,6-diazabicyclo[3.2.1]oct-3-en-7-one (27g)

Under a nitrogen atmosphere, TFA (5.8 mL) was added drop by drop to a solution of benzyl 3-[allyloxy(chlorocarbonyl)amino]-5-(1,3-benzothiazol-2-yl)-3,6-dihydro-2H-pyridine-1-carboxylate (27f) (0.716 mmol) in anhydrous DCM (1.4 mL). After stirring overnight at rt, the reaction mixture was heating 20 h at 40° C. The reaction mixture was concentrated under vacuum and directly purified by flash chromatography on silica gel (cyclohexane/EtOAc 100/0 to 50/50) to afford compound 6-allyloxy-3-(1,3-benzothiazol-2-yl)-1,6-diazabicyclo[3.2.1]oct-3-en-7-one (27g) (85.6 mg, 0.273 mmol, 38% over 2 steps) as an orange gum.

MS m/z ([M+H]⁺) 314, ([2M+H]⁺) 627.

¹H NMR (300 MHz, CDCl₃): δ (ppm) 3.21 (d, J=10.9 Hz, 1H), 3.62 (dd, J=10.9/2.9 Hz, 1H), 4.14 (dd, J=5.2/2.7 Hz, 1H), 4.31 (dd, J=18.0/2.1 Hz, 1H), 4.42-4.57 (m, 3H), 5.31-5.42 (m, 2H), 5.96-6.10 (m, 1H), 7.15 (m, 1H), 7.37-7.49 (m, 2H), 7.82-7.85 (m, 1H), 7.96-7.99 (m, 1H).

Step 8: Preparation of Intermediate triphenyl-(propenyl)-phosphonium [3-(1,3-benzothiazol-2-yl)-7-oxo-1,6-diazabicyclo[3.2.1]oct-3-en-6-yl] sulfate (27h)

Using the procedure described in example 1 (step 6), the intermediate 6-allyloxy-3-(1,3-benzothiazol-2-yl)-1,6-diazabicyclo[3.2.1]oct-3-en-7-one (27g) (98 mg, 0.313 mmol) was converted into triphenyl-(propenyl)-phosphonium [3-(1,3-benzothiazol-2-yl)-7-oxo-1,6-diazabicyclo[3.2.1]oct-3-en-6-yl] sulfate (27h) after purification by flash chromatography on silica gel (DCM/acetone 100/0 to 0/100).

MS m/z ([M−H]⁻) 352.

MS m/z ([M+H]⁺) 303 (triphenyl-propenyl-phosphonium).

Step 9: Preparation of Sodium [3-(1,3-benzothiazol-2-yl)-7-oxo-1,6-diazabicyclo[3.2.1]oct-3-en-6-yl] sulfate (Example 27)

Using the procedure described in example 1 (step 7), triphenyl-(propenyl)-phosphonium [3-(1,3-benzothiazol-2-yl)-7-oxo-1,6-diazabicyclo[3.2.1]oct-3-en-6-yl] sulfate (27h) was converted after ion exchange (Dowex sodium form column) into sodium [3-(1,3-benzothiazol-2-yl)-7-oxo-1,6-diazabicyclo[3.2.1]oct-3-en-6-yl] sulfate (Example 27) (53 mg, 0.141 mmol, 45% over 3 steps) as a white solid, after lyophilization.

MS m/z ([M+H]⁺) 354.

MS m/z ([M−H]⁻) 352.

¹H NMR (300 MHz, D₂O): δ (ppm) 3.41 (d, J=11.4 Hz, 1H), 3.73 (dd, J=11.4/2.9 Hz, 1H), 4.22 (d, J=1.7 Hz, 2H), 4.57 (dd, J=5.3/2.6 Hz, 1H), 7.14 (dd, J=5.4/1.3 Hz, 1H), 7.39-7.48 (m, 2H), 7.61-7.65 (m, 1H), 7.79-7.82 (m, 1H).
Example 28
Synthesis of Sodium [3-(1-methyl-6-oxo-3-pyridyl)-7-oxo-1,6-diazabicyclo[3.2.1]oct-3-en-6-yl] sulfate
Step 1
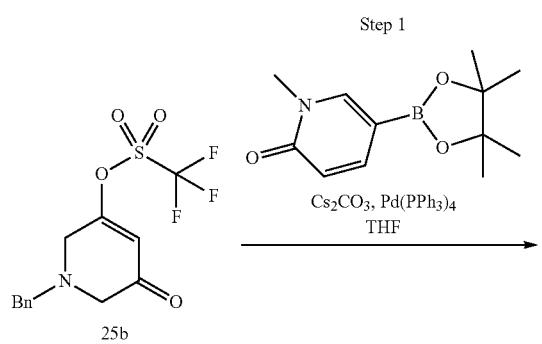
Step 2
CBzCl, DCE
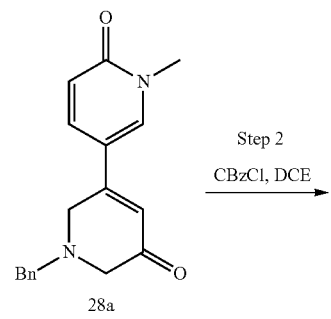
Step 3
NaBH₄, MeOH, 0° C.
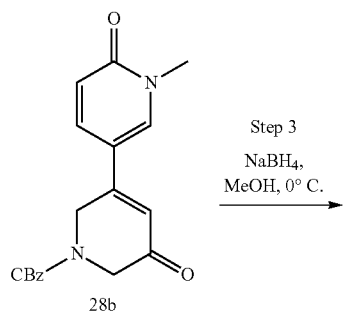
Step 4
PPh₃, DIAD, THF
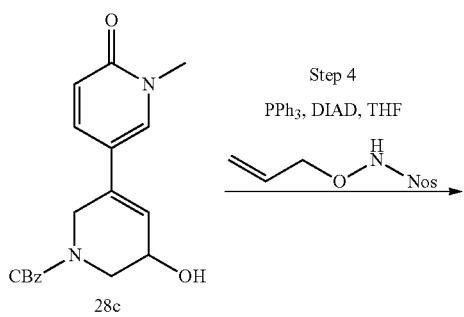
Step 5
PhSH, K₂CO₃
ACN
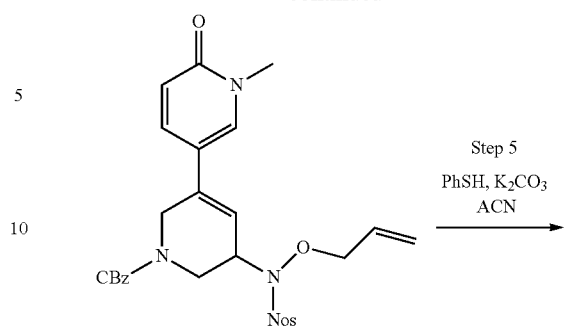
Step 6
Diphosgene, TEA
DCM
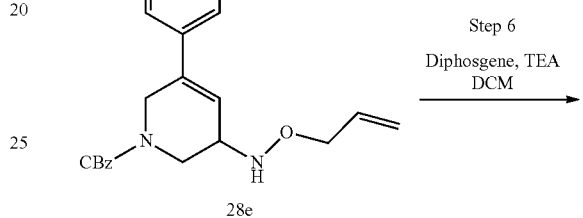
Step 7
TMSOTf, DCM
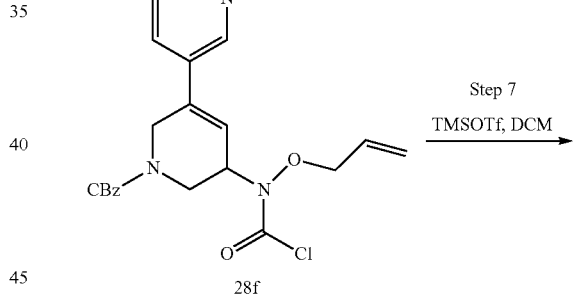
Step 8
1) Pd(PPh₃)₄, AcOH, DCM
2) Sulfur trioxyde pyridine complex, pyridine
3) ion exchange Dowex Na+

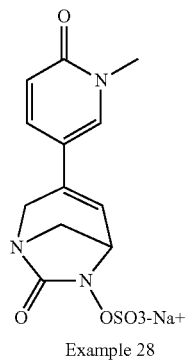

Example 28

Step 1: Preparation of Intermediate 1-benzyl-5-(1-methyl-6-oxo-3-pyridyl)-2,6-dihydropyridin-3-one (28a)

Using the procedure described in example 26 (step 1), the intermediate (1-benzyl-5-oxo-2,6-dihydropyridin-3-yl) trifluoromethanesulfonate (25b) (800 mg, 2.39 mmol) is converted into 1-benzyl-5-(1-methyl-6-oxo-3-pyridyl)-2,6-dihydropyridin-3-one (28a) (395 mg, 1.34 mmol, 56%) as a yellow oil, using 1-methyl-5-(4,4,5,5-tetramethyl-1,3,2-dioxaborolan-2-yl)pyridin-2-one (785 mg, 3.34 mmol) and after purification by flash chromatography on silica gel (DCM/iPrOH 100/0 to 80/20).

MS m/z ([M+H]$^+$) 295.

$^1$H NMR (400 MHz, CDCl$_3$): δ (ppm) 3.25 (bs, 2H), 3.54 (bs, 2H), 3.59 (s, 3H), 3.78 (bs, 2H), 6.33 (t, J=1.5 Hz, 1H), 6.63 (d, J=9.5 Hz, 1H), 7.31-7.41 (m, 5H), 7.47 (d, J=2.7 Hz, 1H), 7.52 (dd, J=9.5/2.7 Hz, 1H).

Step 2: Preparation of Intermediate benzyl 3-(1-methyl-6-oxo-3-pyridyl)-5-oxo-2,6-dihydropyridine-1-carboxylate (28b)

1-benzyl-5-(1-methyl-6-oxo-3-pyridyl)-2,6-dihydropyridin-3-one (28a) (395 mg, 1.34 mmol) was dissolved in DCE (15 mL) and CbzCl (0.67 mL, 4.70 mmol) was added. The reaction mixture was stirred 1 h at 55° C. The reaction was concentrated in vacuo and the crude residue was purified by flash chromatography on silica gel (toluene/acetone 100/0 to 50/50) to give compound benzyl 3-(1-methyl-6-oxo-3-pyridyl)-5-oxo-2,6-dihydropyridine-1-carboxylate (28b) (341 mg, 1.01 mmol, 75%).

MS m/z ([M+H]$^+$) 339.

$^1$H NMR (400 MHz, CDCl$_3$): δ (ppm) 3.62 (s, 3H), 4.22 (bs, 2H), 4.56 (bs, 2H), 5.21 (s, 2H), 6.37 (t, J=1.6 Hz, 1H), 6.65 (d, J=9.6 Hz, 1H), 7.31-7.44 (m, 5H), 7.53-7.75 (m, 2H).

Step 3: Preparation of Intermediate benzyl 3-hydroxy-5-(1-methyl-6-oxo-3-pyridyl)-3,6-dihydro-2H-pyridine-1-carboxylate (28c)

Benzyl 3-(1-methyl-6-oxo-3-pyridyl)-5-oxo-2,6-dihydropyridine-1-carboxylate (28b) (341 mg, 1.01 mmol) was dissolved in MeOH (10 mL) and THF (3 mL) at 0° C. with heptahydrate CeCl$_3$ (431 mg, 1.16 mmol). NaBH$_4$ (44 mg, 1.16 mmol) was added by small portions and the reaction mixture was stirred at 0° C. for 15 min. The reaction was concentrated in vacuo approximately to 4-5 mL of MeOH then diluted with EtOAc. The mixture was filtered off, cooled down to 0° C. The pH was adjusted to 4-5 with a 0.2 N aqueous solution of HCl. The organic layer was dried over Na$_2$SO$_4$, filtered and concentrated. The benzyl 3-hydroxy-5-(1-methyl-6-oxo-3-pyridyl)-3,6-dihydro-2H-pyridine-1-carboxylate (28c) (341 mg, 1.00 mmol, 99%) was used in the next step without further purification.

MS m/z ([M+H]$^+$) 341.

Step 4: Preparation of Intermediate benzyl-3-[allyloxy-(2-nitrophenyl)sulfonyl-amino]-5-(1-methyl-6-oxo-3-pyridyl)-3,6-dihydro-2H-pyridine-1-carboxylate (28d)

Using the procedure described in example 25 (step 5), the intermediate benzyl 3-hydroxy-5-(1-methyl-6-oxo-3-pyridyl)-3,6-dihydro-2H-pyridine-1-carboxylate (28c) (1.00 mmol) was converted into benzyl-3-[allyloxy-(2-nitrophenyl)sulfonyl-amino]-5-(1-methyl-6-oxo-3-pyridyl)-3,6-dihydro-2H-pyridine-1-carboxylate (28d) (431 mg, 0.74 mmol, 74%) as yellow foam, after purification by flash chromatography on silica gel (DCM/iPrOH 100/0 to 70/30).

MS m/z ([M+H]$^+$) 581.

Step 5: Preparation of Intermediate benzyl 3-(allyloxyamino)-5-(1-methyl-6-oxo-3-pyridyl)-3,6-dihydro-2H-pyridine-1-carboxylate (28e)

Using the procedure described in example 25 (step 6), the intermediate benzyl-3-[allyloxy-(2-nitrophenyl)sulfonyl-amino]-5-(1-methyl-6-oxo-3-pyridyl)-3,6-dihydro-2H-pyridine-1-carboxylate (28d) (431 mg, 0.74 mmol) was converted into benzyl 3-(allyloxyamino)-5-(1-methyl-6-oxo-3-pyridyl)-3,6-dihydro-2H-pyridine-1-carboxylate (28e) (199 mg, 0.503 mmol, 68%) as a yellow foam, after purification by chromatography on C18 reverse phase (H$_2$O/ACN 90/10 to 0/100).

MS m/z ([M+H]$^+$) 396.

Step 6: Preparation of Intermediate N-allyloxy-N-[1-methyl-5-(1-methyl-6-oxo-3-pyridyl)-3,6-dihydro-2H-pyridin-3-yl]carbamoyl chloride (28f)

Under inert atmosphere, diphosgene (79 μL, 0.654 mmol) was added to a solution of benzyl 3-(allyloxyamino)-5-(1-methyl-6-oxo-3-pyridyl)-3,6-dihydro-2H-pyridine-1-carboxylate (28e) (199 mg, 0.503 mmol) in anhydrous DCM (5 mL) at 0° C. in presence of TEA (140 μL, 1.01 mmol). After stirring 30 min at rt, the reaction was diluted with DCM (5 mL) and washed with a 2 M aqueous solution of NaH$_2$PO$_4$ (3 mL). The organic layer was dried over Na$_2$SO$_4$, filtered and concentrated. The crude material was purified by chromatography on C18 reverse phase (H$_2$O/ACN 98/2 to 50/50) to give N-allyloxy-N-[1-methyl-5-(1-methyl-6-oxo-3-pyridyl)-3,6-dihydro-2H-pyridin-3-yl]carbamoyl chloride (28f) (183 mg, 0.400 mmol, 80%) as a pale yellow foam.

MS m/z ([M+H]$^+$) 458/460.

Step 7: Preparation of Intermediate 6-allyloxy-3-(1-methyl-6-oxo-3-pyridyl)-1,6-diazabicyclo[3.2.1]oct-3-en-7-one (28g)

Under inert atmosphere, the intermediate N-allyloxy-N-[1-methyl-5-(1-methyl-6-oxo-3-pyridyl)-3,6-dihydro-2H- pyridin-3-yl]carbamoyl chloride (28f) (120 mg, 0.262 mmol) was dissolved in anhydrous DCM (2.6 mL). TBDM-SOTf (237 μL, 1.31 mmol) was added and the resulting solution was warmed up to 45° C. for 24 h. The reaction mixture was cooled down to 0° C., TEA was added (1.18 mL, 8.50 mmol) and concentrated under reduced pressure. The residue was diluted with DCM (5 mL) and washed with a 2 M aqueous solution of NaH$_2$PO$_4$ (3 mL). The organic layer was dried over Na$_2$SO$_4$, filtered, dried under reduced pressure and the crude residue was purified by chromatography on C18 reverse phase (H$_2$O/ACN 98/2 to 50/50) to give 6-allyloxy-3-(1-methyl-6-oxo-3-pyridyl)-1,6-diazabicyclo[3.2.1]oct-3-en-7-one (28g) (41 mg, 0.143 mmol, 54%).

MS m/z ([M+H]$^+$) 288.

Step 8: Preparation of Sodium [3-(1-methyl-6-oxo-3-pyridyl)-7-oxo-1,6-diazabicyclo[3.2.1]oct-3-en-6-yl] sulfate (Example 28)

To a solution of 6-allyloxy-3-(1-methyl-6-oxo-3-pyridyl)-1,6-diazabicyclo[3.2.1]oct-3-en-7-one (28g) (40 mg, 0.140 mmol) under inert atmosphere with glacial AcOH (16 μL, 0.279 mmol) in anhydrous DCM (2.8 mL) was added in one portion Pd(Ph$_3$)$_4$ (81 mg, 0.070 mmol). After stirring 2 h at rt the reaction was completed. To this solution was added anhydrous pyridine (2.8 mL) followed by the sulfur trioxide pyridine complex (111 mg, 0.698 mmol) and the resulting suspension was protected from light and stirred overnight. The reaction mixture was concentrated under vacuum, diluted with DCM and filtered. The filtrate was dried under vacuum and diluted in ACN (0.5 mL) and was applied on a Dowex sodium form column (Dowex® 50WX8 hydrogen form stored with an aqueous solution of 2N NaOH and washed until neutral pH with H$_2$O). The fractions containing the desired compound were combined, frozen and lyophilized to afford finally a mixture of the desired compound as sodium salt and the non-sulfated compound (16 mg). This mixture was diluted with pyridine and sulfur trioxide pyridine complex was added (52 mg, 0.324 mmol). The suspension was protected from light and warmed up to 45° C. for 60 h. The solvent was removed under reduced pressure and the residue was diluted with H$_2$O (5 mL) and concentrated to approximatively 400 μL. This suspension was applied on a Dowex sodium form column (Dowex® 50WX8 hydrogen form stored with an aqueous solution of 2N NaOH and washed until neutral pH with H$_2$O). The fractions were pooled, concentrated to dryness and purified by chromatography on C18 reverse phase (H$_2$O/ACN 98/2 to 80/20). The combined fractions were freeze-dried to give sodium [3-(1-methyl-6-oxo-3-pyridyl)-7-oxo-1,6-diazabicyclo[3.2.1]oct-3-en-6-yl] sulfate (Example 28) (3.8 mg, 0.011 mmol, 7%).

MS m/z ([M–H]$^-$) 326.

$^1$H NMR (400 MHz, D$_2$O): δ (ppm) 3.29 (d, J=11.1 Hz, 1H), 3.45 (s, 3H), 3.55 (dd, J=11.1/2.4 Hz, 1H), 3.96 (d, J=17.7 Hz, 1H), 4.08 (dd, J=17.7/2.4 Hz, 1H), 4.35 (dd, J=5.6/2.7 Hz, 1H), 6.48 (d, J=9.4 Hz, 1H), 6.52-6.54 (m, 1H), 7.51 (d, J=2.4 Hz, 1H), 7.61 (d, J=9.4/2.4 Hz, 1H).

Example 29

Synthesis of Sodium [4-(isothiazol-4-yl)-7-oxo-1,6-diazabicyclo[3.2.1]oct-3-en-6-yl] sulfate

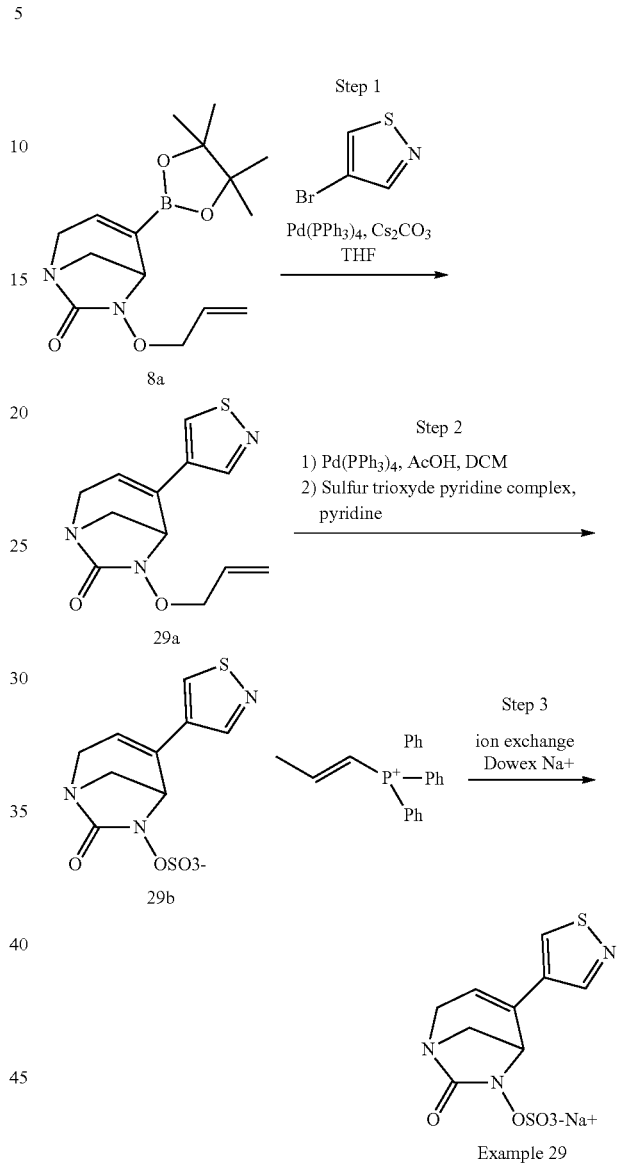

Step 1: Preparation of Intermediate 6-allyloxy-4-(isothiazol-4-yl)-1,6-diazabicyclo[3.2.1]oct-3-en-7-one (29a)

In a Wheaton vial, (6-allyloxy-4-(4,4,5,5-tetramethyl-1,3,2-dioxaborolan-2-yl)-1,6-diazabicyclo[3.2.1]oct-3-en-7-one (8a) (150 mg, 0.490 mmol), 4-bromo-isothiazole (121 mg, 0.735 mmol), dry C$_2$CO$_3$ (319 mg, 0.98 mmol) were dissolved in anhydrous THF (9.8 mL). The solution was degassed under argon for 5 min and Pd(PPh$_3$)$_4$ catalyst (113 mg, 0.098 mmol) was added. The reaction was stirred at 80° C. for 4 h under microwaves. The mixture was filtered and concentrated under reduced pressure to afford a crude material which was purified by preparative TLC (DCM/EtOAc 80/20) to give the desired product 6-allyloxy-4-(isothiazol-4-yl)-1,6-diazabicyclo[3.2.1]oct-3-en-7-one (29a) (61.5 mg, 0.233 mmol, 48%) as a gum.

MS m/z ([M+H]+) 264.
MS m/z ([M–H]−) 262.
¹H NMR (300 MHz, CDCl₃): δ (ppm) 3.15 (d, J=10.8 Hz, 1H), 3.62 (dd, J=10.8/3.0 Hz, 1H), 3.81-4.01 (m, 2H), 4.17-4.18 (m, 1H), 4.39-4.53 (m, 2H), 5.29-5.39 (m, 2H), 5.95-6.08 (m, 2H), 8.45 (s, 1H), 8.53 (s, 1H).

Step 2: Preparation of Intermediate triphenyl-(propenyl)-phosphonium [4-(isothiazol-4-yl)-7-oxo-1,6-diazabicyclo[3.2.1]oct-3-en-6-yl] sulfate (29b)

Using the procedure described in example 1 (step 6), the intermediate 6-allyloxy-4-(isothiazol-4-yl)-1,6-diazabicyclo[3.2.1]oct-3-en-7-one (29a) (61.5 mg, 0.233 mmol) was converted into triphenyl-(propenyl)-phosphonium [4-(isothiazol-4-yl)-7-oxo-1,6-diazabicyclo[3.2.1]oct-3-en-6-yl] sulfate (29b) (95 mg) as an amorphous solid after purification by flash chromatography on silica gel (DCM/acetone 100/0 to 20/80).

MS m/z ([M+H]+) 304.
MS m/z ([M–H]−) 302.
MS m/z ([M+H]+) 303 (triphenyl-propenyl-phosphonium).

Step 3: Preparation of Sodium [4-(isothiazol-4-yl)-7-oxo-1,6-diazabicyclo[3.2.1]oct-3-en-6-yl] sulfate (Example 29)

Using the procedure described in example 1 (step 7), triphenyl-(propenyl)-phosphonium [4-(isothiazol-4-yl)-7-oxo-1,6-diazabicyclo[3.2.1]oct-3-en-6-yl] sulfate (29b) (95 mg) was converted after ion exchange (Dowex sodium form column) into sodium [4-(isothiazol-4-yl)-7-oxo-1,6-diazabicyclo[3.2.1]oct-3-en-6-yl] sulfate (Example 29) (48 mg, 0.147 mmol, 63% over 2 steps) as a white amorphous solid after lyophilization.

MS m/z ([M+H]+) 304.
MS m/z ([M–H]−) 302.
¹H NMR (300 MHz, D₂O): δ (ppm) 3.47 (d, J=11.3 Hz, 1H), 3.74 (dd, J=11.4/3.1 Hz, 1H), 3.86 (dd, J=19.0/3.5 Hz, 1H), 4.04 (dd, J=19.0/2.1 Hz, 1H), 4.76 (d, J=3.6 Hz, 1H), 6.15 (s, 1H), 8.63 (s, 1H), 8.80 (s, 1H).

Example 30

Synthesis of Sodium [4-(isothiazol-5-yl)-7-oxo-1,6-diazabicyclo[3.2.1]oct-3-en-6-yl] sulfate

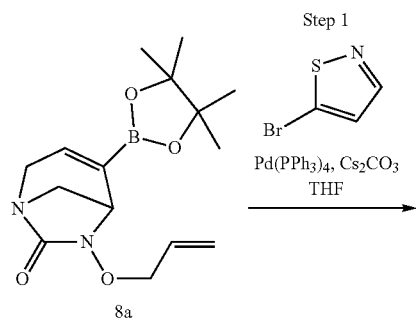
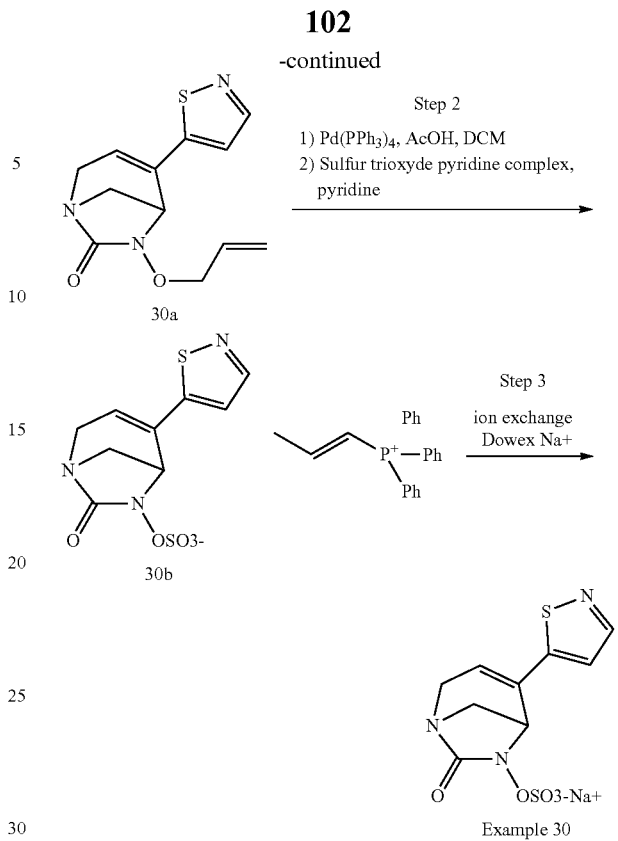

Example 30

Step 1: Preparation of Intermediate 6-allyloxy-4-(isothiazol-5-yl)-1,6-diazabicyclo[3.2.1]oct-3-en-7-one (30a)

In a Wheaton vial, (6-allyloxy-4-(4,4,5,5-tetramethyl-1,3,2-dioxaborolan-2-yl)-1,6-diazabicyclo[3.2.1]oct-3-en-7-one (8a) (150 mg, 0.490 mmol), 5-bromo-isothiazole (121 mg, 0.735 mmol), dry Cs₂CO₃ (319 mg, 0.98 mmol) were dissolved in anhydrous THF (4.9 mL). The solution was degassed under argon for 5 min and Pd(PPh₃)₄ catalyst (113 mg, 0.098 mmol) was added. The reaction was stirred at 80° C. for 1 h30 and at 100° C. for 2 h under microwaves. The reaction mixture was diluted with EtOAc and washed with H₂O. The organic phase was dried over Na₂S₂O₄, filtered and concentrated under reduced pressure to afford a crude material which was purified by preparative TLC (cyclohexane/EtOAc 40/60) to give the desired product 6-allyloxy-4-(isothiazol-5-yl)-1,6-diazabicyclo[3.2.1]oct-3-en-7-one (30a) (64.8 mg, 0.246 mmol, 50%) as a colourless gum.

MS m/z ([M+H]+) 264.
¹H NMR (300 MHz, CDCl₃): δ (ppm) 3.21 (d, J=10.9 Hz, 1H), 3.62 (dd, J=10.9/3.0 Hz, 1H), 3.81-4.02 (m, 2H), 4.18-4.20 (m, 1H), 4.38-4.52 (m, 2H), 5.29-5.39 (m, 2H), 5.95-6.10 (m, 2H), 7.13 (d, J=1.8 Hz, 1H), 8.39 (d, J=1.8 Hz, 1H).

Step 2: Preparation of Intermediate triphenyl-(propenyl)-phosphonium [4-(isothiazol-5-yl)-7-oxo-1,6-diazabicyclo[3.2.1]oct-3-en-6-yl] sulfate (30b)

Using the procedure described in example 1 (step 6), the intermediate 6-allyloxy-4-(isothiazol-5-yl)-1,6-diazabicyclo[3.2.1]oct-3-en-7-one (30a) (65 mg, 0.246 mmol) was converted into triphenyl-(propenyl)-phosphonium [4-(isothiazol-5-yl)-7-oxo-1,6-diazabicyclo[3.2.1]oct-3-en-6-yl] sulfate (30b) (79.3 mg) as an amorphous solid after purification by flash chromatography on silica gel (DCM/acetone 100/0 to 30/70).

MS m/z ([M+H]⁺) 304.
MS m/z ([M–H]⁻) 302.
MS m/z ([M+H]⁺) 303 (triphenyl-propenyl-phosphonium).

Step 3: Preparation of Sodium [4-(isothiazol-5-yl)-7-oxo-1,6-diazabicyclo[3.2.1]oct-3-en-6-yl] sulfate (Example 30)

Using the procedure described in example 1 (step 7), triphenyl-(propenyl)-phosphonium [4-(isothiazol-5-yl)-7-oxo-1,6-diazabicyclo[3.2.1]oct-3-en-6-yl] sulfate (31b) was converted after ion exchange (Dowex sodium form column) into sodium [4-(isothiazol-5-yl)-7-oxo-1,6-diazabicyclo [3.2.1]oct-3-en-6-yl] sulfate (Example 30) (36 mg, 0.111 mmol, 45% over 2 steps) as a white amorphous solid after lyophilization.

MS m/z ([M+H]⁺) 304.
MS m/z ([M–H]⁻) 302.
¹H NMR (300 MHz, D₂O): δ (ppm) 3.50 (d, J=11.4 Hz, 1H), 3.74-3.79 (m, 1H), 3.90 (dd, J=19.4/3.6 Hz, 1H), 4.06 (dd, J=19.4/2.3 Hz, 1H), 4.76-4.77 (m, 1H), 6.15-6.30 (m, 1H), 7.37 (d, J=1.9 Hz, 1H), 8.43 (d, J=1.9 Hz, 1H).

Example 31

Synthesis of Sodium [4-(thiazol-4-yl)-7-oxo-1,6-diazabicyclo[3.2.1]oct-3-en-6-yl] sulfate

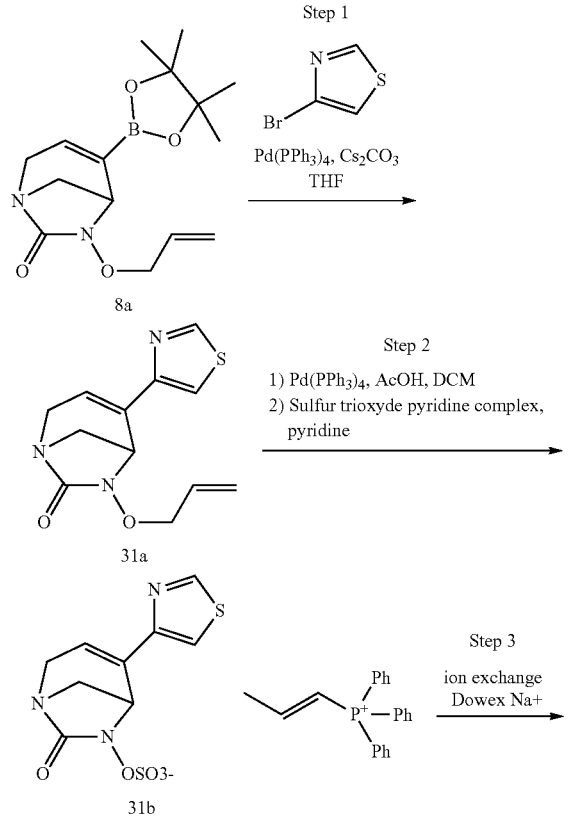

Example 31

Step 1: Preparation of Intermediate 6-allyloxy-4-(thiazol-4-yl)-1,6-diazabicyclo[3.2.1]oct-3-en-7-one (31a)

In a Wheaton vial, (6-allyloxy-4-(4,4,5,5-tetramethyl-1,3,2-dioxaborolan-2-yl)-1,6-diazabicyclo[3.2.1]oct-3-en-7-one (8a) (114 mg, 0.372 mmol), 4-bromothiazole (91 mg, 0.558 mmol), dry Cs₂CO₃ (242 mg, 0.74 mmol) were dissolved in anhydrous THF (3.7 mL). The solution was degassed under argon for 5 min and Pd(PPh₃)₄ catalyst (86 mg, 0.074 mmol) was added. The reaction was stirred at 100° C. for 5 h under microwaves. The reaction mixture was diluted with EtOAc and washed with H₂O. The organic phase was dried over Na₂SO₄, filtered and concentrated under reduced pressure to afford a crude material which was purified by preparative TLC (dichloromethane/EtOAc 60/40) to give the desired product 6-allyloxy-4-(thiazol-4-yl)-1,6-diazabicyclo[3.2.1] oct-3-en-7-one (31a) (31 mg, 0.118 mmol, 32%) as a colourless gum.

MS m/z ([M+H]⁺) 264.
¹H NMR (300 MHz, CDCl₃): δ (ppm) 3.21 (d, J=10.8 Hz, 1H), 3.63 (dd, J=10.8/3.1 Hz, 1H), 3.85-4.04 (m, 2H), 4.36-4.49 (m, 2H), 4.52-4.53 (m, 1H), 5.26-5.36 (m, 2H), 5.93-6.06 (m, 1H), 6.36-6.39 (m, 1H), 7.22 (d, J=1.9 Hz, 1H), 8.77 (d, J=1.9 Hz, 1H).

Step 2: Preparation of Intermediate triphenyl-(propenyl)-phosphonium [4-(thiazol-4-yl)-7-oxo-1,6-diazabicyclo[3.2.1]oct-3-en-6-yl] sulfate (31b)

Using the procedure described in example 1 (step 6), the intermediate 6-allyloxy-4-(thiazol-4-yl)-1,6-diazabicyclo [3.2.1]oct-3-en-7-one (31a) (30 mg, 0.114 mmol) was converted into triphenyl-(propenyl)-phosphonium [4-(thiazol-4-yl)-7-oxo-1,6-diazabicyclo[3.2.1]oct-3-en-6-yl] sulfate (31b) (34.6 mg) as an amorphous solid after purification by flash chromatography on silica gel (DCM/acetone 100/0 to 30/70).

MS m/z ([M+H]⁺) 304.
MS m/z ([M–H]⁻) 302.
MS m/z ([M+H]⁺) 303 (triphenyl-propenyl-phosphonium).

Step 3: Preparation of Sodium [4-(thiazol-4-yl)-7-oxo-1,6-diazabicyclo[3.2.1]oct-3-en-6-yl]sulfate sodium (Example 31)

Using the procedure described in example 1 (step 7), triphenyl-(propenyl)-phosphonium [4-(thiazol-4-yl)-7-oxo-1,6-diazabicyclo[3.2.1]oct-3-en-6-yl] sulfate (31b) (34.6 mg) was converted after ion exchange (Dowex sodium form column) into sodium [4-(thiazol-4-yl)-7-oxo-1,6-diazabicyclo[3.2.1]oct-3-en-6-yl] sulfate (Example 31) (13 mg, 0.040 mmol, 35% over 2 steps) as a white amorphous solid after lyophilization.

MS m/z ([M−H]⁻) 302.

¹H NMR (300 MHz, D₂O): δ (ppm) 3.49 (d, J=11.3 Hz, 1H), 3.74-3.79 (m, 1H), 3.91 (dd, J=19.1/3.6 Hz, 1H), 4.10 (dd, J=19.1/2.2 Hz, 1H), 4.90-4.91 (m, 1H), 6.40-6.43 (m, 1H), 7.60 (d, J=1.9 Hz, 1H), 8.98 (d, J=1.9 Hz, 1H).

Example 32: Synthesis of Sodium [4-[2-(aminomethyl)thiazol-5-yl]-7-oxo-1,6-diazabicyclo[3.2.1]oct-3-en-6-yl] sulfate

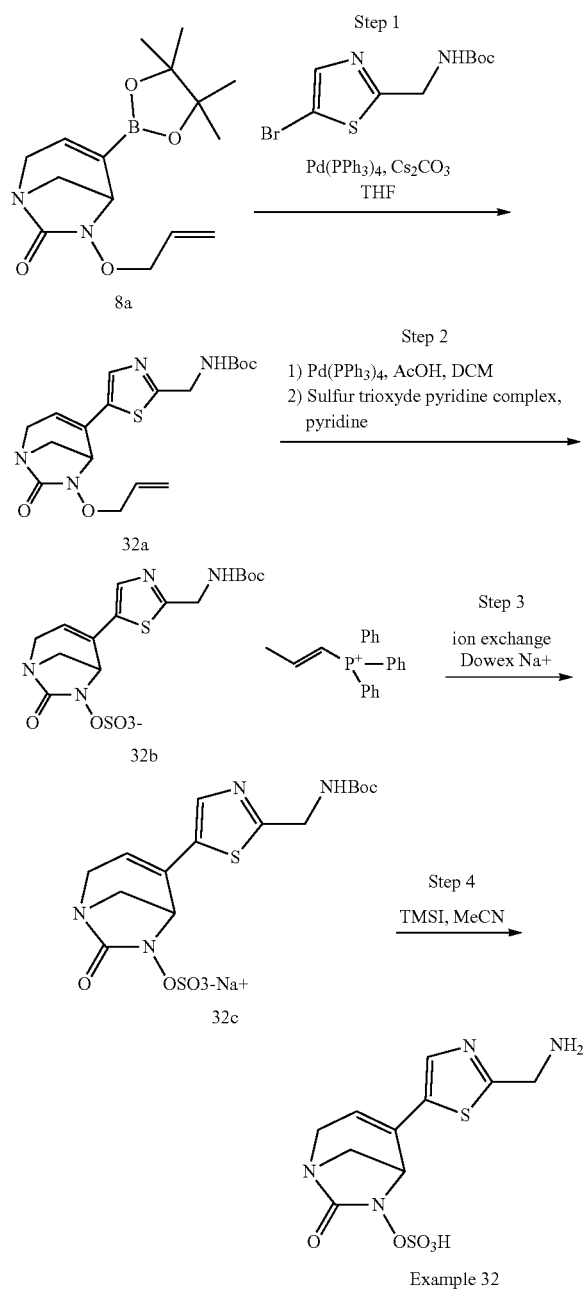

Example 32

Step 1: Preparation of Intermediate 6-allyloxy-4-[2-[(tert-butoxycarbonylamino)methyl]thiazol-5-yl]-1,6-diazabicyclo[3.2.1]oct-3-en-7-one (32a)

In a Wheaton vial, (6-allyloxy-4-(4,4,5,5-tetramethyl-1,3,2-dioxaborolan-2-yl)-1,6-diazabicyclo[3.2.1]oct-3-en-7-one (8a) (269 mg, 0.879 mmol), tert-butyl((2-bromothiazol-5-yl)methyl)carbamate (309 mg, 1.054 mmol), dry CsCO₃ (573 mg, 1.76 mmol) were dissolved in anhydrous THF (8.8 mL). The solution was degassed under argon for 5 min and Pd(PPh₃)₄ (203 mg, 0.176 mmol) was added. The reaction was stirred at 80° C. for 5 h under microwaves. The reaction mixture was diluted with EtOAc and washed with H₂O. The organic phase was dried over Na₂SO₄, filtered and concentrated under reduced pressure to afford a crude material which was purified by flash chromatography on silica gel (cyclohexane/EtOAc 70/30 to 30/70) to give the desired product 6-allyloxy-4-[2-[(tert-butoxycarbonylamino)methyl]thiazol-5-yl]-1,6-diazabicyclo[3.2.1]oct-3-en-7-one (32a) (132 mg, 0.336 mmol, 38%) as a colorless gum.

MS m/z ([M+H]⁺) 393.

¹H NMR (300 MHz, CDCl₃): δ (ppm) 1.39 (s, 9H), 3.08 (d, J=11.0 Hz, 1H), 3.54 (dd, J=11.0/3.0 Hz, 1H), 3.78 (dd, J=19.4/2.4 Hz, 1H), 3.91 (dd, J=19.4/3.4 Hz, 1H), 4.31-4.42 (m, 4H), 4.78-4.79 (m, 1H), 4.91 (bs, 1H), 5.16-5.28 (m, 2H), 5.85-5.99 (m, 1H), 6.20-6.22 (m, 1H), 7.48-7.49 (m, 1H).

Step 2: Preparation of Intermediate triphenyl-(propenyl) phosphonium [4-[2-[(tert-butoxycarbonylamino)methyl]thiazol-5-yl]-7-oxo-1,6-diazabicyclo[3.2.1]oct-3-en-6-yl] sulfate (32b)

Using the procedure described in example 1 (step 6), the intermediate 6-allyloxy-4-[2-[(tert-butoxycarbonylamino)methyl]thiazol-5-yl]-1,6-diazabicyclo[3.2.1]oct-3-en-7-one (32a) (150 mg, 0.382 mmol) was converted into triphenyl-(propenyl) phosphonium [4-[2-[(tert-butoxycarbonylamino)methyl]thiazol-5-yl]-7-oxo-1,6-diazabicyclo[3.2.1]oct-3-en-6-yl] sulfate (32b) as an amorphous solid after purification by flash chromatography on silica gel (DCM/acetone 100/0 to 30/70).

MS m/z ([M+H]⁺) 432.
MS m/z ([M−H]⁻) 431.
MS m/z ([M+H]⁺) 303 (triphenyl-propenyl-phosphonium).

Step 3: Preparation of Sodium [4-[2-[(tert-butoxycarbonylamino)methyl]thiazol-5-yl]-7-oxo-1,6-diazabicyclo[3.2.1]oct-3-en-6-yl] sulfate (32c)

Using the procedure described in example 1 (step 7), triphenyl-(propenyl) phosphonium [4-[2-[(tert-butoxycarbonylamino)methyl]thiazol-5-yl]-7-oxo-1,6-diazabicyclo[3.2.1]oct-3-en-6-yl] sulfate (32b) was converted after ion exchange (Dowex sodium form column) into sodium [4-[2-[(tert-butoxycarbonylamino)methyl]thiazol-5-yl]-7-oxo-1,6-diazabicyclo[3.2.1]oct-3-en-6-yl] sulfate (32c) (43.4 mg, 0.092 mmol, 24% over 2 steps) as a white amorphous solid after lyophilization.

MS m/z ([M−H]⁻) 431.

¹H NMR (300 MHz, D₂O): δ (ppm) 1.41 (s, 9H), 3.43 (d, J=11.3 Hz, 1H), 3.75-3.80 (m, 1H), 3.88 (dd, J=19.6/3.6 Hz, 1H), 4.06 (dd, J=19.6/2.3 Hz, 1H), 4.39 (s, 2H), 4.94 (dd, J=2.8/1.2 Hz, 1H), 6.43 (s, 1H), 7.60 (bs, 1H).

Step 4: Preparation of [4-[2-(aminomethyl)thiazol-5-yl]-7-oxo-1,6-diazabicyclo[3.2.1]oct-3-en-6-yl] hydrogen sulfate (Example 32)

In a Wheaton vial, sodium [4-[2-[(tert-butoxycarbonylamino)methyl]thiazol-5-yl]-7-oxo-1,6-diazabicyclo[3.2.1]oct-3-en-6-yl] sulfate (32c) (20 mg, 48.4 μmop was dissolved in anhydrous ACN (0.485 mL) and TMSI (25 μL, 0.174 mmol) was added. After 6 h at rt, the solid formed was filtered and washed with cold ACN. It was then purified by flash chromatography on C18 reverse phase (H₂O/ACN 98/2) to afford the desired compound [4-[2-(aminomethyl)thiazol-5-yl]-7-oxo-1,6-diazabicyclo[3.2.1]oct-3-en-6-yl] hydrogen sulfate (Example 32) (3.4 mg, 10.2 μmol, 21%) as a white amorphous solid after lyophilization.

MS m/z ([M–H]⁻) 331.

$^1$H NMR (300 MHz, D₂O): δ (ppm) 3.49 (d, J=11.4 Hz, 1H), 3.72-4.16 (m, 3H), 4.42 (s, 2H), 4.97 (dd, J=2.8/1.3 Hz, 1H), 6.59-6.62 (m, 1H), 7.82 (s, 1H).

Example 33

Synthesis of Sodium [3-(4-pyridyl)-7-oxo-1,6-diazabicyclo[3.2.1]oct-3-en-6-yl]sulfate

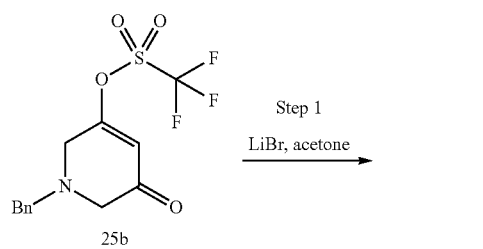

Step 1
LiBr, acetone

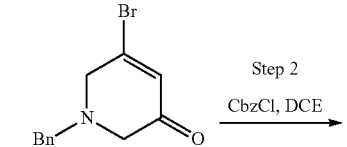
33a

Step 2
CbzCl, DCE

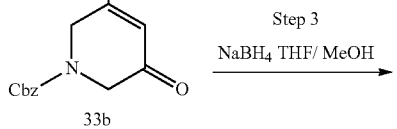
33b

Step 3
NaBH₄ THF/MeOH

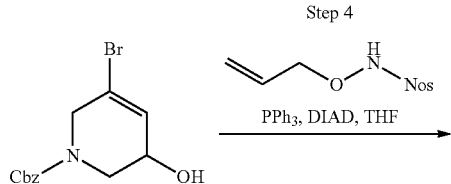
33c

Step 4
PPh₃, DIAD, THF

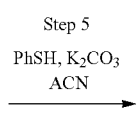
33d

Step 5
PhSH, K₂CO₃
ACN

-continued

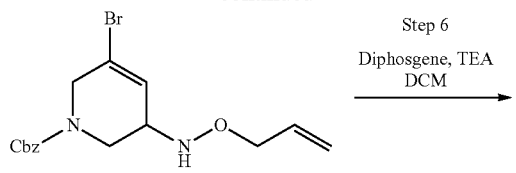
33e

Step 6
Diphosgene, TEA
DCM

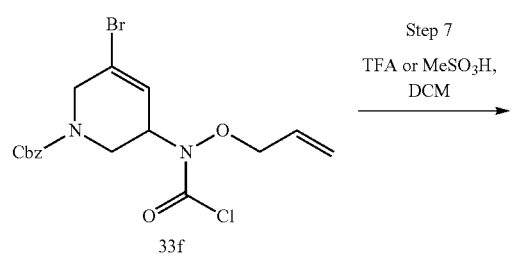
33f

Step 7
TFA or MeSO₃H, DCM

Step 8

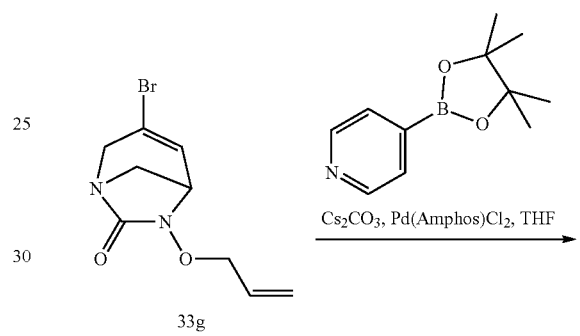
33g

Cs₂CO₃, Pd(Amphos)Cl₂, THF

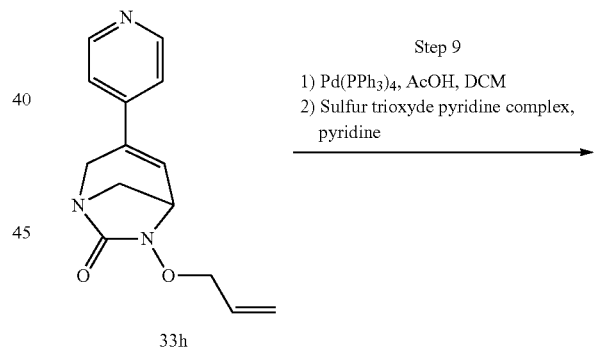
33h

Step 9
1) Pd(PPh₃)₄, AcOH, DCM
2) Sulfur trioxyde pyridine complex, pyridine

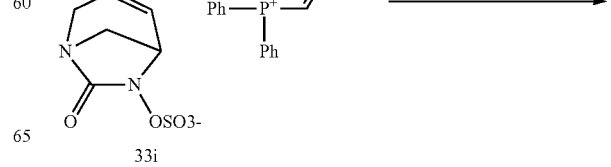
33i

Step 10
ion exchange Dowex Na+

109

-continued

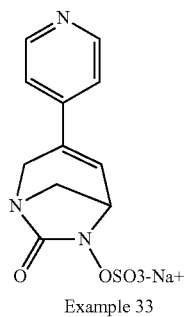

Example 33

Step 1: Preparation of Intermediate 1-benzyl-5-bromo-2,6-dihydropyridin-3-one (33a)

In a 250 mL round bottom flask under nitrogen atmosphere, (1-benzyl-5-oxo-2,6-dihydropyridin-3-yl) trifluoromethanesulfonate (25b) (4.77 g, 14.22 mmol) was diluted with acetone (142 mL). Anhydrous LiBr was added (3.71 g, 42.68 mmol). The resulting pale yellow solution was stirred for 2 h at 45° C. then evaporated to dryness under reduced pressure. The residue was diluted with EtOAc and washed with $H_2O$. The organic layer was concentrated in vacuo then diluted with DCM and filtered over 0.45 μm PTFE. After concentration, 1-benzyl-5-bromo-2,6-dihydropyridin-3-one (33a) was obtained as a yellow oil. After one night at −20° C., the product was a crystalline pale yellow solid and was used in the next step without further purification.

MS m/z ([M+H]$^+$) 266/268.

Step 2: Preparation of Intermediate benzyl 3-bromo-5-oxo-2,6-dihydropyridine-1-carboxylate (33b)

1-benzyl-5-bromo-2,6-dihydropyridin-3-one (33a) (14.22 mmol) was dissolved in DCE (142 mL) and CbzCl (10.1 mL, 71 mmol) was added. The reaction mixture was stirred for 24 h at rt. The reaction was concentrated in vacuo (at low temperature −30° C.) and the crude residue was purified by flash chromatography on silica gel (cyclohexane/EtOAc 100/0 to 40/60) to give benzyl 3-bromo-5-oxo-2,6-dihydropyridine-1-carboxylate (33b) (2.43 g, 7.83 mmol, 55% over 2 steps) as a colorless gum.

MS m/z ([M−H]$^-$) 308/310.

$^1$H NMR (300 MHz, CDCl$_3$): δ (ppm) 4.17 (bs, 2H), 4.52 (bs, 2H), 5.18 (bs, 2H), 6.60-6.61 (m, 1H), 7.36 (bs, 5H).

Step 3: Preparation of Intermediate benzyl 5-bromo-3-hydroxy-3,6-dihydro-2H-pyridine-1-carboxylate (33c)

3-bromo-5-oxo-2,6-dihydropyridine-1-carboxylate (33b) (2.277 g, 7.342 mmol) was dissolved in a mixture of THF/MeOH (2/1, 73 mL) at 0° C. NaBH$_4$ (277 mg, 7.342 mmol) was added by small portions and the reaction mixture was stirred at 0° C. for 10 min. The reaction mixture was concentrated in vacuo to remove the excess of MeOH then diluted with EtOAc and washed with brine. The organic layer was dried over Na$_2$SO$_4$, filtered and concentrated. The intermediate benzyl 5-bromo-3-hydroxy-3,6-dihydro-2H-pyridine-1-carboxylate (33c) was used in the next step without further purification.

MS m/z ([M+H]$^+$) 312/314, ([M+H—H$_2$O]±) 294/296.

110

Step 4: Preparation of Intermediate benzyl 3-[allyloxy-(2-nitrophenyl)sulfonyl-amino]-5-bromo-3,6-dihydro-2H-pyridine-1-carboxylate (33d)

Under a nitrogen atmosphere at rt, DIAD (1.73 mL, 8.81 mmol) was added drop-by-drop to a solution of compound benzyl 5-bromo-3-hydroxy-3,6-dihydro-2H-pyridine-1-carboxylate (33c) (7.342 mmol) dissolved in dry THF (73 mL) in presence of N-allyloxy-2-nitro-benzenesulfonamide (2.27 g, 8.81 mmol) and PPh$_3$ (2.31 g, 8.81 mmol). After stirring overnight, the reaction mixture was concentrated under vacuum and purified by chromatography on silica gel (heptane/EtOAc 100/0 to 40/60) to afford benzyl 3-[allyloxy-(2-nitrophenyl)sulfonyl-amino]-5-bromo-3,6-dihydro-2H-pyridine-1-carboxylate (33d) as a colorless gum contaminated by an excess of unreacted N-allyloxy-2-nitro-benzenesulfonamide which was used as such in the next step.

MS m/z ([M+H]$^+$) 552/554

Step 5: Preparation of Intermediate benzyl 3-(allyloxyamino)-5-bromo-3,6-dihydro-2H-pyridine-1-carboxylate (33e)

Using the procedure described in example 25 (step 6), the intermediate benzyl 3-[allyloxy-(2-nitrophenyl)sulfonyl-amino]-5-bromo-3,6-dihydro-2H-pyridine-1-carboxylate (33d) (7.342 mmol) was converted into benzyl 3-(allyloxyamino)-5-bromo-3,6-dihydro-2H-pyridine-1-carboxylate (33e) (2.04 g, 5.55 mmol, 76% over 3 steps) as a colorless gum, after purification by flash chromatography on silica gel (heptane/EtOAc 100/0 to 40/60).

MS m/z ([M+H]$^+$) 367/369.

$^1$H NMR (300 MHz, CDCl$_3$): δ (ppm) 3.31-3.44 (m, 1H), 3.65 (bs, 1H), 3.93-4.42 (m, 5H), 5.12-5.40 (m, 5H), 5.89 (bs, 1H), 6.13 (bs, 1H), 7.34-7.37 (m, 5H).

Step 6: Preparation of Intermediate benzyl 3-[allyloxy(chlorocarbonyl)amino]-5-bromo-3,6-dihydro-2H-pyridine-1-carboxylate (33f)

To a solution of benzyl 3-(allyloxyamino)-5-bromo-3,6-dihydro-2H-pyridine-1-carboxylate (33e) (139 mg, 0.378 mmol) in anhydrous DCM (3.8 mL) at 0° C. under nitrogen atmosphere were added TEA (106 μL, 0.757 mmol) followed by diphosgene (59 μL, 0.492 mmol). The mixture was stirred at 0° C. for 5-10 min, diluted with DCM (10 mL) and washed with brine (4 mL). The organic layer was dried over Na$_2$SO$_4$ and concentrated in vacuo to provide compound benzyl 3-[allyloxy(chlorocarbonyl)amino]-5-bromo-3,6-dihydro-2H-pyridine-1-carboxylate (33f) which was used in the next step without further purification.

MS m/z ([M+H]$^+$) 429/431.

Step 7: Preparation of Intermediate 6-allyloxy-3-bromo-1,6-diazabicyclo[3.2.1]oct-3-en-7-one (33g)

Under a nitrogen atmosphere, methanesulfonic acid (0.443 mL, 6.82 mmol) was added drop by drop to a solution of benzyl 3-[allyloxy(chlorocarbonyl)amino]-5-bromo-3,6-dihydro-2H-pyridine-1-carboxylate (33f) (0.341 mmol) in anhydrous DCM (3.4 mL). After 2 h at rt, the reaction mixture was cooled to 0° C. and TEA (2.4 mL, 17.05 mmol) was added. After stirring 30 min at 0° C., it was concentrated and directly purified by flash chromatography on silica gel (cyclohexane/EtOAc 100/0 to 0/100) to afford compound 6-allyloxy-3-bromo-1,6-diazabicyclo[3.2.1]oct-3-en-7-one (33g) (77.5 mg, 0.299 mmol, 88% over 2 steps) as a colorless oil.

MS m/z ([M+H]$^+$) 259/261.

$^1$H NMR (300 MHz, CDCl$_3$): δ (ppm) 3.11 (d, J=10.9 Hz, 1H), 3.44 (ddd, J=10.9/2.8/1.0 Hz, 1H), 3.82-4.01 (m, 3H), 4.34-4.47 (m, 2H), 5.28-5.38 (m, 2H), 5.93-6.06 (m, 1H), 6.58-6.62 (m, 1H).

Step 8: Preparation of Intermediate 6-allyloxy-3-(4-pyridyl)-1,6-diazabicyclo[3.2.1]oct-3-en-7-one (33h)

In a wheaton vial, 6-allyloxy-3-bromo-1,6-diazabicyclo[3.2.1]oct-3-en-7-one (33g) (78 mg, 0.301 mmol), pyridine-4-boronic acid pinacol ester (86 mg, 0.421 mmol), dry Cs$_2$CO$_3$ (196 mg, 0.60 mmol) were dissolved in anhydrous THF (3 mL). The solution was degassed under argon for 5 min and bis(di-tert-butyl(4-dimethylaminophenyl)phosphine) dichloropalladium(II) catalyst (Pd(Amphos)Cl$_2$) (21 mg, 0.030 mmol) was added. The reaction was stirred at 55° C. for 30 min. The reaction mixture was filtered on isolute Si-TMT resin and concentrated under reduced pressure to afford a crude material which was purified by flash chromatography on C-18 reverse phase (H$_2$O/ACN 98/2 to 20/80) to give 6-allyloxy-3-(4-pyridyl)-1,6-diazabicyclo[3.2.1]oct-3-en-7-one (33h) (48 mg, 0.185 mmol, 62%) as a clear yellow gum.

MS m/z ([M+H]$^+$) 258.

$^1$H NMR (300 MHz, CDCl$_3$): δ (ppm) 3.12 (d, J=10.8 Hz, 1H), 3.50-3.59 (m, 1H), 4.00-4.24 (m, 3H), 4.35-4.48 (m, 2H), 5.28-5.38 (m, 2H), 5.94-6.07 (m, 1H), 6.82 (d, J=5.2 Hz, 1H), 7.14-7.16 (m, 2H), 8.53-8.55 (m, 2H).

Step 9: Preparation of triphenyl-(propenyl)-phosphonium Salt of [3-(4-pyridyl)-7-oxo-1,6-diazabicyclo[3.2.1]oct-3-en-6-yl] sulfate (33i)

Using the procedure described in example 1 (step 6), the intermediate 6-allyloxy-3-(4-pyridyl)-1,6-diazabicyclo[3.2.1]oct-3-en-7-one (33h) (48 mg, 0.185 mmol) was converted into triphenyl-(propenyl)-phosphonium [3-(4-pyridyl)-7-oxo-1,6-diazabicyclo[3.2.1]oct-3-en-6-yl] sulfate (33i) after purification by flash chromatography on silica gel (DCM/acetone 100/0 to 0/100, then acetone/iPrOH 100/0 to 50/50).

MS m/z ([M−H]$^-$) 296.

MS m/z ([M+H]$^+$) 303 (triphenyl-propenyl-phosphonium).

Step 10: Preparation of Sodium [3-(4-pyridyl)-7-oxo-1,6-diazabicyclo[3.2.1]oct-3-en-6-yl]sulfate (Example 33)

The triphenyl-(propenyl)-phosphonium [3-(4-pyridyl)-7-oxo-1,6-diazabicyclo[3.2.1]oct-3-en-6-yl] sulfate (33i) was applied on a Dowex sodium form column (Dowex® 50WX8 hydrogen form stored with an aqueous solution of 2N NaOH and washed until neutral pH with H$_2$O). The fractions containing the desired compound were combined, freezed and lyophilized to afford the sodium [3-(4-pyridyl)-7-oxo-1,6-diazabicyclo[3.2.1]oct-3-en-6-yl] sulfate (Example 33) (6.1 mg, 0.019 mmol, 10% over 3 steps) as a white solid.

MS m/z ([M−H]$^-$) 296.

$^1$H NMR (300 MHz, D$_2$O): δ (ppm) 3.43 (d, J=11.2 Hz, 1H), 3.69 (dd, J=11.2/3.2 Hz, 1H), 4.15 (d, J=18.3 Hz, 1H), 4.33 (dd, J=17.7/2.2 Hz, 1H), 4.52 (dd, J=5.4/2.7 Hz, 1H), 6.94-7.00 (m, 1H), 7.34-7.36 (m, 2H), 8.44-8.46 (m, 2H).

Example 34

Synthesis of Sodium [3-imidazol-1-yl-7-oxo-1,6-diazabicyclo[3.2.1]oct-3-en-6-yl] sulfate

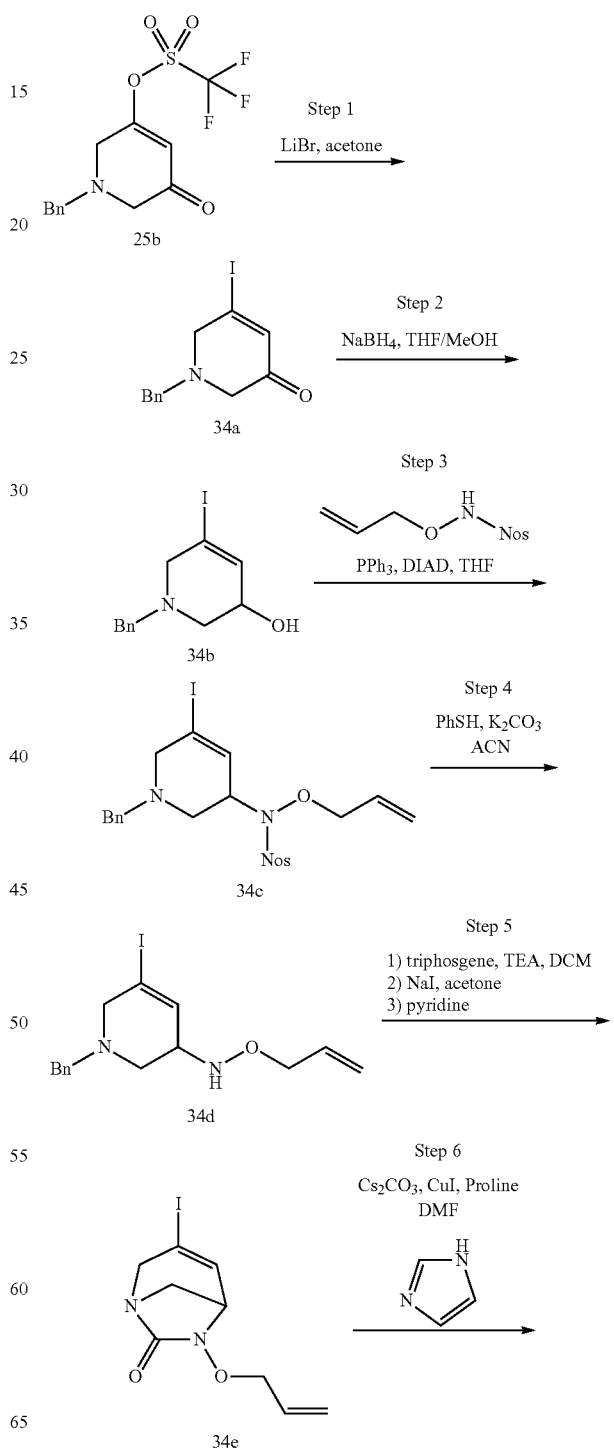

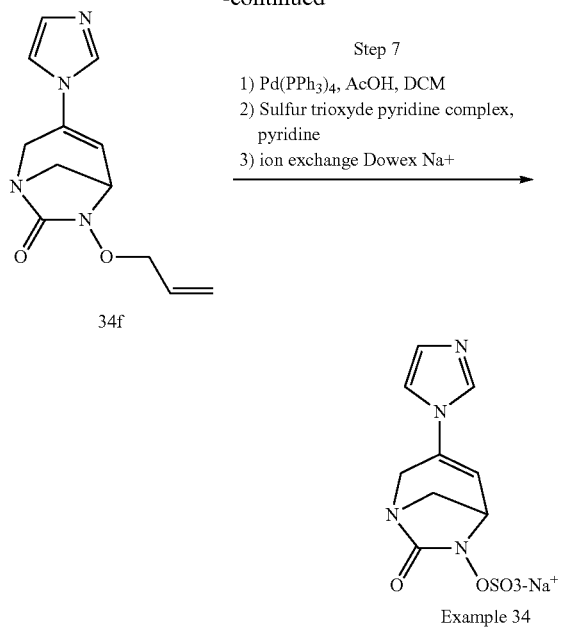

34f

Step 7
1) Pd(PPh$_3$)$_4$, AcOH, DCM
2) Sulfur trioxyde pyridine complex, pyridine
3) ion exchange Dowex Na+

Example 34

Step 1: Preparation of Intermediate 1-benzyl-5-iodo-2,6-dihydropyridin-3-one (34a)

In a 1 L round bottom flask under nitrogen atmosphere, the vinyl triflate (25b) (16.1 g, 48.02 mmol) was diluted with acetone (480 mL). Anhydrous LiI was added (12.9 g, 96.03 mmol) and the resulting pale yellow solution was stirred for 3.5 h at 45° C. It was evaporated to dryness under reduced pressure. The residue was diluted with DCM (350 mL) making salts precipitate which were filtered over a pad of Celite®. The filtrate was washed with H$_2$O (2×100 mL), dried over Na$_2$SO$_4$. After concentration, the 1-benzyl-5-iodo-2,6-dihydropyridin-3-one (34a) (15.3 g, 15.0 g expected) was obtained as pale yellow solid once triturated.

MS m/z ([M+H]$^+$) 314.

$^1$H NMR (300 MHz, CDCl$_3$): δ (ppm) 3.29 (bs, 2H), 3.66 (bs, 2H), 3.73 (bs, 2H), 6.89 (t, J=1.7 Hz, 1H), 7.29-7.37 (m, 5H).

Step 2: Preparation of Intermediate 1-benzyl-5-iodo-3,6-dihydro-2H-pyridin-3-ol (34b)

In a 1 L three-neck round bottom flask under nitrogen atmosphere, 1-benzyl-5-iodo-2,6-dihydropyridin-3-one (34a) (15.3 g, 48.02 mmol theoretical) was dissolved in a 5/1 MeOH/THF mixture (0.16 M) and cooled down to 0° C. After 15 min, NaBH$_4$ (2.1 g, 55.2 mmol) was added by small portions over 10 minutes. The reaction was completed within 10 min. The solvents were removed under reduced pressure at ambient temperature to a volume of approximately 60 mL. The mixture was then diluted with DCM (500 mL) and washed with crushed ice/water (100 mL). Aqueous layer was taken up with DCM (2×30 mL). The combined organic layers were dried over Na$_2$SO$_4$, evaporated to dryness and the crude 1-benzyl-5-iodo-3,6-dihydro-2H-pyridin-3-ol (34b) (15.4 g, 15.1 expected) was obtained as a pale solid and used in the next step without further purification.

MS m/z ([M+H]$^+$) 316.

$^1$H NMR (400 MHz, CDCl$_3$): δ (ppm) 2.36 (bs, 1H), 2.57 (dd, J=12.0/2.4 Hz, 1H), 2.86 (dd, J=12.0/2.4 Hz, 1H), 3.04 (d, J=16.3 Hz, 1H), 3.43 (d, J=16.3 Hz, 1H), 3.61 (d, J=11.5 Hz, 1H), 3.66 (d, J=11.5 Hz, 1H), 3.99-4.06 (m, 1H), 6.52-6.57 (m, 1H), 7.28-7.38 (m, 5H).

Step 3: Preparation of Intermediate N-allyloxy-N-(1-benzyl-5-iodo-3,6-dihydro-2H-pyridin-3-yl)-2-nitro-benzenesulfonamide (34c)

Using the procedure described in example 33 (step 4), the intermediate 1-benzyl-5-iodo-3,6-dihydro-2H-pyridin-3-ol (34b) (15.4 g, 48.02 mmol theoretical) was converted into N-allyloxy-N-(1-benzyl-5-iodo-3,6-dihydro-2H-pyridin-3-yl)-2-nitro-benzenesulfonamide (34c) after purification by flash chromatography on silica gel (petroleum ether/Et$_2$O 100/0 to 40/60) (39.0 g, 26.7 g expected) contaminated by an excess of unreacted N-allyloxy-2-nitro-benzenesulfonamide and reduced DIAD. The oily residue was covered with cold diisopropyl ether making reduced DIAD precipitate partially. After filtration of the white solid, 34 g were recovered and used as such in the next step.

MS m/z ([M+H]$^+$) 556.

Step 4: Preparation of Intermediate N-allyloxy-1-benzyl-5-iodo-3,6-dihydro-2H-pyridin-3-amine (34d)

Under nitrogen atmosphere, K$_2$CO$_3$ (50.0 g, 360.1 mmol) was added to a solution of N-allyloxy-N-(1-benzyl-5-iodo-3,6-dihydro-2H-pyridin-3-yl)-2-nitro-benzenesulfonamide (34c) (48.02 mmol theoretical) in ACN (400 mL) in the presence of PhSH (25.0 mL, 240.1 mmol). After stirring 3 h at rt, the reaction mixture was filtered on Celite® and the cake was washed with DCM (3×150 mL). The filtrate was concentrated and the crude yellow slurry (60 g) was poured in heptane (500 mL) making reduced DIAD precipitate. After filtration and evaporation, clear yellow oil was obtained (51 g). A first purification by flash chromatography on silica gel (petroleum ether/Et$_2$O 100/0 to 40/60) followed by a second purification (DCM 100% then DCM/EtOAc 15/85) gave desired N-allyloxy-1-benzyl-5-iodo-3,6-dihydro-2H-pyridin-3-amine (34d) as a pale yellow solid after trituration (12.2 g, 68% over 4 steps).

MS m/z ([M+H]$^+$) 371.

$^1$H NMR (400 MHz, CDCl$_3$): δ (ppm) 2.48 (dd, J=11.7/3.4 Hz, 1H), 2.96-3.08 (m, 2H), 3.34 (d, J=16.5 Hz, 1H), 3.57 (bs, 1H), 3.60 (d, J=13.5 Hz, 1H), 3.65 (d, J=13.5 Hz, 1H), 4.09-4.22 (m, 2H), 5.15-5.30 (m, 2H), 5.73 (bs, 1H), 5.84-5.96 (m, 1H), 6.37-6.43 (m, 1H), 7.25-7.38 (m, 5H).

Step 5: Preparation of Intermediate 6-allyloxy-3-iodo-1,6-diazabicyclo[3.2.1]oct-3-en-7-one (34e)

In a 2 L three neck round bottom flask under inert atmosphere with an addition funnel and a water condenser, N-allyloxy-1-benzyl-5-iodo-3,6-dihydro-2H-pyridin-3-amine (34d) (12.2 g, 32.96 mmol) was diluted in anhydrous DCE (350 mL). A solution of triphosgene (12.7 g, 42.84 mmol) in DCE (150 mL) was added at rt over 5 min and the solution was stirred until the pale yellow solution turned to a white suspension. The reaction mixture was then heated at 55° C. for 20 min.

A solution of dry NaI (49.2 g, 329.6 mmol) in dry acetone (170 mL) was then added dropwise and the yellow suspension turned to a brown slurry which was heated at 65° C. for 25 min. Pyridine (66 mL, 823.9 mmol) was carefully added dropwise over 10 min. The reaction was stirred for 30 min at 65° C. The reaction was cooled down to 0° C., diluted with DCM (600 mL), filtered on Celite® and concentrated to dryness under reduced pressure. The brown residue was diluted with DCM (600 mL), filtered once more on Celite® and washed with an aqueous 0.2M solution of NaH$_2$PO$_4$ (2×200 mL) and Na$_2$S$_2$O$_3$ 1M aqueous solution (2×200 mL). The organic layer was dried over Na$_2$SO$_4$, concentrated under reduced pressure. The crude compound (14.5 g) was purified by flash chromatography on silica gel (petroleum ether/ether 100/0 to 40/60) to give 6-allyloxy-3-iodo-1,6-diazabicyclo[3.2.1]oct-3-en-7-one (34e) (7.1 g, 23.2 mmol, 70%) as an orange oil. 400 mg of starting material (34d) were also recovered.

MS m/z ([M+H]$^+$) 307.

$^1$H NMR (300 MHz, CDCl$_3$): δ (ppm) 3.21 (d, J=10.8 Hz, 1H), 3.51-3.58 (m, 1H), 3.83-3.86 (m, 1H), 3.90 (dd, J=18.0/2.2 Hz, 1H), 4.07 (dd, J=18.0/1.4 Hz, 1H), 4.36-4.53 (m, 2H), 5.28-5.46 (m, 2H), 5.95-6.13 (m, 1H), 6.87-6.97 (m, 1H).

Step 6: Preparation of Intermediate 6-allyloxy-3-imidazol-1-yl-1,6-diazabicyclo[3.2.1]oct-3-en-7-one (34f)

In a 2 mL sealed tube under inert atmosphere, 6-allyloxy-3-iodo-1,6-diazabicyclo[3.2.1]oct-3-en-7-one (34e) (10 mg, 0.033 mmol) was diluted with anhydrous DMF (650 μL). Imidazole (5.6 mg, 0.082 mmol), proline (1.5 mg, 0.013 mmol) and dry Cs$_2$CO$_3$ (21.3 mg, 0.065 mmol) were successively added and the mixture was degased with argon for 5 min. CuI (1.2 mg, 0.007 mmol) was added. The blue suspension was heated at 85° C. and turned rapidly to green. After 1.5 h, LCMS showed complete conversion of starting material. The mixture was cooled down to rt, diluted with DCM (3 mL) and filtered over 0.20 μm PTFE. The filtrate was poured over TMT scavenger prepacked resin (500 mg) and eluted with DCM. RP18 silica (200 mg) was added to the solution. After evaporation under reduced pressure, the solid-state was purified by chromatohraphy on C-18 reverse phase (H$_2$O/ACN 95/5 to 50/50) to give desired 6-allyloxy-3-imidazol-1-yl-1,6-diazabicyclo[3.2.1]oct-3-en-7-one (34f) (3 mg, 0.012 mmol, 38%) as a yellowish oil.

MS m/z ([M+H]$^+$) 247.

$^1$H NMR (400 MHz, CDCl$_3$): δ (ppm) 3.16 (d, J=11.1 Hz, 1H), 3.58 (dd, J=11.1/2.5 Hz, 1H), 4.06 (dd, J=17.3/1.8 Hz, 1H), 4.12 (dd, J=5.6/2.5 Hz, 1H), 4.27 (d, J=17.3 Hz, 1H), 4.38-4.52 (m, 2H), 5.31-5.53 (m, 2H), 5.98-6.09 (m, 1H), 6.35-6.39 (m, 1H), 7.05 (bs, 1H), 7.12 (bs, 1H), 7.63 (bs, 1H).

Step 7: Preparation of Sodium [3-imidazol-1-yl-7-oxo-1,6-diazabicyclo[3.2.1]oct-3-en-6-yl]sulfate (Example 34)

To a solution of compound 6-allyloxy-3-imidazol-1-yl-1,6-diazabicyclo[3.2.1]oct-3-en-7-one (34f) (3 mg, 0.010 mmol) in anhydrous DCM (210 μL) with glacial AcOH (1.2 μL, 0.023 mmol) was added in one portion Pd(PPh$_3$)$_4$ (6 mg, 0.005 mmol). After stirring 30 min at rt under inert atmosphere the reaction was completed. To this solution was added anhydrous pyridine (210 μL) followed by sulfur trioxide pyridine complex (8.3 mg, 0.052 mmol) and the resulting suspension was protected from light and stirred overnight until the sulfation was completed. The reaction mixture was filtered and concentrated under vacuum, diluted with DCM and filtered. The residue was taken up in ACN (500 μL) and applied on a Dowex sodium form column (Dowex® 50WX8 hydrogen form stored with an aqueous solution of 2N NaOH and washed until neutral pH with H$_2$O). The fractions containing the desired compound were combined, freezed and lyophilized to afford sodium [3-imidazol-1-yl-7-oxo-1,6-diazabicyclo[3.2.1]oct-3-en-6-yl] sulfate (Example 34) (1.5 mg, 0.005 mmol, 47% over 2 steps) as a white solid.

MS m/z ([M–H]$^-$) 285.

$^1$H NMR (300 MHz, D$_2$O): δ (ppm) 3.46 (d, J=11.1 Hz, 1H), 3.67 (dd, J=11.1/2.5 Hz, 1H), 4.23 (d, J=17.5 Hz, 1H), 4.36 (dd, J=17.5/1.9 Hz, 1H), 4.52-4.58 (m, 1H), 6.58-6.60 (m, 1H), 7.07 (bs, 1H), 7.34 (bs, 1H), 7.88 (bs, 1H).

Example 35

Synthesis of Sodium [3-(oxazol-5-yl)-7-oxo-1,6-diazabicyclo[3.2.1]oct-3-en-6-yl] sulfate

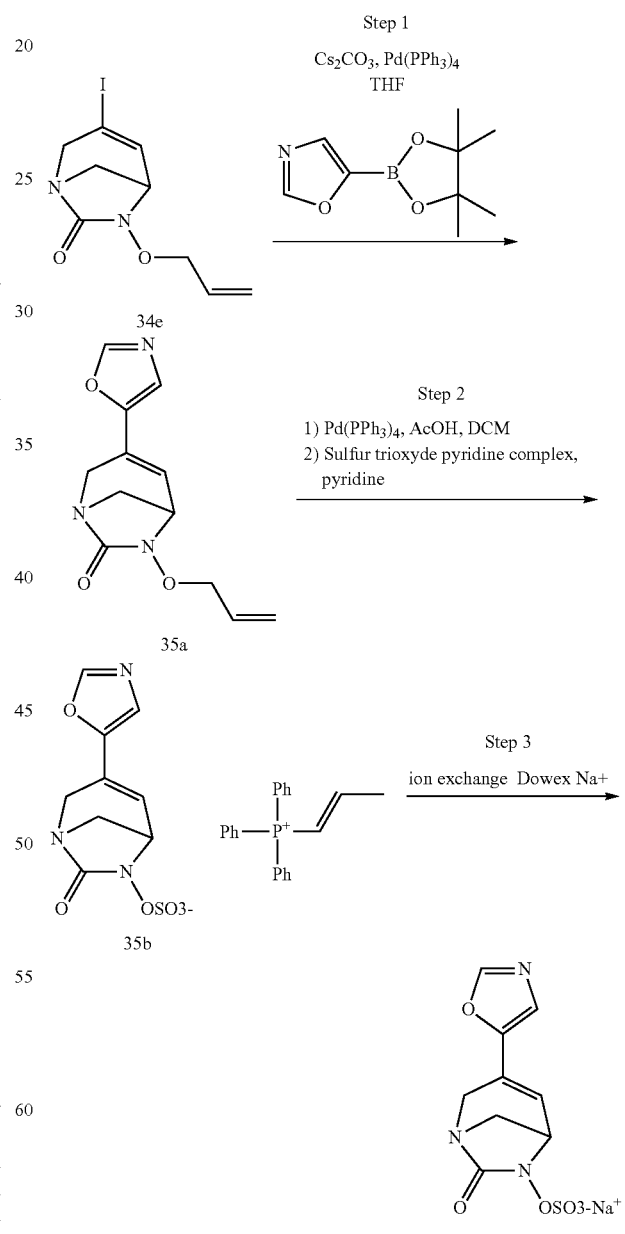

117

Step 1: Preparation of Intermediate 6-allyloxy-3-oxazol-5-yl-1,6-diazabicyclo[3.2.1]oct-3-en-7-one (35a)

In a 25 mL sealed tube under inert atmosphere, 6-allyloxy-3-iodo-1,6-diazabicyclo[3.2.1]oct-3-en-7-one (34e) (250 mg, 0.817 mmol) was diluted with anhydrous THF (9 mL). 5-(4,4,5,5-tetramethyl-1,3,2-dioxaborolan-2-yl)oxazole (203 mg, 1.307 mmol), and dry Cs$_2$CO$_3$ (266 mg, 0.817 mmol) were successively added and the mixture was degased with argon for 5 min. Pd(PPh$_3$)$_4$ (76 mg, 0.065 mmol) was added. The yellow suspension was heated at 60° C. and turned rapidly to orange. After 5 h, LCMS showed complete conversion of starting material. The mixture was cooled down to rt and filtered over 0.20 μm PTFE. The filtrate was poured over TMT scavenger prepacked resin (500 mg) and eluted with DCM. Silica (3 g) was added to the solution. After evaporation under reduced pressure, the solid-state was purified by flash chromatography on silica gel (DCM/acetone 100/0 to 70/30) to give 6-allyloxy-3-oxazol-5-yl-1,6-diazabicyclo[3.2.1]oct-3-en-7-one (35a) (186 mg, 0.752 mmol, 92%) as a yellow solid.

MS m/z ([M+H]$^+$) 248.

$^1$H NMR (400 MHz, CDCl$_3$): δ (ppm) 3.16 (d, J=11.1 Hz, 1H), 3.58 (dd, J=11.1/2.5 Hz, 1H), 4.06 (dd, J=17.3/1.8 Hz, 1H), 4.12 (dd, J=5.6/2.5 Hz, 1H), 4.27 (d, J=17.3 Hz, 1H), 4.38-4.52 (m, 2H), 5.31-5.53 (m, 2H), 5.98-6.09 (m, 1H), 6.74-6.77 (m, 1H), 6.98 (s, 1H), 7.82 (s, 1H).

Step 2: Preparation of Intermediate triphenyl-(propenyl)-phosphonium [3-(oxazol-5-yl)-7-oxo-1,6-diazabicyclo[3.2.1]oct-3-en-6-yl] sulfate (35b)

Using the procedure described in example 1 (step 6), the intermediate 6-allyloxy-3-oxazol-5-yl-1,6-diazabicyclo[3.2.1]oct-3-en-7-one (35a) (186 mg, 0.752 mmol) was converted into triphenyl-(propenyl)-phosphonium [3-(oxazol-5-yl)-7-oxo-1,6-diazabicyclo[3.2.1]oct-3-en-6-yl] sulfate (35b) after purification by flash chromatography on silica gel (DCM/acetone 100/0 to 0/100).

MS m/z ([M−H]$^−$) 286.

MS m/z ([M+H]$^+$) 303 (triphenyl-propenyl-phosphonium).

Step 3: Preparation of Sodium [3-(oxazol-5-yl)-7-oxo-1,6-diazabicyclo[3.2.1]oct-3-en-6-yl]sulfate (Example 35)

Using the procedure described in example 1 (step 7), triphenyl-(propenyl)-phosphonium [3-(oxazol-5-yl)-7-oxo-1,6-diazabicyclo[3.2.1]oct-3-en-6-yl] sulfate (35b) was converted after ion exchange (Dowex sodium form column) into sodium [3-(oxazol-5-yl)-7-oxo-1,6-diazabicyclo[3.2.1]oct-3-en-6-yl] sulfate (Example 35) (67 mg, 0.217 mmol, 29% over 3 steps) as a white solid after lyophilization.

MS m/z ([M−H]$^−$) 286.

$^1$H NMR (400 MHz, D$_2$O): δ (ppm) 3.35 (d, J=11.3 Hz, 1H), 3.58-3.62 (m, 1H), 3.98 (dd, J=17.8/1.5 Hz, 1H), 4.11 (dd, J=17.8/2.0 Hz, 1H), 4.40 (dd, J=5.2/2.5 Hz, 1H), 6.71-6.74 (m, 1H), 7.03 (s, 1H), 8.02 (s, 1H).

118

Example 36

Synthesis of Sodium [3-(1,2,4-oxadiazol-3-yl)-7-oxo-1,6-diazabicyclo[3.2.1]oct-3-en-6-yl] sulfate

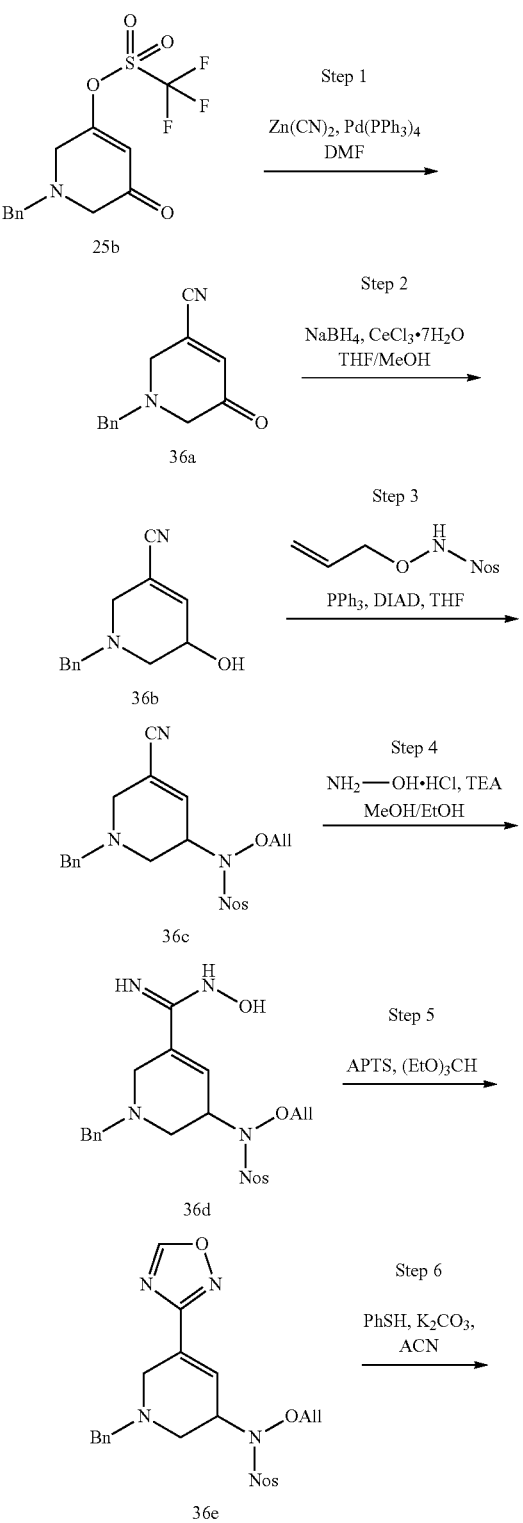

-continued

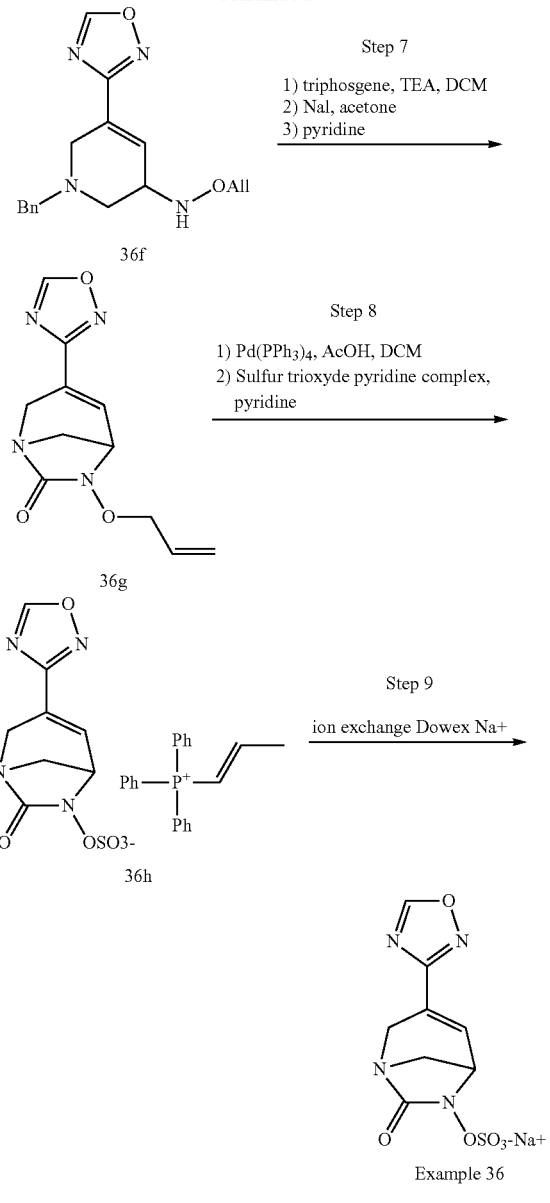

Step 7
1) triphosgene, TEA, DCM
2) NaI, acetone
3) pyridine

36f

Step 8
1) Pd(PPh₃)₄, AcOH, DCM
2) Sulfur trioxyde pyridine complex, pyridine

36g

Step 9
ion exchange Dowex Na+

36h

Example 36

Step 1: Preparation of Intermediate 1-benzyl-5-oxo-2,6-dihydropyridine-3-carbonitrile (36a)

In a 50 mL sealed round bottom flask under inert atmosphere, (1-benzyl-5-oxo-2,6-dihydropyridin-3-yl) trifluoromethanesulfonate (25b) (1.6 g, 4.772 mmol) was diluted in anhydrous DMF (23.9 mL). The reaction mixture was degased with argon for 5 minutes and zinc cyanide (0.672 mg, 5.726 mmol) followed by Pd(PPh₃)₄ (276 mg, 0.239 mmol) were added. The yellow suspension was heated at 60° C. for 2 h. The brown mixture was cooled down to rt and filtered over a pad of Celite® and washed with DCM. After evaporation of the filtrate under reduced pressure, the crude was purified by flash chromatography on silica gel (cyclohexane/EtOAc 100/0 to 60/40) to give 1-benzyl-5-oxo-2,6-dihydropyridine-3-carbonitrile (36a) (487.1 mg, 2.295 mmol, 48%) as a yellow gum.

MS m/z ([M+H]$^+$) 213.
MS m/z ([M−H]$^−$) 211.
$^1$H NMR (300 MHz, CDCl₃): δ (ppm) 3.27 (bs, 2H), 3.39-3.42 (m, 2H), 3.71 (bs, 2H), 6.60 (t, J=2.0 Hz, 1H), 7.26-7.36 (m, 5H).

Step 2: Preparation of Intermediate 1-benzyl-3-hydroxy-3,6-dihydro-2H-pyridine-5-carbonitrile (36b)

1-benzyl-5-oxo-2,6-dihydropyridine-3-carbonitrile (36a) (0.487 g, 2.294 mmol) was dissolved in a mixture of THF/MeOH (2/1, 22.9 mL) at 0° C. with CeCl₃ heptahydrate (0.940 g, 2.524 mmol). NaBH₄ (0.095 g, 2.524 mmol) was added by small portions and the reaction mixture was stirred at 0° C. for 15 min. The reaction mixture was concentrated in vacuo to remove the excess of MeOH then diluted with EtOAc and washed with brine. The organic layer was dried over Na₂SO₄, filtered and concentrated. The intermediate 1-benzyl-3-hydroxy-3,6-dihydro-2H-pyridine-5-carbonitrile (36b) was used in the next step without further purification.

MS m/z ([M+H]$^+$) 215, ([M+H−H₂O]+) 197.

Step 3: Preparation of Intermediate N-allyloxy-N-(1-benzyl-5-cyano-3,6-dihydro-2H-pyridin-3-yl)-2-nitro-benzenesulfonamide (36c)

Under a nitrogen atmosphere at rt, DIAD (0.542 mL, 2.753 mmol) was added drop by drop to a solution of 1-benzyl-3-hydroxy-3,6-dihydro-2H-pyridine-5-carbonitrile (36b) (2.294 mmol) dissolved in dry THF (22.9 mL) in presence of N-allyloxy-2-nitro-benzenesulfonamide (652 mg, 2.523 mmol) and PPh₃ (722 mg, 2.753 mmol). After stirring 3 h, the reaction mixture was concentrated under vacuum and purified by flash chromatography on silica gel (cyclohexane/EtOAc 100/0 to 50/50) to afford N-allyloxy-N-(1-benzyl-5-cyano-3,6-dihydro-2H-pyridin-3-yl)-2-nitro-benzenesulfonamide (36c) as a clear yellow gum contaminated by an excess of unreacted N-allyloxy-2-nitro-benzenesulfonamide which was used as such in the next step.

MS m/z ([M+H]$^+$) 455.

Step 4: Preparation of Intermediate 3-[allyloxy-(2-nitrophenyl)sulfonyl-amino]-1-benzyl-N-hydroxy-3,6-dihydro-2H-pyridine-5-carboxamidine (36d)

A solution of N-allyloxy-N-(1-benzyl-5-cyano-3,6-dihydro-2H-pyridin-3-yl)-2-nitro-benzenesulfonamide (36c) (1.73 mmol), NH₂OH.HCl (162 mg, 2.33 mmol) and TEA (1.30 mL, 9.33 mmol) in MeOH (3.9 mL) and EtOH (3.9 mL) was stirred at rt for 18 h. The reaction mixture was concentrated under vacuum, diluted with DCM and washed with H₂O. The organic layer was dried over Na₂SO₄, filtered, concentrated and purified by flash chromatography on silica gel (cyclohexane/EtOAc 90/10 to 0/90) to afford 3-[allyloxy-(2-nitrophenyl)sulfonyl-amino]-1-benzyl-N-hydroxy-3,6-dihydro-2H-pyridine-5-carboxamidine (36d) (415 mg, 0.851 mmol, 49% over 3 steps) as a pale yellow foam.

MS m/z ([M+H]$^+$) 488.
$^1$H NMR (300 MHz, MeOD): δ (ppm) 2.36-2.64 (m, 2H), 3.00-3.12 (m, 1H), 3.24-3.50 (m, 2H), 3.66 (d, J=12.9 Hz, 1H), 4.43-4.60 (m, 2H), 4.68-4.75 (m, 1H), 5.23-5.33 (m, 2H), 5.84-5.98 (m, 1H), 6.05 (bs, 1H), 7.23-7.33 (m, 3H), 7.64-8.19 (m, 6H).

Step 5: Preparation of Intermediate N-allyloxy-N-[1-benzyl-5-(1,2,4-oxadiazol-3-yl)-3,6-dihydro-2H-pyridin-3-yl]-2-nitro-benzenesulfonamide (36e)

3-[allyloxy-(2-nitrophenyl)sulfonyl-amino]-1-benzyl-N-hydroxy-3,6-dihydro-2H-pyridine-5-carboxamidine (36d) (396 mg, 0.812 mmol) was dissolved in triethyl orthoformate (4.05 mL, 24.4 mmol) with p-toluenesulfonic acid monohydrate (15.5 mg, 0.081 mmol). The reaction mixture was stirred 2 h at 50° C. then concentrated under vacuum. The residue was purified by flash chromatography on silica gel (cyclohexane/EtOAc 100/0 to 50/50) to afford N-allyloxy-N-[1-benzyl-5-(1,2,4-oxadiazol-3-yl)-3,6-dihydro-2H-pyridin-3-yl]-2-nitro-benzenesulfonamide (36e) (294 mg, 0.591 mmol, 73%) as a colorless gum.

MS m/z ([M+H]$^+$) 498.

$^1$H NMR (300 MHz, MeOD): δ (ppm) 2.55-2.90 (m, 2H), 3.25-3.38 (m, 1H), 3.47-3.65 (m, 2H), 3.77 (d, J=12.8 Hz, 1H), 4.45-4.60 (m, 2H), 4.79-4.86 (m, 1H), 5.19-5.30 (m, 2H), 5.81-5.94 (m, 1H), 6.61 (bs, 1H), 7.20-7.37 (m, 5H), 7.67-8.14 (m, 4H), 9.11 (s, 1H).

Step 6: Preparation of Intermediate N-allyloxy-1-benzyl-5-(1,2,4-oxadiazol-3-yl)-3,6-dihydro-2H-pyridin-3-amine (36f)

Under a nitrogen atmosphere, K$_2$CO$_3$ (612 mg, 4.43 mmol) was added to a solution of N-allyloxy-N-[1-benzyl-5-(1,2,4-oxadiazol-3-yl)-3,6-dihydro-2H-pyridin-3-yl]-2-nitro-benzenesulfonamide (36e) (294 mg, 0.591 mmol) in anhydrous ACN (8.9 mL) in presence of PhSH (303 µL, 2.95 mmol). After stirring 4 h at rt, the reaction mixture was filtered and the cake was washed with DCM. The filtrate was concentrated and the crude residue was purified by flash chromatography on silica gel (cyclohexane/ethyl acetate 100/0 to 20/80) to give N-allyloxy-1-benzyl-5-(1,2,4-oxadiazol-3-yl)-3,6-dihydro-2H-pyridin-3-amine (36f) (157 mg, 0.503 mmol, 85%) as a yellow gum.

MS m/z ([M+H]$^+$) 313.

$^1$H NMR (300 MHz, MeOD): δ (ppm) 2.73 (dd, J=11.6/4.4 Hz, 1H), 2.83 (dd, J=11.6/5.3 Hz, 1H), 3.35-3.54 (m, 2H), 3.71-3.85 (m, 3H), 4.15-4.19 (m, 2H), 5.14-5.29 (m, 2H), 5.85-5.99 (m, 1H), 6.95 (dt, J=3.8/1.9 Hz, 1H), 7.28-7.45 (m, 5H), 9.15 (s, 1H).

Step 7: Preparation of Intermediate 6-allyloxy-3-(1,2,4-oxadiazol-3-yl)-1,6-diazabicyclo[3.2.1]oct-3-en-7-one (36g)

In a 20 mL microwave tube, N-allyloxy-1-benzyl-5-(1,2,4-oxadiazol-3-yl)-3,6-dihydro-2H-pyridin-3-amine (36f) (152 mg, 0.485 mmol) was diluted in anhydrous DCE (9.7 mL) under inert atmosphere. Triphosgene (187 mg, 0.631 mmol) was added and the solution was stirred until the pale yellow solution turned to a white suspension. The mixture was then heated at 55° C. for 20 min until almost complete formation of quaternary benzylic ammonium (MS m/z [M]+ 339) was observed by LCMS.

A solution of dry NaI (726 mg, 4.85 mmol) in dry acetone (2.4 mL) was then added. The yellow suspension turned to a brown slurry which was heated at 55° C. for 25 min. Pyridine (980 µL, 12.13 mmol) was carefully added dropwise over 5 min. The reaction was stirred for 4 h at 65° C. The reaction was filtered, concentrated to dryness under reduced pressure and directly purified by flash chromatography on silica gel (cyclohexane/EtOAc 100/0 to 30/70) to give 6-allyloxy-3-(1,2,4-oxadiazol-3-yl)-1,6-diazabicyclo[3.2.1]oct-3-en-7-one (36g) (78.7 mg, 0.317 mmol, 65%) as a brown gum.

MS m/z ([M+H]$^+$) 249, ([2M+H]$^+$) 497.

$^1$H NMR (300 MHz, CDCl$_3$): δ (ppm) 3.17 (d, J=10.9 Hz, 1H), 3.55-3.62 (m, 1H), 4.06-4.15 (m, 2H), 4.32-4.50 (m, 3H), 5.28-5.41 (m, 2H), 5.94-6.08 (m, 1H), 7.38-7.43 (m, 1H), 8.63 (s, 1H).

Step 8: Preparation of triphenyl-(propenyl)-phosphonium [3-(1,2,4-oxadiazol-3-yl)-7-oxo-1,6-diazabicyclo[3.2.1]oct-3-en-6-yl] sulfate (36h)

Using the procedure described in example 1 (step 6), the intermediate 6-allyloxy-3-(1,2,4-oxadiazol-3-yl)-1,6-diazabicyclo[3.2.1]oct-3-en-7-one (36g) (79 mg, 0.317 mmol) was converted into triphenyl-(propenyl)-phosphonium [3-(1,2,4-oxadiazol-3-yl)-7-oxo-1,6-diazabicyclo[3.2.1]oct-3-en-6-yl] sulfate (36h) after purification by flash chromatography on silica gel (DCM/acetone 100/0 to 0/100).

MS m/z ([M−H]$^−$) 287.

MS m/z ([m+H]$^+$) 303 (triphenyl-propenyl-phosphonium).

Step 9: Preparation of Sodium [3-(1,2,4-oxadiazol-3-yl)-7-oxo-1,6-diazabicyclo[3.2.1]oct-3-en-6-yl] sulfate (Example 36)

Using the procedure described in example 1 (step 7), triphenyl-(propenyl)-phosphonium [3-(1,2,4-oxadiazol-3-yl)-7-oxo-1,6-diazabicyclo[3.2.1]oct-3-en-6-yl] sulfate (36h) was converted after ion exchange (Dowex sodium form column) into sodium [3-(1,2,4-oxadiazol-3-yl)-7-oxo-1,6-diazabicyclo[3.2.1]oct-3-en-6-yl] sulfate (Example 36) (31 mg, 0.100 mmol, 32% over 3 steps) as a white solid after lyophilisation followed by chromatography on C-18 reverse phase (H$_2$O/ACN 95/5 to 80/20).

MS m/z ([M−H]$^−$) 287.

$^1$H NMR (300 MHz, D$_2$O): δ (ppm) 3.45 (d, J=11.4 Hz, 1H), 3.67-3.73 (m, 1H), 4.18 (dd, J=17.8/1.2 Hz, 1H), 4.29 (dd, J=17.9/2.1 Hz, 1H), 4.55 (dd, J=5.3/2.7 Hz, 1H), 7.35-7.39 (m, 1H), 9.14 (s, 1H).

Example 37

Synthesis of Lithium difluoro-(3-oxazol-3-yl-7-oxo-1,6-diazabicyclo[3.2.1]oct-3-en-6-yloxy]-acetate

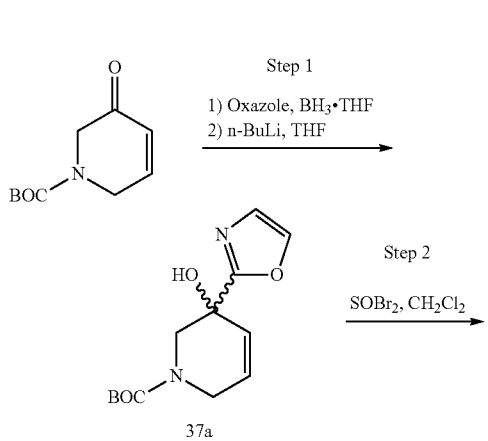

123
-continued

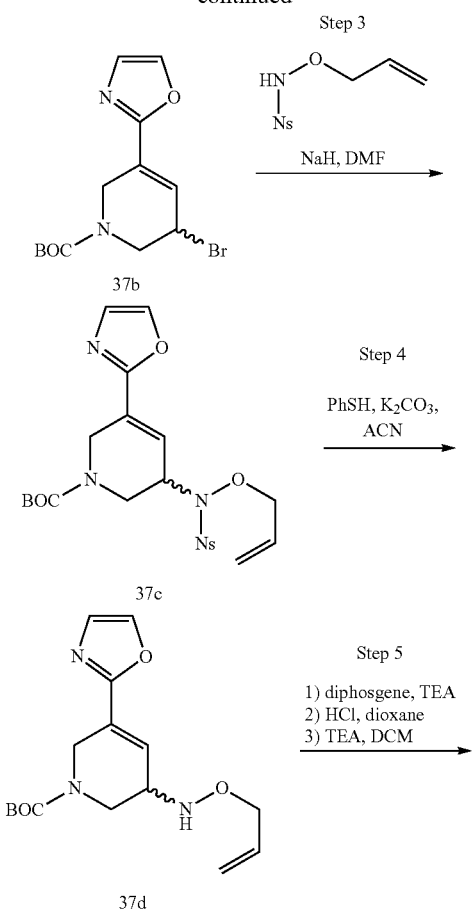

124
-continued

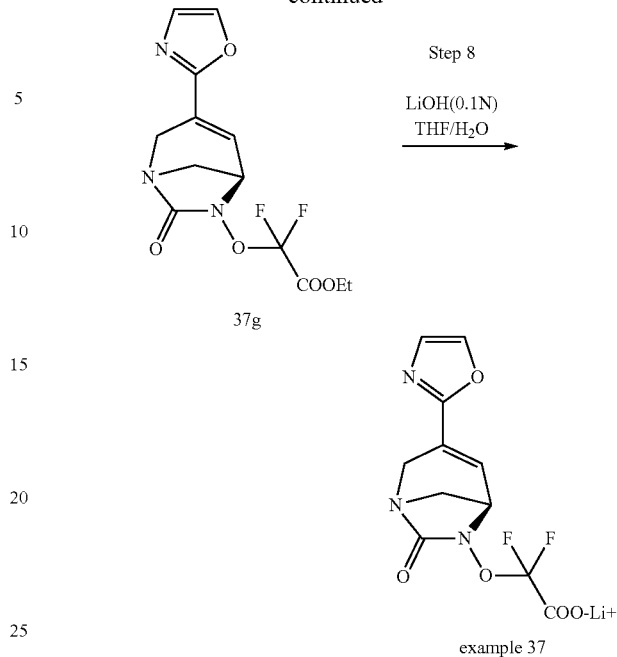

Step 1: Preparation of Intermediate tert-butyl 3-hydroxy-3-oxazol-2-yl-2,6-dihydropyridine-1-carboxylate (37a)

To a solution of borane tetrahydrofuran complex solution 1.0 M in THF (2 mL, 2.0 mmol) under argon atmosphere at rt, was dropwise added oxazole (0.133 mL, 2.0 mmol). The mixture was stirred at rt for 1 h then cooled down to −78° C. A n-butyllithium solution 1.6 M in hexanes (1.33 ml, 2.13 mmol) was dropwise added and the mixture maintained at this temperature for 30 min. A solution of 1-methyl-2,6-dihydropyridin-3-one (200 mg, 1.01 mmol) in anhydrous THF (0.7 mL) was dropwise added. The mixture was stirred at −78° C. for 2 h. EtOH containing 5% AcOH (2.6 mL) was added and the mixture was stirred at rt for 5 h. Water was added. The aqueous layer was extracted with EtOAc. The combined organic layers were washed with a saturated solution of NaHCO$_3$, dried over Na$_2$SO$_4$ and concentrated in vacuo. The residue was purified by flash chromatography on silica gel (petroleum ether/acetone: 100/0 to 80/20) to provide tert-butyl 3-hydroxy-3-oxazol-2-yl-2,6-dihydropyridine-1-carboxylate (37a) (68 mg, 0.26 mmol, 25%).

MS m/z ([M+H]$^+$) 267.

$^1$H NMR (400 MHz, CDCl$_3$) δ (ppm) 1.41-1.44 (m, 9H), 3.70-4.11 (m, 5H), 6.03 (s, 2H), 7.10 (s, 1H), 7.65 (s, 1H).

Step 2: Preparation of Intermediate tert-butyl 3-bromo-5-oxazol-2-yl-3,6-dihydro-2H-pyridine-1-carboxylate (37b)

Thionyl bromide (32 µL, 0.41 mmol) was dropwise added to a solution of TEA (58 µL, 0.41 mmol) and tert-butyl 3-hydroxy-3-oxazol-2-yl-2,6-dihydropyridine-1-carboxylate (37a) (100 mg, 0.38 mmol) in anhydrous DCM (1.38 mL) at 0° C. The mixture was stirred at 0° C. for 50 min then poured in a mixture of ice and H$_2$O. The layers were separated. The aqueous layer was extracted with DCM. The combined organic layers were washed with brine dried over Na$_2$SO$_4$ and concentrated in vacuo to provide tert-butyl

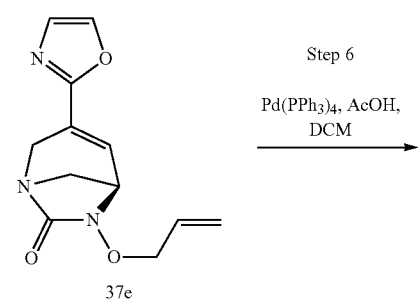

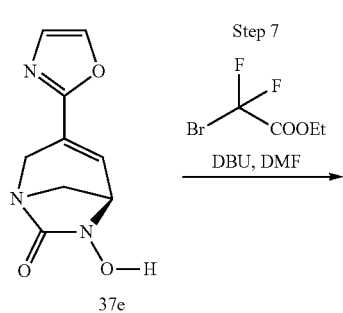

3-bromo-5-oxazol-2-yl-3,6-dihydro-2H-pyridine-1-carboxylate (37b) (124 mg, 0.38 mmol, 99%) as a brown oil which was used without further purification.

$^1$H NMR (400 MHz, CDCl$_3$) δ (ppm) 1.51 (s, 9H), 3.78-3.89 (m, 2H), 3.98-4.06 (m, 1H), 4.20-4.36 (m, 1H), 4.80-4.83 (m, 1H), 6.90-6.91 (m, 1H), 7.18 (s, 1H), 7.63 (s, 1H).

Step 3: Preparation of Intermediate tert-butyl 3-[allyloxy-(2-nitrophenyl)sulfonyl-amino]-5-oxazol-2-yl-3,6-dihydro-2H-pyridine-1-carboxylate (37c)

To a suspension of NaH 60% in oil (97 mg, 2.42 mmol) in anhydrous DMF (4 mL) at 0° C. under nitrogen atmosphere was portionwise added N-allyloxy-2-nitro-benzenesulfonamide (624 mg, 2.42 mmol). The mixture was stirred at 0° C. for 15 min then a solution of tert-butyl 3-bromo-5-oxazol-2-yl-3,6-dihydro-2H-pyridine-1-carboxylate (37b) (692 mg, 2.10 mmol) in anhydrous DMF (2 mL) was dropwise added. The mixture was stirred for 90 min at 0° C. then H$_2$O was added. The mixture was extracted twice with EtOAc. The organic layer was washed with brine, dried over Na$_2$SO$_4$ and concentrated in vacuo. The residue was purified by flash chromatography on silica gel (petroleum ether/acetone: 100/0 to 80/20) to provide tert-butyl 3-[allyloxy-(2-nitrophenyl)sulfonyl-amino]-5-oxazol-2-yl-3,6-dihydro-2H-pyridine-1-carboxylate (37c) (513 mg, 1.01 mmol, 48%) as a solid.

MS m/z ([M+H]$^+$) 507.

$^1$H NMR (400 MHz, CDCl$_3$) δ (ppm) 1.46 (s, 9H), 3.68-3.80 (m, 2H), 4.25-4.50 (m, 4H), 4.68-4.75 (m, 1H), 5.16-5.27 (m, 2H), 5.71-5.83 (m, 1H), 6.48 (bs, 1H), 7.13 (s, 1H), 7.57 (s, 1H), 7.64 (dd, J=7.9/1.3 Hz, 1H), 7.75 (td, J=7.7/1.4 Hz, 1H), 7.82 (td, J=7.7/1.5 Hz, 1H), 8.16 (dd, J=7.9/1.4 Hz, 1H).

Step 4: Preparation of Intermediate tert-butyl 3-(allyloxyamino)-5-oxazol-2-yl-3,6-dihydro-2H-pyridine-1-carboxylate (37d)

The tert-butyl 3-[allyloxy-(2-nitrophenyl)sulfonyl-amino]-5-oxazol-2-yl-3,6-dihydro-2H-pyridine-1-carboxylate (37c) (512 mg, 1.01 mmol) was dissolved in ACN (6.3 mL) and K$_2$CO$_3$ (978 mg, 7.08 mmol) and thiophenol (415 μL, 4.04 mmol) were added. The mixture was stirred at rt for 5h and the mixture was diluted with DCM and filtered on a pad of silica gel to eliminate the excess of thiophenol. Then the pad was washed with (9/1)DCM/MeOH and the filtrate was concentrated in vacuo. The residue was purified by flash chromatography on silica gel (DCM/acetone: 100/0 to 90/10) to provide tert-butyl 3-(allyloxyamino)-5-oxazol-2-yl-3,6-dihydro-2H-pyridine-1-carboxylate (37d) (263 mg, 0.82 mmol, 81%).

MS m/z ([M+H]$^+$) 322.

$^1$H NMR (400 MHz, CDCl$_3$) δ (ppm) 1.50 (s, 9H), 3.35-3.95 (m, 3H), 4.17-4.27 (m, 3H), 4.35-4.60 (m, 1H), 5.17-5.23 (m, 1H), 5.25-5.33 (m, 1H), 5.44 (bs, 1H), 5.89-6.00 (m, 1H), 6.72 (s, 1H), 7.15 (s, 1H), 7.60 (s, 1H).

Step 5: Preparation of Intermediate 6-allyloxy-3-oxazol-2-yl-1,6-diazabicyclo[3.2.1]oct-3-en-7-one (37e)

To a solution of compound tert-butyl 3-(allyloxyamino)-5-oxazol-2-yl-3,6-dihydro-2H-pyridine-1-carboxylate (37d) (257 mg, 0.80 mmol) in anhydrous DCM (4 mL) at 0° C. under argon were added TEA (223 μL, 1.60 mmol) and diphosgene (125.5 μL, 1.04 mmol). The mixture was stirred at 0° C. for 1h, diluted with DCM and washed with brine. The organic layer was dried over Na$_2$SO$_4$ and concentrated in vacuo. The residue was dissolved in anhydrous dioxane (1 mL) and dropwise added to a 4 M HCl solution in dioxane (8 mL). The mixture was stirred at rt for 1 h and concentrated in vacuo. The residue was dissolved in anhydrous dichloromethane (8 mL) cooled at 0° C. and triethylamine (446 μL, 3.20 mmol) was added. The mixture was stirred at rt for 1h then washed with brine. The organic layer was dried over Na$_2$SO$_4$ and concentrated in vacuo. The residue was purified by flash chromatography on silica gel (DCM/Acetone: 100/0 to 80/20) to provide 6-allyloxy-3-oxazol-2-yl-1,6-diazabicyclo[3.2.1]oct-3-en-7-one (37e) (155 mg, 0.63 mmol, 78%).

MS m/z ([M+H]$^+$) 248.

$^1$H NMR (400 MHz, CDCl$_3$): δ (ppm) 3.14 (d, J=10.8 Hz, 1H), 3.54-3.59 (m, 1H), 4.05-4.12 (m, 2H), 4.36 (dd, J=18.2/1.1 Hz, 1H), 4.37-4.49 (m, 2H), 5.28-5.40 (m, 2H), 5.96-6.07 (m, 1H), 7.11-7.15 (m, 2H), 7.58 (s, 1H).

Step 6: Preparation of Intermediate 3-oxazol-2-yl-1,6-diazabicyclo[3.2.1]oct-3-en-7-one (37f)

To a solution of 6-allyloxy-3-oxazol-2-yl-1,6-diazabicyclo[3.2.1]oct-3-en-7-one (37e) (160 mg, 0.65 mmol) and glacial AcOH (59.5 μL, 1.04 mmol) in anhydrous DCM (6.5 mL) was added in one portion Pd(PPh$_3$)$_4$ (374 mg, 0.32 mmol) at rt. After stirring for 30 min, the mixture was concentrated under nitrogen flux. The residue was purified by chromatography on silica gel (DCM/Acetone: 100/0 to 50/50) to afford 3-oxazol-2-yl-1,6-diazabicyclo[3.2.1]oct-3-en-7-one (37f) (122 mg, 0.59 mmol, 91%).

MS m/z ([M+H]$^+$) 208.

Step 7: Preparation of Intermediate ethyl 2,2-difluoro-2-[(3-oxazol-2-yl-7-oxo-1,6-diazabicyclo[3.2.1]oct-3-en-6-yl)oxy]-acetate (37g)

3-oxazol-2-yl-1,6-diazabicyclo[3.2.1]oct-3-en-7-one (37f) (122 mg, 0.59 mmol) was solubilized in DMF (6.5 mL) at −20° C. with DBU (97 μL, 0.65 mmol) and ethyl 2-bromo-2,2-difluoro-acetate (340 μL, 2.65 mmol). The reaction was stirred for 1h15 at −20° C. H$_2$O was added and the mixture was extracted twice with EtOAc. The organic layer was dried over Na$_2$SO$_4$, filtered, and concentrated in vacuo. The crude was purified by flash chromatography on silica gel (petroleum ether/acetone 100/0 to 70/30) to provide ethyl 2,2-difluoro-2-[(3-oxazol-2-yl-7-oxo-1,6-diazabicyclo[3.2.1]oct-3-en-6-yl)oxy]-acetate (37g) (121 mg, 0.37 mmol, 63.5%).

MS m/z ([M+H]$^+$) 330.

$^1$H NMR (400 MHz, CDCl$_3$): δ (ppm) 1.37 (t, J=7.2 Hz, 3H), 3.23 (d, J=11.2 Hz, 1H), 3.67-3.70 (m, 1H), 4.17 (dd, J=18.0/2.1 Hz, 1H), 4.28 (dd, J=5.3/2.5 Hz, 1H), 4.33-4.41 (m, 2H), 4.45 (dd, J=18.0/1.4 Hz, 1H), 7.08-7.11 (m, 1H), 7.15 (s, 1H), 7.62 (s, 1H).

Step 8: Preparation of Lithium 2,2-difluoro-2-[(3-oxazol-2-yl-7-oxo-1,6-diazabicyclo[3.2.1]oct-3-en-6-yloxy]acetate (Example 37)

Ethyl 2,2-difluoro-2-[(3-oxazol-2-yl-7-oxo-1,6-diazabicyclo[3.2.1]oct-3-en-6-yl)oxy]-acetate (37g) (10 mg, 0.03 mmol) was solubilized in THF (0.25 mL) and H$_2$O (2 μL) at 0° C. A solution of LiOH 0.1N (320 μL, 0.73 mmol) was then dropwise added. The mixture was stirred for 2 h at 0°

C. H₂O was added (0.5 mL) and the aqueous layer was washed with EtOAc. The resulting aqueous layer was frozen and lyophilized to provide lithium 2,2-difluoro-2-[(3-oxazol-2-yl-7-oxo-1,6-diazabicyclo[3.2.1]oct-3-en-6-yloxy] acetate (Example 37) (8 mg, 0.03 mmol, 86%) as a white solid.

MS m/z ([M+H]⁺) 302.

MS m/z ([M−H]⁻) 300.

¹H NMR (400 MHz, D₂O): δ (ppm) 3.44 (d, J=11.4 Hz, 1H), 3.67-3.71 (m, 1H), 4.21 (dd, J=17.8/1.5 Hz, 2H), 4.28 (dd, J=17.8/2.1 Hz, 1H), 4.48 (dd, J=5.4/2.7 Hz, 1H), 7.19 (s, 1H), 7.20-7.24 (m, 1H), 7.83 (s, 1H).

Example 38

Synthesis of [3-[5-(aminomethyl)thiazol-2-yl]-7-oxo-1,6-diazabicyclo[3.2.1]oct-3-en-6-yl] hydrogen sulfate

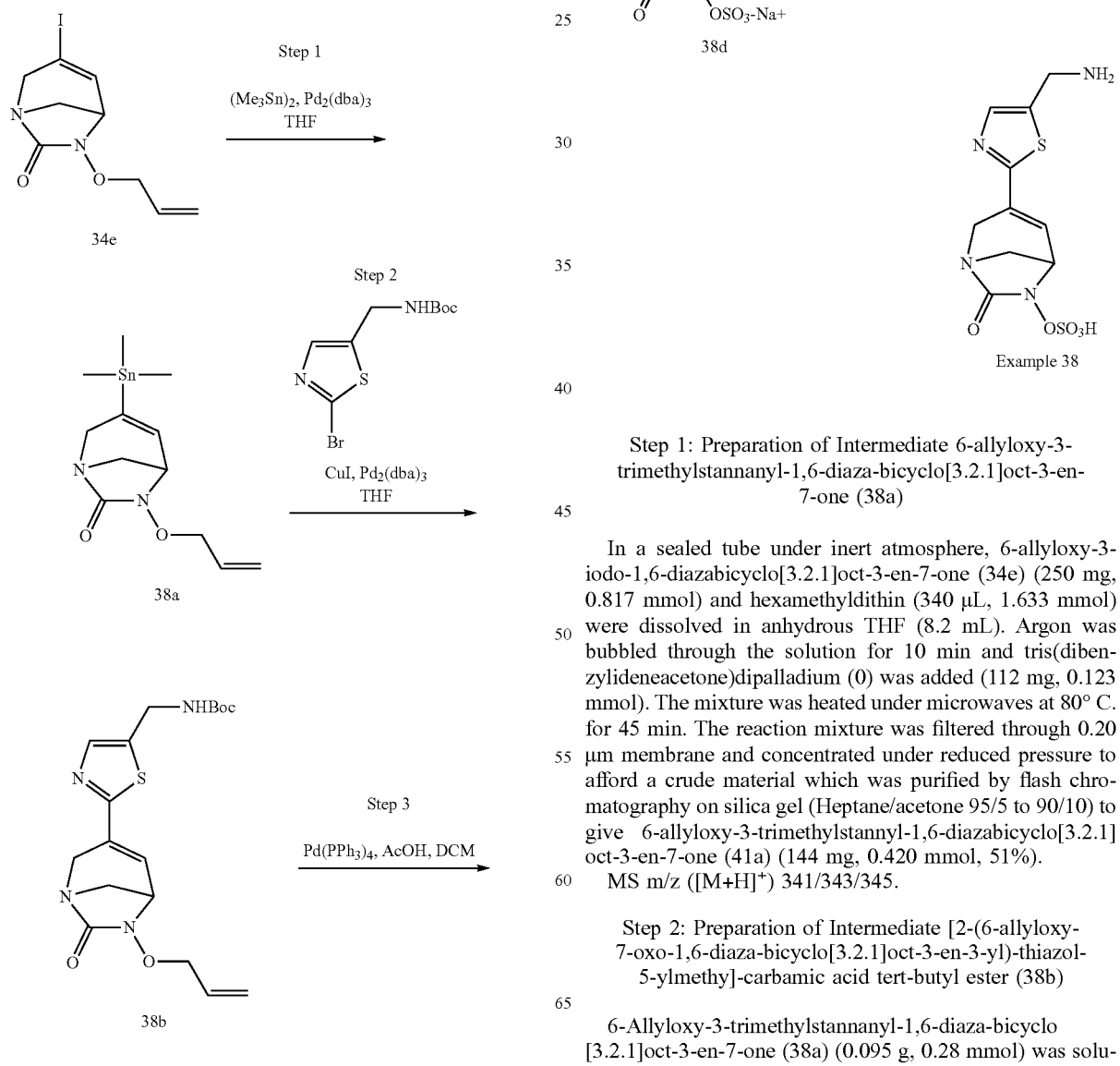

Step 1: Preparation of Intermediate 6-allyloxy-3-trimethylstannanyl-1,6-diaza-bicyclo[3.2.1]oct-3-en-7-one (38a)

In a sealed tube under inert atmosphere, 6-allyloxy-3-iodo-1,6-diazabicyclo[3.2.1]oct-3-en-7-one (34e) (250 mg, 0.817 mmol) and hexamethyldithin (340 µL, 1.633 mmol) were dissolved in anhydrous THF (8.2 mL). Argon was bubbled through the solution for 10 min and tris(dibenzylideneacetone)dipalladium (0) was added (112 mg, 0.123 mmol). The mixture was heated under microwaves at 80° C. for 45 min. The reaction mixture was filtered through 0.20 µm membrane and concentrated under reduced pressure to afford a crude material which was purified by flash chromatography on silica gel (Heptane/acetone 95/5 to 90/10) to give 6-allyloxy-3-trimethylstannyl-1,6-diazabicyclo[3.2.1]oct-3-en-7-one (41a) (144 mg, 0.420 mmol, 51%).

MS m/z ([M+H]⁺) 341/343/345.

Step 2: Preparation of Intermediate [2-(6-allyloxy-7-oxo-1,6-diaza-bicyclo[3.2.1]oct-3-en-3-yl)-thiazol-5-ylmethyl]-carbamic acid tert-butyl ester (38b)

6-Allyloxy-3-trimethylstannanyl-1,6-diaza-bicyclo[3.2.1]oct-3-en-7-one (38a) (0.095 g, 0.28 mmol) was solubilised in THF (6 mL) with (2-bromo-thiazol-5-ylmethyl)-carbamic acid tert-butyl ester (97 mg, 0.33 mmol) and the solution was degassed for 15 min under argon.

Tris(dibenzylideneacetone)dipalladium(0) (0.038 g, 0.04 mmol) and dry CuI (0.008 g, 0.04 mmol) were added. The mixture was heated for 1 h at 100° C. under microwaves. The reaction was filtered over PTFE and the filtrate was evaporated under nitrogen flux. The crude product was purified on silica gel (heptane/acetone: 100/0 to 60/40) to provide [2-(6-allyloxy-7-oxo-1,6-diaza-bicyclo[3.2.1]oct-3-en-3-yl)-thiazol-5-ylmethyl]-carbamic acid tert-butyl ester (1b) (43 mg, 0.11 mmol, 40%).

MS m/z ([M+H]$^+$) 393

$^1$H NMR (400 MHz, CDCl$_3$) δ (ppm): 1.45 (s, 9H), 3.13 (d, J=10.8 Hz, 1H), 3.54 (dd, J=1.6/10.8 Hz, 1H), 4.04 (dd, J=2.6/5.2 Hz, 1H), 4.14 (dd, J=2.0/18.0 Hz, 1H), 4.33-4.44 (m, 5H), 4.93 (bs, 1H), 4.29-4.31 (m, 1H), 5.26-5.40 (m, 1H), 5.94-6.02 (m, 1H), 6.83-6.94 (m, 1H), 7.52 (s, 1H).

Step 3: Preparation of Intermediate 2-(6-Hydroxy-7-oxo-1,6-diaza-bicyclo[3.2.1]oct-3-en-3-yl)-thiazol-5-ylmethyl]-carbamic acid tert-butyl ester (38c)

To a solution of [2-(6-allyloxy-7-oxo-1,6-diaza-bicyclo[3.2.1]oct-3-en-3-yl)-thiazol-5-ylmethyl]-carbamic acid tert-butyl ester (38b) (52 mg, 0.132 mmol) in anhydrous DCM (3 mL) under inert atmosphere were successively added AcOH (0.015 mL, 0.264 mmol) and Pd(PPh$_3$)$_4$ (0.076 g, 0.066 mmol). After stirring for 20 min at rt, the mixture was concentrated in vacuo. The residue was purified by flash chromatography on silica gel (DCM/Acetone 80/20 to 0/100) to provide 2-(6-hydroxy-7-oxo-1,6-diaza-bicyclo[3.2.1]oct-3-en-3-yl)-thiazol-5-ylmethyl]-carbamic acid tert-butyl ester (38c) (25 mg, 0.07 mmol, 54%).

MS m/z ([M+H]$^+$) 353.

$^1$H NMR (400 MHz, CDCl$_3$) δ (ppm): 1.44 (s, 9H), 3.12 (d, J=10.8 Hz, 1H), 3.55 (dd, J=1.7/10.9 Hz, 1H), 4.04 (dd, J=5.2/2.7 Hz, 1H), 4.10 (dd, J=17.9/2.1 Hz, 1H), 4.32 (dd, J=18.0/1.2 Hz, 1H), 4.40 (m, 2H), 5.25 (bs, 1H), 6.96 (d, J=4.9 Hz, 1H), 7.53 (s, 1H).

Step 4: Preparation of Intermediate Sodium [2-(7-oxo-6-sulfooxy-1,6-diaza-bicyclo[3.2.1]oct-3-en-3-yl)-thiazol-5-ylmethyl]-carbamic acid tert-butyl ester (38d)

To a solution of 2-(6-hydroxy-7-oxo-1,6-diaza-bicyclo[3.2.1]oct-3-en-3-yl)-thiazol-5-ylmethyl]-carbamic acid tert-butyl ester (38c) (25 mg, 0.07 mmol) in anhydrous pyridine (1 mL) under inert atmosphere was added sulfur trioxide pyridine complex (0.046 g, 0.287 mmol). After stirring for 16 h, the heterogeneous mixture was concentrated in vacuo. DCM was added to the residue and the solids were filtered. The crude residue was purified by flash chromatography on silica gel (DCM/MeOH: 100/0 to 80/20) to give 0.04 g of a solid which are applied on a Dowex sodium form column (Dowex® 50WX8 hydrogen form stored with an aqueous solution of 2N NaOH and washed until neutral pH with water). The fractions containing the desired compound were combined, freezed and lyophilized to provide sodium [2-(7-oxo-6-sulfooxy-1,6-diaza-bicyclo[3.2.1]oct-3-en-3-yl)-thiazol-5-ylmethyl]-carbamic acid tert-butyl ester (38d) (17 mg, 0.04 mmol, 53%).

MS m/z ([M+H]$^+$) 433.

Step 5: Preparation of [3-[5-(aminomethyl)thiazol-2-yl]-7-oxo-1,6-diazabicyclo[3.2.1]oct-3-en-6-yl] hydrogen sulfate (Example 38)

Sodium [2-(7-oxo-6-sulfooxy-1,6-diaza-bicyclo[3.2.1]oct-3-en-3-yl)-thiazol-5-ylmethyl]-carbamic acid tert-butyl ester (38d) (17 mg, 0.037 mmol) was dissolved in TFA (0.3 mL, 3.92 mmol) at 0° C. under inert atmosphere. After stirring for 10 min at rt, the mixture was concentrated in vacuo. The solid was triturated in ACN for 20 min. The white solid was filtered and washed with ACN. The solid was triturated with water MilliQ® and lyophilized to provide [3-[5-(aminomethyl)thiazol-2-yl]-7-oxo-1,6-diazabicyclo[3.2.1]oct-3-en-6-yl] hydrogen sulfate (Example 1) (11.4 g, 0.034 mmol, 95%).

MS m/z ([M−H]$^-$) 331

$^1$H NMR (300 MHz, DMSO) δ (ppm): 3.27 (d, J=10.8 Hz, 1H), 3.41-3.46 (m, 1H), 4.03 (dd, J=0.6/17.4 Hz, 1H), 4.16 (dd, J=2.1/17.4 Hz, 1H), 4.32 (bs, 2H), 4.35 (dd, J=5.4/2.5 Hz, 1H), 7.06 (d, J=5.1 Hz, 1H), 7.85 (s, 1H), 8.18 bs, 3H).

Example 39

Synthesis of Sodium [3-(2-methoxythiazol-5-yl)-7-oxo-1,6-diazabicyclo[3.2.1]oct-3-en-6-yl] sulfate

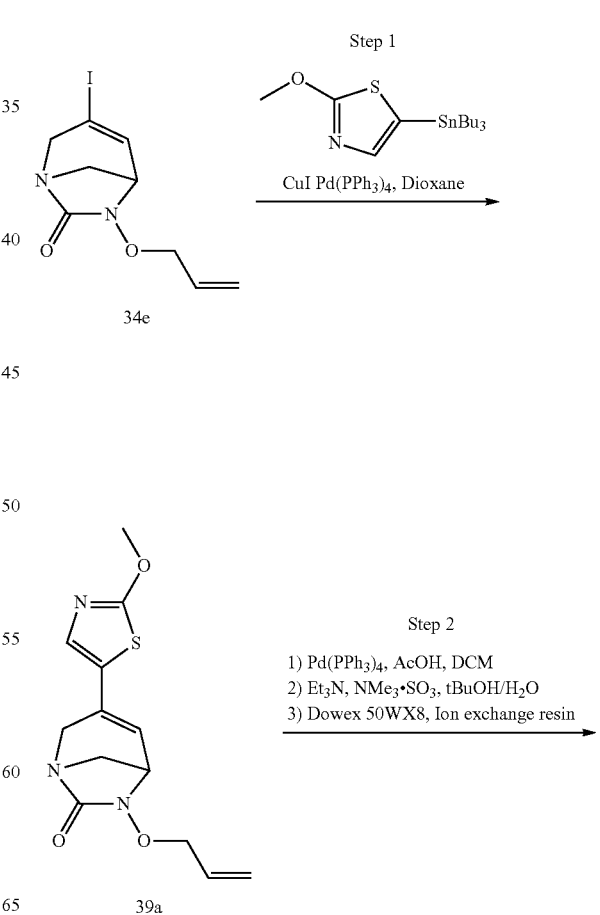

<sup>1</sup>H NMR (400 MHz, D₂O): δ (ppm) 3.35 (d, J=11.2 Hz, 1H), 3.59 (dd, J=11.2/2.3 Hz, 1H), 3.97 (s, 3H), 4.08 (d, J=17.4 Hz, 1H), 4.17 (dd, J=17.4/1.8 Hz, 1H), 4.34 (dd, J=5.4/2.7 Hz, 1H), 6.36 (d, J=5.3 Hz, 1H), 7.00 (s, 1H).

Example 40

Synthesis of Sodium (7-oxo-3-thiazolo[5,4-b]pyridin-2-yl-1,6-diazabicyclo[3.2.1]oct-3-en-6-yl) sulfate

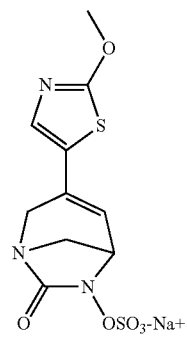

Example 39

Step 1: Preparation of Intermediate 6-allyloxy-3-(2-methoxythiazol-5-yl)-1,6-diazabicyclo[3.2.1]oct-3-en-7-one (39a)

In a wheaton vial, 6-allyloxy-3-iodo-1,6-diazabicyclo[3.2.1]oct-3-en-7-one (34e) (500 mg, 1.63 mmol), 2-methoxy-5-(tributylstannyl)thiazole (725 mg, 2.45 mmol), CuI (325 mg, 1.63 mmol) were dissolved in anhydrous dioxane (12.5 mL). The solution was degassed under argon for 5 min and Pd(PPh₃)₄ (188 mg, 0.163 mmol) was added. The reaction was stirred at 70° C. overnight. The reaction mixture was concentrated under reduced pressure to afford a crude material which was purified by flash chromatography on silica gel (Heptane/acetone 50/50) to give 6-allyloxy-3-(2-methoxythiazol-5-yl)-1,6-diazabicyclo[3.2.1]oct-3-en-7-one (39a) (240 mg, 0.818 mmol, 50%).

MS m/z ([M+H]⁺) 294.

<sup>1</sup>H NMR (400 MHz, CDCl₃): δ (ppm) 3.14 (d, J=10.7 Hz, 1H), 3.47-3.57 (m, 1H), 3.95-4.03 (m, 2H), 4.07 (s, 3H), 4.22 (dd, J=17.3/1.1 Hz, 1H), 4.37-4.49 (m, 2H), 5.25-5.43 (m, 2H), 5.98-6.08 (m, 1H), 6.28 (dd, J=5.4/1.6 Hz, 1H), 6.92 (s, 1H).

Step 2: Preparation of Sodium [3-(2-methoxythiazol-5-yl)-7-oxo-1,6-diazabicyclo[3.2.1]oct-3-en-6-yl] sulfate (Example 39)

To a solution of 6-allyloxy-3-(2-methoxythiazol-5-yl)-1,6-diazabicyclo[3.2.1]oct-3-en-7-one (39a) (240 mg, 0.818 mmol) in anhydrous DCM (12 mL) under nitrogen atmosphere were successively added AcOH (94 μL, 0.818 mmol) and Pd(PPh₃)₄ (476 mg, 0.082 mmol). The mixture was stirred at rt for 2 h then concentrated in vacuo. The residue was purified by flash chromatography on silica gel (DCM/acetone: 75/25 to 50/50) to provide a mixture of expected intermediate and triphenylphosphine oxide. The mixture was dissolved in a mixture of t-BuOH (2.6 mL) and H₂O (2.6 mL). TEA (28.4 μL, 0.204 mmol) and sulfur trioxide trimethylamine complex (136 mg, 0.982 mmol) was added. The mixture was stirred at rt overnight then concentrated in vacuo. The reaction mixture was filtered. The filtrate was concentrated and the residue was purified by preparative TLC (DCM/acetone: 50/50). The fractions containing the expected intermediate were combined and concentrated in vacuo. The residue was dissolved in H₂O (1 mL) and converted after ion exchange (Dowex sodium form column) to sodium [3-(2-methoxythiazol-5-yl)-7-oxo-1,6-diazabicyclo[3.2.1]oct-3-en-6-yl] sulfate (Example 39) (10 mg, 0.028 mmol, 3.4%).

MS m/z ([M−H]⁻) 332.

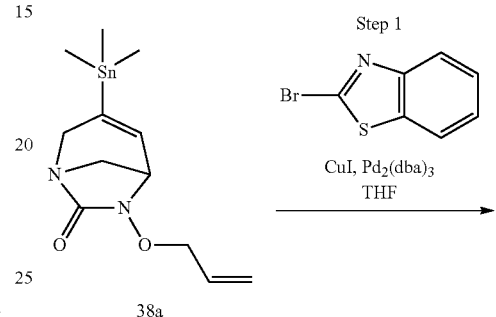

38a

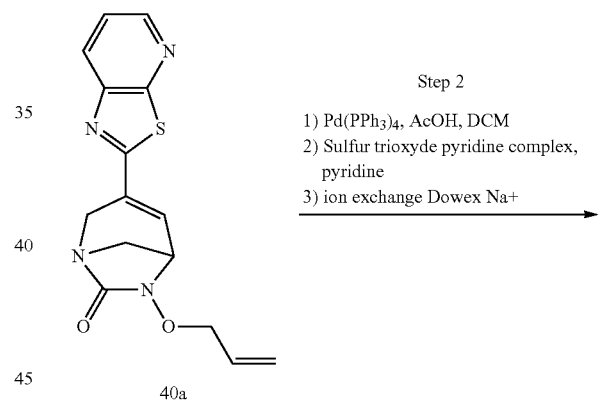

40a

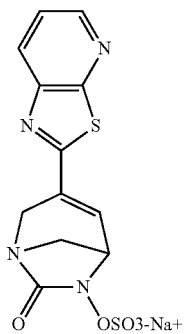

Example 40

Step 1: Preparation of Intermediate 6-allyloxy-3-thiazolo[5,4-b]pyridin-2-yl-1,6-diazabicyclo[3.2.1]oct-3-en-7-one (40a)

In a sealed tube under inert atmosphere, 6-allyloxy-3-trimethylstannyl-1,6-diazabicyclo[3.2.1]oct-3-en-7-one (38a) (144 mg, 0.420 mmol) and 2-bromothiazolo[5,4-b]pyridine (108 mg, 0.504 mmol) were dissolved in anhydrous THF (4.2 mL). Argon was bubbled through the solution for 10 min, then copper iodide (12 mg, 0.063 mmol) and tris(dibenzylideneacetone)dipalladium (0) (58 mg, 0.063 mmol) were added. The mixture was heated under microwaves at 80° C. for 60 min. The reaction mixture was filtered through 0.20 μm membrane and concentrated under reduced pressure to afford a crude material which was purified by flash chromatography on silica gel (Heptane/acetone 90/10 to 50/50) to give 6-allyloxy-3-thiazolo[5,4-b]pyridin-2-yl-1,6-diazabicyclo[3.2.1]oct-3-en-7-one (40a) (20 mg, 0.064 mmol, 15%).

MS m/z ([M+H]$^+$) 315.

$^1$H NMR (300 MHz, CDCl$_3$): δ (ppm) 3.17 (d, J=10.8 Hz, 1H), 3.60 (dd, J=10.8/2.1 Hz, 1H), 4.13 (dd, J=5.4/2.7 Hz, 1H), 4.26 (dd, J=18.0/2.1 Hz, 1H), 4.40-4.57 (m, 3H), 5.33-5.37 (m, 2H), 6.00-6.06 (m, 1H), 7.16-7.19 (m, 1H), 7.40 (dd, J=8.1/4.5 Hz, 1H), 8.18 (dd, J=8.1/1.5 Hz, 1H), 8.55 (dd, J=4.5/1.5 Hz, 1H).

Step 2: Preparation of Sodium (7-oxo-3-thiazolo[5,4-b]pyridin-2-yl-1,6-diazabicyclo[3.2.1]oct-3-en-6-yl) sulfate (Example 40)

To a solution of 6-allyloxy-3-thiazolo[5,4-b]pyridin-2-yl-1,6-diazabicyclo[3.2.1]oct-3-en-7-one (40a) (50 mg, 0.159 mmol) under inert atmosphere with glacial AcOH (20 μL, 0.318 mmol) in anhydrous DCM (1.6 mL) was added in one portion Pd(PPh$_3$)$_4$ (92 mg, 0.080 mmol). After stirring 30 min at rt the reaction was completed. To this solution was added anhydrous pyridine (1.6 mL) followed by the sulfur trioxide pyridine complex (127 mg, 0.795 mmol) and the resulting suspension was protected from light and stirred at 40° C. overnight. The reaction mixture was concentrated under vacuum, diluted with DCM and filtered. The filtrate was concentrated under vacuum and then purified by flash chromatography on silica gel (DCM/acetone: 100/0 to 0/100). The fractions containing the expected intermediate were combined and concentrated in vacuo. The residue was dissolved in an ACN/water mixture and applied on a Dowex sodium form column (Dowex® 50WX8 hydrogen form stored with an aqueous solution of 2N NaOH and washed until neutral pH with water). The fractions containing the desired compound were combined, freezed and lyophilized to afford sodium (7-oxo-3-thiazolo[5,4-b]pyridin-2-yl-1,6-diazabicyclo[3.2.1]oct-3-en-6-yl) sulfate (Example 40) (23 mg, 0.061 mmol, 38% over 2 steps) as a yellow light solid.

MS m/z ([M−H]$^−$) 353.

MS m/z ([M+H]$^+$) 355.

$^1$H NMR (300 MHz, DMSO-d$_6$): δ (ppm) 3.30-3.36 (m, 1H), 3.47 (dd, J=11.0/1.8 Hz, 1H), 4.18 (d, J=17.6 Hz, 1H), 4.29 (dd, J=17.6/1.8 Hz, 1H), 4.43 (dd, J=5.2/2.5 Hz, 1H), 7.35 (d, J=5.0 Hz, 1H), 7.58 (dd, J=8.2/4.7 Hz, 1H), 8.40 (dd, J=8.2/1.4 Hz, 1H), 8.62 (dd, J=4.7/1.4 Hz, 1H).

Example 41

Synthesis of Sodium [3-(3-pyridyl)-7-oxo-1,6-diazabicyclo[3.2.1]oct-3-en-6-yl]sulfate

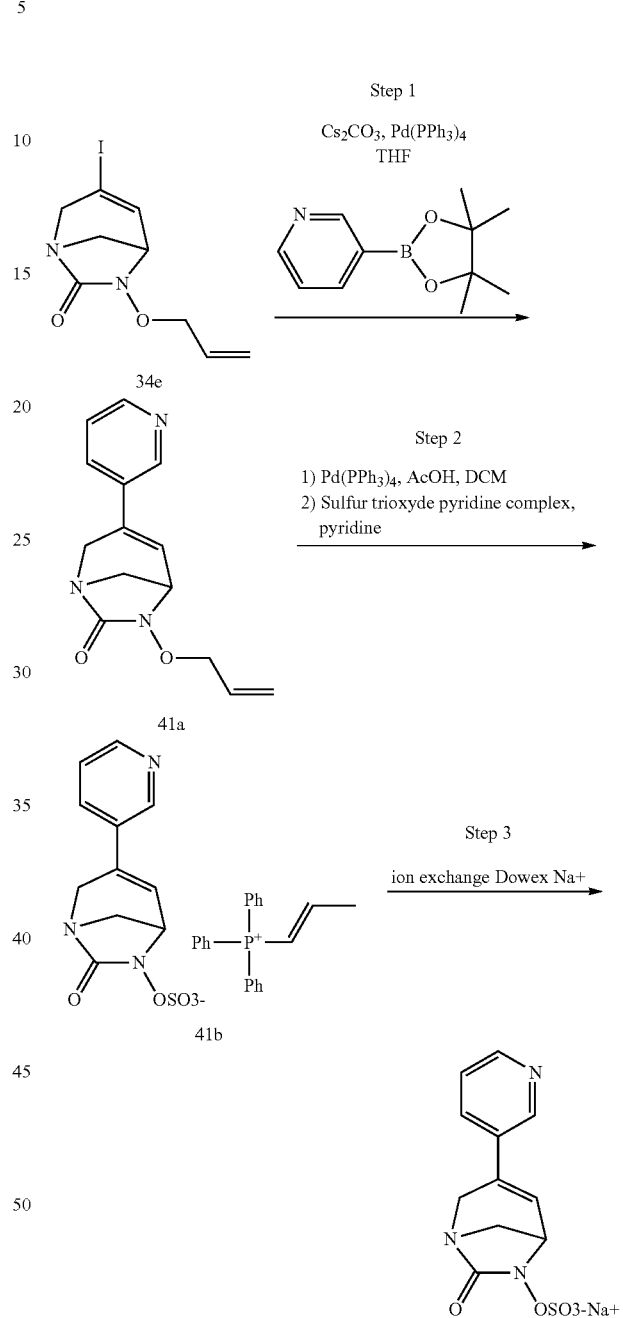

Step 1: Preparation of Intermediate 6-allyloxy-3-(3-pyridyl)-1,6-diazabicyclo[3.2.1]oct-3-en-7-one (41a)

In a wheaton vial, 6-allyloxy-3-iodo-1,6-diazabicyclo[3.2.1]oct-3-en-7-one (34e) (200 mg, 0.653 mmol), pyridine-3-boronic acid pinacol ester (161 mg, 0.784 mmol), dry Cs$_2$CO$_3$ (426 mg, 1.31 mmol) were dissolved in anhydrous THF (6.5 mL). The solution was degassed under argon for 5 min and [1,1'-Bis(diphenylphosphino)ferrocene] dichloropalladium(II) (107 mg, 0.131 mmol) was added. The reaction was stirred at 60° C. overnight. The reaction mixture was filtered on isolute Si-TMT resin and concentrated under reduced pressure to afford a crude material which was purified by flash chromatography on C-18 reverse phase (H$_2$O/ACN 90/10 to 0/100) to give 6-allyloxy-3-(3-pyridyl)-1,6-diazabicyclo[3.2.1]oct-3-en-7-one (41a) (85 mg, 0.329 mmol, 50%) as a clear yellow gum.

MS m/z ([M+H]$^+$) 258.

$^1$H NMR (300 MHz, CDCl$_3$): δ (ppm) 3.15 (d, J=10.1 Hz, 1H), 3.55 (ddd, J=10.7/2.9/1.2 Hz, 1H), 4.04 (ddd, J=11.2/6.0/2.1 Hz, 2H), 4.24 (dd, J=17.6/1.2 Hz, 1H), 4.35-4.50 (m, 2H), 5.26-5.32 (m, 1H), 5.36 (dq, J=17.6/1.5 Hz, 1H), 5.94-6.10 (m, 1H), 6.64-6.70 (m, 1H), 7.25 (ddd, J=8.0/4.8, 0.8 Hz, 1H), 7.57 (ddd, J=8.0/2.4, 1.6 Hz, 1H), 8.52 (dd, J=4.8/1.6 Hz, 1H), 8.56 (dd, J=2.4/0.8 Hz, 1H).

Step 2: Preparation of triphenyl-(propenyl)-phosphonium [3-(3-pyridyl)-7-oxo-1,6-diazabicyclo [3.2.1]oct-3-en-6-yl] sulfate (41b)

Using the procedure described in example 1 (step 6), the intermediate 6-allyloxy-3-(3-pyridyl)-1,6-diazabicyclo [3.2.1]oct-3-en-7-one (41a) (85 mg, 0.329 mmol) was converted into triphenyl-(propenyl)-phosphonium [3-(3-pyridyl)-7-oxo-1,6-diazabicyclo[3.2.1]oct-3-en-6-yl] sulfate (41b) after purification by flash chromatography on silica gel (DCM/acetone 100/0 to 0/100).

MS m/z ([M−H]$^-$) 296.

MS m/z ([M+H]$^+$) 303 (triphenyl-propenyl-phosphonium).

Step 3: Preparation of Sodium [3-(3-pyridyl)-7-oxo-1,6-diazabicyclo[3.2.1]oct-3-en-6-yl]sulfate (Example 41)

Using the procedure described in example 1 (step 7), triphenyl-(propenyl)-phosphonium [3-(3-pyridyl)-7-oxo-1, 6-diazabicyclo[3.2.1]oct-3-en-6-yl] sulfate (41b) was converted after ion exchange (Dowex sodium form column) into sodium [3-(3-pyridyl)-7-oxo-1,6-diazabicyclo[3.2.1]oct-3-en-6-yl] sulfate (Example 41) (19.8 mg, 0.062 mmol, 19% over 3 steps) as a white solid after lyophilization.

MS m/z ([M−H]$^-$) 296.

$^1$H NMR (300 MHz, D$_2$O): δ (ppm) 3.43 (d, J=11.2 Hz, 1H), 3.65-3.72 (m, 1H), 4.12 (d, J=17.8 Hz, 1H), 4.28 (dd, J=17.8/2.1 Hz, 1H), 4.50 (dd, J=5.4/2.7 Hz, 1H), 6.72 (d, J=5.3 Hz, 1H), 7.38 (dd, J=8.2/4.9 Hz, 1H), 7.74 (dt, J=8.2/2.0 Hz, 1H), 8.37-8.44 (m, 2H).

Example 42

Synthesis of Sodium [7-oxo-3-(2-pyridyl)-1,6-diazabicyclo[3.2.1]oct-3-en-6-yl]sulfate

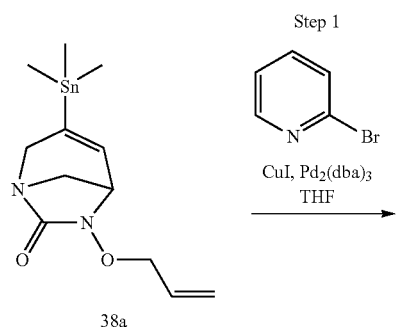

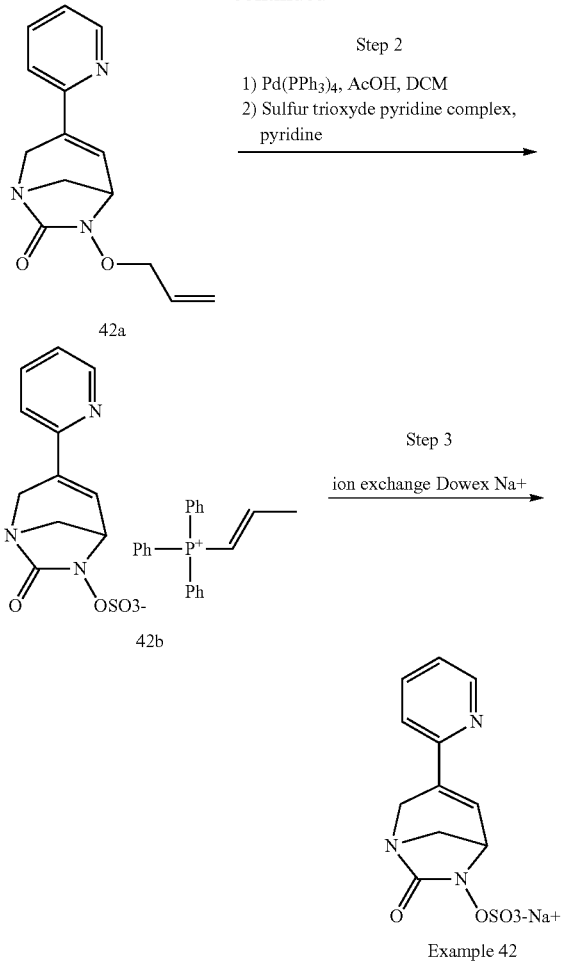

Step 1: Preparation of Intermediate 6-allyloxy-3-(2-pyridyl)-1,6-diazabicyclo[3.2.1]oct-3-en-7-one (42a)

6-Allyloxy-3-trimethylstannanyl-1,6-diaza-bicyclo [3.2.1]oct-3-en-7-one (38a) (150 mg, 0.437 mmol) was solubilised in anhydrous THF (4.5 mL) with 2-bromopyridine (83 mg, 0.525 mmol) and the solution was degassed for 15 min under argon. Tris(dibenzylideneacetone)dipalladium (0) (60 mg, 0.066 mmol) and dry CuI (12.5 mg, 0.066 mmol) were added. The mixture was heated for 16 h at 70° C. The reaction was poured over SiTMT scavenger cartridge (500 mg) and eluted with DCM (3×2 mL). The filtrate was evaporated to dryness under reduced pressure. The crude product was purified on silica gel (DCM/acetone 100/0 to 80/20) to provide 6-allyloxy-3-(2-pyridyl)-1,6-diazabicyclo [3.2.1]oct-3-en-7-one (42a) (35 mg, 0.136 mmol, 31%).

MS m/z ([M+H]$^+$) 258.

Step 2: Preparation of Intermediate triphenyl-(propenyl)-phosphonium [3-(2-pyridyl)-7-oxo-1,6-diazabicyclo[3.2.1]oct-3-en-6-yl] sulfate (42b)

Using the procedure described in example 1 (step 6), the intermediate 6-allyloxy-3-(2-pyridyl)-1,6-diazabicyclo [3.2.1]oct-3-en-7-one (41a) (85 mg, 0.329 mmol) was converted into triphenyl-(propenyl)-phosphonium [3-(2-pyridyl)-7-oxo-1,6-diazabicyclo[3.2.1]oct-3-en-6-yl] sulfate (42b) after purification by flash chromatography on silica gel (DCM/acetone 100/0 to 0/100) as a white foam.

MS m/z ([M−H]⁻) 296.

MS m/z ([M+H]⁺) 298.

MS m/z ([M+H]⁺) 303 (triphenyl-propenyl-phosphonium).

Step 3: Preparation of Sodium [7-oxo-3-(2-pyridyl)-1,6-diazabicyclo[3.2.1]oct-3-en-6-yl]sulfate (Example 42)

Using the procedure described in example 1 (step 7), Triphenyl-(propenyl)-phosphonium [3-(2-pyridyl)-7-oxo-1,6-diazabicyclo[3.2.1]oct-3-en-6-yl] sulfate (42b) was converted after ion exchange (Dowex sodium form column) into sodium [7-oxo-3-(2-pyridyl)-1,6-diazabicyclo[3.2.1]oct-3-en-6-yl] sulfate (Example 42) (17.7 mg, 0.055 mmol, 41% over 3 steps) as a white solid.

MS m/z ([M−H]⁻) 296, ([2M−H]⁻) 593.

MS m/z ([M+H]⁺) 298.

$^1$H NMR (400 MHz, D$_2$O): δ (ppm) 3.35 (d, J=11.2 Hz, 1H), 3.62 (dd, J=11.2/2.1 Hz, 1H), 4.16 (d, J=17.8 Hz, 1H), 4.26 (dd, J=17.8/1.6 Hz, 1H), 4.44-4.48 (m, 1H), 6.98 (d, J=5.1 Hz, 1H), 7.34 (dd, J=7.9/5.4 Hz, 1H), 7.49 (d, J=7.9 Hz, 1H), 7.78-7.84 (m, 1H), 8.35 (d, J=4.8 Hz, 1H).

Example 43

Synthesis of Sodium [7-oxo-3-(1H-pyrazol-4-yl)-1,6-diazabicyclo[3.2.1]oct-3-en-6-yl] sulfate

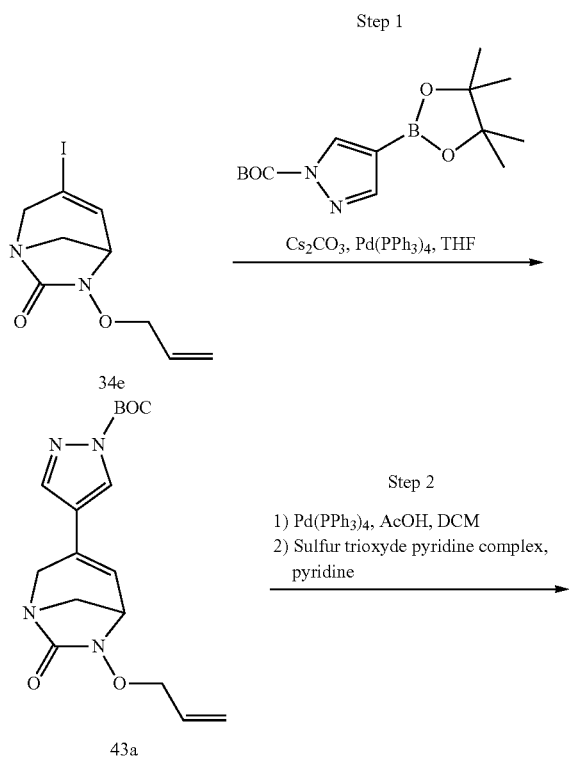

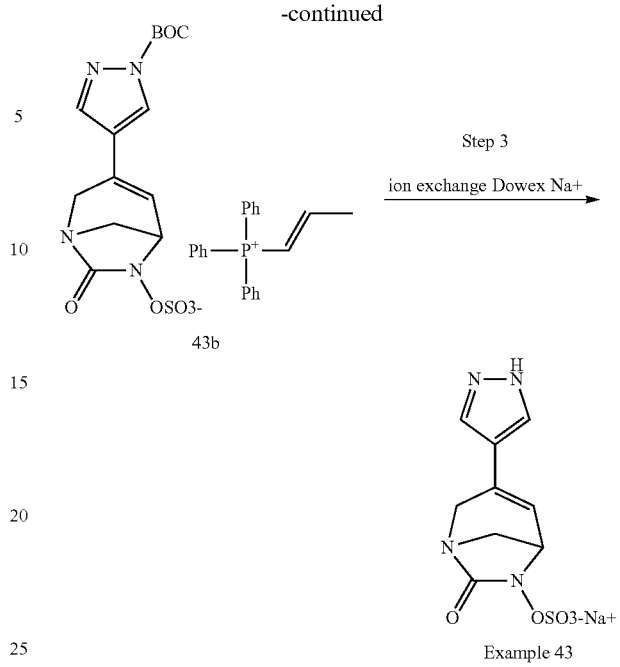

Example 43

Step 1: Preparation of Intermediate tert-butyl 4-(6-allyloxy-7-oxo-1,6-diazabicyclo[3.2.1]oct-3-en-3-yl)pyrazole-1-carboxylate (43a)

In a wheaton vial, 6-allyloxy-3-iodo-1,6-diazabicyclo[3.2.1]oct-3-en-7-one (34e) (200 mg, 0.653 mmol), tert-butyl 4-(4,4,5,5-tetramethyl-1,3,2-dioxaborolan-2-yl)pyrazole-1-carboxylate (230 mg, 0.784 mmol), dry Cs$_2$CO$_3$ (425 mg, 1.30 mmol) were dissolved in anhydrous THF (6.5 mL). The solution was degassed under nitrogen for 5 min and Pd(PPh$_3$)$_4$ (37 mg, 0.032 mmol) was added. The reaction was stirred at 55° C. for 22 h. The reaction mixture was filtered and concentrated under reduced pressure to afford a crude material which was purified by flash chromatography on silica gel (dichloromethane/EtOAc 100/0 to 80/20) to give tert-butyl 4-(6-allyloxy-7-oxo-1,6-diazabicyclo[3.2.1] oct-3-en-3-yl)pyrazole-1-carboxylate (43a) (107 mg, 0.309 mmol, 47%) as a white solid.

MS m/z ([M+H]⁺) 347.

$^1$H NMR (300 MHz, CDCl$_3$): δ (ppm) 1.63 (s, 9H), 3.13 (d, J=10.7 Hz, 1H), 3.53 (ddd, J=10.7/2.8/1.3 Hz, 1H), 3.84-4.02 (m, 2H), 4.08 (dt, J=17.4/1.3 Hz, 1H), 4.30-4.51 (m, 2H), 5.23-5.42 (m, 2H), 5.91-6.11 (m, 1H), 6.49-6.59 (m, 1H), 7.73 (d, J=0.9 Hz, 1H), 7.92 (d, J=0.9 Hz, 1H).

Step 2: Preparation of Intermediate triphenyl-(propenyl)-phosphonium [3-(1-tert-butoxycarbonylpyrazol-4-yl)-7-oxo-1,6-diazabicyclo[3.2.1]oct-3-en-6-yl] sulfate (43b)

Using the procedure described in example 1 (step 6), the intermediate tert-butyl 4-(6-allyloxy-7-oxo-1,6-diazabicyclo[3.2.1]oct-3-en-3-yl)pyrazole-1-carboxylate (43a) (83 mg, 0.240 mmol) was converted into 30 mg of triphenyl-(propenyl)-phosphonium [3-(1-tert-butoxycarbonylpyrazol-4-yl)-7-oxo-1,6-diazabicyclo[3.2.1]oct-3-en-6-yl] sulfate (43b) as a colorless oil after purification by flash chromatography on silica gel (dichloromethane/acetone 100/0 to 0/100, then acetone/iPrOH 100/0 to 50/50).

MS m/z ([M−H]−) 385.
MS m/z ([M+H]+) 303 (triphenyl-propenyl-phosphonium).

Step 3: Preparation of Sodium [7-oxo-3-(1H-pyrazol-4-yl)-1,6-diazabicyclo[3.2.1]oct-3-en-6-yl] sulfate (Example 43)

Triphenyl-(propenyl)-phosphonium [3-(1-tert-butoxycarbonylpyrazol-4-yl)-7-oxo-1,6-diazabicyclo[3.2.1]oct-3-en-6-yl] sulfate (43b) was applied on a Dowex sodium form column (Dowex® 50WX8 hydrogen form stored with an aqueous solution of 2N NaOH and washed until neutral pH with water). The fractions containing the desired compound were combined and concentrated to give 10 mg of white solid. This solid was purified by flash chromatography on C-18 reverse phase (water/acetonitrile 95/5 to 0/100) The fractions containing the desired compound were combined, freezed and lyophilized to afford sodium [7-oxo-3-(1H-pyrazol-4-yl)-1,6-diazabicyclo[3.2.1]oct-3-en-6-yl] sulfate (Example 43) (3 mg, 0.010 mmol, 4% over 3 steps) as a white solid.

MS m/z ([M−H]−) 285, ([2M−H]−) 571.
MS m/z ([M+H]+) 287.

1H NMR (400 MHz, D2O): δ (ppm) 3.33-3.53 (m, 1H), 3.63-3.73 (m, 1H), 4.09 (dd, J=17.6/1.3 Hz, 1H), 4.21 (dd, J=17.6/2.1 Hz, 1H), 4.42 (dd, J=5.3/2.8 Hz, 1H), 6.58 (dt, J=4.9/1.4 Hz, 1H), 7.79 (s, 2H).

Example 44

Synthesis of Sodium [(5R)-3-(oxazol-2-yl)-7-oxo-1,6-diazabicyclo[3.2.1]oct-3-en-6-yl] sulfate (example 44)

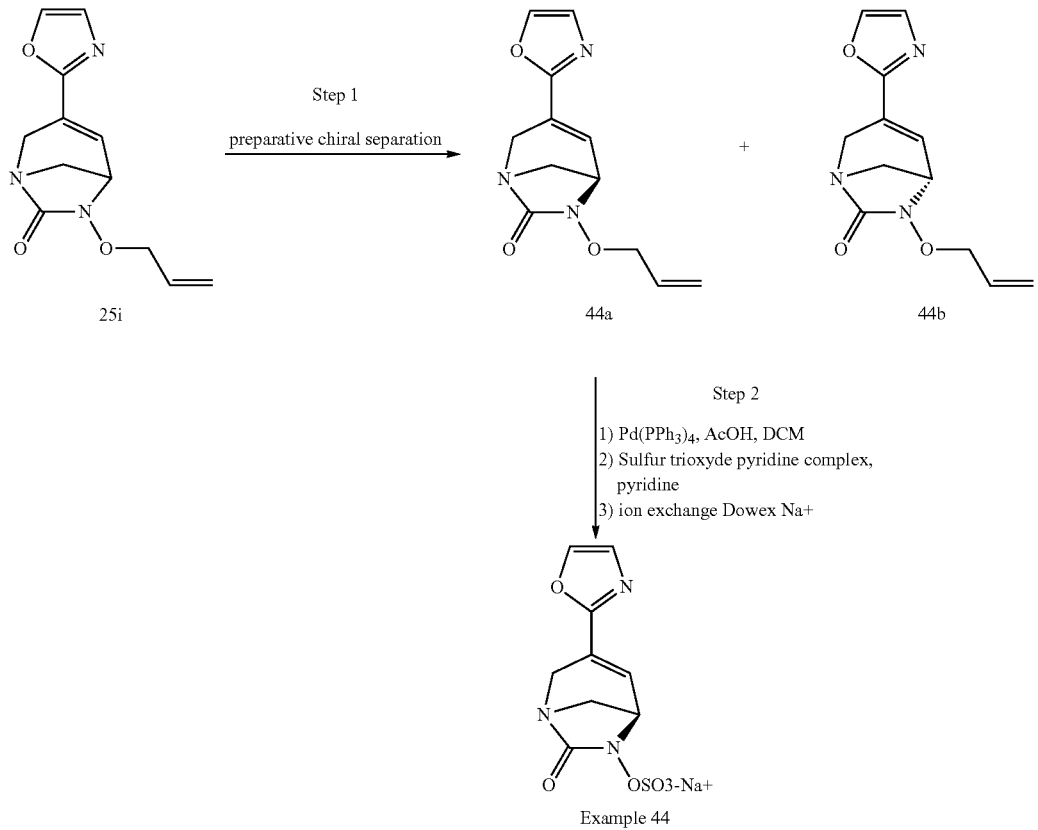

Example 44

Step 1: Preparation of Intermediates (5R)-6-allyloxy-3-oxazol-2-yl-1,6-diazabicyclo[3.2.1]oct-3-en-7-one (44a) and (5S)-6-allyloxy-3-oxazol-2-yl-1,6-diazabicyclo[3.2.1]oct-3-en-7-one (44b)

Both enantiomers of 6-allyloxy-3-oxazol-2-yl-1,6-diazabicyclo[3.2.1]oct-3-en-7-one (25i) (3.94 g, 15.9 mmol) were separated using preparative chiral chromatography (CHIRALPAK® ID 5 µm, 250*30 mm, Heptane/DCM 30/70, 42.5 mL/min) to provide (5R)-6-allyloxy-3-oxazol-2-yl-1,6-diazabicyclo[3.2.1]oct-3-en-7-one (44a) (1.70 g, 6.88 mmol, 43%, 98.7 ee) and (5S)-6-allyloxy-3-oxazol-2-yl-1,6-diazabicyclo[3.2.1]oct-3-en-7-one (44b) (1.55 g, 6.27 mmol, 39%, 99.4 ee).

MS m/z ([M+H]+) 248.

(44a) (44b) 1H NMR (400 MHz, CDCl3): δ (ppm) 3.17 (d, J=10.9 Hz, 1H), 3.56-3.54 (m, 1H), 4.07-4.17 (m, 2H), 4.34-4.51 (m, 3H), 5.31-5.45 (m, 2H), 5.97-6.14 (m, 1H), 7.16 (d, J=0.7 Hz, 1H), 7.17-7.19 (m, 1H), 7.62 (d, J=0.7 Hz, 1H).

Step 2: Preparation of Sodium [(5R)-3-(oxazol-2-yl)-7-oxo-1,6-diazabicyclo[3.2.1]oct-3-en-6-yl] sulfate (Example 44)

Using the procedure described in example 34 (step 7), the intermediate (5R)-6-allyloxy-3-oxazol-2-yl-1,6-diazabicyclo[3.2.1]oct-3-en-7-one (44a) (1.60 g, 6.47 mmol) was converted into sodium [(5R)-3-(oxazol-2-yl)-7-oxo-1,6-diazabicyclo[3.2.1]oct-3-en-6-yl] sulfate (example 44) (0.82 g, 2.65 mmol, 41%) after lyophilization.

MS m/z ([M–H]$^-$) 286.

$^1$H NMR (400 MHz, D$_2$O): δ (ppm) 3.23 (d, J=11.3 Hz, 1H), 3.45-3.53 (m, 1H), 3.96 (dd, J=17.8/1.5 Hz, 1H), 4.05 (dd, J=17.8/2.0 Hz, 1H), 4.34 (dd, J=5.2/2.5 Hz, 1H), 6.97 (d, J=0.8 Hz, 1H), 6.99-7.04 (m, 1H), 7.62 (d, J=0.8 Hz, 1H).

Example 45

Synthesis of Sodium [7-oxo-3-(2-oxopyrrolidin-1-yl)-1,6-diazabicyclo[3.2.1]oct-3-en-6-yl]sulfate

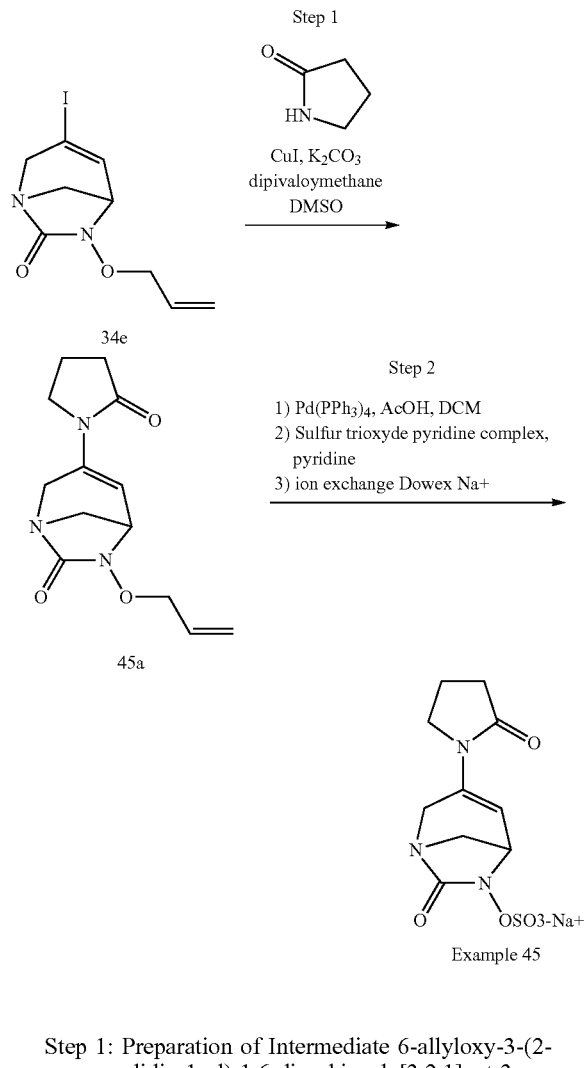

Step 1: Preparation of Intermediate 6-allyloxy-3-(2-oxopyrrolidin-1-yl)-1,6-diazabicyclo[3.2.1]oct-3-en-7-one (45a)

In a wheaton vial under argon atmosphere, 6-allyloxy-3-iodo-1,6-diazabicyclo[3.2.1]oct-3-en-7-one (34e) (206 mg, 0.67 mmol), 2-pyrrolidinone (86 mg, 1.01 mmol), dry CuI (13 mg, 0.067 mmol), K$_2$CO$_3$ (186 mg, 1.35 mmol) and dipivaloymethane (27 µL, 0.13 mmol) were dissolved in DMSO (3.3 mL). The reaction was stirred at 100° C. overnight, filtered, washed with DCM and concentrated in vacuo. The crude was purified by flash chromatography on silica gel (DCM/MeOH 100/0 to 95/5) followed by a preparative TLC (DCM/MeOH 97/3) to provide 6-allyloxy-3-(2-oxopyrrolidin-1-yl)-1,6-diazabicyclo[3.2.1]oct-3-en-7-one (45a) (47 mg, 0.179 mmol, 27%) as an lightly coloured oil.

MS m/z ([M+H]$^+$) 264, ([2M+H]$^+$) 527.

$^1$H NMR (300 MHz, CDCl$_3$): δ (ppm) 1.99-2.11 (m, 2H), 2.38-2.46 (m, 2H), 3.04 (d, J=10.5 Hz, 1H), 3.38-3.54 (m, 3H), 3.96 (dd, J=5.4/2.5 Hz, 1H), 4.33-4.44 (m, 2H), 4.44-4.49 (m, 2H), 5.25-5.30 (m, 1H), 5.34 (dq, J=17.2/1.4 Hz, 1H), 5.50 (dd, J=5.6/1.3 Hz, 1H), 5.92-6.08 (m, 1H).

Step 2: Preparation of Sodium [7-oxo-3-(2-oxopyrrolidin-1-yl)-1,6-diazabicyclo[3.2.1]oct-3-en-6-yl] sulfate (Example 45)

Using the procedure described in example 34 (step 7), the intermediate 6-allyloxy-3-(2-oxopyrrolidin-1-yl)-1,6-diazabicyclo[3.2.1]oct-3-en-7-one (Xa) (47 mg, 0.179 mmol) could be converted into sodium [7-oxo-3-(2-oxopyrrolidin-1-yl)-1,6-diazabicyclo[3.2.1]oct-3-en-6-yl] sulfate (example 45).

Example 46

Synthesis of Sodium [7-oxo-3-(2-oxoazetidin-1-yl)-1,6-diazabicyclo[3.2.1]oct-3-en-6-yl] sulfate

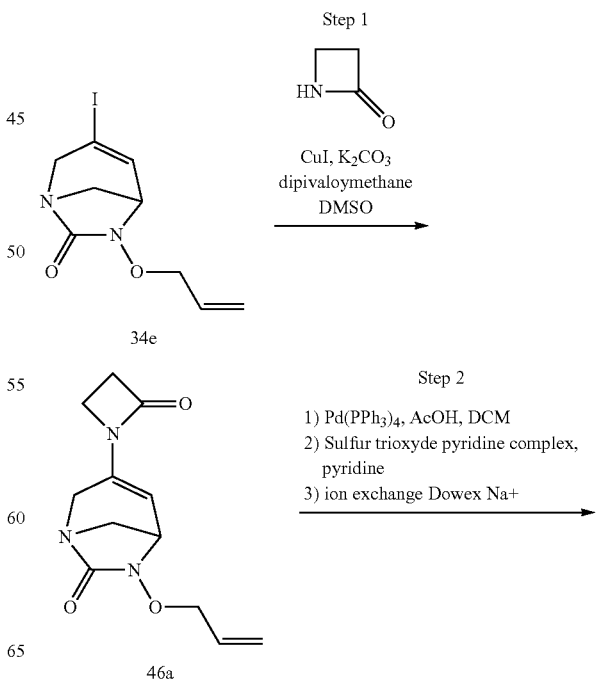

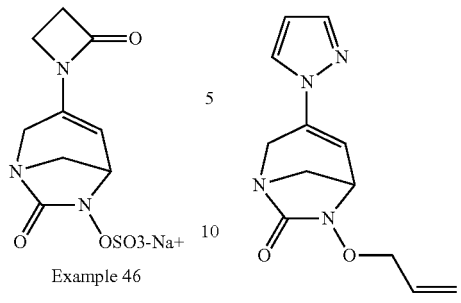

Example 46

Step 1: Preparation of Intermediate 6-allyloxy-3-(2-oxoazetidin-1-yl)-1,6-diazabicyclo[3.2.1]oct-3-en-7-one (46a)

Using the procedure described in example 45 (step 1), the intermediate 6-allyloxy-3-iodo-1,6-diazabicyclo[3.2.1]oct-3-en-7-one (34e) (250 mg, 0.817 mmol) was converted into 6-allyloxy-3-(2-oxoazetidin-1-yl)-1,6-diazabicyclo[3.2.1]oct-3-en-7-one (46a) (114 mg, 0.457 mmol, 56%) as an lightly coloured oil, using 2-azetidinone (87 mg, 1.224 mmol) and after purification by flash chromatography on silica gel (DCM/Acetone 98/2 to 0/100) followed by preparative TLC (DCM/Acetone 75/25).

MS m/z ([M+H]$^+$) 250.

$^1$H NMR (400 MHz, CDCl$_3$): δ (ppm) 2.91-2.95 (m, 2H), 3.10 (d, J=10.7 Hz, 1H), 3.25-3.32 (m, 1H), 3.32-3.38 (m, 1H), 3.44 (dd, J=10.8/2.8 Hz, 1H), 3.93 (dd, J=5.4/2.8 Hz, 1H), 4.07 (dd, J=17.8/1.8 Hz, 1H), 4.28-4.47 (m, 3H), 5.23-5.38 (m, 2H), 5.42 (d, J=5.4 Hz, 1H), 5.92-6.05 (m, 1H).

Step 2: Preparation of Sodium [7-oxo-3-(2-oxoazetidin-1-yl)-1,6-diazabicyclo[3.2.1]oct-3-en-6-yl] sulfate (Example 46)

Using the procedure described in example 34 (step 7), the intermediate 6-allyloxy-3-(2-oxoazetidin-1-yl)-1,6-diazabicyclo[3.2.1]oct-3-en-7-one (46a) (114 mg, 0.457 mmol) could be converted into sodium [7-oxo-3-(2-oxoazetidin-1-yl)-1,6-diazabicyclo[3.2.1]oct-3-en-6-yl] sulfate (example 46).

Example 47

Synthesis of Sodium (7-oxo-3-pyrazol-1-yl-1,6-diazabicyclo[3.2.1]oct-3-en-6-yl) sulfate

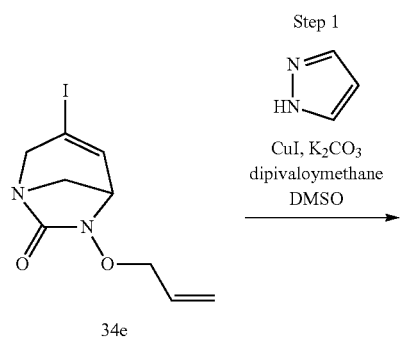

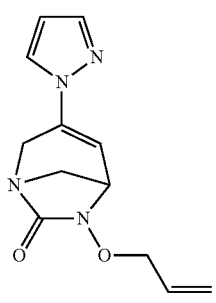

47a

Step 2

1) Pd(PPh$_3$)$_4$, AcOH, DCM
2) Sulfur trioxyde pyridine complex, pyridine
3) ion exchange Dowex Na+

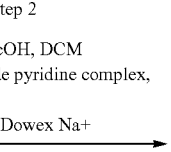

Example 47

Step 1: Preparation of Intermediate 6-allyloxy-3-pyrazol-1-yl-1,6-diazabicyclo[3.2.1]oct-3-en-7-one (47a)

Using the procedure described in example 45 (step 1), 6-allyloxy-3-iodo-1,6-diazabicyclo[3.2.1]oct-3-en-7-one (34e) (20 mg, 0.065 mmol) was converted into 6-allyloxy-3-pyrazol-1-yl-1,6-diazabicyclo[3.2.1]oct-3-en-7-one (47a) (5 mg, 0.020 mmol, 31%) using pyrazole (5 mg, 0.078 mmol) and after purification by preparative TLC (Cyclohexane/EtOAc 50/50) as a yellow oil.

MS m/z ([M+H]$^+$) 247.

$^1$H NMR (400 MHz, CDCl$_3$): δ (ppm) 3.15 (d, J=10.8 Hz, 1H), 3.53 (dd, J=10.8/2.2 Hz, 1H), 4.10 (dd, J=5.6/2.7 Hz, 1H), 4.22 (dd, J=17.6/1.9 Hz, 1H), 4.37-4.50 (m, 3H), 5.28-5.31 (m, 1H), 5.34-5.41 (m, 1H), 5.97-6.08 (m, 1H), 6.35 (dd, J=2.4/1.9 Hz, 1H), 6.46 (d, J=5.5 Hz, 1H), 7.57 (d, J=1.7 Hz, 1H), 7.61 (d, J=2.5 Hz, 1H).

Step 2: Preparation of Sodium (7-oxo-3-pyrazol-1-yl-1,6-diazabicyclo[3.2.1]oct-3-en-6-yl) sulfate (Example 47)

Using the procedure described in example 34 (step 7), the intermediate 6-allyloxy-3-pyrazol-1-yl-1,6-diazabicyclo[3.2.1]oct-3-en-7-one (47a) (105 mg, 0.427 mmol) was converted into sodium (7-oxo-3-pyrazol-1-yl-1,6-diazabicyclo[3.2.1]oct-3-en-6-yl) sulfate (example 47) (69 mg, 0.224 mmol, 52%) as a light yellow solid after lyophilization.

MS m/z ([M–H]$^-$) 285.

$^1$H NMR (400 MHz, D$_2$O): δ (ppm) 3.48 (d, J=11.3 Hz, 1H), 3.71 (dd, J=11.3/2.8 Hz, 1H), 4.34-4.46 (m, 2H), 4.60 (dd, J=5.6/2.7 Hz, 1H), 6.52 (t, J=2.3 Hz, 1H), 6.63 (d, J=5.6 Hz, 1H), 7.73 (d, J=1.8 Hz, 1H), 7.95 (d, J=2.7 Hz, 1H).

Example 48

Synthesis of Sodium [3-(1H-imidazol-2-yl)-7-oxo-1,6-diazabicyclo[3.2.1]oct-3-en-6-yl] sulfate

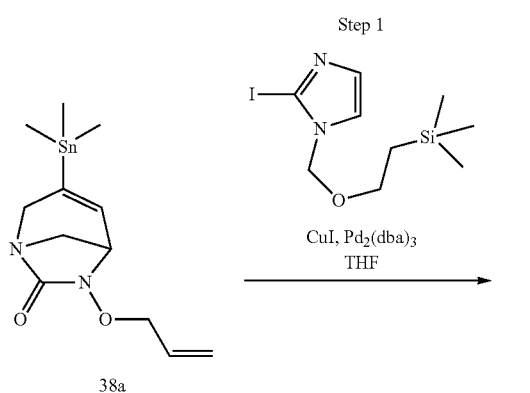

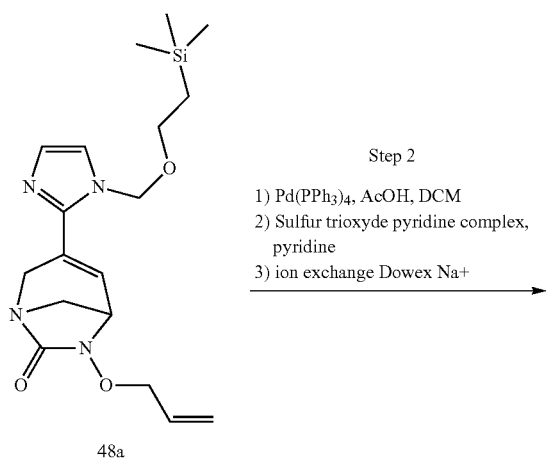

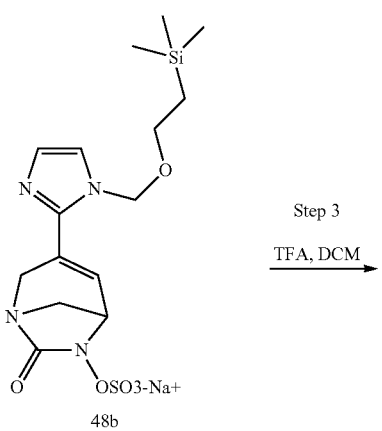

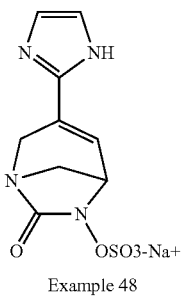

Example 48

Step 1: Preparation of Intermediate 6-allyloxy-3-[1-(2-trimethylsilylethoxymethyl)imidazol-2-yl]-1,6-diazabicyclo[3.2.1]oct-3-en-7-one (48a)

In a sealed tube under inert atmosphere, 6-allyloxy-3-trimethylstannyl-1,6-diazabicyclo[3.2.1]oct-3-en-7-one (38a) (100 mg, 0.291 mmol) and 2-[(2-iodoimidazol-1-yl)methoxy]ethyl-trimethyl-silane (114 mg, 0.349 mmol) were dissolved in anhydrous THF (2.9 mL). Argon was bubbled through the solution for 10 min, then CuI (9 mg, 0.043 mmol) and tris(dibenzylideneacetone)dipalladium (0) (40 mg, 0.0.43 mmol) were added. The mixture was heated at 80° C. overnight. The reaction mixture was filtered on Si-TMT resin and concentrated under reduced pressure to afford a crude material which was purified by flash chromatography on silica gel (DCM/Acetone 100/0 to 0/100) to give 6-allyloxy-3-[1-(2-trimethylsilylethoxymethyl)imidazol-2-yl]-1,6-diazabicyclo[3.2.1]oct-3-en-7-one (48a) (15 mg, 0.040 mmol, 14%).

MS m/z ([M+H]$^+$) 377.

$^1$H NMR (300 MHz, CDCl$_3$): δ (ppm) 0.00 (s, 9H), 0.82-0.99 (m, 2H), 3.25 (d, J=10.8 Hz, 1H), 3.50-3.62 (m, 3H), 4.04 (dd, J=5.3/2.6 Hz, 1H), 4.13 (dd, J=17.9/0.9 Hz, 1H), 4.29 (dd, J=17.9/2.1 Hz, 1H), 4.35-4.51 (m, 2H), 5.18 (d, J=11.0 Hz, 1H), 5.26-5.41 (m, 3H), 5.94-6.10 (m, 1H), 6.78-6.87 (m, 1H), 7.02 (d, J=1.4 Hz, 1H), 7.05 (d, J=1.4 Hz, 1H).

Step 2: Preparation of Intermediate Sodium [7-oxo-3-[1-(2-trimethylsilylethoxymethyl)imidazol-2-yl]-1,6-diazabicyclo[3.2.1]oct-3-en-6-yl] sulfate (48b)

Using the procedure described in example 34 (step 7), the intermediate 6-allyloxy-3-[1-(2-trimethylsilylethoxymethyl)imidazol-2-yl]-1,6-diazabicyclo[3.2.1]oct-3-en-7-one (48a) (15 mg, 0.040 mmol) could be converted into sodium [7-oxo-3-[1-(2-trimethylsilylethoxymethyl)imidazol-2-yl]-1,6-diazabicyclo[3.2.1]oct-3-en-6-yl] sulfate (48b).

Step 3: Preparation of Sodium [3-(1H-imidazol-2-yl)-7-oxo-1,6-diazabicyclo[3.2.1]oct-3-en-6-yl] sulfate (Example 48)

Using the procedure described in example 39 (step 5), the intermediate sodium [7-oxo-3-[1-(2-trimethylsilylethoxymethyl)imidazol-2-yl]-1,6-diazabicyclo[3.2.1]oct-3-en-6-yl] sulfate (48b) could be converted into sodium [3-(1H-imidazol-2-yl)-7-oxo-1,6-diazabicyclo[3.2.1]oct-3-en-6-yl] sulfate (Example 48).

Example 49

Synthesis of Sodium [3-(1-methyl-6-oxo-pyridazin-4-yl)-7-oxo-1,6-diazabicyclo[3.2.1]oct-3-en-6-yl] sulfate

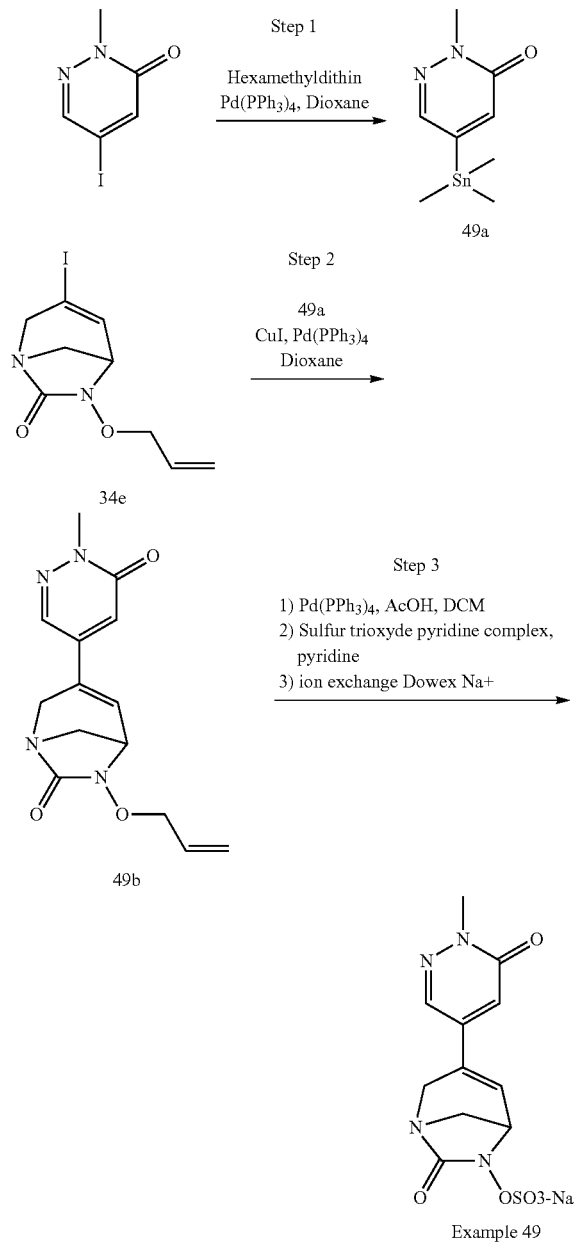

Example 49

Step 1: Preparation of Intermediate 2-methyl-5-trimethylstannyl-pyridazin-3-one (49a)

In a wheaton vial, hexamethylditin (0.26 mL, 1.27 mmol) and Pd(PPh$_3$)$_4$ (24 mg, 0.02 mmol) were added to a solution of 5-iodo-2-methyl-pyridazin-3-one (100 mg, 0.42 mmol) in dioxane (2.5 mL). The reaction was heated a 110° C. for 5 h, and concentrated in vacuo. The crude was purified by flash chromatography on silica gel (DCM/Acetone 100/0 to 40/60) to provide 2-methyl-5-trimethylstannyl-pyridazin-3-one (49a) (106 mg, 0.39 mmol, 92%).

$^1$H NMR (400 MHz, CDCl$_3$): δ (ppm) 0.37 (s, 9H), 3.78 (s, 3H), 7.06 (d, J=1.4 Hz, 1H), 7.71 (d, J=1.4 Hz, 1H).

Step 2: Preparation of Intermediate 6-allyloxy-3-(1-methyl-6-oxo-pyridazin-4-yl)-1,6-diazabicyclo[3.2.1]oct-3-en-7-one (49b)

In a wheaton vial, 6-allyloxy-3-iodo-1,6-diazabicyclo[3.2.1]oct-3-en-7-one (34e) (99 mg, 0.323 mmol), 2-methyl-5-trimethylstannyl-pyridazin-3-one (49a) (106 mg, 0.388 mmol) were dissolved in dioxane (4 mL). The solution was degassed under argon for 5 min then CuI (61 mg, 0.323 mmol) and Pd(PPh$_3$)$_4$ (45 mg, 0.039 mmol) were added. The reaction was heated at 70° C. for 4 h and stirred at rt overnight. The mixture was concentrated in vacuo and purified by flash chromatography on silica gel (DCM/Acetone 100/0 to 0/100) to provide 6-allyloxy-3-(1-methyl-6-oxo-pyridazin-4-yl)-1,6-diazabicyclo[3.2.1]oct-3-en-7-one (49b) (20 mg, 0.068 mmol, 18%).

MS m/z ([M+H]$^+$) 289.

$^1$H NMR (400 MHz, CDCl$_3$): δ (ppm) 3.11 (d, J=10.9 Hz, 1H), 3.54-3.60 (m, 1H), 3.75 (s, 3H), 3.96 (dd, J=17.6/2.1 Hz, 1H), 4.06-4.15 (m, 2H), 4.38-4.48 (m, 2H), 5.31-5.41 (m, 2H), 5.97-6.07 (m, 1H), 6.63 (d, J=2.3 Hz, 1H), 6.90 (d, J=5.3 Hz, 1H), 7.79 (d, J=2.3 Hz, 1H).

Step 3: Preparation of Sodium [3-(1-methyl-6-oxo-pyridazin-4-yl)-7-oxo-1,6-diazabicyclo[3.2.1]oct-3-en-6-yl] sulfate (Example 49)

Using the procedure described in example 34 (step 7), the intermediate 6-allyloxy-3-(1-methyl-6-oxo-pyridazin-4-yl)-1,6-diazabicyclo[3.2.1]oct-3-en-7-one (49b) (47 mg, 0.179 mmol) could be converted into sodium [3-(1-methyl-6-oxo-pyridazin-4-yl)-7-oxo-1,6-diazabicyclo[3.2.1]oct-3-en-6-yl] sulfate (example 49).

Example 50

Synthesis of Sodium [3-(4-carbamoyloxazol-2-yl)-7-oxo-1,6-diazabicyclo[3.2.1]oct-3-en-6-yl] sulfate

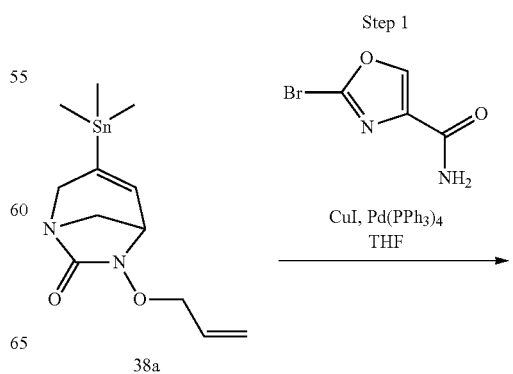

149
-continued

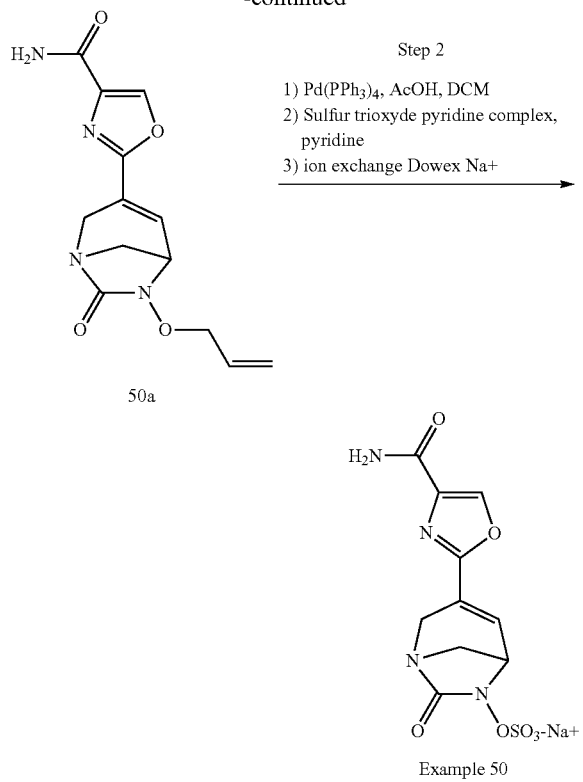

Step 2
1) Pd(PPh₃)₄, AcOH, DCM
2) Sulfur trioxyde pyridine complex, pyridine
3) ion exchange Dowex Na+

50a

Example 50

Step 1: Preparation of Intermediate 2-(6-allyloxy-7-oxo-1,6-diazabicyclo[3.2.1]oct-3-en-3-yl)oxazole-4-carboxamide (50a)

6-Allyloxy-3-trimethylstannanyl-1,6-diaza-bicyclo[3.2.1]oct-3-en-7-one (38a) (0.160 g, 0.47 mmol) was solubilised in THF (10 mL) with 2-bromooxazole-4-carboxamide (107 mg, 0.56 mmol) and the solution was degassed for 15 min under argon. Pd(PPh₃)₄ (0.081 g, 0.07 mmol) and dry CuI (0.013 g, 0.07 mmol) were added. The mixture was heated at 80° C. overnight. The reaction was filtered over PTFE and the filtrate was evaporated under nitrogen flux to provide 2-(6-allyloxy-7-oxo-1,6-diazabicyclo[3.2.1]oct-3-en-3-yl)oxazole-4-carboxamide (50a) (44 mg, 0.15 mmol, 32%).

MS m/z ([M+H]⁺) 291.

150

Step 2: Preparation of Sodium [3-(4-carbamoyloxazol-2-yl)-7-oxo-1,6-diazabicyclo[3.2.1]oct-3-en-6-yl] sulfate (Example 50)

Using the procedure described in example 34 (step 7), the intermediate 2-(6-allyloxy-7-oxo-1,6-diazabicyclo[3.2.1]oct-3-en-3-yl)oxazole-4-carboxamide (50a) (44 mg, 0.151 mmol) was converted into sodium [3-(4-carbamoyloxazol-2-yl)-7-oxo-1,6-diazabicyclo[3.2.1]oct-3-en-6-yl] sulfate (Example 50) (10.5 mg, 0.030 mmol, 20%) after lyophilization.

MS m/z ([M−H]⁻) 329.
$^1$H NMR (300 MHz, D₂O): δ (ppm) 3.46 (d, J=11.4 Hz, 1H), 3.69-3.77 (m, 1H), 4.21 (dd, J=18.0/1.5 Hz, 1H), 4.29 (dd, J=15.9/2.0 Hz, 1H), 4.58 (dd, J=5.3/2.7 Hz, 1H), 7.29-7.35 (m, 1H), 8.34 (s, 1H).

Example 51

Biological Activity

Method 1: β-lactamase inhibitory activity, determination of IC₅₀ (table 1)

Enzyme activity was monitored by spectrophotometric measurement of nitrocefin (NCF-TOKU-E, N005) hydrolysis at 485 nm, at room temperature and in assay buffer A: 100 mM Phosphate $pH_{7.2}$ 2% glycerol and 0.1 mg/mL Bovine serum albumin (Sigma, B4287). Enzymes were cloned in *E. coli* expression vector, expressed and purified in house using classical procedures. To a transparent polystyrene plate (Corning, 3628) were added in each well 5 μL DMSO or inhibitor dilutions in DMSO and 80 μL enzyme in buffer A. Plates were immediately read at 485 nm in a microplate spectrophotometer (BioTek, PowerWave HT) to enable background subtraction. After 30 min of pre-incubation at room temperature, 15 μL of NCF (200 μM final) were finally added in each well. Final enzyme concentrations were 0.1 nM (TEM-1), 0.075 nM (SHV-1), 0.4 nM (CTX-M-15), 1 nM (KPC-2), 0.2 nM (P99 AmpC), 0.2 nM (CMY-37), 0.4 nM (AmpC *P. aeruginosa*), 0.2 nM (OXA-1), 1.2 nM (OXA-11), 0.4 nM (OXA-15) and 0.3 nM (OXA-48). After 20 min incubation at room temperature, plates were once again read at 485 nm. Enzyme activity was obtained by subtracting the final signal by the background, and was converted to enzyme inhibition using non inhibited wells. IC₅₀ curves were fitted to a classical Langmuir equilibrium model with Hill slope using XLFIT (IDBS).

TABLE 1

IC₅₀ (μM) for β-lactamase Inhibitory Activity

| | IC₅₀ β-lactamase (μM) | | | | | | | | | |
|---|---|---|---|---|---|---|---|---|---|---|
| | (A) | | | | (C) | | | (D) | | | |
| | TEM-1 | SHV-1 | CTX-M-15 | KPC-2 | AmpC (P99) | CMY-37 | AmpC (PAE) | OXA-1 | OXA-11 | OXA-15 | OXA-48 |
| Example 1 | 0.013 | 0.029 | 0.026 | 0.77 | 6.1 | 2.7 | 9.3 | 1.4 | 2.9 | 0.59 | 0.0089 |
| Example 2 | 0.0027 | 0.0064 | 0.033 | 1.2 | 0.67 | 0.28 | 0.96 | 0.064 | 0.91 | 0.0098 | 0.0028 |
| Example 3 | 0.0034 | 0.0069 | 0.0028 | 0.29 | 0.77 | 0.39 | 2.0 | 0.21 | 1.1 | 0.033 | 0.0035 |
| Example 4 | 0.0029 | 0.0084 | 0.0075 | 0.39 | 1.5 | 0.59 | 0.94 | 0.26 | 0.80 | 0.046 | 0.0029 |
| Example 5 | 0.011 | 0.025 | 0.0069 | 0.27 | 0.67 | 0.38 | 1.5 | 0.45 | 2.2 | 0.094 | 0.0057 |
| Example 6 | 0.0073 | 0.018 | 0.0017 | 0.46 | 1.8 | 2.4 | 4.2 | 1.7 | 0.18 | 0.028 | 0.0037 |
| Example 7 | 0.012 | 0.030 | 0.013 | 0.15 | 1.7 | 0.75 | 2.2 | 0.25 | 2.3 | 0.095 | 0.0049 |
| Example 8 | 0.0082 | 0.019 | 0.012 | 0.17 | 1.9 | 0.87 | 3.3 | 0.69 | 1.4 | 0.14 | 0.0022 |
| Example 9 | 0.0038 | 0.011 | 0.0048 | 0.068 | 0.77 | 0.27 | 0.81 | 0.13 | 0.73 | 0.052 | 0.0014 |
| Example 10 | 0.0077 | 0.021 | 0.0083 | 0.13 | 1.1 | 0.43 | 2.6 | 0.20 | 1.3 | 0.14 | 0.0061 |
| Example 11 | 0.027 | 0.056 | 0.029 | 1.8 | 8.9 | 2.1 | 4.6 | 1.3 | 6.4 | 0.31 | 0.0051 |

TABLE 1-continued

IC$_{50}$ (μM) for β-lactamase Inhibitory Activity

| | IC$_{50}$ β-lactamase (μM) | | | | | | | | | | |
|---|---|---|---|---|---|---|---|---|---|---|---|
| | (A) | | | | (C) | | | (D) | | | |
| | TEM-1 | SHV-1 | CTX-M-15 | KPC-2 | AmpC (P99) | CMY-37 | AmpC (PAE) | OXA-1 | OXA-11 | OXA-15 | OXA-48 |
| Example 12 | 0.0031 | 0.0069 | 0.0057 | 0.31 | 1.4 | 0.55 | 1.6 | 0.35 | 1.2 | 0.066 | 0.0032 |
| Example 13 | 0.0061 | 0.0088 | 0.0060 | 0.063 | 2.8 | 1.5 | 3.2 | 0.82 | 0.73 | 0.23 | 0.0023 |
| Example 14 | 0.0016 | 0.0029 | 0.0027 | 0.052 | 0.89 | 0.73 | 1.9 | 0.73 | 0.92 | 0.033 | 0.0014 |
| Example 15 | 0.0099 | 0.012 | 0.0063 | 0.11 | 2.0 | 1.0 | 3.5 | 1.1 | 2.6 | 0.29 | 0.0079 |
| Example 16 | 0.056 | 0.12 | 0.10 | 4.5 | 7.3 | 3.6 | 7.1 | 0.72 | 7.4 | 0.027 | 0.010 |
| Example 17 | 0.0012 | 0.0028 | 0.0057 | 0.13 | 2.3 | 0.92 | 0.91 | 0.33 | 1.4 | 0.057 | 0.0039 |
| Example 18 | 0.0027 | 0.011 | 0.017 | 1.8 | 0.23 | 0.13 | 2.7 | 0.035 | 0.54 | 0.014 | 0.020 |
| Example 19 | 0.0040 | 0.0089 | 0.0054 | 0.046 | 0.94 | 0.64 | 1.8 | 0.38 | 0.29 | 0.075 | 0.0047 |
| Example 20 | 0.0010 | 0.0067 | 0.0035 | 0.087 | 1.9 | 1.2 | 3.2 | 1.9 | 0.43 | 0.094 | 0.0022 |
| Example 21 | 0.0052 | 0.030 | 0.014 | 3.5 | 0.18 | 0.14 | 0.73 | 0.17 | 1.6 | 0.057 | 0.0010 |
| Example 22 | 0.0050 | 0.019 | 0.0065 | 0.34 | 0.16 | 0.084 | 5.5 | 0.068 | 0.37 | 0.012 | 0.0039 |
| Example 23 | 0.0015 | 0.0031 | 0.012 | 0.097 | 0.58 | 0.31 | 1.6 | 0.87 | 2.2 | 0.11 | 0.0048 |
| Example 24 | 0.012 | 0.020 | 0.014 | 0.16 | 1.1 | 0.50 | 1.4 | 0.38 | 1.2 | 0.048 | 0.0036 |
| Example 25 | 0.0038 | 0.015 | 0.015 | 0.030 | 0.064 | 0.043 | 0.097 | 0.31 | 0.19 | 0.30 | 0.0066 |
| Example 26 | 0.0048 | 0.013 | 0.0057 | 0.0042 | 0.051 | 0.042 | 0.074 | 0.37 | 0.14 | 0.21 | 0.0066 |
| Example 27 | 0.00021 | 0.0021 | 0.0014 | 0.0027 | 0.0091 | 0.0092 | 0.068 | 0.56 | 0.15 | 0.099 | 0.0064 |
| Example 28 | 0.0016 | 0.0038 | 0.0044 | 0.0065 | 0.077 | 0.073 | 0.52 | 1.0 | 0.43 | 0.018 | 0.054 |
| Example 29 | 0.011 | 0.020 | 0.0058 | 0.15 | 0.95 | 0.48 | 1.2 | 0.33 | 1.7 | 0.091 | 0.0028 |
| Example 30 | 0.0052 | 0.015 | 0.0018 | 0.063 | 0.20 | 0.16 | 0.78 | 0.15 | 0.72 | 0.023 | 0.0025 |
| Example 31 | 0.0049 | 0.011 | 0.0055 | 0.36 | 0.94 | 0.79 | 1.5 | 1.1 | 0.99 | 0.097 | 0.0023 |
| Example 32 | 0.0075 | 0.033 | 0.014 | 0.30 | 4.4 | 2.2 | 3.2 | 0.67 | 3.5 | 0.17 | 0.0089 |
| Example 33 | 0.0010 | 0.0023 | 0.00079 | 0.0090 | 0.031 | 0.029 | 0.090 | 0.69 | 0.21 | 0.11 | 0.012 |
| Example 34 | 0.0072 | 0.021 | 0.0027 | 0.024 | 0.059 | 0.13 | 0.50 | 0.41 | 0.65 | 0.22 | 0.22 |
| Example 35 | 0.0023 | 0.0084 | 0.00081 | 0.0082 | 0.051 | 0.058 | 0.21 | 1.4 | 0.30 | 0.074 | 0.0025 |
| Example 36 | 0.0023 | 0.016 | 0.0011 | 0.039 | 0.043 | 0.056 | 0.16 | 2.4 | 0.92 | 0.66 | 0.0021 |
| Example 37 | 0.0016 | 0.013 | 0.00057 | 0.053 | 0.63 | 0.52 | 0.24 | 7.4 | 0.21 | 0.059 | 0.0018 |
| Example 38 | 0.00070 | 0.0043 | 0.00079 | 0.019 | 0.031 | 0.037 | 0.32 | 0.63 | 0.56 | 0.28 | 0.0077 |
| Example 39 | 0.0014 | 0.0032 | 0.00062 | 0.011 | 0.046 | 0.022 | 0.24 | 0.22 | 0.14 | 0.079 | 0.00099 |
| Example 40 | 0.00035 | 0.0011 | 0.0012 | 0.0022 | 0.010 | 0.022 | 0.23 | 0.12 | 0.061 | 0.077 | 0.0027 |
| Example 41 | 0.0018 | 0.0036 | 0.0026 | 0.0090 | 0.040 | 0.054 | 0.19 | 1.4 | 0.84 | 0.15 | 0.0014 |
| Example 42 | 0.0024 | 0.0029 | 0.00089 | 0.0080 | 0.025 | 0.023 | 0.075 | 0.64 | 0.12 | 0.37 | 0.031 |
| Example 43 | 0.00077 | 0.0017 | 0.0029 | 0.030 | 0.18 | 0.11 | 0.44 | 1.2 | 0.37 | 0.54 | 0.0094 |
| Example 44 | 0.00069 | 0.0060 | 0.00061 | 0.011 | 0.010 | 0.017 | 0.075 | 0.087 | 0.046 | 0.067 | 0.0015 |

Method 2: MIC of Compounds and Synergy with Ceftazidime Against Bacterial Isolates (Table 2 and 3)

Compounds of the present invention were assessed against genotyped bacterial strains alone or in combination with the β-lactam ceftazidime (CAZ). In the assays, MICs of said compounds, or of ceftazidime at fixed concentrations of said compounds were determined by the broth microdilution method according to the Clinical Laboratory Standards Institute (CLSI-M7-A7). Briefly, compounds alone according to the invention were prepared in DMSO and spotted (2 μL each) on sterile polystyrene plates (Corning, 3788). Compounds and ceftazidime dilutions were prepared in DMSO and spotted (1 μL each) on sterile polystyrene plates (Corning, 3788). Log phase bacterial suspensions were adjusted to a final density of 5×10$^5$ cfu/mL in cation-adjusted Mueller-Hinton broth (Becton-Dickinson) and added to each well (98 μL). Microplates were incubated for 16-20 h at 35° C. in ambient air. The MIC of the compounds was defined as the lowest concentration of said compounds that prevented bacterial growth as read by visual inspection. The MIC of ceftazidime at each compound concentration was defined as the lowest concentration of ceftazidime that prevented bacterial growth as read by visual inspection.

TABLE 2

Bacterial species used in MIC determination

| Strains | | Resistance mechanism |
|---|---|---|
| E. cloacae | 260508 | TEM-1, CTX-M-15 |
| E. coli | UFR61O | TEM-1, KPC-2 |
| K. pneumoniae | BAA-1898 | TEM-1, SHV-11, SHV-12, KPC-2 |
| K. pneumoniae | 160143 | TEM-1, SHV-1, CTX-M-15, KPC-2, OXA-1 |
| K. pneumoniae | UFR68 | TEM-1, SHV-11, CTX-M-15, KPC-3 |
| E. cloacae | P99 | AmpC |
| E. cloacae | UFR85 | TEM-1, CTX-M-15, AmpC |
| E. cloacae | UFR70 | TEM-1, CTX-M-15, CMY-2, OXA-1, Porin loss |
| K. pneumoniae | UFR77 | CMY-2 |
| E. coli | UFR74 | SHV-1, DHA-1 |
| E. coli | UFR18 | CTX-M-15, OXA-204 |
| E. coli | 131119 | TEM-1, OXA-48 |
| K. oxytoca | UFR21 | TEM-1, CTX-M-15, OXA-48 |
| K. pneumoniae | UFR24 | TEM-1, SHV-2, SHV-11, OXA-1, OXA-48, OXA-47 |
| K. pneumoniae | 6299 | TEM-1, SHV-11, OXA-163 |
| E. coli | RGN238 | OXA-1 |
| K. pneumoniae | 200047 | TEM-1, SHV-32, CTX-M-15, OXA-1 |
| E. coli | 190317 | TEM-1, SHV-12, CTX-M-15, OXA-1 |
| E. coli | UFR32 | TEM-1, VEB-1, OXA-10 |
| K. pneumoniae | UFR39 | CTX-M-15, NDM-1 |
| E. coli | UFR41 | TEM-1, CTX-M-15, CMY-2, OXA-1, NDM-4 |
| E. cloacae | UFR51 | SHV-12, IMP-8 |
| P. aeruginosa | CIP107051 | TEM-24 |

TABLE 3

| | MIC of compounds | | | | | | | | | | | |
|---|---|---|---|---|---|---|---|---|---|---|---|---|
| | MIC compounds of the invention alone (µg/mL) | | | | | | | | | | | |
| Strains | Example 1 | Example 2 | Example 3 | Example 4 | Example 5 | Example 6 | Example 7 | Example 8 | Example 9 | Example 10 | Example 11 | Example 12 |
| 260508 | | | 16 | | 16 | 4 | | | | | | |
| UFR61O | | | 16 | | 8 | 8 | | | | | | |
| BAA-1898 | >32 | >32 | >32 | >32 | >32 | >32 | >32 | >32 | >32 | >32 | >32 | >32 |
| 160143 | | | >32 | | >32 | >32 | | | | | | |
| UFR68 | | | >32 | | >32 | >32 | | | | | | |
| P99 | >32 | >32 | 8 | 16 | 8 | 4 | >32 | >32 | >32 | 16 | >32 | >32 |
| UFR85 | | | >32 | | >32 | >32 | | | | | | |
| UFR70 | | | 8 | | 16 | 16 | | | | | | |
| UFR77 | | | >32 | | >32 | >32 | | | | | | |
| UFR74 | | | >32 | | >32 | >32 | | | | | | |
| UFR18 | | | 2 | | 1 | 2 | | | | | | |
| 131119 | >32 | >32 | 4 | 16 | 16 | 4 | >32 | >32 | 16 | 16 | >32 | 16 |
| UFR21 | | | >32 | | >32 | >32 | | | | | | |
| UFR24 | | | >32 | | >32 | >32 | | | | | | |
| 6299 | >32 | >32 | >32 | >32 | >32 | >32 | >32 | >32 | >32 | >32 | >32 | >32 |
| RGN238 | >32 | >32 | 16 | 32 | >32 | 16 | >32 | >32 | >32 | >32 | >32 | >32 |
| 200047 | | | >32 | | >32 | 32 | | | | | | |
| 190317 | 32 | >32 | 2 | 8 | 16 | 2 | 8 | 8 | 16 | >32 | >32 | >32 |
| UFR32 | | | >32 | | 1 | 2 | | | | | | |
| UFR39 | | | 4 | | 2 | 4 | | | | | | |
| UFR41 | | | >32 | | >32 | >32 | | | | | | |
| UFR51 | | | 2 | | 2 | 2 | | | | | | |
| CIP107051 | >32 | >32 | >32 | >32 | >32 | >32 | >32 | >32 | >32 | >32 | >32 | >32 |

| | MIC compounds of the invention alone (µg/mL) | | | | | | | | | | | |
|---|---|---|---|---|---|---|---|---|---|---|---|---|
| Strains | Example 13 | Example 14 | Example 15 | Example 16 | Example 17 | Example 18 | Example 19 | Example 20 | Example 21 | Example 22 | Example 23 | Example 24 |
| 260508 | | | 2 | | | | 8 | | | | | |
| UFR61O | | | 8 | | | | >32 | | | | | |
| BAA-1898 | >32 | >32 | >32 | >32 | >32 | >32 | >32 | >32 | >32 | >32 | >32 | >32 |
| 160143 | | | >32 | | | | >32 | | | | | |
| UFR68 | | | >32 | | | | >32 | | | | | |
| P99 | 16 | 8 | 2 | >32 | 16 | 16 | 8 | 32 | >32 | >32 | >32 | >32 |
| UFR85 | | | >32 | | | | >32 | | | | | |
| UFR70 | | | 8 | | | | 16 | | | | | |
| UFR77 | | | >32 | | | | >32 | | | | | |
| UFR74 | | | >32 | | | | >32 | | | | | |
| UFR18 | | | 0.5 | | | | 4 | | | | | |
| 131119 | 8 | 8 | 4 | >32 | 16 | >32 | 2 | 32 | >32 | >32 | 32 | >32 |
| UFR21 | | | 32 | | | | >32 | | | | | |
| UFR24 | | | >32 | | | | >32 | | | | | |
| 6299 | >32 | >32 | >32 | >32 | >32 | >32 | >32 | >32 | >32 | >32 | >32 | >32 |
| RGN238 | >32 | >32 | 16 | >32 | 32 | >32 | 32 | >32 | >32 | >32 | >32 | >32 |
| 200047 | | | >32 | | | | >32 | | | | | |
| 190317 | 8 | 8 | 1 | >32 | 4 | >32 | 2 | 8 | >32 | >32 | >32 | 16 |
| UFR32 | | | 1 | | | | >32 | | | | | |
| UFR39 | | | 0.5 | | | | 4 | | | | | |
| UFR41 | | | >32 | | | | >32 | | | | | |
| UFR51 | | | 0.5 | | | | 4 | | | | | |
| CIP107051 | >32 | >32 | >32 | >32 | >32 | >32 | >32 | >32 | >32 | >32 | >32 | >32 |

| | MIC compounds of the invention alone (µg/mL) | | | | | | | | | | | |
|---|---|---|---|---|---|---|---|---|---|---|---|---|
| Strains | Example 25 | Example 26 | Example 27 | Example 28 | Example 29 | Example 30 | Example 31 | Example 32 | Example 33 | Example 34 | Example 35 | Example 36 |
| 260508 | 4 | | | | | | | | 16 | | | |
| UFR61O | 8 | | | | | | | | 16 | | | |
| BAA-1898 | 4 | 8 | >32 | >32 | >32 | >32 | >32 | >32 | 8 | 16 | 4 | 8 |
| 160143 | 4 | | | | | | | | 8 | | | |
| UFR68 | 4 | | | | | | | | 16 | | | |
| P99 | 8 | 8 | >32 | >32 | >32 | 8 | 16 | 16 | 8 | 8 | 8 | 8 |
| UFR85 | 2 | | | | | | | | 8 | | | |
| UFR70 | 2 | | | | | | | | 4 | | | |
| UFR77 | 4 | | | | | | | | 16 | | | |
| UFR74 | 4 | | | | | | | | 8 | | | |
| UFR18 | 2 | | | | | | | | 4 | | | |
| 131119 | 2 | 2 | >32 | >32 | >32 | 4 | 16 | >32 | 4 | 8 | 2 | 1 |
| UFR21 | 4 | | | | | | | | 32 | | | |
| UFR24 | 4 | | | | | | | | 32 | | | |
| 6299 | 8 | 8 | >32 | >32 | >32 | >32 | >32 | >32 | 16 | 32 | 8 | 16 |

TABLE 3-continued

| MIC of compounds | | | | | | | | | | | | |
|---|---|---|---|---|---|---|---|---|---|---|---|---|
| RGN238 | 2 | 4 | >32 | >32 | >32 | >32 | >32 | >32 | 4 | 16 | 4 | 4 |
| 200047 | 2 | | | | | | | | 8 | | | |
| 190317 | 2 | 2 | >32 | >32 | >32 | 4 | 16 | 8 | 4 | 8 | 2 | 1 |
| UFR32 | 2 | | | | | | | | 8 | | | |
| UFR39 | 8 | | | | | | | | 16 | | | |
| UFR41 | 16 | | | | | | | | 16 | | | |
| UFR51 | 4 | | | | | | | | 16 | | | |
| CIP107051 | >128 | >32 | >32 | >32 | >32 | >32 | >32 | >32 | >32 | >32 | >32 | >32 |

| | MIC compounds of the invention alone (μg/mL) | | | | | | | |
|---|---|---|---|---|---|---|---|---|
| Strains | Example 37 | Example 38 | Example 39 | Example 40 | Example 41 | Example 42 | Example 43 | Example 44 |
| 260508 | 4 | >32 | | | 16 | | | 4 |
| UFR61O | 8 | 2 | | | 16 | | | 4 |
| BAA-1898 | 4 | >32 | >32 | >32 | 8 | 32 | >32 | 4 |
| 160143 | 4 | 8 | | | 8 | | | 1 |
| UFR68 | 4 | 32 | | | 16 | | | 4 |
| P99 | 8 | 4 | >32 | >32 | 8 | >32 | >32 | 4 |
| UFR85 | 2 | 1 | | | 16 | | | 2 |
| UFR70 | 2 | 4 | | | 8 | | | 1 |
| UFR77 | 4 | 32 | | | 8 | | | 2 |
| UFR74 | 4 | 32 | | | 16 | | | 2 |
| UFR18 | 2 | 0.5 | | | 4 | | | 1 |
| 131119 | 2 | 4 | | | 4 | | | 0.5 |
| UFR21 | 4 | 16 | | | 16 | | | 4 |
| UFR24 | 4 | >32 | | | 16 | | | 2 |
| 6299 | 8 | >32 | >32 | >32 | 16 | >32 | >32 | 4 |
| RGN238 | 2 | 32 | | | 32 | | | 1 |
| 200047 | 2 | 8 | | | 8 | | | 1 |
| 190317 | 2 | 1 | >32 | >32 | 8 | 16 | >32 | 0.5 |
| UFR32 | 2 | 32 | | | 8 | | | 1 |
| UFR39 | 8 | 0.5 | >32 | >32 | 4 | 32 | >32 | 4 |
| UFR41 | 16 | 1 | | | 8 | | | 4 |
| UFR51 | 4 | 1 | | | 4 | | | 1 |
| CIP107051 | >128 | >32 | >32 | >32 | >32 | >32 | >32 | >32 |

TABLE 4

| MIC of Ceftazidime/compound combinations | | | | | | | | | | | | |
|---|---|---|---|---|---|---|---|---|---|---|---|---|
| MIC combination of CAZ and compounds of the invention at 4 μg/mL | | | | | | | | | | | | |
| Strains | CAZ | Example 1 | Example 2 | Example 3 | Example 4 | Example 5 | Example 6 | Example 7 | Example 8 | Example 9 | Example 10 | Example 11 |
| 260508 | 128 | | | <=0.125 | | <=0.25 | <=0.25 | | | | | |
| UFR61O | 128 | | | 0.5 | | <0.25 | <0.25 | | | | | |
| BAA-1898 | 256 | 32 | 32 | <=0.125 | 2 | 0.5 | 8 | 4 | 32 | 16 | 4 | 32 |
| 160143 | 128 | | | <=0.125 | | <=0.25 | <=0.25 | | | | | |
| UFR68 | >128 | | | 0.5 | | <=0.25 | 32 | | | | | |
| P99 | 128 | 16 | 16 | <=0.125 | 4 | <=0.125 | <0.25 | 1 | 2 | 32 | 2 | 64 |
| UFR85 | 128 | | | <=0.125 | | <=0.25 | 1 | | | | | |
| UFR70 | >128 | | | 0.25 | | 0.5 | 8 | | | | | |
| UFR77 | 64 | | | 1 | | <=0.25 | 2 | | | | | |
| UFR74 | 64 | | | 0.5 | | <=0.25 | 1 | | | | | |
| UFR18 | >128 | | | <0.25 | | <=0.25 | <=0.25 | | | | | |
| 131119 | 0.5 | | | <0.25 | | <=0.25 | <=0.25 | | | | | |
| UFR21 | 128 | | | <=0.125 | | <=0.25 | <=0.25 | | | | | |
| UFR24 | >128 | | | 2 | | 0.5 | 0.5 | | | | | |
| 6299 | 256 | 1 | 2 | 0.25 | 0.25 | 1 | <=0.125 | 4 | 1 | 4 | 0.5 | 4 |
| RGN238 | 0.5 | | | <=0.125 | | <=0.25 | <=0.25 | | | | | |
| 200047 | 128 | | | <=0.125 | | <=0.25 | <=0.25 | | | | | |
| 190317 | 128 | 0.25 | 1 | <0.25 | <=0.125 | <=0.125 | <=0.25 | <=0.125 | <=0.125 | 0.25 | <=0.125 | 2 |
| UFR32 | >128 | | | <0.25 | | <0.25 | <0.25 | | | | | |
| UFR39 | >1024 | | | >64 | | | | | | | | |
| UFR41 | >128 | | | >64 | | | | | | | | |
| UFR51 | >128 | | | <0.25 | | | | | | | | |
| CIP107051 | 256 | 64 | 128 | 8 | 16 | 32 | 16 | 64 | 64 | 64 | 32 | >128 |

TABLE 4-continued

MIC of Ceftazidime/compound combinations

MIC combination of CAZ and compounds of the invention at 4 µg/mL

| Strains | CAZ | Example 12 | Example 13 | Example 14 | Example 15 | Example 16 | Example 17 | Example 18 | Example 19 | Example 20 | Example 21 | Example 22 |
|---|---|---|---|---|---|---|---|---|---|---|---|---|
| 260508 | 128 | | | | <0.25 | | | | <=0.125 | | | |
| UFR61O | 128 | | | | <=0.25 | | | | 2 | | | |
| BAA-1898 | 256 | 8 | 4 | 1 | <=0.125 | 64 | 1 | 32 | 4 | 32 | 64 | 128 |
| 160143 | 128 | | | | <=0.25 | | | | <=0.125 | | | |
| UFR68 | >128 | | | | <=0.25 | | | | 2 | | | |
| P99 | 128 | 8 | 16 | <=0.125 | <=0.125 | 128 | 4 | 16 | 0.25 | 16 | 64 | 128 |
| UFR85 | 128 | | | | 0.5 | | | | 0.25 | | | |
| UFR70 | >128 | | | | 0.5 | | | | 0.5 | | | |
| UFR77 | 64 | | | | 0.5 | | | | 1 | | | |
| UFR74 | 64 | | | | 0.5 | | | | 1 | | | |
| UFR18 | >128 | | | | <=0.25 | | | | <0.25 | | | |
| 131119 | 0.5 | | | | <=0.25 | | | | <0.25 | | | |
| UFR21 | 128 | | | | <=0.25 | | | | 8 | | | |
| UFR24 | >128 | | | | 0.5 | | | | 16 | | | |
| 6299 | 256 | 2 | 0.25 | 0.25 | <=0.125 | 32 | 0.25 | 8 | 0.25 | 0.25 | 2 | 128 |
| RGN238 | 0.5 | | | | <=0.25 | | | | <=0.125 | | | |
| 200047 | 128 | | | | <=0.25 | | | | <=0.125 | | | |
| 190317 | 128 | <=0.125 | <=0.125 | <0.25 | <=0.25 | 4 | <=0.125 | 1 | <=0.125 | <=0.125 | 4 | 16 |
| UFR32 | >128 | | | | <0.25 | | | | 0.25 | | | |
| UFR39 | >1024 | | | | >128 | | | | >64 | | | |
| UFR41 | >128 | | | | >128 | | | | >64 | | | |
| UFR51 | >128 | | | | 1 | | | | <0.25 | | | |
| CIP107051 | 256 | 64 | 64 | 32 | 16 | 128 | 16 | 128 | 64 | 32 | >128 | >128 |

MIC combination of CAZ and compounds of the invention at 4 µg/mL

| Strains | CAZ | Example 23 | Example 24 | Example 25 | Example 26 | Example 27 | Example 28 | Example 29 | Example 30 | Example 31 | Example 32 | Example 33 |
|---|---|---|---|---|---|---|---|---|---|---|---|---|
| 260508 | 128 | | | <0.25 | | | | | | | | 0.5 |
| UFR61O | 128 | | | <=0.125 | | | | | | | | <=0.25 |
| BAA-1898 | 256 | 32 | 64 | <=0.125 | 0.25 | 32 | 128 | 16 | 4 | 16 | 2 | <=0.125 |
| 160143 | 128 | | | <0.25 | | | | | | | | <=0.25 |
| UFR68 | >128 | | | <0.25 | | | | | | | | 0.5 |
| P99 | 128 | 32 | 128 | <0.25 | 0.5 | 32 | 32 | 8 | <=0.125 | 8 | 0.25 | 0.5 |
| UFR85 | 128 | | | <0.25 | | | | | | | | <0.25 |
| UFR70 | >128 | | | <0.25 | | | | | | | | <0.25 |
| UFR77 | 64 | | | <0.25 | | | | | | | | 0.5 |
| UFR74 | 64 | | | <0.25 | | | | | | | | 0.5 |
| UFR18 | >128 | | | <0.25 | | | | | | | | <0.25 |
| 131119 | 0.5 | | | <0.25 | | | | | | | | <0.25 |
| UFR21 | 128 | | | 0.25 | | | | | | | | 0.5 |
| UFR24 | >128 | | | <0.25 | | | | | | | | 0.5 |
| 6299 | 256 | 16 | 8 | <=0.125 | <=0.125 | 64 | 16 | 4 | 0.25 | 0.25 | 0.5 | 0.5 |
| RGN238 | 0.5 | | | <0.25 | | | | | | | | <=0.25 |
| 200047 | 128 | | | <0.25 | | | | | | | | <0.25 |
| 190317 | 128 | 2 | 1 | <0.25 | <0.25 | 4 | 1 | <=0.125 | <0.25 | 0.25 | <=0.125 | <0.25 |
| UFR32 | >128 | | | <=0.125 | | | | | | | | <0.25 |
| UFR39 | >1024 | | | <=0.125 | | | | | | | | 1 |
| UFR41 | >128 | | | 0.25 | | | | | | | | >128 |
| UFR51 | >128 | | | <0.25 | | | | | | | | >128 |
| CIP107051 | 256 | 128 | 128 | 4 | 4 | 8 | 8 | 64 | 64 | 128 | 8 | 4 |

MIC combination of CAZ and compounds of the invention at 4 µg/mL

| Strains | CAZ | Example 34 | Example 35 | Example 36 | Example 37 | Example 38 | Example 39 | Example 40 | Example 41 | Example 42 | Example 43 | Example 44 |
|---|---|---|---|---|---|---|---|---|---|---|---|---|
| 260508 | 128 | | | | | <=0.25 | | | 0.5 | | | <0.25 |
| UFR61O | 128 | | | | | <0.25 | | | 0.5 | | | <0.25 |
| BAA-1898 | 256 | 0.5 | <=0.125 | <=0.125 | 1 | <=0.125 | 32 | 8 | <=0.125 | 2 | 32 | <0.25 |
| 160143 | 128 | | | | | <=0.25 | | | <=0.25 | | | <0.25 |
| UFR68 | >128 | | | | | <=0.25 | | | <=0.25 | | | <0.25 |
| P99 | 128 | 0.5 | <=0.125 | <=0.125 | 4 | <0.25 | 64 | 32 | 0.5 | 4 | 16 | <0.25 |
| UFR85 | 128 | | | | | <0.25 | | | 0.5 | | | <0.25 |
| UFR70 | >128 | | | | | <0.25 | | | <=0.25 | | | <0.25 |
| UFR77 | 64 | | | | | <0.25 | | | 0.5 | | | <0.25 |
| UFR74 | 64 | | | | | <0.25 | | | <=0.25 | | | <0.25 |
| UFR18 | >128 | | | | | <0.25 | | | <0.25 | | | <0.25 |
| 131119 | 0.5 | | | | | <0.25 | | | <0.25 | | | <0.25 |
| UFR21 | 128 | | | | | <0.25 | | | 1 | | | <0.25 |
| UFR24 | >128 | | | | | <0.25 | | | 0.5 | | | <0.25 |
| 6299 | 256 | 0.5 | <=0.125 | <=0.125 | <=0.125 | <=0.125 | 16 | 32 | 0.25 | 1 | 8 | <0.25 |

TABLE 4-continued

MIC of Ceftazidime/compound combinations

| RGN238 | 0.5 | | | | | <=0.25 | | | <=0.25 | | | <0.25 |
|---|---|---|---|---|---|---|---|---|---|---|---|---|
| 200047 | 128 | | | | | <=0.25 | | | <=0.25 | | | <=0.25 |
| 190317 | 128 | <=0.125 | <0.25 | <0.25 | <0.25 | <0.25 | 1 | 1 | <0.25 | 0.25 | 1 | <0.25 |
| UFR32 | >128 | | | | | <=0.25 | | | <0.25 | | | <0.25 |
| UFR39 | >1024 | | | | | <0.25 | >128 | >128 | <0.25 | >128 | >128 | <0.25 |
| UFR41 | >128 | | | | | <=0.25 | | | <0.25 | | | <0.25 |
| UFR51 | >128 | | | | | <0.25 | | | <0.25 | | | <0.25 |
| CIP107051 | 256 | 4 | 4 | 4 | 8 | 4 | 16 | 8 | 4 | 8 | 32 | 4 |

The invention claimed is:

1. A compound of formula (I)

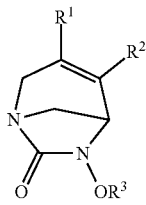

(I)

wherein:
R¹ represents A and R² represents B, or R¹ represents B and R² represents A;

A is a 4- to 10-member heterocycle that has at least one heteroatom/heteroatomic group selected from the group consisting of O, S, S(O), S(O)₂, and N, and is monocyclic or bicyclic, unsubstituted or substituted by one or more T¹, and is a saturated or partially unsaturated or totally unsaturated or aromatic;

B is one of the following:
B is selected from the group consisting of H, F, —(CH₂)$_m$OQ¹, —(CH₂)$_m$—CN, —(CH₂)$_m$—OC(O)Q¹, —(CH₂)$_m$—C(O)OQ¹, —(CH₂)$_m$—OC(O)OQ¹, —(CH₂)$_m$—OC(O)NQ¹Q², —(CH₂)$_m$—C(O)NQ¹Q², —(CH₂)$_m$—C(O)ONQ¹Q², —(CH₂)$_m$—C(O)NQ¹OQ², —(CH₂)$_m$—C(O)NQ¹-NQ¹Q², —(CH₂)$_m$—NQ¹C(O)Q², —(CH₂)$_m$—NQ¹S(O)₂NQ¹Q², —(CH₂)$_m$—NQ¹S(O)₂Q², —(CH₂)$_m$—NQ¹C(O)OQ², —(CH₂)$_m$—NQ¹C(O)NQ¹Q², —(CH₂)$_n$—NQ¹Q², —(CH₂)$_n$—NH—C(NHQ³)=NQ⁴, —(CH₂)$_n$—NH—CH=NQ³, —(CH₂)$_m$—C(NHQ³)=NQ⁴; or B is selected from the group consisting of (C₁-C₃)-alkyl that is unsubstituted or substituted by one or more T², (C₁-C₃)-fluoroalkyl, O-(C₁-C₃)-fluoroalkyl, —(CH₂)$_m$-(C₃-C₆)-cycloalkyl, and —(CH₂)$_m$-(C₃-C₆)-cyclofluoroalkyl;

Q¹ and Q² are one of the following:
Q¹ and Q², identical or different, are independently selected from the group consisting of H, —(CH₂)$_r$—NHQ³, —(CH₂)$_r$—NH—C(NHQ³)=NQ⁴, —(CH₂)$_r$—NH—CH=NQ³, (CH₂)$_n$—C(NHQ³)=NQ⁴, —(CH₂)$_r$—OQ³, and —(CH₂)$_n$—CONHQ³; or Q¹ and Q², identical or different, are independently selected from the group consisting of (C₁-C₃)-alkyl that is unsubstituted or substituted by one or more T², (C₁-C₃)-fluoroalkyl, and —(CH₂)$_m$-(4-, 5- or 6-member heterocycle having at least one nitrogen heteroatom) that is monocyclic, and saturated or partially unsaturated or totally unsaturated or aromatic; or Q¹ and Q² and the nitrogen atom to which they are bonded form a monocyclic, saturated or partially unsaturated 4-, 5-, or 6-member heterocycle that has 1, 2, or 3 heteroatom(s)/heteroatomic groups (s), wherein, in addition to said nitrogen atom being the first of said heteroatom(s)/heteroatomic group(s), the second and third of said heteroatom(s)/heteroatomic group(s) is/are each selected from the group consisting of O, S, S(O), S(O)₂, and N;

Q³ and Q⁴, identical or different, are independently selected from the group consisting of H and (C₁-C₃)-alkyl;

T¹ is one of the following:
T¹, identical or different, is independently selected from the group consisting of F, —(CH₂)$_m$OQ¹, —(CH₂)$_m$—CN, —(CH₂)$_m$—OC(O)Q¹, —(CH₂)$_m$ —C(O)OQ¹, —(CH₂)$_m$—OC(O)OQ¹, —(CH₂)$_m$ —OC(O)NQ¹Q², —(CH₂)$_m$—C(O)NQ¹Q², —(CH₂)$_m$—C(O)ONQ¹Q², —(CH₂)$_m$—C(O)NQ¹OQ², —(CH₂)$_m$—C(O)NQ¹—NQ¹Q², —(CH₂)$_m$—NQ¹C(O)Q², —(CH₂)$_m$—NQ¹S(O)₂NQ¹Q², —(CH₂)$_m$—NQ¹S(O)₂Q², —(CH₂)$_m$—NQ¹C(O)OQ², —(CH₂)$_m$—NQ¹C(O)NQ¹Q², —(CH₂)$_m$—NQ¹Q², —(CH₂)$_m$—NH—C(NHQ³)=NQ⁴, —(CH₂)$_m$—NH—CH=NQ³, —(CH₂)$_m$—C(NHQ³)=NQ⁴, —(X)—(CH₂)$_p$OQ¹, —(X)—(CH₂)$_n$—CN, —(X)—(CH₂)$_p$—OC(O)Q¹, —(X)—(CH₂)$_n$—C(O)OQ¹, —(X)—(CH₂)$_p$—OC(O)OQ¹, —(X)—(CH₂)$_p$—OC(O)NQ¹Q², —(X)—(CH₂)$_n$—C(O)NQ¹Q², —(X)—(CH₂)$_n$—C(O)ONQ¹Q², —(X)—(CH₂)$_n$—C(O)NQ¹OQ², —(X)—(CH₂)$_n$—C(O)NQ¹—NQ¹Q², —(X)—(CH₂)$_p$—NQ¹C(O)Q², —(X)—(CH₂)$_p$—NQ¹S(O)₂NQ¹Q², —(X)—(CH₂)$_p$—NQ¹S(O)₂Q², —(X)—(CH₂)$_p$—NQ¹C(O)OQ², —(X)—(CH₂)$_p$—NQ¹C(O)NQ¹Q², —(X)—(CH₂)$_p$—NQ¹Q², —(X)—(CH₂)$_p$—NH—C(NHQ³)=NQ⁴, —(X)—(CH₂)$_p$—NH—CH=NQ³, —(X)—(CH₂)$_n$—C(NHQ³)=NQ⁴, —C(O)—(CH₂)$_n$OQ¹, —C(O)—(CH₂)$_n$—CN, —C(O)—(CH₂)$_n$—OC(O)Q¹, —C(O)—(CH₂)$_n$—C(O)OQ¹, —C(O)—(CH₂)$_n$—OC(O)OQ¹, —C(O)—(CH₂)$_n$—OC(O)NQ¹Q², —C(O)—(CH₂)$_n$—C(O)NQ¹Q², —C(O)—(CH₂)$_n$—C(O)ONQ¹Q², —C(O)—(CH₂)$_n$—C(O)NQ¹OQ², —C(O)—(CH₂)$_n$—C(O)NQ¹—NQ¹Q², —C(O)—(CH₂)$_n$—NQ¹C(O)Q², —C(O)—(CH₂)$_n$—NQ¹S(O)₂NQ¹Q², —C(O)—(CH₂)$_n$—NQ¹S(O)₂Q², —C(O)—(CH₂)$_n$—NQ¹C(O)OQ², —C(O)—(CH₂)$_n$—NQ¹C(O)NQ¹Q², —C(O)—(CH₂)$_n$—NQ¹Q², —C(O)—(CH₂)$_n$—NH—C(NHQ³)=NQ⁴, —C(O)—(CH₂)$_n$—NH—CH=NQ³, and —C(O)—(CH₂)$_n$—C(NHQ³)=NQ⁴; or T¹, identical or different, is independently selected from the group consisting of —(CH₂)ₘ-(4-, 5- or 6-member heterocycle that has at least one heteratom/heteroatomic group that is selected from the group consisting of O, S, S(O)₂, and N, and is monocyclic, and saturated or partially unsaturated or totally unsaturated or aromatic) that is unsubstituted or substituted by one or more T², —(X)—(CH₂)ₘ-(4-, 5- or 6-member heterocycle that has at least one heteroatom/heteratomic group that is selected from the group consisting of O, S, S(O), S(O)₂, and N, and is monocyclic is saturated or partially unsaturated or totally unsaturated or aromatic), (C₁-C₃)-alkyl, (C₁-C₃)-fluoroalkyl, —(X)—(C₁-C₃)-alkyl, —(X)—(C₁-C₃)-fluoroalkyl, —(CH₂)ₘ—(C₃-C₆)-cycloalkyl, —(X)—(CH₂)ₘ—(C₃-C₆)-cycloalkyl, —(CH₂)ₘ—(C₃-C₆)-cyclofluoroalkyl, —(X)—(CH₂)ₘ—(C₃-C₆)-cyclofluoroalkyl, —C(O)—(CH₂)ₘ-(4-, 5- or 6-member heterocycle that has at least one heteroatom/heteratomic group that is selected from the group consisting of O, S, S(O), S(O)₂, and N, and is monocyclic, and saturated or partially unsaturated or totally unsaturated or aromatic), —C(O)—(C₁-C₃)-alkyl, —C(O)—(C₁-C₃)-fluoroalkyl, —C(O)O—(C₁-C₃)-fluoroalkyl, —C(O)—(CH₂)ₘ—(C₃-C₆)-cycloalkyl, —C(O)—(CH₂)ₘ—(C₃-C₆)-cycloalkyl, —C(O)—(CH₂)ₘ—(C₃-C₆)-cyclofluoroalkyl, and —C(O)—(CH₂)ₘ—(C₃-C₆)-cyclofluoroalkyl;

T², identical or different, is independently selected from the group consisting of —OH, —NH₂, and —CONH₂;

m, identical or different, independently is 0, 1, 2, or 3;

n, identical or different, independently is 1, 2, or 3;

p, identical or different, independently is 2 or 3;

r is 1, 2, or 3 when the (CH₂)ᵣ is directly linked to a carbon atom, or 2 or 3 otherwise;

X, identical or different, is independently selected from the group consisting of O, S, S(O), S(O)₂, and N(Q³); and R³ is selected from the group consisting of —SO₃H, —CFHCOOH, and —CF₂COOH;

wherein any carbon atom present within any of the foregoing alkyls, cycloalkyls, fluoroalkyls, cyclofluoroalkyls, and heterocycles may be oxidized to form a C=O group;

wherein any sulphur atom present within a heterocycle may be oxidized to form a S=O group or a S(O)₂ group; and wherein any nitrogen atom present within a heterocycle or a tertiary amino group may be further quaternized by a methyl group; or a racemate, an enantiomer, a diastereoisomer, a geometric isomer, or a pharmaceutically acceptable salt thereof.

2. The compound according to claim 1, wherein:

A is one of the following:

A is a 4-, 5- or 6-member heterocycle that has at least one nitrogen heteroatom, is unsubstituted or substituted by one or more T¹, and is monocyclic, and is saturated or partially unsaturated or totally unsaturated or aromatic; or A is a 4-, 5- or 6-member heterocycle that has at least one nitrogen heteroatom and at least one further heteroatom/heteratomic group selected from the group consisting of O, S, S(O), S(O)₂, and N, is unsubstituted or substituted by one or more T¹, is monocyclic, and is saturated or partially unsaturated or totally unsaturated or aromatic.

3. The compound according to claim 1 selected from the group consisting of compounds of formulae (I*), (D), (B), (D*), and (B*)

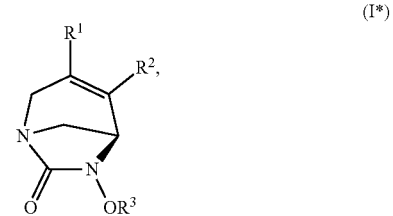

(I*)

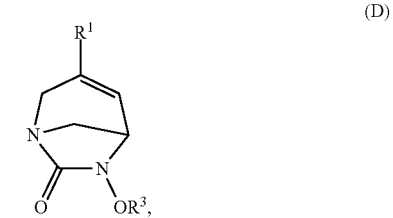

(D)

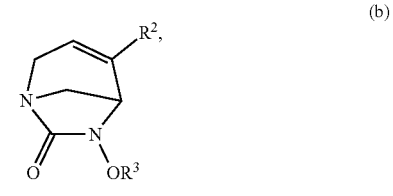

(b)

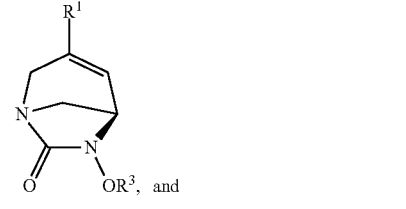

(D*)

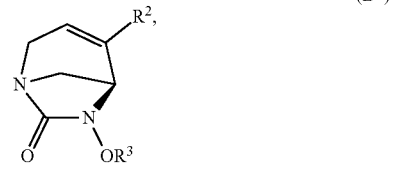

(B*)

wherein, for formulae (D), (B), (D*), and (B*), the depicted R¹ or R², as the case may be, represents A.

4. The compound according to claim 1 selected from the group consisting of compounds of formulae (C) and (C*)

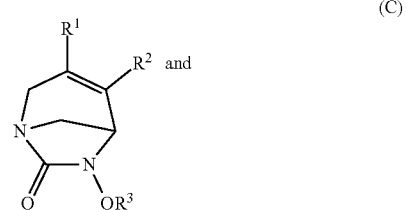

(C)

-continued (C*)

wherein B is not H.

5. The compound according to claim 1, wherein:
B is selected from the group consisting of H, $(C_1-C_3)$-alkyl that is unsubstituted or substituted by one or more $T^2$, $—(CH_2)_m—C(O)NQ^1Q^2$, and $—(CH_2)_m—NQ^1C(O)Q^2$; and
$Q^1$ and $Q^2$ are H or $(C_1-C_3)$-alkyl.

6. The compound according to claim 1, wherein:
$T^1$ is selected from the group consisting of $(C_1-C_3)$-alkyl that is unsubstituted or substituted by one or more $T^2$, $(CH_2)_mOQ^1$, $(CH_2)_mC(O)OQ^1$, $(CH_2)_mNQ^1Q^2$, $—(CH_2)_m—C(O)NQ^1OQ^2$, $—(CH_2)_m—C(O)NQ^1Q^2$, $—(CH_2)_m—C(O)NQ^1-NQ^1Q^2$, $—(CH_2)_m—NQ^1C(O)Q^2$, $—(CH_2)_m—NQ^1S(O)_2NQ^1Q^2$, $—(CH_2)_m—NQ^1C(O)NQ^1Q^2$, $—(CH_2)_m—NQ^1Q^2$, $—(CH_2)_m—NH—C(NHQ^3)=NQ^4$, $—C(O)(C_1-C_3)$-alkyl that is unsubstituted or substituted by one or more $T^2$, $—C(O)(CH_2)_nOQ^1$, $—C(O)(CH_2)_n—C(O)OQ^1$, $—C(O)(CH_2)_n—NQ^1Q^2$, $—C(O)—(CH_2)_n—C(O)NQ^1OQ^2$, $—C(O)(CH_2)_n—C(O)NQ^1-NQ^1Q^2$, $—C(O)(CH_2)_n—NQ^1C(O)Q^2$, $—C(O)(CH_2)_n—NQ^1S(O)_2NQ^1Q^2$, $—C(O)(CH_2)_n—NQ^1C(O)NQ^1Q^2$, $—C(O)(CH_2)_n—NQ^1Q^2$, $—C(O)(CH_2)_n—NH—C(NHQ^3)=NQ^4$, $—(X)—(C_1-C_3)$-alkyl, $—(X)—(CH_2)_pOQ^1$, $—(X)—(CH_2)_nC(O)OQ^1$, $—(X)—(CH_2)_pNQ^1Q^2$, $—(X)—(CH_2)_n—C(O)NQ^1OQ^2$, $—(X)—(CH_2)_n—C(O)NQ^1-NQ^1Q^2$, $—(X)—(CH_2)_p—NQ^1C(O)Q^2$, $—(X)—(CH_2)_p—NQ^1S(O)_2NQ^1Q^2$, $—(X)—(CH_2)_p—NQ^1C(O)NQ^1Q^2$, $—(X)—(CH_2)_p—NQ^1Q^2$, and $—(X)—(CH_2)_p—NH—C(NHQ^3)=NQ^4$; and
$Q^1$, $Q^2$, $Q^3$, and $Q^4$ are independently selected from the group consisting of H and $—(C_1-C_3)$-alkyl.

7. The compound according to claim 1, wherein:
$T^1$ is selected from the group consisting of $—(C_1-C_3)$-alkyl, $—(CH_2)_mOQ^1$, $—(CH_2)_m—C(O)OQ^1$, $—(CH_2)_m—C(O)NQ^1Q^2$, $—(CH_2)_m—NQ^1C(O)Q^2$, $—(CH_2)_m—NQ^1C(O)NQ^1Q^2$, $—(CH_2)_m—NQ^1Q^2$, $—C(O)—(C_1-C_3)$-alkyl, $—C(O)—(CH_2)_nOQ^1$, $—C(O)—(CH_2)_n—C(O)OQ^1$, $—C(O)—(CH_2)_n—C(O)NQ^1Q^2$, $—C(O)—(CH_2)_n—NQ^1C(O)Q^2$, $—C(O)—(CH_2)_n—NQ^1C(O)NQ^1Q^2$, $—C(O)—(CH_2)_n—NQ^1Q^2$, $—(X)—(C_1-C_3)$-alkyl, $—(X)—(CH_2)_p OQ^1$, $—(X)—(CH_2)_n—C(O)OQ^1$, $—(X)—(CH_2)_n—C(O)NQ^1Q^2$, $—(X)—(CH_2)_p—NQ^1C(O)Q^2$, $—(X)—(CH_2)_p—NQ^1C(O)NQ^1Q^2$, and $—(X)—(CH_2)_p—NQ^1Q^2$; and
$Q^1$, $Q^2$, $Q^3$, and $Q^4$ are independently selected from the group consisting of H and $—(C_1-C_3)$-alkyl.

8. The compound according to claim 1, wherein $T^1$ is selected from the group consisting of $—(C_1-C_3)$-alkyl, $—(CH_2)_mOQ^1$, $—(CH_2)_mC(O)OQ^1$, $—(CH_2)_m—C(O)NQ^1Q^2$, and $—(CH_2)_mNQ^1Q^2$.

9. The compound according to claim 1, wherein:
$T^1$ is selected from the group consisting of represents a $(C_1-C_3)$-alkyl, $OQ^1$, $C(O)OQ^1$, $(CH_2)_mNQ^1Q^2$, $—C(O)NQ^1Q^2$; and $Q^1$ and $Q^2$ are selected from the group consisting of H and $—(C_1-C_3)$-alkyl.

10. The compound according to claim 1, wherein:
A is one of the following:
A is a 5- or 6-member monocyclic heterocycle that has at least one nitrogen heteroatom and at least one further heteroatom/heteroatomic group selected from the group consisting of O, S, S(O), S(O)$_2$, and N, and that is unsubstituted or substituted by one or more $T^1$; or
A is an 8- to 10-member bicyclic heterocycle having at least one nitrogen heteroatom and at least one further heteroatom/heteroatomic group selected from the group consisting of O, S, S(O), S(O)$_2$ and N;
B is selected from the group consisting of H, $(C_1-C_3)$-alkyl that is unsubstituted or substituted by one or more $T^2$, and $—(CH_2)_m—C(O)NQ^1Q^2$;
$T^1$ is selected from the group consisting of $—(C_1-C_3)$-alkyl, $—(CH_2)_mOQ^1$, $—(CH_2)_m—C(O)OQ^1$, $—(CH_2)_m—C(O)NQ^1Q^2$, $—(CH_2)_m—NQ^1C(O)Q^2$, $—(CH_2)_m—NQ^1C(O)NQ^1Q^2$, $—(CH_2)_m—NQ^1Q^2$, $—C(O)—(C_1-C_3)$-alkyl, $—C(O)—(CH_2)_nOQ^1$, $—C(O)—(CH_2)_n—C(O)OQ^1$, $—C(O)—(CH_2)_n—C(O)NQ^1Q^2$, $—C(O)—(CH_2)_n—NQ^1C(O)Q^2$, $—C(O)—(CH_2)_n—NQ^1C(O)NQ^1Q^2$, $—C(O)—(CH_2)_n—NQ^1Q^2$, $—(X)—(C_1-C_3)$-alkyl, $—(X)—(CH_2)_pOQ^1$, $—(X)—(CH_2)_n—C(O)OQ^1$, $—(X)—(CH_2)_n—C(O)NQ^1Q^2$, $—(X)—(CH_2)_p—NQ^1C(O)Q^2$, $—(X)—(CH_2)_p—NQ^1C(O)NQ^1Q^2$, and $—(X)—(CH_2)_p—NQ^1Q^2$; and
$Q^1$, $Q^2$, $Q^3$, and $Q^4$ are independently selected from the group consisting of H and $—(C_1-C_3)$-alkyl.

11. The compound according to claim 1, wherein $T^1$ is selected from the group consisting of $(C_1-C_3)$-alkyl that is unsubstituted or substituted by one or more $T^2$, $(CH_2)_mOQ^1$, $—(CH_2)_m—C(O)NQ^1Q^2$, $(CH_2)_mC(O)OQ^1$, and $(CH_2)_mNQ^1Q^2$.

12. The compound according to claim 1, wherein:
$T^1$ is selected from the group consisting of $(C_1-C_3)$-alkyl, $OQ^1$, $C(O)OQ^1$, $(CH_2)_mNQ^1Q^2$, $—C(O)NQ^1Q^2$; and
$Q^1$ and $Q^2$ are selected from the group consisting of H and $—(C_1-C_3)$-alkyl.

13. The compound according to claim 1, wherein B is H.

14. A pharmaceutical composition comprising an effective amount of at least one compound according to claim 1 and a pharmaceutically acceptable excipient.

15. The pharmaceutical composition according to claim 14 further comprising an antibacterial compound.

16. The pharmaceutical composition according to claim 15, wherein the antibacterial compound is selected from the group consisting of aminoglycosides, β-lactams, glycylcyclines, tetracyclines, quinolones, fluoroquinolones, glycopeptides, lipopeptides, macrolides, ketolides, lincosamides, streptogramins, oxazolidinones, polymyxins, and mixtures thereof.

17. The pharmaceutical composition of claim 16, wherein the antibacterial compound is a β-lactam.

18. The pharmaceutical composition of claim 17, wherein the β-lactam is selected from the group consisting of penicillin, cephalosporins, penems, carbapenems, monobactam, and mixtures thereof.

19. A pharmaceutical composition comprising at least a compound according to claim 1 and ceftazidime.

20. A kit comprising:
a first pharmaceutical composition comprising a first compound according to claim 1, wherein the first compound is such that B is not H; and a second pharmaceutical composition comprising a second compound according to claim 1, wherein the second compound is such that B is H.

21. A kit comprising:
a first pharmaceutical composition comprising at least one compound according to claim 1; and
a second pharmaceutical composition comprising ceftazidime.

22. A method for the treatment or prevention of a bacterial infection, the method comprising administering a therapeutically effective amount of a compound of claim 1 to a patient in need thereof.

23. A method for the treatment or prevention of a bacterial infection, the method comprising administering, either simultaneously or separately or sequentially, therapeutically effective amounts of the first pharmaceutical composition and the second pharmaceutical composition of the kit of claim 20 to a patient in need thereof.

24. A compound selected from the group consisting of the following:

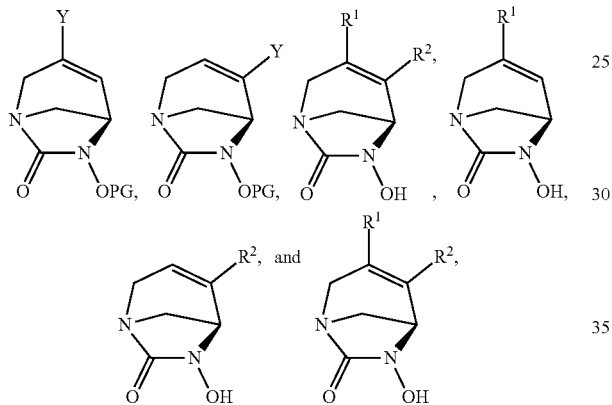

wherein:
R$^1$ represents A and R$^2$ represents B, or R$^1$ represents B and R$^2$ represents A;
A is a 4- to 10-member heterocycle that has at least one heteroatom/heteratomic group selected from the group consisting of O, S, S(O), S(O)$_2$ and N, and is monocyclic or bicyclic, is unsubstituted or substituted by one or more T$^1$, and is a saturated or partially unsaturated or totally unsaturated or aromatic;
B is one of the following:
B is selected from the group consisting of H, F, —(CH$_2$)$_m$OQ$^1$, —(CH$_2$)$_m$—CN, —(CH$_2$)$_m$—OC(O)Q$^1$, —(CH$_2$)$_m$—C(O)OQ$^1$, —(CH$_2$)$_m$—OC(O)OQ$^1$, —(CH$_2$)$_m$—OC(O)NQ$^1$Q$^2$, —(CH$_2$)$_m$—C(O)NQ$^1$Q$^2$, —(CH$_2$)$_m$—C(O)ONQ$^1$Q$^2$, —(CH$_2$)$_m$—C(O)NQ$^1$OQ$^2$, —(CH$_2$)$_m$—C(O)NQ$^1$-NQ$^1$Q$^2$, —(CH$_2$)$_m$NQ$^1$C(O)Q$^2$, —(CH$_2$)$_m$—NQ$^1$S(O)$_2$NQ$^1$Q$^2$, —(CH$_2$)$_m$—NQ$^1$S(O)$_2$Q$^2$, —(CH$_2$)$_m$—NQ$^1$C(O)OQ$^2$, —(CH$_2$)$_m$—NQ$^1$C(O)NQ$^1$Q$^2$, —(CH$_2$)$_n$—NQ$^1$Q$^2$, —(CH$_2$)$_n$—NH—C(NHQ$^3$)=NQ$^4$, —(CH$_2$)$_n$—NH—CH=NQ$^3$, —(CH$_2$)$_m$—C(NHQ$^3$)=NQ$^4$; or
B is selected from the group consisting of (C$_1$-C$_3$)-alkyl that is unsubstituted or substituted by one or more T$^2$, (C$_1$-C$_3$)-fluoroalkyl, O—(C$_1$-C$_3$)-fluoroalkyl, —(CH$_2$)$_m$—(C$_3$-C$_6$)-cycloalkyl, and —(CH$_2$)$_m$—(C$_3$-C$_6$)-cyclofluoroalkyl;

Q$^1$ and Q$^2$ are one of the following:
Q$^1$ and Q$^2$, identical or different, are independently selected from the group consisting of H, —(CH$_2$)$_r$—NHQ$^3$, —(CH$_2$)$_r$—NH—C(NHQ$^3$)=NQ$^4$, —(CH$_2$)$_r$—NH—CH=NQ$^3$, (CH$_2$)$_n$—C(NHQ$^3$)=NQ$^4$, —(CH$_2$)$_r$—OQ$^3$, and —(CH$_2$)$_n$—CONHQ$^3$; or
Q$^1$ and Q$^2$, identical or different, are independently selected from the group consisting of (C$_1$-C$_3$)-alkyl that is unsubstituted or substituted by one or more T$^2$, (C$_1$-C$_3$)-fluoroalkyl, and —(CH$_2$)$_m$-(4-, 5- or 6-member heterocycle having at least one nitrogen heteroatom) that is monocyclic, and saturated or partially unsaturated or totally unsaturated or aromatic; or
Q$^1$ and Q$^2$ and the nitrogen atom to which they are bonded form a is monocyclic, saturated or partially unsaturated 4-, 5-, or 6-member heterocycle that has 1, 2, or 3 heteroatom(s)/heteroatomic groups, wherein, in addition to said nitrogen atom being the first of said heteroatom(s)/heteroatomic group(s), the second and third od said heteroatom(s)/heteroatomic group(s) is/are each selected from the group consisting of O, S, S(O), S(O)$_2$, and N;
Q$^3$ and Q$^4$, identical or different, are independently selected from the group consisting of H and (C$_1$-C$_3$)-alkyl;
T$^1$ is one of the following:
T$^1$, identical or different, is independently selected from the group consisting of F, —(CH$_2$)$_m$OQ$^1$, —(CH$_2$)$_m$—CN, —(CH$_2$)$_m$—OC(O)Q$^1$, —(CH$_2$)$_m$—C(O)OQ$^1$, —(CH$_2$)$_m$—OC(O)OQ$^1$, —(CH$_2$)$_m$—OC(O)NQ$^1$Q$^2$, —(CH$_2$)$_m$—C(O)NQ$^1$Q$^2$, —(CH$_2$)$_m$—C(O)ONQ$^1$Q$^2$, —(CH$_2$)$_m$—C(O)NQ$^1$OQ$^2$, —(CH$_2$)$_m$—C(O)NQ$^1$-NQ$^1$Q$^2$, —(CH$_2$)$_m$—NQ$^1$C(O)Q$^2$, —(CH$_2$)$_m$—NQ$^1$S(O)$_2$NQ$^1$Q$^2$, —(CH$_2$)$_m$—NQ$^1$S(O)$_2$Q$^2$, —(CH$_2$)$_m$—NQ$^1$C(O)OQ$^2$, —(CH$_2$)$_m$—NQ$^1$C(O)NQ$^1$Q$^2$, —(CH$_2$)$_m$—NQ$^1$Q$^2$, —(CH$_2$)$_m$—NH—C(NHQ$^3$)=NQ$^4$, —(CH$_2$)$_m$—NH—CH=NQ$^3$, —(CH$_2$)$_m$—C(NHQ$^3$)=NQ$^4$, —(X)—(CH$_2$)$_p$OQ$^1$, —(X)—(CH$_2$)$_n$—CN, —(X)—(CH$_2$)$_p$—OC(O)Q$^1$, —(X)—(CH$_2$)$_n$—C(O)OQ$^1$, —(X)—(CH$_2$)$_p$—OC(O)OQ$^1$, —(X)—(CH$_2$)$_p$—OC(O)NQ$^1$Q$^2$, —(X)—(CH$_2$)$_n$—C(O)NQ$^1$Q$^2$, —(X)—(CH$_2$)$_n$—C(O)ONQ$^1$Q$^2$, —(X)—(CH$_2$)$_n$—C(O)NQ$^1$OQ$^2$, —(X)—(CH$_2$)$_n$—C(O)NQ$^1$—NQ$^1$Q$^2$, —(X)—(CH$_2$)$_p$—NQ$^1$C(O)Q$^2$, —(X)—(CH$_2$)$_p$—NQ$^1$S(O)$_2$NQ$^1$Q$^2$, —(X)—(CH$_2$)$_p$—NQ$^1$S(O)$_2$Q$^2$, —(X)—(CH$_2$)$_p$—NQ$^1$C(O)OQ$^2$, —(X)—(CH$_2$)$_p$—NQ$^1$C(O)NQ$^1$Q$^2$, —(X)—(CH$_2$)$_p$—NQ$^1$Q$^2$, —(X)—(CH$_2$)$_p$—NH—C(NHQ$^3$)=NQ$^4$, —(X)—(CH$_2$)$_p$—NH—CH=NQ$^3$, —(X)—(CH$_2$)$_n$—C(NHQ$^3$)=NQ$^4$, —C(O)—(CH$_2$)$_n$OQ$^1$, —C(O)—(CH$_2$)$_n$—CN, —C(O)—(CH$_2$)$_n$—OC(O)Q$^1$, —C(O)—(CH$_2$)$_n$—C(O)OQ$^1$, —C(O)—(CH$_2$)$_n$—OC(O)OQ$^1$, —C(O)—(CH$_2$)$_n$—OC(O)NQ$^1$Q$^2$, —C(O)—(CH$_2$)$_n$—C(O)NQ$^1$Q$^2$, —C(O)—(CH$_2$)$_n$—C(O)ONQ$^1$Q$^2$, —C(O)—(CH$_2$)$_n$—C(O)NQ$^1$OQ$^2$, —C(O)—(CH$_2$)$_n$—C(O)NQ$^1$-NQ$^1$Q$^2$, —C(O)—(CH$_2$)$_n$—NQ$^1$C(O)Q$^2$, —C(O)—(CH$_2$)$_n$—NQ$^1$S(O)$_2$NQ$^1$Q$^2$, —C(O)—(CH$_2$)$_n$—NQ$^1$S(O)$_2$Q$^2$, —C(O)—(CH$_2$)$_n$—NQ$^1$C(O)OQ$^2$, —C(O)—(CH$_2$)$_n$—NQ$^1$C(O)NQ$^1$Q$^2$, —C(O)—(CH$_2$)$_n$—NQ$^1$Q$^2$, —C(O)—(CH$_2$)$_n$—

NH—C(NHQ³)=NQ⁴, —C(O)—(CH₂)ₙ—NH—CH=NQ³, and —C(O)—(CH₂)ₙ—C(NHQ³)=NQ⁴; or

T¹, identical or different, is independently selected from the group consisting of —(CH₂)ₘ-(4-, 5- or 6-member heterocycle that has at least one heteroatom/heteroatomic group that is selected from the group consisting of O, S, S(O), S(O)₂, and N, and is monocyclic, and saturated or partially unsaturated or totally unsaturated or aromatic) that is unsubstituted or substituted by one or more T², —(X)—(CH₂)ₘ-(4-, 5- or 6-member heterocycle that has at least one heteroatom/heteroatomic group that is selected from the group consisting of O, S, S(O), S(O)₂, and N, and is monocyclic, and saturated or partially unsaturated or totally unsaturated or aromatic), (C₁-C₃)-alkyl, (C₁-C₃)-fluoroalkyl, —(X)—(C₁-C₃)-alkyl, —(X)—(C₁-C₃)-fluoroalkyl, —(CH₂)ₘ—(C₃-C₆)-cycloalkyl, —(X)—(CH₂)ₘ—(C₃-C₆)-cycloalkyl, —(CH₂)ₘ—(C₃-C₆)-cyclofluoroalkyl, —(X)—(CH₂)ₘ—(C₃-C₆)-cyclofluoroalkyl, —C(O)—(CH₂)ₘ-(4-, 5- or 6-member heterocycle that has at least one heteroatom/heteroatomic group that is selected from the group consisting of O, S, S(O), S(O)₂, and N, and is monocyclic, and saturated or partially unsaturated or totally unsaturated or aromatic), —C(O)—(C₁-C₃)-alkyl, —C(O)—(C₁-C₃)-fluoroalkyl, —C(O)O—(C₁-C₃)-fluoroalkyl, —C(O)—(CH₂)ₘ—(C₃-C₆)-cycloalkyl, —C(O)—(CH₂)ₘ—(C₃-C₆)-cycloalkyl, —C(O)—(CH₂)ₘ—(C₃-C₆)-cyclofluoroalkyl, and —C(O)—(CH₂)ₘ—(C₃-C₆)-cyclofluoroalkyl;

T², identical or different, is independently selected from the group consisting of —OH, —NH₂, and —CONH₂;

m, identical or different, independently is 0, 1, 2, or 3;

n, identical or different, independently is 1, 2, or 3;

p, identical or different, independently is 2 or 3;

r is 1, 2, or 3 when the (CH₂)ᵣ is directly linked to a carbon atom, or 2 or 3 otherwise; and X, identical or different, is independently selected from the group consisting of O, S, S(O), S(O)₂, and N(Q³);

R³ is selected from the group consisting of —SO₃H, —CFHCOOH, and —CF₂COOH;

Y is selected from the group consisting of a halogen, —B(OR)₂ in which R is alkyl or the OR are linked together with the B to form a cycle, and SnR₃; and PG is a protective group selected from the group consisting of allyl, benzyl, tertbutyldimethylsilyl (TBDMS), and tert-butoxycarbonyl (Boc);

wherein any carbon atom present within any of the foregoing alkyls, cycloalkyls, fluoroalkyls, cyclofluoroalkyls, and heterocycles may be oxidized to form a C=O group;

wherein any sulphur atom present within a heterocycle may be oxidized to form a S=O group or a S(O)₂ group; and wherein any nitrogen atom present within a heterocycle or a tertiary amino group may be further quaternized by a methyl group; or a racemate, an enantiomer, a diastereoisomer, a geometric isomer, or a pharmaceutically acceptable salt thereof.

\* \* \* \* \*